US012716090B2

(12) United States Patent
Kirkizlar et al.

(10) Patent No.: US 12,716,090 B2
(45) Date of Patent: Aug. 25, 2026

(54) METHODS AND COMPOSITIONS FOR DETERMINING PLOIDY

(71) Applicant: Natera, Inc., San Carlos, CA (US)

(72) Inventors: Huseyin Eser Kirkizlar, Los Angeles, CA (US); Raheleh Salari, San Carlos, CA (US); Styrmir Sigurjonsson, San Jose, CA (US); Bernhard Zimmermann, Manteca, CA (US); Allison Ryan, Belmont, CA (US); Naresh Vankayalapati, San Francisco, CA (US)

(73) Assignee: Natera, Inc., San Carlos, CA (US)

( * ) Notice: Subject to any disclaimer, the term of this patent is extended or adjusted under 35 U.S.C. 154(b) by 64 days.

(21) Appl. No.: 18/441,502

(22) Filed: Feb. 14, 2024

(65) Prior Publication Data

US 2024/0301482 A1 Sep. 12, 2024

Related U.S. Application Data

(60) Continuation of application No. 17/845,169, filed on Jun. 21, 2022, now Pat. No. 11,946,101, which is a division of application No. 15/573,800, filed as application No. PCT/US2016/031686 on May 10, 2016, now Pat. No. 11,479,812.

(60) Provisional application No. 62/159,958, filed on May 11, 2015.

(51) Int. Cl.

| | |
|---|---|
| ***C12Q 1/68*** | (2018.01) |
| ***C12Q 1/6853*** | (2018.01) |
| ***C12Q 1/6858*** | (2018.01) |
| ***C12Q 1/6869*** | (2018.01) |
| ***C12Q 1/6886*** | (2018.01) |
| ***G16B 20/00*** | (2019.01) |
| ***G16B 20/10*** | (2019.01) |
| ***G16H 10/40*** | (2018.01) |

(52) U.S. Cl.

CPC ......... *C12Q 1/6858* (2013.01); *C12Q 1/6853* (2013.01); *C12Q 1/6869* (2013.01); *C12Q 1/6886* (2013.01); *G16B 20/00* (2019.02); *G16B 20/10* (2019.02); *G16H 10/40* (2018.01); *C12Q 2539/10* (2013.01); *C12Q 2600/106* (2013.01); *C12Q 2600/156* (2013.01); *Y02A 90/10* (2018.01)

(58) Field of Classification Search

CPC .. C12Q 1/6858; C12Q 1/6853; C12Q 1/6869; C12Q 1/6886; C12Q 2539/10; C12Q 2600/106; C12Q 2600/156; G16H 10/40; G16B 20/00; G16B 20/10; Y02A 90/10

See application file for complete search history.

(56) References Cited

U.S. PATENT DOCUMENTS

| | | | |
|---|---|---|---|
| 3,957,654 | A | 5/1976 | Ayres |
| 4,040,785 | A | 8/1977 | Kim et al. |
| 4,683,195 | A | 7/1987 | Mullis et al. |
| 4,942,124 | A | 7/1990 | Church |
| 5,180,812 | A | 1/1993 | Dower et al. |
| 5,314,809 | A | 5/1994 | Erlich et al. |
| 5,319,071 | A | 6/1994 | Dower et al. |
| 5,464,937 | A | 11/1995 | Sims et al. |
| 5,486,477 | A | 1/1996 | Carver, Jr. |
| 5,488,032 | A | 1/1996 | Dower et al. |
| 5,492,888 | A | 2/1996 | Dower et al. |
| 5,569,582 | A | 10/1996 | Tavernarakis et al. |
| 5,595,890 | A | 1/1997 | Newton et al. |
| 5,635,366 | A | 6/1997 | Cooke et al. |
| 5,645,988 | A | 7/1997 | Vande Woude et al. |
| 5,648,220 | A | 7/1997 | Bianchi et al. |
| 5,714,320 | A | 2/1998 | Kool |
| 5,716,776 | A | 2/1998 | Bogart |
| 5,736,033 | A | 4/1998 | Coleman et al. |
| 5,753,467 | A | 5/1998 | Jensen et al. |
| 5,824,467 | A | 10/1998 | Mascarenhas |
| 5,854,033 | A | 12/1998 | Lizardi |
| 5,860,917 | A | 1/1999 | Comanor et al. |
| 5,891,734 | A | 4/1999 | Gill et al. |
| 5,952,170 | A | 9/1999 | Stroun et al. |
| 5,962,223 | A | 10/1999 | Whiteley et al. |
| 5,972,602 | A | 10/1999 | Hyland et al. |
| 5,976,790 | A | 11/1999 | Pinkel et al. |
| 5,994,148 | A | 11/1999 | Stewart et al. |

(Continued)

FOREIGN PATENT DOCUMENTS

| | | |
|---|---|---|
| CA | 2875281 A1 | 12/2013 |
| CN | 1650032 A | 8/2005 |

(Continued)

OTHER PUBLICATIONS

US 8,501,409 B2, 08/2013, Birgitte (withdrawn)

(Continued)

*Primary Examiner* — Catherine S Hibbert

(57) ABSTRACT

The invention provides improved methods, compositions, and kits for detecting ploidy of chromosome regions, e.g. for detecting cancer or a chromosomal abnormality in a gestating fetus. The methods can utilize a set of more than 200 SNPs that are found within haploblocks and can include analyzing a series of target chromosomal regions related to cancer or a chromosomal abnormality in a gestating fetus. Finally the method may use knowledge about chromosome crossover locations or a best fit algorithm for the analysis. The compositions may comprise more than 200 primers located within haplotype blocks known to show CNV.

20 Claims, 11 Drawing Sheets

Specification includes a Sequence Listing.

(56) References Cited

U.S. PATENT DOCUMENTS 6,001,611 A 12/1999 Will
6,025,128 A 2/2000 Veltri et al.
6,066,454 A 5/2000 Lipshutz et al.
6,100,029 A 8/2000 Lapidus et al.
6,108,635 A 8/2000 Herren et al.
6,124,120 A 9/2000 Lizardi
6,143,496 A 11/2000 Brown et al.
6,156,504 A 12/2000 Gocke et al.
6,180,349 B1 1/2001 Ginzinger et al.
6,214,558 B1 4/2001 Shuber et al.
6,221,603 B1 4/2001 Mahtani
6,235,472 B1 5/2001 Landegren et al.
6,258,540 B1 7/2001 Lo et al.
6,300,077 B1 10/2001 Shuber et al.
6,329,179 B1 12/2001 Kopreski
6,335,167 B1 1/2002 Pinkel et al.
6,440,706 B1 8/2002 Vogelstein et al.
6,479,235 B1 11/2002 Schumm et al.
6,489,135 B1 12/2002 Parrott
6,605,451 B1 8/2003 Marmaro et al.
6,617,137 B2 9/2003 Dean et al.
6,720,140 B1 4/2004 Hartley et al.
6,794,140 B1 9/2004 Goldsborough
6,807,491 B2 10/2004 Pavlovic et al.
6,852,487 B1 2/2005 Barany et al.
6,858,412 B2 2/2005 Willis et al.
6,927,028 B2 8/2005 Dennis et al.
6,958,211 B2 10/2005 Vingerhoets et al.
6,964,847 B1 11/2005 Englert
7,035,739 B2 4/2006 Schadt et al.
7,058,517 B1 6/2006 Denton et al.
7,058,616 B1 6/2006 Larder et al.
7,101,663 B2 9/2006 Godfrey et al.
7,153,656 B2 12/2006 Nolan et al.
7,218,764 B2 5/2007 Vaisberg et al.
7,297,485 B2 11/2007 Bornarth et al.
7,332,277 B2 2/2008 Dhallan
7,410,764 B2 8/2008 Gocke et al.
7,414,118 B1 8/2008 Mullah et al.
7,442,506 B2 10/2008 Dhallan
7,459,273 B2 12/2008 Jones et al.
7,537,897 B2 5/2009 Brenner et al.
7,645,576 B2 1/2010 Lo et al.
7,655,399 B2 2/2010 Cantor et al.
7,700,325 B2 4/2010 Cantor et al.
7,718,367 B2 5/2010 Lo et al.
7,718,370 B2 5/2010 Dhallan
7,727,720 B2 6/2010 Dhallan
7,741,463 B2 6/2010 Gormley et al.
7,785,798 B2 8/2010 Cantor et al.
7,790,393 B2 9/2010 Lyamichev et al.
7,790,418 B2 9/2010 Mayer
7,805,282 B2 9/2010 Casey
7,838,647 B2 11/2010 Hahn et al.
7,888,017 B2 2/2011 Quake et al.
7,981,609 B2 7/2011 Rubin et al.
8,008,018 B2 8/2011 Quake et al.
8,024,128 B2 9/2011 Rabinowitz et al.
8,133,719 B2 3/2012 Drmanac et al.
8,137,912 B2 3/2012 Kapur et al.
8,168,389 B2 5/2012 Shoemaker et al.
8,173,370 B2 5/2012 Oeth et al.
8,195,415 B2 6/2012 Fan et al.
8,236,503 B2 8/2012 Faham et al.
8,296,076 B2 10/2012 Fan et al.
8,304,187 B2 11/2012 Fernando
8,318,430 B2 11/2012 Chuu et al.
8,318,434 B2 11/2012 Cuppens
8,323,897 B2 12/2012 Andersen et al.
8,372,584 B2 2/2013 Shoemaker et al.
8,389,557 B2 3/2013 Singh et al.
8,389,578 B2 3/2013 Went et al.
8,450,063 B2 5/2013 Dube et al.
8,467,976 B2 6/2013 Lo et al.
8,515,679 B2 8/2013 Rabinowitz et al.
8,532,930 B2 9/2013 Rabinowitz et al.
8,609,338 B2 12/2013 Mitchell et al.
8,679,741 B2 3/2014 Hoyal-Wrightson et al.
8,682,592 B2 3/2014 Rabinowitz et al.
8,703,652 B2 4/2014 Quake et al.
8,706,422 B2 4/2014 Lo et al.
8,748,103 B2 6/2014 Faham et al.
8,822,153 B2 9/2014 Hayes et al.
8,825,412 B2 9/2014 Rabinowitz et al.
9,005,894 B2 4/2015 Ladner et al.
9,051,602 B2 6/2015 Oliphant et al.
9,085,798 B2 7/2015 Chee
9,206,475 B2 12/2015 Gerdes et al.
9,228,234 B2 1/2016 Rabinowitz et al.
9,290,815 B2 3/2016 Di Pasquale et al.
9,323,888 B2 4/2016 Rava et al.
9,364,829 B2 6/2016 Heid et al.
9,404,150 B2 8/2016 Lee et al.
9,424,392 B2 8/2016 Rabinowitz et al.
9,453,257 B2 9/2016 Hoyal-Wrightson et al.
9,476,095 B2 10/2016 Vogelstein et al.
9,487,829 B2 11/2016 Vogelstein et al.
9,493,828 B2 11/2016 Rava et al.
9,506,119 B2 11/2016 Faham et al.
9,598,731 B2 3/2017 Talasaz
9,677,118 B2 6/2017 Zimmermann et al.
9,784,742 B2 10/2017 Benz et al.
9,926,593 B2 3/2018 Ehrich et al.
9,957,558 B2 5/2018 Leamon et al.
10,011,870 B2 7/2018 Zimmermann et al.
10,017,810 B2 7/2018 Iafrate et al.
10,041,127 B2 8/2018 Talasaz
10,061,890 B2 8/2018 Rabinowitz et al.
10,081,839 B2 9/2018 Rabinowitz et al.
10,083,273 B2 9/2018 Rabinowitz et al.
10,174,369 B2 1/2019 Rabinowitz et al.
10,179,937 B2 1/2019 Babiarz et al.
10,227,652 B2 3/2019 Rabinowitz et al.
10,229,244 B2 3/2019 Ghosh
10,240,202 B2 3/2019 Rabinowitz et al.
10,260,096 B2 4/2019 Rabinowitz et al.
10,262,755 B2 4/2019 Babiarz et al.
10,266,893 B2 4/2019 Rabinowitz et al.
10,308,981 B2 6/2019 Sparks et al.
10,316,362 B2 6/2019 Babiarz et al.
10,351,906 B2 7/2019 Zimmermann et al.
10,385,396 B2 8/2019 Mitchell et al.
10,392,664 B2 8/2019 Rabinowitz et al.
10,450,597 B2 10/2019 Iafrate et al.
10,472,680 B2 11/2019 Mitchell et al.
10,522,242 B2 12/2019 Rabinowitz et al.
10,526,658 B2 1/2020 Babiarz et al.
10,538,814 B2 1/2020 Babiarz et al.
10,557,172 B2 2/2020 Babiarz et al.
10,597,708 B2 3/2020 Zimmermann et al.
10,597,709 B2 3/2020 Zimmermann et al.
10,597,723 B2 3/2020 Babiarz et al.
10,640,819 B2 5/2020 Rosenfeld et al.
10,655,180 B2 5/2020 Babiarz et al.
10,683,552 B2 6/2020 McCarroll et al.
10,711,309 B2 7/2020 Rabinowitz et al.
10,731,220 B2 8/2020 Babiarz et al.
10,774,380 B2 9/2020 Ryan et al.
10,793,912 B2 10/2020 Babiarz et al.
10,894,976 B2 1/2021 Stray et al.
11,111,543 B2 9/2021 Rabinowitz et al.
11,111,544 B2 9/2021 Rabinowitz et al.
11,111,545 B2 9/2021 Babiarz et al.
11,130,995 B2 9/2021 Quake et al.
11,319,596 B2 5/2022 Babiarz et al.
11,371,100 B2 6/2022 Babiarz et al.
11,519,035 B2 12/2022 Rabinowitz et al.
2001/0051341 A1 12/2001 Lo et al.
2001/0053519 A1 12/2001 Fodor et al.
2002/0006622 A1 1/2002 Bradley et al.
2002/0107640 A1 8/2002 Ideker et al.
2002/0119478 A1 8/2002 Umansky et al.
2002/0182622 A1 12/2002 Nakamura et al.
2002/0197630 A1 12/2002 Knapp et al.

(56) References Cited

U.S. PATENT DOCUMENTS

2003/0009295 A1 1/2003 Markowitz et al.
2003/0040620 A1 2/2003 Langmore et al.
2003/0044388 A1 3/2003 Dennis et al.
2003/0065535 A1 4/2003 Karlov et al.
2003/0077586 A1 4/2003 Pavlovic et al.
2003/0087276 A1 5/2003 Kopreski
2003/0101000 A1 5/2003 Bader et al.
2003/0108900 A1 6/2003 Oliphant et al.
2003/0119004 A1 6/2003 Wenz et al.
2003/0138780 A1 7/2003 Gill et al.
2003/0148301 A1 8/2003 Aono et al.
2003/0191005 A1 10/2003 Coelho et al.
2003/0211489 A1 11/2003 Shen et al.
2003/0228613 A1 12/2003 Bornarth et al.
2003/0232348 A1 12/2003 Jones et al.
2003/0232353 A1 12/2003 Kennedy
2003/0235848 A1 12/2003 Neville et al.
2004/0009518 A1 1/2004 Lo et al.
2004/0033596 A1 2/2004 Threadgill et al.
2004/0067493 A1 4/2004 Matsuzaki et al.
2004/0096874 A1 5/2004 Neville et al.
2004/0115629 A1 6/2004 Panzer et al.
2004/0117346 A1 6/2004 Stoffel et al.
2004/0126760 A1 7/2004 Broude
2004/0136967 A1 7/2004 Weiss et al.
2004/0137470 A1 7/2004 Dhallan
2004/0146866 A1 7/2004 Fu
2004/0157243 A1 8/2004 Huang et al.
2004/0185495 A1 9/2004 Schueler et al.
2004/0197797 A1 10/2004 Inoko et al.
2004/0209299 A1 10/2004 Pinter et al.
2004/0229231 A1 11/2004 Frudakis et al.
2004/0236518 A1 11/2004 Pavlovic et al.
2004/0259100 A1 12/2004 Gunderson et al.
2005/0009069 A1 1/2005 Liu et al.
2005/0043894 A1 2/2005 Fernandez
2005/0049793 A1 3/2005 Paterlini-Brechot
2005/0053950 A1 3/2005 Zudaire Ubani et al.
2005/0064476 A1 3/2005 Huang et al.
2005/0079521 A1 4/2005 Beaulieu et al.
2005/0079535 A1 4/2005 Kirchgesser et al.
2005/0123914 A1 6/2005 Katz et al.
2005/0130173 A1 6/2005 Leamon et al.
2005/0142577 A1 6/2005 Jones et al.
2005/0144664 A1 6/2005 Smith et al.
2005/0164241 A1 7/2005 Hahn et al.
2005/0164252 A1 7/2005 Yeung
2005/0216207 A1 9/2005 Kermani
2005/0221341 A1 10/2005 Shimkets et al.
2005/0227263 A1 10/2005 Green et al.
2005/0250111 A1 11/2005 Xie et al.
2005/0255508 A1 11/2005 Casey
2005/0272073 A1 12/2005 Vaisberg et al.
2005/0282185 A1 12/2005 Lo Yuk-Ming et al.
2006/0014179 A1 1/2006 Roberts
2006/0019278 A1 1/2006 Lo et al.
2006/0040300 A1 2/2006 Dapprich et al.
2006/0046258 A1 3/2006 Lapidus et al.
2006/0051799 A1 3/2006 Iwaki et al.
2006/0052945 A1 3/2006 Rabinowitz et al.
2006/0057618 A1 3/2006 Piper et al.
2006/0068369 A1 3/2006 Coelho et al.
2006/0068394 A1 3/2006 Langmore et al.
2006/0088574 A1 4/2006 Manning et al.
2006/0088871 A1 4/2006 Finkelstein et al.
2006/0088912 A1 4/2006 Yan et al.
2006/0094010 A1 5/2006 Giles et al.
2006/0099614 A1 5/2006 Gill et al.
2006/0121452 A1 6/2006 Dhallan
2006/0134662 A1 6/2006 Pratt et al.
2006/0141499 A1 6/2006 Sher et al.
2006/0210997 A1 9/2006 Myerson et al.
2006/0216153 A1 9/2006 Wobben
2006/0216738 A1 9/2006 Wada et al.
2006/0228721 A1 10/2006 Leamon et al.
2006/0229823 A1 10/2006 Liu et al.
2006/0234264 A1 10/2006 Hardenbol
2006/0248031 A1 11/2006 Kates et al.
2006/0281105 A1 12/2006 Li et al.
2006/0292599 A1 12/2006 Ritz et al.
2007/0020640 A1 1/2007 McCloskey et al.
2007/0027636 A1 2/2007 Rabinowitz
2007/0031857 A1 2/2007 Makarov et al.
2007/0037166 A1 2/2007 Wohlgemuth et al.
2007/0042384 A1 2/2007 Li et al.
2007/0059700 A1 3/2007 Tao et al.
2007/0059707 A1 3/2007 Cantor et al.
2007/0122805 A1 5/2007 Cantor et al.
2007/0128624 A1 6/2007 Gormley et al.
2007/0134658 A1 6/2007 Bohmer
2007/0178478 A1 8/2007 Dhallan et al.
2007/0178501 A1 8/2007 Rabinowitz et al.
2007/0184467 A1 8/2007 Rabinowitz et al.
2007/0202525 A1 8/2007 Quake et al.
2007/0202536 A1 8/2007 Yamanishi et al.
2007/0207466 A1 9/2007 Cantor et al.
2007/0212689 A1 9/2007 Bianchi et al.
2007/0231823 A1 10/2007 McKernan et al.
2007/0243549 A1 10/2007 Bischoff
2007/0259351 A1 11/2007 Chinitz et al.
2008/0020390 A1 1/2008 Mitchell et al.
2008/0026390 A1 1/2008 Stoughton et al.
2008/0038733 A1 2/2008 Bischoff et al.
2008/0050739 A1 2/2008 Stoughton et al.
2008/0070792 A1 3/2008 Stoughton et al.
2008/0071076 A1 3/2008 Hahn et al.
2008/0085836 A1 4/2008 Kearns et al.
2008/0090239 A1 4/2008 Shoemaker et al.
2008/0096766 A1 4/2008 Lee
2008/0102455 A1 5/2008 Poetter
2008/0138809 A1 6/2008 Kapur et al.
2008/0161420 A1 7/2008 Shuber
2008/0164204 A1 7/2008 Hatamian et al.
2008/0182244 A1 7/2008 Tafas et al.
2008/0193927 A1 8/2008 Mann et al.
2008/0220422 A1 9/2008 Shoemaker et al.
2008/0234142 A1 9/2008 Lietz
2008/0243398 A1 10/2008 Rabinowitz et al.
2008/0280292 A1 11/2008 Wangh et al.
2008/0286783 A1 11/2008 Hosono et al.
2008/0293589 A1 11/2008 Shapero
2008/0299562 A1 12/2008 Oeth et al.
2008/0305473 A1 12/2008 Chowdary et al.
2009/0023190 A1 1/2009 Lao et al.
2009/0029377 A1 1/2009 Lo et al.
2009/0053719 A1 2/2009 Lo et al.
2009/0087847 A1 4/2009 Lo et al.
2009/0098534 A1 4/2009 Weier et al.
2009/0099041 A1 4/2009 Church et al.
2009/0143570 A1 6/2009 Jiang et al.
2009/0176234 A1 7/2009 Drmanac et al.
2009/0176662 A1 7/2009 Rigatti et al.
2009/0221620 A1 9/2009 Luke et al.
2009/0228299 A1 9/2009 Kangarloo et al.
2009/0233802 A1 9/2009 Bignell et al.
2009/0253183 A1 10/2009 Han
2009/0263800 A1 10/2009 Wohlgemuth et al.
2009/0280479 A1 11/2009 Hoon et al.
2009/0317817 A1 12/2009 Oeth et al.
2010/0012598 A1 1/2010 DiCesare et al.
2010/0035232 A1 2/2010 Ecker et al.
2010/0041048 A1 2/2010 Diehl et al.
2010/0086914 A1 4/2010 Bentley et al.
2010/0105049 A1 4/2010 Ehrich et al.
2010/0112575 A1 5/2010 Fan et al.
2010/0112586 A1 5/2010 Stoughton et al.
2010/0112590 A1 5/2010 Lo et al.
2010/0120038 A1 5/2010 Mir et al.
2010/0124751 A1 5/2010 Quake et al.
2010/0129792 A1 5/2010 Makrigiorgos
2010/0129874 A1 5/2010 Mitra et al.
2010/0138165 A1 6/2010 Fan et al.
2010/0155343 A1 6/2010 Battles et al.
2010/0171954 A1 7/2010 Quake et al.

(56) References Cited

U.S. PATENT DOCUMENTS

2010/0173394 A1 7/2010 Colston, Jr. et al.
2010/0184043 A1 7/2010 Mitchell et al.
2010/0184069 A1 7/2010 Fernando et al.
2010/0184152 A1 7/2010 Sandler et al.
2010/0196892 A1 8/2010 Quake et al.
2010/0203538 A1 8/2010 Dube et al.
2010/0216145 A1 8/2010 Duvdevani
2010/0216151 A1 8/2010 Lapidus et al.
2010/0216153 A1 8/2010 Lapidus et al.
2010/0227329 A1 9/2010 Cuppens
2010/0248231 A1 9/2010 Wei et al.
2010/0255492 A1 10/2010 Quake et al.
2010/0256013 A1 10/2010 Quake et al.
2010/0273159 A1 10/2010 Melo et al.
2010/0273219 A1 10/2010 May et al.
2010/0273678 A1 10/2010 Alexandre et al.
2010/0285478 A1 11/2010 Chen et al.
2010/0285537 A1 11/2010 Zimmermann
2010/0291572 A1 11/2010 Stoughton et al.
2010/0291635 A1 11/2010 Peleg
2010/0323352 A1 12/2010 Lo et al.
2010/0326218 A1 12/2010 Boeckh et al.
2011/0015096 A1 1/2011 Chiu
2011/0033862 A1 2/2011 Rabinowitz et al.
2011/0039724 A1 2/2011 Lo et al.
2011/0045462 A1 2/2011 Fu et al.
2011/0064824 A1 3/2011 Lascoste et al.
2011/0071031 A1 3/2011 Khripin et al.
2011/0086769 A1 4/2011 Oliphant et al.
2011/0092763 A1 4/2011 Rabinowitz et al.
2011/0105353 A1 5/2011 Lo et al.
2011/0110931 A1 5/2011 Matsui
2011/0111410 A1 5/2011 Ryan et al.
2011/0130558 A1 6/2011 Ritt et al.
2011/0151442 A1 6/2011 Fan et al.
2011/0159499 A1 6/2011 Hindson et al.
2011/0160078 A1 6/2011 Fodor et al.
2011/0178719 A1 7/2011 Rabinowitz et al.
2011/0189677 A1 8/2011 Adli et al.
2011/0201507 A1 8/2011 Rava et al.
2011/0212446 A1 9/2011 Wang et al.
2011/0212846 A1 9/2011 Spier
2011/0224087 A1 9/2011 Quake et al.
2011/0230358 A1 9/2011 Rava
2011/0246083 A1 10/2011 Fan et al.
2011/0251149 A1 10/2011 Perrine et al.
2011/0288780 A1 11/2011 Rabinowitz et al.
2011/0294699 A1 12/2011 Lee et al.
2011/0300608 A1 12/2011 Ryan et al.
2011/0301854 A1* 12/2011 Curry .................... G16B 20/20 702/19
2011/0312503 A1 12/2011 Chuu et al.
2011/0318734 A1 12/2011 Lo et al.
2012/0003635 A1 1/2012 Lo et al.
2012/0003637 A1 1/2012 Lo et al.
2012/0010085 A1 1/2012 Rava et al.
2012/0021442 A1 1/2012 Buhimschi et al.
2012/0028814 A1 2/2012 Toloue et al.
2012/0034603 A1 2/2012 Oliphant et al.
2012/0034685 A1 2/2012 Sparks et al.
2012/0108460 A1 5/2012 Quake et al.
2012/0115140 A1 5/2012 Rivkees et al.
2012/0122701 A1 5/2012 Ryan et al.
2012/0122702 A1 5/2012 Leproust et al.
2012/0135872 A1 5/2012 Chuu et al.
2012/0165203 A1 6/2012 Quake et al.
2012/0185176 A1 7/2012 Rabinowitz et al.
2012/0190020 A1 7/2012 Oliphant et al.
2012/0190021 A1 7/2012 Oliphant et al.
2012/0190557 A1 7/2012 Oliphant et al.
2012/0191358 A1 7/2012 Oliphant et al.
2012/0196754 A1 8/2012 Quake et al.
2012/0208706 A1 8/2012 Downing et al.
2012/0214678 A1 8/2012 Rava et al.
2012/0251411 A1 10/2012 Jeon
2012/0264121 A1 10/2012 Rava et al.
2012/0264618 A1 10/2012 Nygren
2012/0270212 A1 10/2012 Rabinowitz et al.
2012/0270739 A1 10/2012 Rava et al.
2012/0295810 A1 11/2012 Quake et al.
2012/0295819 A1 11/2012 Leamon et al.
2013/0017549 A1 1/2013 Hong
2013/0022973 A1 1/2013 Hansen et al.
2013/0024127 A1 1/2013 Stuelpnagel et al.
2013/0034546 A1 2/2013 Rava et al.
2013/0040375 A1 2/2013 Sparks et al.
2013/0059733 A1 3/2013 Lo et al.
2013/0060483 A1 3/2013 Struble et al.
2013/0069869 A1 3/2013 Akao et al.
2013/0071844 A1 3/2013 Makino et al.
2013/0073214 A1 3/2013 Hyland et al.
2013/0085681 A1 4/2013 Deciu et al.
2013/0090250 A1 4/2013 Sparks et al.
2013/0116130 A1 5/2013 Fu et al.
2013/0123120 A1* 5/2013 Zimmermann ........ G16B 20/20 506/26
2013/0130923 A1 5/2013 Ehrich et al.
2013/0143219 A1 6/2013 Mitchell et al.
2013/0150253 A1 6/2013 Deciu et al.
2013/0157870 A1 6/2013 Pushkarev et al.
2013/0172211 A1 7/2013 Oliphant et al.
2013/0178373 A1 7/2013 Rabinowitz et al.
2013/0190653 A1 7/2013 Alvarez Ramos
2013/0196862 A1 8/2013 Rabinowitz et al.
2013/0210644 A1 8/2013 Stoughton et al.
2013/0225422 A1 8/2013 Rabinowitz et al.
2013/0231252 A1 9/2013 Mitchell et al.
2013/0237431 A1 9/2013 Lo et al.
2013/0252824 A1 9/2013 Rabinowitz et al.
2013/0253369 A1 9/2013 Rabinowitz et al.
2013/0261004 A1 10/2013 Ryan et al.
2013/0274116 A1 10/2013 Rabinowitz et al.
2013/0274135 A1 10/2013 Zhang et al.
2013/0288252 A1 10/2013 Sparks et al.
2013/0303461 A1 11/2013 Iafrate et al.
2013/0310260 A1 11/2013 Kim et al.
2013/0323727 A1 12/2013 Huang et al.
2013/0323731 A1 12/2013 Lo et al.
2013/0325360 A1 12/2013 Deciu et al.
2013/0344066 A1 12/2013 Faham et al.
2014/0032128 A1 1/2014 Rabinowitz et al.
2014/0038830 A1 2/2014 Srinivasan et al.
2014/0045181 A1 2/2014 Lo et al.
2014/0051585 A1 2/2014 Prosen et al.
2014/0065621 A1 3/2014 Mhatre et al.
2014/0066317 A1 3/2014 Talasaz
2014/0087385 A1 3/2014 Rabinowitz et al.
2014/0094373 A1 4/2014 Zimmermann et al.
2014/0100121 A1 4/2014 Lo et al.
2014/0100126 A1 4/2014 Rabinowitz
2014/0100134 A1 4/2014 Rabinowitz et al.
2014/0106975 A1 4/2014 Stoughton et al.
2014/0113795 A1 4/2014 Emerson et al.
2014/0141981 A1 5/2014 Zimmermann et al.
2014/0154682 A1 6/2014 Rabinowitz et al.
2014/0155274 A1 6/2014 Xie et al.
2014/0162269 A1 6/2014 Rabinowitz et al.
2014/0186827 A1 7/2014 Pieprzyk et al.
2014/0193816 A1 7/2014 Rabinowitz et al.
2014/0206552 A1 7/2014 Rabinowitz et al.
2014/0227691 A1 8/2014 May et al.
2014/0227705 A1 8/2014 Vogelstein et al.
2014/0242588 A1 8/2014 Van Den Boom et al.
2014/0256558 A1 9/2014 Varley et al.
2014/0256569 A1 9/2014 Rabinowitz et al.
2014/0272956 A1 9/2014 Huang et al.
2014/0274740 A1 9/2014 Srinivasan et al.
2014/0287934 A1 9/2014 Szelinger et al.
2014/0296081 A1 10/2014 Diehn et al.
2014/0329245 A1 11/2014 Spier et al.
2014/0336060 A1 11/2014 Rabinowitz et al.
2015/0051087 A1 2/2015 Rabinowitz et al.
2015/0056617 A1 2/2015 Whitt et al.
2015/0064695 A1 3/2015 Katz et al.

(56) References Cited

U.S. PATENT DOCUMENTS

2015/0086477 A1 3/2015 Mitchell et al.
2015/0087535 A1 3/2015 Patel
2015/0099673 A1 4/2015 Fodor et al.
2015/0147815 A1 5/2015 Babiarz et al.
2015/0167069 A1 6/2015 Schutz et al.
2015/0167077 A1 6/2015 Fehr et al.
2015/0197786 A1 7/2015 Osborne et al.
2015/0211050 A1 7/2015 Iafrate et al.
2015/0218631 A1 8/2015 Chuu et al.
2015/0232938 A1 8/2015 Mhatre et al.
2015/0246103 A1 9/2015 Hazout
2015/0265995 A1 9/2015 Head et al.
2015/0299812 A1 10/2015 Talasaz
2015/0315657 A1 11/2015 Rhodes et al.
2015/0322507 A1 11/2015 Zimmermann et al.
2015/0329891 A1 11/2015 Tan et al.
2016/0024581 A1 1/2016 Sarwal et al.
2016/0032396 A1 2/2016 Diehn et al.
2016/0046986 A1 2/2016 Eltoukhy et al.
2016/0053320 A1 2/2016 Schuh et al.
2016/0115541 A1 4/2016 Schutz et al.
2016/0138112 A1 5/2016 Janne et al.
2016/0145682 A1 5/2016 Woodward et al.
2016/0186239 A1 6/2016 Sinha
2016/0186253 A1 6/2016 Talasaz et al.
2016/0201124 A1 7/2016 Donahue et al.
2016/0239602 A1 8/2016 Shendure et al.
2016/0244838 A1 8/2016 Babiarz et al.
2016/0257993 A1 9/2016 Fu et al.
2016/0265042 A1 9/2016 Schroeder et al.
2016/0289740 A1 10/2016 Fu et al.
2016/0289753 A1 10/2016 Osborne et al.
2016/0312276 A1 10/2016 Fu et al.
2016/0319345 A1 11/2016 Gnerre et al.
2016/0369333 A1 12/2016 Babiarz et al.
2017/0011166 A1 1/2017 Rabinowitz et al.
2017/0107576 A1 4/2017 Babiarz et al.
2017/0114411 A1 4/2017 Mitchell et al.
2017/0121716 A1 5/2017 Rodi
2017/0137882 A1 5/2017 Goossens et al.
2017/0145475 A1 5/2017 Hunsley et al.
2017/0152561 A1 6/2017 Hamamah et al.
2017/0218458 A1 8/2017 Fan et al.
2017/0275689 A1 9/2017 Maguire et al.
2017/0283788 A1 10/2017 Khoja et al.
2017/0298427 A1 10/2017 Buis et al.
2017/0314014 A1 11/2017 Green et al.
2017/0342477 A1 11/2017 Jensen et al.
2017/0362649 A1 12/2017 Lieberman-Aiden et al.
2018/0023128 A1 1/2018 Yanai et al.
2018/0025109 A1 1/2018 Rabinowitz et al.
2018/0105807 A1 4/2018 Lo et al.
2018/0127744 A1 5/2018 Hu et al.
2018/0142296 A1 5/2018 Mitchell et al.
2018/0148777 A1 5/2018 Kirkizlar et al.
2018/0155775 A1 6/2018 Zimmermann et al.
2018/0155776 A1 6/2018 Zimmermann et al.
2018/0155779 A1 6/2018 Zimmermann et al.
2018/0155785 A1 6/2018 Rabinowitz et al.
2018/0155786 A1 6/2018 Rabinowitz et al.
2018/0155792 A1 6/2018 Rabinowitz et al.
2018/0171409 A1 6/2018 Rabinowitz et al.
2018/0171420 A1 6/2018 Babiarz et al.
2018/0173845 A1 6/2018 Sigurjonsson et al.
2018/0173846 A1 6/2018 Sigurjonsson et al.
2018/0187241 A1 7/2018 Selvaraj et al.
2018/0201995 A1 7/2018 Rabinowitz et al.
2018/0237841 A1 8/2018 Stray et al.
2018/0251553 A1 9/2018 Mcgranahan et al.
2018/0265917 A1 9/2018 Barany et al.
2018/0288982 A1 10/2018 Sinha
2018/0298439 A1 10/2018 Ryan et al.
2018/0300448 A1 10/2018 Rabinowitz et al.
2018/0303870 A1 10/2018 Golobish et al.
2018/0320171 A1 11/2018 Withey
2018/0320239 A1 11/2018 Babiarz et al.
2018/0371531 A1 12/2018 Quake et al.
2019/0010543 A1 1/2019 Babiarz et al.
2019/0106737 A1 4/2019 Underhill
2019/0106751 A1 4/2019 Zimmermann et al.
2019/0112661 A1 4/2019 Khan et al.
2019/0153521 A1 5/2019 Mitchell et al.
2019/0153525 A1 5/2019 Mitchell et al.
2019/0185913 A1 6/2019 Zimmermann et al.
2019/0185936 A1 6/2019 Babiarz et al.
2019/0194743 A1 6/2019 Ryan et al.
2019/0194758 A1 6/2019 Babiarz et al.
2019/0194759 A1 6/2019 Babiarz et al.
2019/0203290 A1 7/2019 Rabinowitz et al.
2019/0203294 A1 7/2019 Babiarz et al.
2019/0211376 A1 7/2019 Quake et al.
2019/0211385 A1 7/2019 Sarwal et al.
2019/0211391 A1 7/2019 Rabinowitz et al.
2019/0211392 A1 7/2019 Rabinowitz et al.
2019/0211393 A1 7/2019 Rabinowitz et al.
2019/0211399 A1 7/2019 Rabinowitz et al.
2019/0211402 A1 7/2019 Babiarz et al.
2019/0211406 A1 7/2019 Babiarz et al.
2019/0249241 A1 8/2019 Rabinowitz et al.
2019/0256894 A1 8/2019 Zimmermann et al.
2019/0256906 A1 8/2019 Rabinowitz et al.
2019/0256907 A1 8/2019 Ryan et al.
2019/0256908 A1 8/2019 Rabinowitz et al.
2019/0256909 A1 8/2019 Rabinowitz et al.
2019/0256912 A1 8/2019 Rabinowitz et al.
2019/0256916 A1 8/2019 Babiarz et al.
2019/0256917 A1 8/2019 Babiarz et al.
2019/0256919 A1 8/2019 Babiarz et al.
2019/0256924 A1 8/2019 Vogelstein et al.
2019/0256931 A1 8/2019 Babiarz et al.
2019/0264277 A1 8/2019 Rabinowitz et al.
2019/0264280 A1 8/2019 Rabinowitz et al.
2019/0264288 A1 8/2019 Rabinowitz et al.
2019/0271043 A1 9/2019 Babiarz et al.
2019/0276888 A1 9/2019 Rabinowitz et al.
2019/0284623 A1 9/2019 Rabinowitz et al.
2019/0300950 A1 10/2019 Rabinowitz et al.
2019/0309358 A1 10/2019 Rabinowitz et al.
2019/0309359 A1 10/2019 Zimmermann et al.
2019/0309365 A1 10/2019 Babiarz et al.
2019/0316177 A1 10/2019 Zimmermann et al.
2019/0316184 A1 10/2019 Zimmermann et al.
2019/0316200 A1 10/2019 Rabinowitz et al.
2019/0323076 A1 10/2019 Rabinowitz et al.
2019/0360033 A1 11/2019 Stamm et al.
2019/0360036 A1 11/2019 Rabinowitz et al.
2019/0367972 A1 12/2019 Mitchell et al.
2020/0024653 A1 1/2020 Bethke
2020/0032323 A1 1/2020 Talasaz et al.
2020/0032340 A1 1/2020 Mitchell et al.
2020/0109449 A1 4/2020 Stamm et al.
2020/0121718 A1 4/2020 Novik et al.
2020/0123612 A1 4/2020 Babiarz et al.
2020/0126634 A1 4/2020 Sigurjonsson et al.
2020/0140950 A1 5/2020 Babiarz et al.
2020/0141925 A1 5/2020 Liaw et al.
2020/0149111 A1 5/2020 Babiarz et al.
2020/0157629 A1 5/2020 Babiarz et al.
2020/0165678 A1 5/2020 Mitchell et al.
2020/0172977 A1 6/2020 Rabinowitz et al.
2020/0181681 A1 6/2020 Mitchell et al.
2020/0181697 A1 6/2020 Rabinowitz et al.
2020/0190570 A1 6/2020 Ryan et al.
2020/0190573 A1 6/2020 Rabinowitz et al.
2020/0190591 A1 6/2020 Rabinowitz et al.
2020/0208196 A1 7/2020 Zimmermann et al.
2020/0208221 A1 7/2020 Babiarz et al.
2020/0224273 A1 7/2020 Rabinowitz et al.
2020/0232036 A1 7/2020 Rabinowitz et al.
2020/0232037 A1 7/2020 Babiarz et al.
2020/0248264 A1 8/2020 Rabinowitz et al.
2020/0248266 A1 8/2020 Swanton et al.
2020/0316498 A1 10/2020 Tomita Mitchell
2020/0318191 A1 10/2020 Babiarz et al.

(56) References Cited

U.S. PATENT DOCUMENTS

2020/0347454 A1 11/2020 Babiarz et al.
2020/0350034 A1 11/2020 Rabinowitz
2020/0362415 A1 11/2020 Rabinowitz et al.
2020/0370129 A1 11/2020 Quinn et al.
2020/0385809 A1 12/2020 Ramani
2020/0407788 A1 12/2020 Ryan et al.
2020/0407798 A1 12/2020 Babiarz et al.
2021/0009990 A1 1/2021 Stray et al.
2021/0025005 A1 1/2021 Babiarz et al.
2021/0054459 A1 2/2021 Rabinowitz et al.
2021/0071246 A1 3/2021 Zimmermann et al.
2021/0139969 A1 5/2021 Mitchell et al.
2021/0139983 A1 5/2021 Mitchell et al.
2021/0139988 A1 5/2021 Mitchell et al.
2021/0155988 A1 5/2021 Rabinowitz et al.
2021/0189498 A1 6/2021 Babiarz et al.
2021/0198733 A1 7/2021 Moshkevich et al.
2021/0198742 A1 7/2021 Babiarz et al.
2021/0198743 A1 7/2021 Babiarz et al.
2021/0222230 A1 7/2021 Zimmermann et al.
2021/0222240 A1 7/2021 Moshkevich et al.
2021/0257048 A1 8/2021 Zimmermann et al.
2021/0269879 A1 9/2021 Mitchell et al.
2021/0301320 A1 9/2021 Mitchell et al.
2021/0324463 A1 10/2021 Rabinowitz et al.
2021/0327538 A1 10/2021 Egilsson et al.
2021/0327542 A1 10/2021 Ryan et al.
2021/0355536 A1 11/2021 Rabinowitz et al.
2022/0025455 A1 1/2022 Zimmermann et al.
2022/0025456 A1 1/2022 Rabinowitz et al.
2022/0033908 A1 2/2022 Rabinowitz et al.
2022/0033909 A1 2/2022 Babiarz et al.
2022/0042103 A1 2/2022 Rabinowitz et al.
2022/0056509 A1 2/2022 Zimmermann et al.
2022/0056534 A1 2/2022 Rivers et al.
2022/0073978 A1 3/2022 Rabinowitz et al.
2022/0073979 A1 3/2022 Rabinowitz et al.
2022/0098667 A1 3/2022 Rabinowitz et al.
2022/0139495 A1 5/2022 Rabinowitz et al.
2022/0145391 A1 5/2022 Mitchell et al.
2022/0154249 A1 5/2022 Zimmermann et al.
2022/0154290 A1 5/2022 Babiarz et al.
2022/0195526 A1 6/2022 Rabinowitz et al.
2022/0213561 A1 7/2022 Babiarz et al.
2022/0251654 A1 8/2022 Hafez et al.
2022/0267849 A1 8/2022 Mitchell et al.
2022/0282335 A1 9/2022 Babiarz et al.
2022/0307086 A1 9/2022 Babiarz et al.
2022/0340963 A1 10/2022 North et al.
2022/0356522 A1 11/2022 Mitchell et al.
2022/0356526 A1 11/2022 Babiarz et al.
2022/0356530 A1 11/2022 Sharma et al.
2022/0403461 A1 12/2022 Kirkizlar et al.
2022/0411875 A1 12/2022 Rabinowitz et al.
2023/0054494 A1 2/2023 Rabinowitz et al.
2023/0060579 A1 3/2023 Bethke
2023/0193387 A1 6/2023 Rabinowitz et al.
2023/0203573 A1 6/2023 Swenerton et al.
2023/0212693 A1 7/2023 Rabinowitz et al.
2023/0242998 A1 8/2023 Babiarz et al.
2023/0343411 A1 10/2023 Rabinowitz et al.

FOREIGN PATENT DOCUMENTS

CN 102892901 A 1/2013
EP 1325963 B1 9/2006
EP 1524321 B1 7/2009
EP 2551356 A1 1/2013
EP 2902500 A1 8/2015
EP 2315849 B1 11/2017
EP 2877594 B1 12/2019
EP 3760730 A1 1/2021
EP 3760731 A1 1/2021
EP 3760732 A1 1/2021
GB 2488358 A 8/2012
JP 2002530121 A 9/2002
JP 2002300894 A 10/2002
JP 2003521252 A 7/2003
JP 2004502466 A 1/2004
JP 2004121087 A 4/2004
JP 2005514956 A 5/2005
JP 2005160470 A 6/2005
JP 2006254912 A 9/2006
JP 2008263974 A 11/2008
JP 2008271980 A 11/2008
JP 2010509922 A 4/2010
JP 2011516069 A 5/2011
JP 2012085556 A 5/2012
JP 2013509883 A 3/2013
JP 2014118334 A 6/2014
JP 2015535681 A 12/2015
JP 2016502849 A 2/2016
WO WO-2001007640 A2 2/2001
WO WO-2001057269 A2 8/2001
WO WO-2001090419 A2 11/2001
WO WO-2002004672 A2 1/2002
WO WO-2002044411 A1 6/2002
WO WO-2002070751 A1 9/2002
WO WO-2003000919 A2 1/2003
WO WO-2003031646 A1 4/2003
WO WO-2003062441 A1 7/2003
WO WO-2003018757 A3 9/2003
WO WO-2003020974 A3 9/2003
WO WO-2004051218 A2 6/2004
WO WO-2004069849 A2 8/2004
WO WO-2004070005 A2 8/2004
WO WO-2004070007 A2 8/2004
WO WO-2004078999 A1 9/2004
WO WO-2004081183 A2 9/2004
WO WO-2005003375 A2 1/2005
WO WO-2005021793 A1 3/2005
WO WO-2005023091 A2 3/2005
WO WO-2005035725 A2 4/2005
WO WO-2005039389 A3 11/2005
WO WO-2006110855 A2 10/2006
WO WO-2007052006 A1 5/2007
WO WO-2007057647 A1 5/2007
WO WO-2007073171 A2 6/2007
WO WO-2007075836 A2 7/2007
WO WO-2007086935 A2 8/2007
WO WO-2007092473 A2 8/2007
WO WO-2007100911 A2 9/2007
WO WO-2007062164 A3 11/2007
WO WO-2007132167 A2 11/2007
WO WO-2007140417 A2 12/2007
WO WO-2007145612 A1 12/2007
WO WO-2007147073 A2 12/2007
WO WO-2007147074 A2 12/2007
WO WO-2007147076 A2 12/2007
WO WO-2007147079 A2 12/2007
WO WO-2008024473 A2 2/2008
WO WO-2008051928 A2 5/2008
WO WO-2008059578 A1 5/2008
WO WO-2008061213 A2 5/2008
WO WO-2008079374 A2 7/2008
WO WO-2008081451 A2 7/2008
WO WO-2008115497 A2 9/2008
WO WO-2008118988 A1 10/2008
WO WO-2008135837 A2 11/2008
WO WO-2008157264 A2 12/2008
WO WO-2009009769 A2 1/2009
WO WO-2009013492 A1 1/2009
WO WO-2009013496 A1 1/2009
WO WO-2009017784 A2 2/2009
WO WO-2009019215 A1 2/2009
WO WO-2009019455 A2 2/2009
WO WO-2009030100 A1 3/2009
WO WO-2009032779 A2 3/2009
WO WO-2009032781 A2 3/2009
WO WO-2009033178 A1 3/2009
WO WO-2009036525 A2 3/2009
WO WO-2009049889 A1 4/2009
WO WO-2009064897 A2 5/2009
WO WO-2009091934 A1 7/2009

(56) References Cited

FOREIGN PATENT DOCUMENTS

WO WO-2009092035 A2 7/2009
WO WO-2009099602 A1 8/2009
WO WO-2009100029 A1 8/2009
WO WO-2009105531 A1 8/2009
WO WO-2009117122 A2 9/2009
WO WO-2009120808 A2 10/2009
WO WO-2009145828 A2 12/2009
WO WO-2010014920 A1 2/2010
WO WO-2010017214 A1 2/2010
WO WO-2010033578 A2 3/2010
WO WO-2010033639 A2 3/2010
WO WO-2010042831 A2 4/2010
WO WO-2010045617 A2 4/2010
WO WO-2010075459 A1 7/2010
WO WO-2010088288 A2 8/2010
WO WO-2010115016 A2 10/2010
WO WO-2010115154 A1 10/2010
WO WO-2010118016 A2 10/2010
WO WO-2010127186 A1 11/2010
WO WO-2011015944 A2 2/2011
WO WO-2011041485 A1 4/2011
WO WO-2011051283 A1 5/2011
WO WO-2011057061 A1 5/2011
WO WO-2011057094 A1 5/2011
WO WO-2011087760 A2 7/2011
WO WO-2011090556 A1 7/2011
WO WO-2011094646 A1 8/2011
WO WO-2011102998 A2 8/2011
WO WO-2011109440 A1 9/2011
WO WO-2011118603 A1 9/2011
WO WO-2011130751 A1 10/2011
WO WO-2011140433 A2 11/2011
WO WO-2011142836 A2 11/2011
WO WO-2011146632 A1 11/2011
WO WO-2011146942 A1 11/2011
WO WO-2011153254 A2 12/2011
WO WO-2012019200 A2 2/2012
WO WO-2012028746 A1 3/2012
WO WO-2012042374 A2 4/2012
WO WO-2012071621 A1 6/2012
WO WO-2012083189 A2 6/2012
WO WO-2012088456 A2 6/2012
WO WO-2012092426 A1 7/2012
WO WO-2012108920 A1 * 8/2012 ............ C12Q 1/686
WO WO-2012122374 A2 9/2012
WO WO-2012142531 A2 10/2012
WO WO-2013030577 A1 3/2013
WO WO-2013049892 A1 4/2013
WO WO-2013052557 A2 4/2013
WO WO-2013086464 A1 6/2013
WO WO-2013123220 A1 8/2013
WO WO-2013130848 A1 * 9/2013 ............ G16B 20/10
WO WO-2013159035 A2 10/2013
WO WO-2013169339 A1 11/2013
WO WO-2013190441 A2 12/2013
WO WO-2014004726 A1 1/2014
WO WO-2014014497 A1 1/2014
WO WO-2014018080 A1 * 1/2014 ............ G16B 20/00
WO WO-2014026277 A1 2/2014
WO WO-2014039556 A1 3/2014
WO WO-2014099919 A2 6/2014
WO WO-2013138510 A9 7/2014
WO WO-2014143989 A1 9/2014
WO WO-2014149134 A2 9/2014
WO WO-2014151117 A1 9/2014
WO WO-2014194113 A2 12/2014
WO WO-2015006668 A1 1/2015
WO WO-2015069933 A1 5/2015
WO WO-2015100427 A1 7/2015
WO WO-2015134552 A1 9/2015
WO WO-2015138997 A1 9/2015
WO WO-2015164432 A1 10/2015
WO WO-2015169947 A1 11/2015
WO WO-2015178978 A2 11/2015
WO WO-2016001411 A1 1/2016
WO WO-2016009224 A1 1/2016
WO WO-2016028316 A1 2/2016
WO WO-2016063122 A1 4/2016
WO WO-2016077313 A1 5/2016

OTHER PUBLICATIONS

Kirsch-Gerweck et al in "HaploBlocks: Efficient Detection of Positive Selection in Large Population Genomic Datasets" (Mol. Biol. Evol. Feb. 25, 2023). (Year: 2023).*

Ge et al in "Haplotype block: a new type of forensic DNA markers" (J Legal Med 2010, vol. 124: pp. 353-361). (Year: 2010).*

Slatkin_Nat_Rev_Genet_2008 (Year: 2008).*

Su et al: "Inferring combined CNV/SNP haplotypes from genotype data", Bioinformatics, vol. 26, No. 11, Jun. 1, 2010: pp. 1437-1445) (Year: 2010).*

"Abstracts for CNAPS IV Circulating Nucleic Acids in Plasma/Serum," Fourth International Conference on Circulating Nucleic Acids in Plasma/Serum (CNAPS-IV), London, Sep. 4-6, 2005, 40 Pages.

Alkan C., et al., "Personalized Copy Number and Segmental Duplication Maps Using Next-Generation Sequencing," Nature Genetics, Oct. 2009, vol. 41, No. 10, pp. 1061-1068.

Amicucci P., et al., "Prenatal Diagnosis of Myotonic Dystrophy Using Fetal DNA Obtained from Maternal Plasma," Clinical Chemistry, 2000, vol. 46, No. 2, pp. 301-302.

Andras S.C., et al., "Strategies for Signal Amplification in Nucleic Acid Detection," Molecular Biotechnology, 2001, vol. 19, pp. 29-44.

Anker P., et al., "Circulating DNA in Plasma or Serum," Medicina, 2000, vol. 60, pp. 699-702, 10 Pages.

Anker P., et al., "The Second International Symposium on Circulating Nucleic Acids in Plasma and Serum (CNAPS-2) held in Conjunction with the 6th Annual Scientific Symposium of the Hong Kong Cancer Institute", Clinical Chemistry, Hong Kong, Feb. 20-21, 2001, vol. 47, No. 2, pp. 361-370.

Ansorge W.J., "Next-Generation DNA Sequencing Techniques," New Biotechnology, Feb. 2, 2009, vol. 25, No. 4, pp. 195-203, ( Apr. 2009).

Arandjelovic M., et al., "Two-Step Multiplex Polymerase Chain Reaction improves the Speed and Accuracy of Genotyping Using DNA from Noninvasive and Museum Samples," Molecular Ecology Resources, 2009, vol. 9, pp. 28-36.

Ashoor G., et al., "Chromosome-selective Sequencing of Maternal Plasma Cell-free DNA for First-trimester Detection of Trisomy 21 and Trisomy 18," American Journal of Obstetrics & Gynecology, Apr. 2012, vol. 206, pp. 322.e1-322.e5.

Ashoor G., et al., "Fetal Fraction in Maternal Plasma Cell-Free DNA at 11-13 Weeks' Gestation: Effect of Maternal and Fetal Factors," Fetal Diagnosis and Therapy, 2012, pp. 1-7, Published Online May 4, 2012.

Ashoor G., et al., "Fetal Fraction in Maternal Plasma Cell-free DNA at 11-13 Weeks' Gestation: Relation to Maternal and Fetal Characteristics," Ultrasound in Obstetrics and Gynecology, 2013, vol. 41, pp. 26-32.

Avent N.D., et al., "Cell-free Fetal DNA in The Maternal Serum And Plasma: Current And Evolving Applications," Current Opinion in Obstretrics and Gynecology, Apr. 1, 2009, vol. 21, No. 2, pp. 175-179.

Avgidou K., et al., "Prospective First-trimester Screening for Trisomy 21 in 30,564 Pregnancies," American Journal of Obstetrics and Gynecology, 2005, vol. 192, pp. 1761-1767 (13 Pages).pp. 1761.

Ayala R., et al., "Long-Term Follow-Up of Donor Chimerism Tolerance After Human Liver Transplantation," Liver Transplantation, May 28, 2009, vol. 15, No. 6, pp. 581-591.

Balduini A., et al., "Utility of Biochemical Markers in The Follow-Up Heart Transplant Recipients," Transplantation Proceedings, Dec. 1, 2003, vol. 35, No. 8, pp. 3075-3078.

Bau S., et al., "Targeted Next-Generation Sequencing by Specific Capture of Multiple Genomic Loci using Low-Volume Microfluidic DNA Arrays," Analytical and Bioanalytical Chemistry, 2009, vol. 393, pp. 171-175.

(56) References Cited

OTHER PUBLICATIONS

Bauer M., et al., "A Prospective Analysis of Cell-Free Fetal DNA Concentration in Maternal Plasma as an Indicator for Adverse Pregnancy Outcome," Prenatal Diagnosis, 2006, vol. 26, pp. 831-836.
Baxter-Lowe L.A., et al., "Tracking Microchimeric DNA In Plasma To Diagnose And Manage Organ Transplant Rejection," Clinical Chemistry, Apr. 1, 2006, vol. 52, No. 4, pp. 559-561.
Beck J., et al., "Digital Droplet PCR for Rapid Quantification of Donor DNA in the Circulation of Transplant Recipients as a Potential Universal Biomarker of Graft Injury," Clinical Chemistry, Dec. 2013, vol. 59, No. 12, pp. 1732-1741, DOI: 10.1373/clinchem.2013.210328, EPublished Sep. 23, 2013.
Beck J., et al., "Next Generation Sequencing of Serum Circulating Nucleic Acids from Patients with Invasive Ductal Breast Cancer Reveals Differences to Healthy and Nonmalignant Controls," Molecular Cancer Research, Mar. 1, 2010, vol. 8, No. 3, pp. 335-342, 9 Pages.
Beck J., et al., "Profile of the Circulating DNA in Apparently Healthy Individuals," Clinical Chemistry, 2009, vol. 55, No. 4, pp. 730-738.
Bender K., et al., "A Multiplex SNP Typing Approach For The DNA Pyrosequencing Technology," International Congress Series, Apr. 20, 2006, vol. 1288, pp. 73-75.
Benesova L., et al., "Mutation-based Detection and Monitoring of Cell-free Tumor DNA in Peripheral Blood of Cancer Patients," Analytical Biochemistry, 2013, vol. 433, pp. 227-234.
Benn P., et al., "Non-Invasive Prenatal Diagnosis for Down Syndrome: The Paradigm Will Shift, but Slowly," Ultrasound in Obstetrics & Gynecology, 2012, vol. 39, pp. 127-130.
Benn P., et al., "Non-Invasive Prenatal Testing for Aneuploidy: Current Status and Future Prospects," Ultrasound in Obstetrics & Gynecology, 2013, vol. 42, pp. 15-33.
Bentley G., et al., "High-Resolution, High-throughput HLA Genotyping by Next-Generation Sequencing," Tissue Antigens, Nov. 1, 2009, vol. 74, No. 5, pp. 393-403.
Bergen A.W., et al., "Effects of DNA Mass on Multiple Displacement Whole Genome Amplification and Genotyping Performance," BMC Biotechnology, Sep. 16, 2005, vol. 5, No. 24, 11 Pages.
Bianchi D.W., "Circulating Fetal DNA: Its Origin and Diagnostic Potential-A Review," Placenta, May 2004, vol. 25, vol. 18, Supplemental A, S93-S101.
Bianchi D.W., et al., "Genome-Wide Fetal Aneuploidy Detection by Maternal Plasma DNA Sequencing," Obstetrics & Gynecology, May 2012, vol. 119, No. 5. pp. 890-901.
Bianchi D.W., et al., "Insights into Fetal and Neonatal Development Through Analysis of Cell-Free RNA in Body Fluids," Early Human Development, Nov. 2010, vol. 86, No. 11, pp. 747-752, 11 Pages.
Bianchi D.W., et al., "Noninvasive Prenatal Testing and Incidental Detection of Occult Maternal Malignancies," JAMA the Journal of the American Medical Association, Jul. 14, 2015, vol. 314, No. 2, pp. 162-169.
Binladen J., et al., "The Use of Coded PCR Primers Enables High-Throughput Sequencing of Multiple Homolog Amplification Products by 454 Parallel Sequencing," PLOS One, Feb. 2007, Issue No. 2, Article No. e197, 9 Pages.
Birch L., et al., "Accurate and Robust Quantification of Circulating Fetal and Total DNA in Maternal Plasma from 5 to 41 Weeks of Gestation," Clinical Chemistry, 2005, vol. 51, No. 2, pp. 312-320.
Bisignano A., et al., "PGD and Aneuploidy Screening for 24 Chromosomes: Advantages and Disadvantages of Competing Platforms," Reproductive BioMedicine Online, 2011, vol. 23, pp. 677-685.
Blomquist T.M., et al., "Targeted RNA-Sequencing with Competitive Multiplex-PCR Amplicon Libraries," Plos One, Nov. 13, 2013, vol. 8, Issue 11(e79120), 14 Pages.
Bordoni R., et al., "Evaluation of Human Gene Variant Detection in Amplicon Pools by the GS-FLX Parallel Pyrosequencer," BMC Genomics, Oct. 8, 2008, vol. 9, pp. 1-8 (8 Pages).
Brockman W., et al., "Quality Scores and SNP Detection in Sequencing-by- synthesis Systems," Genome Research, May 1, 2008, vol. 18, No. 5, pp. 763-770.
Broude N.E., et al., "High Multiplexity PCR Based on PCR Suppression," DNA Amplification Current Technologies and Applications, 2004, pp. 61-76.
Broude N.E., et al., "High-Level Multiplex DNA Amplification," Antisense & Nucleic Acid Drug Development, 2001, vol. 11, pp. 327-332.
Broude N.E., et al., "Multiplex Allele-Specific Target Amplification based on PCR Suppression," Proceedings of the National Academy of Sciences of the United States of America, Jan. 2, 2001, vol. 98, No. 1, pp. 206-211.
Bustamante-Aragones A., et al., "New Strategy for The Prenatal Detection/Exclusion of Paternal Cystic Fibrosis Mutations in Maternal Plasma," Journal of Cystic Fibrosis, Nov. 1, 2008, vol. 7, Issue 6, pp. 505-510.
Butt A.N., et al., "Overview of Circulating Nucleic Acids in Plasma/Serum: Update on Potential Prognostic and Diagnostic Value in Diseases Excluding Fetal Medicine and Oncology," Annals of the New York Academy of Sciences, 2008, vol. 1137, pp. 236-242.
Caliendo A.M., "Multiplex PCR and Emerging Technologies for the Detection of Respiratory Pathogens," Clinical Infectious Diseases, 2011, vol. 52, Supp. 4, pp. S326-S330.
Campbell P.J., et al., "Subclonal Phylogenetic Structures in Cancer Revealed by Ultra-Deep Sequencing," Proceedings of the National Academy of Sciences of the United States of America, Sep. 2, 2008, vol. 105, No. 35, pp. 13081-13086.
Canick J.A., et al., "The Impact of Maternal Plasma DNA Fetal Fraction on Next Generation Sequencing Tests for Common Fetal Aneuploidies," Prenatal Diagnosis, 2013, vol. 33, pp. 667-674.
Casbon J.A., et al., "A Method for Counting PCR Template Molecules with Application to Next-generation Sequencing," Nucleic Acids Research, Apr. 13, 2011, vol. 39, No. 12, pp. 1-8.
Castleberry C.D., et al., "Quantification of Circulating Cell-Free DNA in Pediatric Heart Transplant Recipients," Journal of Heart and Lung Transplantation, Apr. 1, 2011 vol. 30, No. 4, p. S139, DOI: 10.1016/j.healun.2011.01.415, ISSN: 1053-2498.
Chan A.K.C., et al., "Cell-Free Nucleic Acids in Plasma, Serum and Urine: A New Tool in Molecular Diagnosis," Annals of Clinical Biochemistry, Mar. 1, 2003, vol. 40, Issue 2, pp. 122-130.
Chan K.C.A., "Scanning for Cancer Genomic Changes in Plasma: Toward an Era of Personalized Blood-Based Tumor Markers," Clinical Chemistry, 2013, vol. 59, No. 11, pp. 1553-1555.
Chan K.C.A., et al., "Cancer Genome Scanning in Plasma: Detection of Tumor-Associated Copy Number Aberrations, Single-Nucleotide Variants, and Tumoral Heterogeneity by Massively Parallel Sequencing," Clinical Chemistry, 2013, vol. 59, No. 1, pp. 211-224.
Chan K.C.A., et al., "Size Distributions of Maternal and Fetal DNA in Maternal Plasma," Clinical Chemistry, 2004, vol. 50, No. 1, pp. 88-92.
Chen C.P., et al., "Fetal DNA in Maternal Plasma: The Prenatal Detection of a Paternally Inherited Fetal Aneuploidy," Prenatal Diagnosis, 2000, vol. 20, pp. 353-357, 4 Pages.
Chen E.Z., et al., "Noninvasive Prenatal Diagnosis of Fetal Trisomy 18 and Trisomy 13 by Maternal Plasma DNA Sequencing," PLoS One, Jul. 6, 2011, vol. 6, Issue 7, e21791, pp. 1-7.
Chen J.J., et al., "Non-Invasive Prenatal Diagnosis using Fetal DNA in Maternal Plasma: A Preliminary Study for Identification of Paternally-Inherited Alleles using Single Nucleotide Polymorphisms," BMJ Open, Jul. 22, 2015, vol. 5, No. 7 (e007648), 8 Pages, DOI: 10.1136/bmjopen-2015-007648.
Chetty S., et al., "Uptake of Noninvasive Prenatal Testing (NIPT) in Women Following Positive Aneuploidy Screening," Prenatal Diagnosis, 2013, vol. 33, pp. 542-546.
Chitty L.S., et al., "Noninvasive Prenatal Screening for Genetic Diseases Using Massively Parallel Sequencing of Maternal Plasma DNA," Cold Spring Harbor Perspectives in Medicine, 2015, vol. 5, No. 9(a023085), 20 Pages.

(56) References Cited

OTHER PUBLICATIONS

Chiu R.W.K., et al., "Effects of Blood-Processing Protocols on Fetal and Total DNA Quantification in Maternal Plasma," Clinical Chemistry, Sep. 2001, vol. 47, No. 9, pp. 1607-1613, PubMed PMID: 11514393.
Chiu R.W.K., et al., "Maternal Plasma DNA Analysis With Massively Parallel Sequencing by Litigation for Noninvasive Prenatal Diagnosis of Trisomy 21," Clinical Chemistry, 2010, vol. 56, No. 3, pp. 459-463.
Chiu R.W.K., et al., "Non-Invasive Prenatal Assessment of Trisomy 21 by Multiplexed Maternal Plasma DNA Sequencing: Large Scale Validity Study," BMJ, 2011, vol. 342, c7401, 9 Pages.
Chiu R.W.K., et al., "Non-Invasive Prenatal Diagnosis by Single Molecule Counting Technologies," Trends in Genetics, 2009, vol. 25, No. 7, pp. 324-331.
Chiu R.W.K., et al., "Noninvasive Prenatal Diagnosis of Fetal Chromosomal Aneuploidy by Massively Parallel Genomic Sequencing of DNA in Maternal Plasma (With Supporting Information)," Proceedings of the National Academy of Sciences, Dec. 23, 2008, vol. 105, No. 51,23 Pages.
Choi M., et al., "Genetic Diagnosis by Whole Exome Capture and Massively Parallel DNA Sequencing," Proceedings of the National Academy of Sciences, Nov. 10, 2009, vol. 106, No. 45, p. 19096-19101.
Chu T., et al., "A Novel Approach Toward the Challenge of Accurately Quantifying Fetal DNA in Maternal Plasma," Prenatal Diagnosis, Nov. 11, 2010, vol. 30, pp. 1226-1229.
Chu T., et al., "Statistical Considerations for Digital Approaches to Non- Invasive Fetal Genotyping," Bioinformatics, Advance Access publication Sep. 23, 2010, vol. 26, No. 22, pp. 2863-2866.
Chu T., et al., "Statistical Model for Whole Genome Sequencing and its Application to Minimally Invasive Diagnosis of Fetal Genetic Disease," Bioinformatics, Advance Access Publication Mar. 23, 2009, vol. 25, No. 10, pp. 1244-1250.
Colella S., et al., "QuantiSNP: an Objectives Bayes Hidden-Markov Model to Detect and Accurately Map Copy Number Variation Using SNP Genotyping Data," Nucleic Acids Research, 2007, vol. 35, No. 6, pp. 2013-2025.
Costa J-M., et al., "Fetal RHD Genotyping in Maternal Serum during the First Trimester of Pregnancy," British Journal of Haematology, 2002, vol. 119, pp. 255-260.
Courad S., et al., "Supplementary Data for Noninvasive Diagnosis of Actionable Mutations by Deep Sequencing of Circulating Free DNA in lung Cancer from Never-Smokers: A Proof-of-Concept Study from BioCAST/IFCT-1002," American Association for Cancer Research, Clinical Cancer Research, Sep. 1, 2014, vol. 20, No. 17, 13 Pages.
Couraud S., et al., "Noninvasive Diagnosis of Actionable Mutations by Deep Sequencing of Circulating Free DNA in lung Cancer from Never-Smokers: A Proof-of-Concept Study from BioCAST / IFCT-1002," Clinical Cancer Research, Sep. 1, 2014, vol. 20, No. 17, pp. 4613-4624, 13 Pages, Jul. 10, 2014.
Craig D.W., et al., "Identification of Genetic Variants using Bar-Coded Multiplexed Sequencing," Nature Methods, Oct. 2008, vol. 5, No. 10, pp. 887-893.
Crespo-Leiro M.G., et al., "Gene Expression Profiling for Monitoring Graft Rejection in Heart Transplant Recipients," Transplantation Proceedings, Jul. 1, 2009, vol. 41, No. 6, pp. 2240-2243.
Croft D.T., Jr., et al., "Performance of Whole-Genome Amplified DNA Isolated from Serum and Plasma on High-Density Single Nucleotide Polymorphism Arrays," Journal of Molecular Diagnostics, May 2008, vol. 10, No. 3, pp. 249-257.
Cross J., et al., "Resolution of Trisomic Mosaicism in Prenatal Diagnosis: Estimated Performance of a 50k SNP Microarray," Prenatal Diagnosis, 2007, vol. 27, pp. 1197-1204.
Dahl F., et al., "Multigene Amplification and Massively Parallel Sequencing for Cancer Mutation Discovery," Proceedings of the National Academy of Sciences of the United States of America, May 29, 2007, vol. 104, No. 22, pp. 9387-9392, DOI: 10.1073/pnas.0702165104. Epub: May 17, 2007.
Daniels G., et al., "Fetal Blood Group Genotyping from DNA from Maternal Plasma: An Important Advance in the Management and Prevention of Haemolytic disease of the Fetus and Newbornm," Vox Sanguinis, 2004, vol. 87, pp. 225-232.
Daruwala R-S., et al., "A Versatile Statistical Analysis Algorithm to Detect Genome Copy Number Variation," Proceedings of the National Academy of Sciences, Nov. 16, 2004, vol. 101, No. 46, pp. 16292-16297.
Dawson S-J., et al., "Analysis of Circulating Tumor DNA to Monitor Metastatic Breast Cancer," The New England Journal of Medicine, Mar. 28, 2013, vol. 368, No. 13, pp. 1199-1209.
De Vlaminck I., et al., "Circulating Cell-Free DNA Enables Noninvasive Diagnosis of Heart Transplant Rejection," Science Translational Medicine, Jun. 18, 2014, vol. 6, No. 241, 26 Pages.
Delgado P.O., et al., "Characterization of Cell-Free Circulating DNA in Plasma in Patients with Prostate Cancer," Tumor Biology, Apr. 2013, vol. 34, No. 2, pp. 983-986, DOI: 10.1007/s13277-012-0634-6, Epub Dec. 27, 2012.
Deutsch S., et al., "Detection of Aneuploidies by Paralogous Sequence Quantification," Journal of Medical Genetics, 2004, vol. 41, pp. 908-915.
Devaney S.A., et al., "Noninvasive Fetal Sex Determination Using Cell-free Fetal Dna: A Systematic Review and Meta-analysis," JAMA, Aug. 10, 2011, vol. 306, No. 6, pp. 627-636.
Dhallan R., et al., "A Non-Invasive Test for Prenatal Diagnosis Based on Fetal DNA Present in Maternal Blood: A Preliminary Study," Lancet, Feb. 10, 2007, vol. 369, No. 9560, pp. 474-481.
Dhallan R., et al., "Methods to Increase the Percentage of Free Fetal DNA Recovered From the Maternal Circulation," JAMA, Mar. 3, 2004, vol. 291, No. 9, pp. 1114-1119.
Diaz L.A., Jr., et al., "Liquid Biopsies: Genotyping Circulating Tumor DNA," Journal of Clinical Oncology, Feb. 20, 2014, vol. 32, No. 6, pp. 579-586.
Diehl F., et al., "Circulating Mutant DNA to Assess Tumor Dynamics," Nature Medicine, Sep. 2008, vol. 14, No. 9, pp. 985-990, Published Jul. 31, 2008.
Diehl F., et al., "Detection and Quantification of Mutations in the Plasma of Patients with Colorectal Tumors," Proceedings of the National Academy of Sciences, Nov. 8, 2005, vol. 102, No. 45, pp. 16368-16373.
Donaghue C., et al., "Detection of Mosaicism for Primary Trisomies in Prenatal Samples by QF-PCR and Karyotype Analysis," Prenatal Diagnosis, 2005, vol. 25, pp. 65-72.
Doostzadeh J., et al., "High Throughput Automated Allele Frequency Estimation by Pyrosequencing," Plos One, Jul. 16, 2008, vol. 3, Issue. 7, e2693, pp. 1-4.
Ehrich M., et al., "Noninvasive Detection of Fetal Trisomy 21 by Sequencing of DNA in Maternal Blood: A Study in a Clinical Setting," American Journal of Obstetrics & Gynecology, Mar. 2011, vol. 204, pp. 205.e1-205.e11.
Ellonen P., et al., "Development of SNP Microarray for Supplementary Paternity Testing," International Congress Series, 2004, vol. 1261, pp. 12-14.
Erlich R.L., "Next-Generation Sequencing for HLA Typing of Class Loci," BMC Genomics, Jan. 18, 2011, vol. 12, No. 42, 13 Pages.
Eronen L., et al., "HaploRec: Efficient and Accurate Large-Scale Reconstruction of Haplotypes," BMC Bioinformatics, Dec. 22, 2006, vol. 7, No. 542, 18 Pages.
European Commission: "The 7th International Conference on Circulating Nucleic Acids in Plasma and Serum (CNAPS VII) in Madrid-Spain," The International Conference on Circulating Nucleic Acids in Plasma and Serum, Oct. 24-25, 2011,2 Pages.
Fan C.H., et al., "Non-Invasive Prenatal Measurement of the Fetal Genome," Nature, 2012, 26 Pages, DOI:10.1038/nature11251.
Fan H.C., et al., "Detection of Aneuploidy with Digital Polymerase Chain Reaction," Analytical Chemistry, Oct. 1, 2007, vol. 79, No. 19, pp. 7576-7579.
Fan H.C., et al., "Sensitivity of Noninvasive Prenatal Detection of Fetal Aneuploidy from Maternal Plasma Using Shotgun Sequencing is Limited only by Counting Statistics," PLoS One, Mar. 2010, vol. 5, Issue 5 (e10439), pp. 1-6 (7 Pages), Published May 3, 2010.
Fan H.C., et al., "In Principle Method for Noninvasive Determination of the Fetal Genome," National Precisionss, 2010, 16 Pages.

(56) References Cited

OTHER PUBLICATIONS

Fan H.C., et al., "Microfluidic Digital PCR Enables Rapid Prenatal Diagnosis of Fetal Aneuploidy," American Journal of Obstetrics & Gynecology, May 2009, vol. 200, pp. 543e1-543e7.
Fan H.C., "Noninvasive Diagnosis of Fetal Aneuploidy by Shotgun Sequencing DNA from Maternal Blood," Proceedings of the National Academy of Sciences, USA, Oct. 21, 2008, vol. 105, No. 42, pp. 16266-16271, DOI: 10.1073/pnas.0808319105 Published Online (Oct. 6, 2008).
Fan J-B., et al., "Highly Parallel Genomic Assays," Nature Reviews, Aug. 2006, vol. 7, pp. 632-644.
Fan J-B., et al., "Highly Parallel SNP Genotyping," Cold Spring Harbor Symposia on Quantitative Biology, vol. LXVIII, Feb. 2003, pp. 69-78.
Forshew T., et al., "Noninvasive Identification and Monitoring of Cancer Mutations by Targeted Deep Sequencing of Plasma DNA," Science Translational Medicine, May 30, 2012, vol. 4, Issue No. 136, 33 pages.
Forshew, T., et al., "Supplementary Materials for Noninvasive Identification and Monitoring of Cancer Mutations by Targeted Deep Sequencing of Plasma DNA", Science Translational Medicine, May 30, 2012, vol. 4, No. 136:136ra68, pp. 1-13.
Fredriksson M., et al., "Assessing Hematopoietic Chimerism After Allogeneic Stem Cell Transplantation by Multiplexed SNP Genotyping Using Microarrays and Quantitive Analysis of SNP Alleles," Leukemia, Dec. 4, 2003, vol. 18, Issue 2, pp. 255-266.
Fredriksson S., et al., "Multiplex Amplification of All Coding Sequences Within 10 Cancer Genes by Gene-collector," Nucleic Acids Research, 2007, vol. 35, No. 7, Article e47, pp. 1-6.
Fu X-H., et al., "Advances on Circulating Fetal DNA In Maternal Plasma," Chinese Medical Journal, Jul. 2, 2007, vol. 120, No. 14, pp. 1256-1259.
Fu Y-W., et al., "Presence of Donor-and-recipient Derived DNA Microchimerism in The Cell-free Blood Samples of Renal Transplantation Recipients Associates with The Acceptance Of Transplanted Kidneys," Asian Journal of Andrology, Jul. 1, 2006, vol. 8, No. 4, pp. 477-482.
Gadi V.K., et al., "Soluble Donor DNA Concentrations in Recipient Serum Correlate with Pancreas-Kidney Rejection," Clinical Chemistry, 2006, vol. 52, No. 3, pp. 379-382.
Gautier E., et al., "Fetal RhD Genotyping by Maternal Serum Analysis: A Two-Year Experience," American Journal of Obstetrics and Gynecology, 2005, vol. 192, pp. 666-669.
Geifman-Holtzman O., et al., "Prenatal Diagnosis: Update on Invasive Versus Noninvasive Fetal Diagnostic Testing From Maternal Blood," Expert Review of Molecular Diagnostics, Nov. 1, 2008, vol. 8, No. 6, pp. 727-751.
Genovese G., et al., "Hematopoiesis and Blood-Cancer Risk Inferred from Blood DNA Sequence," The New England Journal of Medicine, Dec. 25, 2014, vol. 371, No. 26, pp. 2477-2487.
Ghanta S., et al., "Non-invasive Prenatal Detection of Trisomy 21using Tandem Single Nucleotide Polymorphisms," PLoS One, Oct. 8, 2010, vol. 5, No. 10:e. 13184, 10 Pages, doi: 10.1371/journal.pone.0013184.
Gielis E.M., et al., "Cell-Free DNA: An Upcoming Biomarker in Transplantation," American Journal of Transplantation, 2015, vol. 15, pp. 2541-2551, 12 Pages.
Gnirke A., et al., "Solution Hybrid Selection with Ultra-Long Oligonucleotides for Massively Parallel Targeted Sequencing," Nature Biotechnology, Feb. 2009, vol. 27, No. 2, pp. 182-189.
Go A.T.J.I., et al., "Non-invasive Aneuploidy Detection using Free Fetal DNA and RNA in Maternal Plasma: Recent Progress and Future Possibilities," Human Reproduction Update, 2011, vol. 17, No. 3, pp. 372-382.
Goessl C et al., "DNA Alterations in Body Fluids as Molecular Tumor Markers for Urological Malignancies," European Urology, 2002, vol. 41, pp. 668-676.
Gormally E., et al., "Amount of DNA in Plasma and Cancer Risk: A Prospective Study," International Journal of Cancer, Sep. 20, 2004, vol. 111, No. 5, DOI: 10.1002/ijc.20327, pp. 746-749.
Gu H., et al., "Diagnostic Role of MicroRNA Expression Profile in the Serum of Pregnant Women with Fetuses with Neural Tube Defects," Journal of Neurochemistry, 2012, vol. 122, pp. 641-649.
Gwee P-C., et al., "Simultaneous Genotyping of Seven Single-nucleotide Polymorphisms in the Mdr1 Gene by Single-tube Multiplex Minisequencing," Clinical Chemistry, Apr. 1, 2003, vol. 49, Issue. 3, pp. 672-676.
Hall M.P., "Panorama(TM) Non-Invasive Prenatal Screening for Microdeletion Syndromes," Panaroma Prenatal Screen, Apr. 1, 2014, 5 Pages, XP055157224, [Retrieved on Dec. 8, 2014], Retrieved from URL: http://www.panoramatest.com/sites/default/files/files/PanoramaMicrodeletionsWhitePaper-2.pdf.
Handley D., et al., "Noninvasive Prenatal Chromosomal Aneuploidy Detection using Plasma Cell-Free Nucleic Acid," Expert Review of Obstetrics & Gynecology, 2010, vol. 5, No. 5, pp. 581-590, 12 Pages.
Hardenbol P., et al., "Highly Multiplexed Molecular Inversion Probe Genotyping: Over 10,000 Targeted SNPs Genotyped in a Singled Tube Assay," Genome Research, 2005, vol. 15, pp. 269-275.
Hardenbol P., et al., "Multiplexed Genotyping with Sequence-Tagged Molecular Inversion Probes," Nature Biotechnology, Jun. 2003, vol. 21, No. 6, pp. 673-678 (7 Pages).
Harismendy O., et al., "Method for Improving Sequence Coverage Uniformity of Targeted Genomic Intervals Amplified by LR-PCR Using Illumina GA Sequencing-by-synthesis Technology," Bio Techniques, 2009, vol. 46, No. 3, pp. 229-231.
Hayden M.J., et al., "Multiplex-Ready PCR: A New Method for Multiplexed SSR and SNP Genotyping," BMC Genomics, Feb. 18, 2008, vol. 9, No. 80, pp. 1-12 (12 Pages).
Heidary M., et al., "The Dynamic Range of Circulating Tumor DNA in Metastatic Breast Cancer," Breast Cancer Research, Aug. 9, 2014, vol. 16, No. 421, 10 Pages.
Hidestrand M., et al., "Highly Sensitive Noninvasive Cardiac Transplant Rejection Monitoring Using Targeted Quantification of Donor-Specific Cell-Free Deoxyribonucleic Acid," Journal of the American College of Cardiology, 2014, vol. 63, No. 12, 1224-1226.
Hochberg E.P., et al., "A Novel Rapid Single Nucleotide Polymorphism (SNP)-Based Method For Assessment Of Hematopoietic Chimerism After Allogeneic Stem Cell Transplantation," Jan. 1, 2003, Blood, vol. 101, No. 1, pp. 363-369.
Hodgkinson C.L., et al., "Tumorigenicity and Genetic Profiling of Circulating Tumor Cells in Small-Cell Lung Cancer," Nature Medicine, Aug. 2014, vol. 20, No. 8, pp. 897-905.
Hoffmann S., et al., "Donor Genomics Influence Graft Events: The Effect Of Donor Polymorphisms On Acute Rejection And Chronic Allograft Nephropathy," Kidney International, Oct. 1, 2004, vol. 66, No. 4, pp. 1686-1693.
Hosono S., et al., "Unbiased Whole-Genome Amplification Directly from Clinical Samples," Genome Research, Jun. 2003, vol. 13, pp. 954-964, 12 Pages.
Hu D.G., et al., "Aneuploidy Detection in Single Cells Using DNA Array-Based Comparative Genomic Hybridization," Molecular Human Reproduction, 2004, vol. 10, No. 4, pp. 283-289.
Huang D.J., et al., "Use of an Automated Method Improves the Yield and Quality of Cell-Free Fetal DNA Extracted from Maternal Plasma," Clinical Chemistry, 2005, vol. 51, No. 12, pp. 2419-2420.
Huang J., et al., "Whole Genome DNA Copy Number Changes Identified by High Density Oligonucleotide Arrays," Human Genomics, May 2004, vol. 1, No. 4, pp. 287-299, 13 Pages.
Hubacek J.A., et al., "Detection of Donor DNA After Heart Transplantation: How Far Could It Be Affected by Blood Transfusion and Donor Chimerism?," Transplantation Proceedings, Jun. 1, 2007, vol. 39, pp. 1593-1595.
Hung E.C.W., et al., "Detection of Circulating Fetal Nucleic Acids: A Review of Methods and Applications," Journal of Clinical Pathology, 2009, vol. 62, pp. 308-313.
Imielinski M., et al., "Mapping the Hallmarks of Lung Adenocarcinoma with Massively Parallel Sequencing," Cell, Sep. 14, 2012, vol. 150, pp. 1107-1120, Published Sep. 13, 2012.

(56) References Cited

OTHER PUBLICATIONS

Ingman M., et al., "SNP Frequency Estimation using Massively Parallel Sequencing of Pooled DNA," European Journal of Human Genetics, 2009, vol. 17, No. 3, pp. 383-386, Published Online Oct. 15, 2008.
Interewicz B., et al., "DNA Released from Ischemic and Rejecting Organs as an Indicator of Graft Cellular Damage," Annals of Transplantation, May 1, 2004, vol. 9, No. 2, pp. 42-45.
Ishii K., et al., "Optimization of Annealing Temperature to Reduce Bias Caused by a Primer Mismatch in Multitemplate PCR," Applied and Environmental Microbiology, Aug. 2001, vol. 67 (8), pp. 3753-3755.
Ito T., et al., "Estimation of Haplotype Frequencies, Linkage-Disequilibrium Measures, and Combination of Haplotype Copies in Each Pool By Use Of Pooled DNA Data," American Journal of Human Genetics, Jan. 17, 2003, vol. 72, pp. 384-398.
Jamal-Hanjani M., et al., "Tracking Genomic Cancer Evolution for Precision Medicine: The Lung TRACERx Study," PLOS Biology, Jul. 2014, vol. 12, No. 7, pp. 1-7.
Jarvie T., "Next Generation Sequencing Technologies," Drug Discovery Today: Technologies, 2005, vol. 2, No. 3, pp. 255-260.
Jen J., et al., "An Overview on the Isolation and Analysis of Circulating Tumor DNA in Plasma and Serum," Annals New York Academy of Sciences, 2000, pp. 8-12.
Jung K., et al., "Increased Cell-free DNA in Plasma of Patients with Metastatic Spread in Prostate Cancer," Cancer Letters, 2004, vol. 205, pp. 173-180.
Kamat A.A., et al., "Quantification of Total Plasma Cell-Free DNA in Ovarian Cancer using Real-Time PCR," Annals of the New York Academy of Sciences, Sep. 2006, vol. 1075, pp. 230-234.
Kaper F., et al., "Abstract 1164: Parallel Preparation of Targeted Resequencing Libraries from 480 Genomic Regions Using Multiplex PCR on the Access Array System," American Association for Cancer Research, Apr. 17-21, 2010, vol. 70, Supplement. 8, No. 1164, pp. 1-2.
Kaper F., et al., "Parallel Preparation of Targeted Resequencing Libraries from 480 Genomic Regions Using Multiplex PCR on the Access Array(TM) System," Fluidigm Poster, 2011, 1 Page.
Kennedy S.R., et al., "Detecting Ultralow-Frequency Mutations by Duplex Sequencing," Nature Protocols, 2014, vol. 9, No. 11, pp. 2586-2606, 22 Pages.
Khater N., et al., "Pseudorejection and True Rejection after Kidney Transplantation: Classification and Clinical Significance," Urologia Internationalis, 2013, vol. 90, No. 4, pp. 373-380, 2012.
Kinde I., et al., "Detection and Quantification of Rare Mutations with Massively Parallel Sequencing," Proceedings of the National Academy of Sciences of the United States of America, Jun. 7, 2011, vol. 108, No. 23, pp. 9530-9535.
Kinnings S.L., et al., "Factors Affecting Levels of Circulating Cell-Free Fetal DNA in Maternal Plasma and Their Implications for Noninvasive Prenatal Testing," Prenatal Diagnosis, 2015, vol. 35, pp. 816-822.
Kircher M., et al., "Improved Base Calling for the Illumina Genome Analyzer Using Machine Learning Strategies," Genome Biology, Aug. 14, 2009, vol. 10, Issue 8, Article No. R83, pp. R83.2-R83.9, (9 Pages).
Kittler R., et al., "A Whole Genome Amplification Method to Generate Long Fragments from Low Quantities of Genomic DNA," Analytical Biochemistry, 2002, vol. 300, pp. 237-244.
Kivioja T., et al., "Counting Absolute Nos. of Molecules Using Unique Molecular Identifiers," Nature Methods, Advance Online Publication, Nov. 20, 2011, pp. 1-5 (18 Pages).
Kivioja T., et al., "Counting Absolute Nos. of Molecules using Unique Molecular Identifiers," Nature Methods, Jan. 2012, vol. 9, No. 1, pp. 72-76.
Koboldt D.C., et al., "VarScan: Variant Detection In Massively Parallel Sequencing Of Individual And Pooled Samples," Bioinformatics, Jun. 19, 2009, vol. 25, No. 17, pp. 2283-2285.
Koelman C.A., et al., "Donor-Derived Soluble HLA Plasma Levels Can Not Be Used To Monitor Graft Rejection In Heart Transplant Recipients," Transplant Immunology, Mar. 1, 2000, vol. 8, No. 1, pp. 57-64.
Kohler C., et al., "Levels of Plasma Circulating Cell Free Nuclear and Mitochondrial DNA as Potential Biomarkers for Breast Tumors," Molecular Cancer, Nov. 17, 2009, vol. 8, No. 105, 9 Pages.
Koide K., et al., "Fragmentation of Cell-Free Fetal DNA in Plasma and Urine of Pregnant Women," Prenatal Diagnosis, 2005, vol. 25, pp. 604-607.
Koldehoff M., et al., "Quantitative Analysis of Chimerism After Allogeneic Stem Cell Transplantation by Real-time Polymerase Chain Reaction With Single Nucleotide Polymorphisms, Standard Tandem Repeats, and Y- Chromosome-specific Sequences," American Journal of Hematology, Jul. 12, 2006, vol. 18, No. 10, pp. 735-746.
Korn J.M., et al., "Integrated Genotype Calling And Association Analysis Of SNPS, Common Copy Number Polymorphisms And Rare CNVS," Nature Genetics, Oct. 1, 2008, vol. 40, No. 10, pp. 1253-1260.
Krishnakumar S., et al., "A Comprehensive Assay for Targeted Multiplex Amplification of Human DNA Sequences," The Proceedings of the National Academy of Sciences, Jul. 8, 2008, vol. 105, No. 27, pp. 9296-9301.
Krjutskov K., et al., "Development of a Single Tube 640-plex Genotyping Method for Detection of Nucleic Acid Variations on Microarrays," Nucleic Acids Research, May 23, 2008, vol. 36, No. 12, pp. e75-e75 (7 Pages), XP055207208, ISSN: 0305-1048, DOI: 10.1093/nar/gkn357.
Lanman R.B., et al., "Analytical and Clinical Validation of a Digital Sequencing Panel for Quantitative, Highly Accurate Evaluation of Cell- Free Circulating Tumor DNA," Plos One, Oct. 16, 2015, vol. 10, No. 10, e0140712, pp. 1-27, DOI:10.1371/journal.pone.0140712.
Lavebratt C., et al., "Single Nucleotide Polymorphism (SNP) Allele Frequency Estimation in DNA Pools Using Pyrosequencing(TM)," Nature Protocols, Jan. 11, 2007, vol. 1, No. 6, pp. 2573-2582.
Lavebratt C., et al., "Pyrosequencing(TM)-based SNP Allele Frequency Estimation In DNA Pools," Human Mutation, Dec. 19, 2003, vol. 23, Issue 1, pp. 92-97.
Leamon J.H., et al., "A Massively Parallel Pico TiterPlate based Platform for Discrete Picoliter-scale Polymerase Chain Reactions," Electrophoresis, Nov. 1, 2003, vol. 24, No. 21, pp. 3769-3777.
Leary R.J., et al., "Detection of Chromosomal Alterations in the Circulation of Cancer Patients with Whole-Genome Sequencing," Science Translational Medicine, Nov. 28, 2012, vol. 4, No. 162(162ra154), 14 Pages, DOI: 10.1126/scitranslmed.3004742.
Leary R.J., et al., "Development of Personalized Tumor Biomarkers Using Massively Parallel Sequencing," Science Translational Medicine, Feb. 24, 2010, vol. 2, Issue. 20 (20ra14), pp. 1-8.
Lecomte T., et al., "Detection of Free-Circulating Tumor-Associated DNA in Plasma of Colorectal Cancer Patients and its Association with Prognosis," International Journal of Cancer, Aug. 10, 2002, vol. 100, No. 5, pp. 542-548, DOI: 10.1002/ijc. 10526.
Lee T., et al., "Down Syndrome and Cell-Free Fetal DNA in Archived Maternal Serum," American Journal of Obstetrics & Gynecology, Nov. 2002, vol. 187, No. 5, pp. 1217-1221.
Lee T.H., et al., "Quantitation of Genomic DNA in Plasma and Serum Samples: Higher Concentrations of Genomic DNA found in Serum than in Plasma," Transfusion, Feb. 2001, vol. 41, pp. 276-282.
Lefebure B., et al., "Prognostic Value of Circulating Mutant DNA in Unresectable Metastatic Colorectal Cancer," Annals of Surgery, Feb. 2010, vol. 251, No. 2, pp. 275-280, DOI: 10.1097/SLA.0b013e3181c35c87.
Li R., et al., "SNP Detection For Massively Parallel Whole-Genome Resequencing," Genome Research, 2009, vol. 19, pp. 1124-1132 (10 Pages).
Li Y., et al., "Detection of Donor-specific DNA Polymorphisms in the Urine of Renal Transplant Recipients," Clinical Chemistry, Apr. 1, 2003, vol. 49, No. 4, pp. 655-658.
Li Y., et al., "Detection of Paternally Inherited Fetal Point Mutations for Beta-Thalassemia Using Size-Fractionated Cell-Free DNA in

(56) References Cited

OTHER PUBLICATIONS

Maternal Plasma," JAMA, Feb. 16, 2005, vol. 293, No. 7, pp. 843-849, 8 Pages, Apr. 13, 2005.
Li Y., et al., "Detection of SNPs in the Plasma of Pregnant Women and in the Urine of Kidney Transplant Recipients by Mass Spectrometry," Annals of the New York Academy of Sciences, Sep. 5, 2006, vol. 1075, pp. 144-147.
Li Y., et al., "Size Separation of Circulatory DNA in Maternal Plasma Permits Ready Detection of Fetal DNA Polymorphisms," Clinical Chemistry, 2004, vol. 50, No. 6, pp. 1002-1011.
Li Y., et al., "Non-invasive Prenatal Diagnosis Using Cell-free Fetal DNA in Maternal Plasma From PGD Pregnancies," Reproductive Bio Medicine Online, 2009, vol. 19, No. 5, pp. 714-720 (8 Pages).
Liao G.J.W., et al., "Targeted Massively Parallel Sequencing of Maternal Plasma DNA Permits Efficient and Unbiased Detection of Fetal Alleles," Clinical Chemistry, 2011, vol. 92, No. 1, pp. 92-101.
Lichtenstein A.V., et al., "Circulating Nucleic Acids and Apoptosis," Annals New York Academy of Sciences, Aug. 1, 2001, vol. 945, pp. 239-249.
Liew M., et al., "Genotyping of Single-Nucleotide Polymorphisms by High-Resolution Melting of Small Amplicons," Clinical Chemistry, 2004, vol. 50, No. 7, pp. 1156-1164.
Liljedahl U., et al., "Detecting Imbalanced Expression of SNP Alleles by Minisequencing On Microarrays," BMC Biotechnology, Oct. 22, 2004, vol. 4, Article No. 24, pp. 1-10.
Lindroos K., et al., "Genotyping SNPs by Minisequencing Primer Extension Using Oligonucleotide Microarrays," Methods in Molecular Biology, Single Nucleotide Polymorphisms: Methods and Protocols, P-K Kwok (ed.), Humana Press, Inc., Totowa, NJ, 2003, vol. 212, pp. 149-165.
Lo Y., "Noninvasive Prenatal Detection of Fetal Chromosomal Aneuploidies by Maternal Plasma Nucleic Acid Analysis: A Review of the Current State of the Art," BJOG An International Journal of Obstetrics and Gynaecology, 2009, vol. 116, pp. 152-157.
Lo Y.M.D., et al., "Circulating Nucleic Acids in Plasma and Serum: An Overview," Annals of the New York Academy of Sciences, Sep. 1, 2001, vol. 945, pp. 1-7.
Lo Y.M.D., et al., "Digital PCR for the Molecular Detection of Fetal Chromosomal Aneuploidy," Proceedings of the National Academy of Sciences, Aug. 7, 2007, vol. 104, No. 32, pp. 13116-13121.
Lo Y.M.D., et al., "Fetal Nucleic Acids in Maternal Blood: The Promises," Clinical Chemistry and Laboratory Medicine, 2012, vol. 50, No. 6, pp. 995-998 (5 Pages).
Lo Y.M.D., et al., "Free Fetal DNA in Maternal Circulation," JAMA (Letters to the Editor), Dec. 15, 2004, vol. 292, No. 23, pp. 2835-2836 (3 Pages).
Lo Y.M.D., et al., "Maternal Plasma DNA Sequencing Reveals the Genome-Wide Genetic and Mutational Profile of the Fetus," Science Translational Medicine, Dec. 8, 2010, vol. 2, No. 61, 13 Pages.
Lo Y.M.D., et al., "Next-Generation Sequencing Of Plasma/Serum DNA: An Emerging Research And Molecular Diagnostic Tool," Clinical Chemistry, Apr. 1, 2009, vol. 55, No. 4, pp. 607-608.
Lo Y.M.D., et al., "Non-Invasive Prenatal Diagnosis by Massively Parallel Sequencing of Maternal Plasma DNA," Open Biology, 2012, vol. 2, Article 120086, pp. 1-5.
Lo Y.M.D., et al., "Plasma Placental RNA Allelic Ration Permits Noninvasive Prenatal Chromosomal Aneuploidy Detection," Nature Medicine, Feb. 2007, vol. 13, No. 2, pp. 218-224 (6 Pages).
Lo Y.M.D., et al., "Prenatal Diagnosis: Progress through Plasma Nucleic Acids," Nature Reviews, Jan. 2007, vol. 8, pp. 71-77.
Lo Y.M.D., et al., "Transplantation Monitoring by Plasma DNA Sequencing," Clinical Chemistry, Jul. 2011, vol. 57, No. 7, pp. 941-942, DOI: 10.1373/clinchem.2011.166686, PubMed PMID: 21566070.
Lo Y.M.D., "Fetal DNA in Maternal Plasma: Biology and Diagnostic Applications," Clinical Chemistry, 2000, vol. 46, No. 12, pp. 1903-1906.
Lo Y.M.D., "Fetal Nucleic Acids in Maternal Plasma: Toward the Development of Noninvasive Prenatal Diagnosis of Fetal Chromosomal Aneuploidies," Annals of the New York Academy of Sciences, 2008, vol. 1137, pp. 140-143.
Lovmar L., et al., "Quantitative Evaluation by Minisequencing and Microarrays Reveals Accurate Multiplexed SNP Genotyping of Whole Genome Amplified DNA," Nucleic Acids Research, 2003, vol. 31, No. 21(e129), 9 Pages.
Lui Y.Y.N., et al., "Circulating DNA in Plasma and Serum: Biology, Preanalytical Issues And Diagnostic Applications," Clinical Chemistry and Laboratory Medicine, Oct. 29, 2002, vol. 40, No. 10, pp. 962-968.
Lui Y.Y.N., et al., "Origin of Plasma Cell-Free DNA after Solid Organ Transplantation," Clinical Chemistry, Mar. 1, 2003, vol. 49, No. 3, pp. 495-496.
Lui Y.Y.N., et al., "Predominant Hematopoietic Origin of Cell-Free DNA in Plasma and Serum after Sex-Mismatched Bone Marrow Transplantation," Clinical Chemistry, 2002, vol. 48, vol. 3, pp. 421-427.
Lun F M F., et al., "Microfluidics Digital PCR Reveals A Higher Than Expected Fraction Of Fetal DNA In Maternal Plasma," Clinical Chemistry, Aug. 14, 2008, vol. 54, No. 10, pp. 1664-1672.
Lun F.M.F., et al., "Noninvasive Prenatal Diagnosis of Monogenic Diseases by Digital Size Selection and Relative Mutation Dosage on DNA in Maternal Plasma," PNAS, Dec. 16, 2008, vol. 105, No. 50, pp. 19920-19925.
Mamanova L., et al., "Target-Enrichment Strategies for Next-Generation Sequencing," Nature Methods, Feb. 2010, vol. 7, No. 2, pp. 111-118 (9 Pages) DOI: 10.1038/nmeth.1419.
Mamon H., et al., "Letters to the Editor: Preferential Amplification of Apoptotic DNA from Plasma: Potential for Enhancing Detection of Minor DNA Alterations in Circulating DNA," Clinical Chemistry, 2008, vol. 54, No. 9, pp. 1582-1584.
Maron J.L., et al., "Cell-free Fetal DNA Plasma Extraction and Realtime Polymerase Chain Reaction Quantification," Methods In Molecular Medicine, Aug. 1, 2007, vol. 132, pp. 51-63.
Matsuzaki H., et al., "Genotyping over 100,000 SNPs on a Pair of Oligonucleotide Arrays," Nature Methods, Nov. 2004, vol. 1, No. 2, pp. 109-111.
Mcbride D.J., et al., "Use of Cancer-Specific Genomic Rearrangements to Quantify Disease Burden in Plasma from Patients with Solid Tumors," Genes, Chromosomes & Cancer, Aug. 19, 2010, vol. 49, pp. 1062-1069.
Mccloskey M.L., et al., "Encoding PCR Products with Batch-Stamps and Barcodes," Biochemical Genetics, Oct. 23, 2007, vol. 45, pp. 761-767.
Mersy E., et al., "Noninvasive Detection of Fetal Trisomy 21: Systematic Review and Report of Quality and Outcomes of Diagnostic Accuracy Studies Performed Between 1997 and 2012," Human Reproduction Update, 2013, vol. 19, No. 4, pp. 318-329.
Mertes F., et al., "Targeted Enrichment of Genomic DNA Regions for Next-Generation sequencing," Briefings in Functional Genomics, Nov. 26, 2011, vol. 10, No. 6, pp. 374-386.
Meuzelaar L.S., et al., "Megaplex Pcr: A Strategy for Multiplex Amplification," Nature Methods, 2007, vol. 4, pp. 835-837, 8 Pages.
Milani L., et al., "Genotyping Single Nucleotide Polymorphisms By Multiplex Minisequencing Using Tag-Arrays," DNA Microarrays for Biomedical Research, Jan. 16, 2009, vol. 529, pp. 215-229.
Miner B.E., et al., "Molecular Barcodes Detect Redundancy and Contamination in Hairpin- Bisulfite PCR," Nucleic Acids Research, Sep. 30, 2004, vol. 32(17), pp. 1-4.
Moreira V.G., et al., "Cell-Free DNA as a Noninvasive Acute Rejection Marker in Renal Transplantation," Clinical Chemistry, 2009, vol. 55, No. 11, pp. 1958-1966.
Murtaza M., et al., "Non-Invasive Analysis of Acquired Resistance to Cancer Therapy by Sequencing of Plasma DNA," Nature, May 2, 2013, vol. 497, 6 Pages, DOI:10.1038/nature12065).
Nannya Y., et al., "A Robust Algorithm for Copy Number Detection Using High-density Oligonucleotide Single Nucleotide Polymorphism Genotyping Arrays," Cancer Research, Jul. 15, 2005, vol. 65, No. 14, pp. 6071-6079.
Narayan A., et al., "Ultrasensitive Measurement of Hotspot Mutations in Tumor DNA in Blood using Error-Suppressed Multiplexed Deep Sequencing," Cancer Research, Jul. 15, 2012, vol. 72, No. 14, pp. 3492-3498 (8 Pages).

(56) References Cited

OTHER PUBLICATIONS

Nguyen-Dumont T., et al., "A High-Plex PCR Approach for Massively Parallel Sequencing," BioTechniques, Aug. 2013, vol. 55, No. 2, pp. 69-74 (5 Pages).
Nicolaides K.H., et al., "Noninvasive Prenatal Testing for Fetal Trisomies in a Routinely Screened First-Trimester Population," American Journal of Obstetrics and Gynecology, (Article in Press), 2012, vol. 207, pp. 1.e1-1.e6.
Nicolaides K.H., et al., "Prenatal Detection of Fetal Triploidy from Cell-Free DNA Testing in Maternal Blood," Fetal Diagnosis and Therapy, Oct. 10, 2013, pp. 1-6.
Nicolaides K.H., et al., "Validation of Targeted Sequencing of Single-Nucleotide Polymorphisms for Non-Invasive Prenatal Detection of Aneuploidy of Chromosomes 13, 18, 21, X, and Y," Prenatal Diagnosis, Jun. 2013, vol. 33, No. 6, pp. 575-579.
No Author Listed, "Abstracts for CNAPS III Circulating Nucleic Acids in Plasma and Serum and Serum Proteomics," Loews Santa Monica Beach Hotel, Clinical Chemistry, Nov. 9-12, 2003, vol. 49, No. 11, 33 Pages.
Owczarzy R., et al., "Melting Temperatures of Nucleic Acids Discrepancies in Analysis," Biophysical Chemistry, 2005, vol. 117, pp. 207-215.
Palomaki G., et al., "DNA Sequencing of Maternal Plasma Reliably Identifies Trisomy 18 and Trisomy 13 as Well as Down Syndrome: an International Collaborative Study," Genetics in Medicine, Mar. 2012, vol. 14, No. 3, 10 Pages.
Palomaki G.E., et al., "DNA Sequencing of Maternal Plasma to Detect Down Syndrome: An International Clinical Validation Study," Genetics in Medicine, Nov. 2001, vol. 13, No. 11, pp. 913-920.
Panjkovich A., et al., "Comparison of Different Melting Temperature Calculation Methods for Short DNA Sequences," Bioinformatics, 2005, vol. 21, No. 6, pp. 711-722.
Papadopoulou E., et al., "Cell-Free DNA and RNA in Plasma as a New Molecular Marker for Prostate Cancer," Oncology Research, 2004, vol. 14, pp. 439-445.
Papageorgiou E.A., et al., Fetal-Specific DNA Methylation Ratio Permits Noninvasive Prenatal Diagnosis of Trisomy 21, Nature Medicine, Advanced Online Publication, Mar. 6, 2011, vol. 17, pp. 510-513 (5 Pages).
Parameswaran P., et al., "A Pyrosequencing-Tailored Nucleotide Barcode Design Unveils Opportunities for Large-Scale Sample Multiplexing," Nucleic Acids Research, Oct. 11, 2007, vol. 35, No. 19(e130), 9 Pages.
Pathak A.K., et al., "Circulating Cell-Free DNA in Plasma/Serum of Lung Cancer Patients as a Potential Screening and Prognostic Tool," Clinical Chemistry, 2006, vol. 52, No. 10, pp. 1833-1842.
Peng Q., et al., "Reducing Amplification Artifacts in High Multiplex Amplicon Sequencing by using Molecular Barcodes," BMC Genomics, Aug. 7, 2015, vol. 16, No. 1, 589, 12 Pages, DOI: 10.1186/s12864-015-1806-8.
Pergament E., et al., "Single-Nucleotide Polymorphism-Based Noninvasive Prenatal Screening in a High-Risk and Low-Risk Cohort," Obstetrics & Gynecology, Aug. 2014, vol. 124, No. 2, Part 1, pp. 210-218 (26 Pages), Appendix.
Perkel J.M., "Overcoming the Challenges of Multiplex PCR," Biocompare Editorial Article, Oct. 23, 2012, pp. 1-5.
Peters D., et al., "Noninvasive Prenatal Diagnosis of a Fetal Microdeletion Syndrome," New England Journal of Medicine, 2011, vol. 365, No. 11, pp. 1847-1848.
Pinard R., et al., "Assessment of Whole Genome Amplification-induced Bias Through High-throughput, Massively Parallel Whole Genome Sequencing," BMC Genomics, Aug. 23, 2006, vol. 7, No. 216, pp. 1-21.
Podder M., et al., "Robust SNP Genotyping by Multiplex PCR and Arrayed Primer," BMC Medical Genomics, 2008, vol. 1, No. 5, pp. 1-15.
Pont-Kingdon., G., et al., "Rapid Detection of Aneuploidy (Trisomy 21) by Allele Quantification Combined with Melting Curves Analysis of Single-Nucleotide Polymorphism Loci," Clinical Chemistry, 2003, vol. 49, No. 7, pp. 1087-1094.
Pourmand N., et al., "Multiplex Pyrosequencing," Nucleic Acid Research, Apr. 1, 2002, vol. 30, No. 7(e31), pp. 1-5.
Puszyk W.M., et al., "Noninvasive Prenatal Diagnosis Of Aneuploidy Using Cell-free Nucleic Acids In Maternal Blood: Promises And Unanswered Questions," Prenatal Diagnosis, 2008, vol. 28, No. 1, pp. 1-6, Nov. 16, 2007.
Rabinowitz M., et al., "Non-Invasive Prenatal Aneuploidy Testing of Chromosomes 13, 18, 21, X, and Y Using Targeted Sequencing of Polymorphic Loci," The American Society of Human Genetics, Meeting poster, 2012, 1 Page.
Rabinowitz M., et al., "Origins and Rates of Aneuploidy in Human Blastomeres," Fertility and Sterility, Elsevier Science Inc, New York, NY, USA, Feb. 2012, vol. 97, No. 2, pp. 395-401, DOI: 10.1016/J.FERTNSTERT.2011.11.034, ISSN: 0015-0282, XP028453561, [Retrieved on Nov. 30, 2011], Nov. 24, 2011.
Roedder S., et al., "Biomarkers in Solid Organ Transplantation: Establishing Personalized Transplantation Medicine," Genome Medicine, Jun. 8, 2011, vol. 3, No. 6 (37), 12 Pages.
Ryan A., et al., "Informatics-Based, Highly Accurate, Noninvasive Prenatal Paternity Testing," Genetics in Medicine, (Advance Online Publication), 2012, 5 Pages.
Saito H., et al., "Prenatal DNA Diagnosis of a Single-Gene Disorder from Maternal Plasma," The Lancet, Sep. 30, 2000, vol. 356, p. 1170.
Samango-Sprouse C., et al., "SNP-Based Non-Invasive Prenatal Testing Detects Sex Chromosome Aneuploidies With High Accuracy," Prenatal Diagnosis, 2013, vol. 33, 643-649.
Samura O., et al., "Diagnosis of Trisomy 21 in Fetal Nucleated Erythrocytes from Maternal Blood by Use of Short Tandem Repeat Sequences," Clinical Chemistry, 2001, vol. 47, No. 9, pp. 1622-1626.
Schmitt M.W., "Detection of Ultra-Rare Mutations by the Next Generation Sequencing," Proceedings of the National Academy of Sciences of the United States of America, Sep. 4, 2012, vol. 109, No. 36, p. 14508-14513 (9 Pages), Supporting Information.
Schoske R., et al., "Multiplex PCR Design Strategy used for the Simultaneous Amplification of 10 Y Chromosome Short Tandem Repeat (STR) Loci," Analytical and Bioanalytical Chemistry, 2003, vol. 375, pp. 333-343.
Schwarzenbach H., et al., "Cell-Free Nucleic Acids as Biomarkers in Cancer Patients," Nature Reviews Cancer, Jun. 2011, vol. 11, No. 6, pp. 426-437, DOI: 10.1038/nrc3066m EPublished May 12, 2011.
Schwarzenbach H., et al., "Detection and Characterization of Circulating Microsatellite-DNA in Blood of Patients with Breast Cancer," Annals of the New York Academy of Sciences, 2004, vol. 1022, pp. 25-32.
Schwarzenbach H., et al., "Evaluation of Cell-Free Tumour DNA and RNA in Patients with Breast Cancer and Benign Breast Disease," Molecular BioSystems, Jul. 2011, vol. 7, pp. 2848-2854, 8 Pages.
Sehnert A.J., et al., Optimal Detection of Fetal Chromosomal Abnormalities by Massively Parallel DNA Sequencing of Cell-Free Fetal DNA from Maternal Blood, Clinical Chemistry, Apr. 25, 2011, vol. 57, No. 7, pp. 1-8.
Seppo A., et al., "Detection of Circulating Fetal Cells Utilizing Automated Microscopy: Potential for Noninvasive Prenatal Diagnosis of Chromosomal Aneuploidies," Prenatal Diagnosis, vol. 28, pp. 815-821, Published Online on Jul. 22, 2008.
Shen Z., et al., "MPprimer: A Program for Reliable Multiplex PCR Primer Design," BMC Bioinformatics, Mar. 18, 2010, vol. 11, No. 143, pp. 1-7.
Shendure J., et al., "Next-Generation DNA Sequencing," Nature Biotechnology, Oct. 2008, vol. 26, No. 10, pp. 1135-1145.
Shiroguchi K., et al., "Digital RNA Sequencing Minimizes Sequence-Dependent Bias and Amplification Noise with Optimized Single-Molecule Barcodes," PNAS, Jan. 24, 2012, vol. 109, No. 4, pp. 1347-1352.
Shokralla S., et al., "Next-generation DNA Barcoding: Using Next-Generation Sequencing to Enhance and Accelerate DNA Barcode Capture from Single Specimens," Molecular Ecology Resources, 2014, vol. 14, pp. 892-901.

(56) References Cited

OTHER PUBLICATIONS

Sint D., et al., "Advances in Multiplex PCR: Balancing Primer Efficiencies and Improving Detection Success," Methods in Ecology and Evolution, 2012, vol. 3, pp. 898-905.
Smith D.R., et al., "Rapid Whole-genome Mutational Profiling using Next-generation Sequencing Technologies," Genome Research, Sep. 4, 2008, vol. 18, pp. 1638-1642.
Smith J.F., et al., "Cell-Free Fetal DNA in Maternal Plasma," Progress and Potential, Neo Reviews, Aug. 1, 2008, vol. 9, No. 8, pp. e332-e337 (8 Pages).
Snyder T.M., et al., "Universal Noninvasive Detection of Solid Organ Transplant Rejection," Proceedings of the National Academy of Sciences of the United States of America, Apr. 12, 2011, vol. 108, No. 15, pp. 6229-6234.
Sparks A.B., et al., "Selective Analysis of Cell-free DNA in Maternal Blood for Evaluation of Fetal Trisomy," Prenatal Diagnosis, 2012, vol. 32, No. (1-7), pp. 3-9 (7 Pages), Epublished on Jan. 6, 2012.
Sparks A.B., et al., "Non-invasive Prenatal Detection and Selective Analysis of Cell-free DNA Obtained From Maternal Blood: Evaluation for Trisomy 21 and Trisomy 18," American Journal of Obstetrics & Gynecology, Apr. 2012, vol. 206, pp. 319.e1-319.e9.
Spindler K-L G., et al., "Cell-Free DNA in Healthy Individuals, Noncancerous Disease and Strong Prognostic Value in Colorectal Cancer," International Journal of Cancer, Dec. 15, 2014, vol. 135, No. 12, pp. 2984-2991, DOI: 10.1002/ijc.28946, Epub Jun. 17, 2014.
Spits C., et al., "Optimization and Evaluation of Single-Cell Whole Genome Multiple Displacement Amplification," Human Mutation, 2006, vol. 27, No. 5, pp. 496-503.
Srinivasan A., et al., "Noninvasive Detection of Fetal Subchromosome Abnormalities via Deep Sequencing of Maternal Plasma," The American Journal of Human Genetics, Feb. 7, 2013, vol. 92, pp. 167-176, Published Jan. 10, 2013.
Stiller M., et al., "Direct Multiplex Sequencing (DMPS)—A Novel Method for Targeted High-throughput Sequencing of Ancient and Highly Degraded DNA," Genome Research, Oct. 2009, vol. 19, No. 10, pp. 1843-1848.
Swarup V., et al., "Circulating (Cell-Free) Nucleic Acids—A Promising, Non-Invasive Tool for Early Detection of Several Human Diseases," FEBS Letters, 2007, vol. 581, pp. 795-799.
Swinkels D.W., et al., "Effects of Blood-Processing Protocols on Cell-Free DNA Quantification in Plasma," Clinical Chemistry, Mar. 2003, vol. 49, No. 3, pp. 525-526, PubMed PMID: 12600978.
Taback B., et al., "Quantification of Circulating DNA in the Plasma and Serum of Cancer Patients," Annals of the New York Academy of Sciences, 2004, vol. 1022, pp. 17-24.
Taliun D., et al., "Efficient Haplotype Block Recognition of Very Long and Dense Genetic Sequences," BMC Bioinformatics, Jan. 14, 2014, vol. 15, No. 10, pp. 1-18.
Tamkovich S.N., et al., "Circulating Nucleic Acids in Blood of Healthy Male and Female Donors," Clinical Chemistry, Jul. 2005, vol. 51, No. 7, pp. 1317-1319, PubMed PMID: 15976134.
Ten Bosch J.R., et al., "Keeping Up With the Next Generation Massively Parallel Sequencing in Clinical Diagnostics," Journal of Molecular Diagnostics, Nov. 2008, vol. 10, No. 6, pp. 484-492.
Tewhey R., et al., "Microdroplet-Based PCR Enrichment for Large-Scale Targeted Sequencing," Nature Biotechnology, Nov. 2009, vol. 27, No. 11, pp. 1025-1031, 11 Pages, DOI: 10.1038/nbt. 1583, EPublished Nov. 1, 2009.
Tewhey R., et al., "The Importance of Phase Information for Human Genomics," Nature Reviews Genetics, Mar. 1, 2011, vol. 12, No. 3, pp. 215-223.
Tie J., et al., "Circulating Tumor DNA as an Early Marker of Therapeutic Response in Patients with Metastatic Colorectal Cancer," Annals of Oncology, 2015, vol. 26, No. 8, pp. 1715-1722.
Tong Y-K., et al., "Diagnostic Developments Involving Cell-Free (Circulating) Nucleic Acids," Clinica Chimica Acta, Jan. 2006, vol. 363, No. 1-2, pp. 187-196, Epub Aug. 26, 2005 Review. PubMed PMID: 16126188.
Tong Y.K., et al., "Noninvasive Prenatal Detection of Fetal Trisomy 18 by Epigenetic Allelic Ratio Analysis in Maternal Plasma: Theoretical and Empirical Considerations," Clinical Chemistry, 2006, vol. 52, No. 12, pp. 2194-2202.
Tong Y.K., et al., "Noninvasive Prenatal Detection of Trisomy 21 by an Epigenetic-Genetic Chromosome-Dosage Approach," Clinical Chemistry, Jan. 2010, vol. 56, No. 1, pp. 90-98.
Tounta G., et al., "A Multiplex PCR for Non-invasive Fetal RHD Genotyping Using Cell-free Fetal DNA," In Vivo, 2011, vol. 25, pp. 411-418, 7 Pages.
Tounta G., et al., "Non-Invasive Prenatal Diagnosis using Cell-free Fetal Nucleic Acids in Maternal Plasma: Progress Overview beyond Predictive and Personalized Diagnosis," EPMA Journal, 2011, vol. 2, Issue. 2, pp. 163-171.
Tsang J.C.H., et al., "Circulating Nucleic Acids in Plasma/Serum," Pathology, Apr. 1, 2007, vol. 39, No. 2, pp. 197-207.
Tu J., et al., "Pair-barcode High-throughput Sequencing for Large-scale Multiplexed Sample Analysis," BMC Genomics, Jan. 25, 2012, vol. 13, No. 43, pp. 1-9.
Tufan N.L.S., et al., "Analysis of Cell-Free Fetal DNA from Maternal Plasma and Serum Using a Conventional Multiplex PCR: Factors Influencing Success," The Turkish Journal of Medical Sciences, 2005, vol. 35, pp. 85-92.
Tungwiwat W., et al., Non-Invasive Fetal Sex Determination using a Conventional Nested PCR Analysis of Fetal DNA in Maternal Plasma, Clinica Chimica Acta, 2003, vol. 334, No. 1-2, pp. 173-177.
Tynan J.A., et al., "Restriction Enzyme-Mediated Enhanced Detection of Circulating Cell-Free Fetal DNA in Maternal Plasma," The Journal of Molecular Diagnostics, Jul. 2011, vol. 13, No. 4, pp. 382-389.
Tzimagiorgis G., et al., "Recovering Circulating Extracellular or Cell-Free RNA from Bodily Fluids," Cancer Epidemiology, 2011, vol. 35, pp. 580-589.
Urbanova M., et al., "Circulating Nucleic Acids as a New Diagnostic Tool," Cellular & Molecular Biology Letters, 2010, vol. 15, No. 2, pp. 242-259.
Vallone P.M., et al., "Demonstration of Rapid Multiplex PCR Amplification Involving 16 Genetic Loci," Forensic Science International: Genetics, 2008, vol. 3, pp. 42-45.
Van Den Oever J.M.E., et al., "Single Molecule Sequencing of Free DNA from Maternal Plasma for Noninvasive Trisomy 21 Detection," Clinical Chemistry, 2012, vol. 58, No. 4, pp. 699-706.
Varley K.E., et al., "Nested Patch PCR Enables Highly Multiplexed Mutation Discovery in Candidate Genes," Genome Research, Nov. 2008, vol. 18, No. 11, pp. 1844-1850, DOI: 10.1101/gr.078204.108.
Veselovska L., "The Use of Cell-Free Nucleic Acids in Maternal Plasma for Non-Invasive Prenatal Diagnosis of Monogenic Diseases, Placental Insufficiency-Related Complications and Down Syndrome," Thesis from Charles University in Prague, Apr. 25, 2011, 104 Pages.
Wagner F.F., et al., "RHD Gene Deletion Occurred in the Rhesus box," Blood, Jun. 15, 2000, vol. 95, No. 12, pp. 3662-3668.
Wagner J., et al., "Non-invasive Prenatal Paternity Testing From Maternal Blood," International Journal of Legal Medicine, 2009, vol. 123, pp. 75-79 (3 Pages), Published Online Oct. 24, 2008.
Wang E., et al., "Gestational Age and Maternal Weight Effects on Fetal Cell-Free DNA in Maternal Plasma," Prenatal Diagnosis, 2013, vol. 33, pp. 662-666.
Wang H-Y., et al., "A Genotyping System Capable of Simultaneously Analyzing 1000 Single Nucleotide Polymorphisms in a Haploid Genome," Genome Research, 2005, vol. 15, pp. 276-283, 9 Pages.
Wang W-P., et al., "Multiplex Single Nucleotide Polymorphism Genotyping by Adapter Ligation-Mediated Allele-Specific Amplification," Analytical Biochemistry, May 5, 2006, vol. 355, pp. 240-248.
Wang Y., et al., "Allele Quantification Using Molecular Inversion Probes (MIP)," Nucleic Acids Research, Oxford University 1 Press, GB, Nov. 1, 2005, vol. 33, No. 21, pp. e183/1-14, XP009127259, ISSN: 1362-4962, DOI: 10.1093/NAR/GNI177 [retrieved on Nov. 28, 2005], Abstract.

(56) References Cited

OTHER PUBLICATIONS

Wang Y., et al., Molecular Inversion Probes: A Novel Microarray Technology and its Application in Cancer Research, Cancer Genetics, 2012, vol. 205, pp. 341-355.
Wapner R., et al., "First-Trimester Screening forTrisomies 21 and 18," The New England Journal of Medicine, Oct. 9, 2003, vol. 349, No. 15, pp. 1405-1413.
Wapner R.J., et al., "Expanding the Scope of Noninvasive Prenatal Testing: Detection of Fetal Microdeletion Syndromes," American Journal of Obstetrics and Gynecology, Mar. 2015, vol. 212, No. 3, pp. 332.e1-332.e9, DOI: 10.1016/j.ajog.2014.11.041, Epub Dec. 2, 2014.
Wasson J., et al., "Assessing Allele Frequencies of Single Nucleotide Polymorphisms in DNA Pools by Pyrosequencing(TM) Technology," Bio Techniques, May 1, 2022, vol. 32, No. 5, pp. 1144-1152, 6 Pages.
Wei C., et al., "Detection and Quantification by Homogeneous PCR of Cell- free Fetal DNA in Maternal Plasma," Clinical Chemistry, 2001, vol. 47, No. 2, pp. 336-338.
Wen D., et al., "Universal Multiplex Pcr: A Novel Method of Simultaneous Amplification of Multiple DNA Fragments," Plant Methods, Null, Aug. 15, 2012, vol. 8, No. 32, pp. 1-9.
Wilkening., et al., "Determination of Allele Frequency in Pooled DNA: Comparison of Three PCR-based Methods," Bio Techniques, May 30, 2005, vol. 39, No. 6, pp. 853-857, (Dec. 2005).
Wong K.H., et al., "Multiplex Illumina Sequencing Using DNA Barcoding," Current Protocols in Molecular Biology, Jan. 2013, Supplement 101, pp. 7.11.1-7.11.11, 12 Pages.
Wong K-K., et al., "Allelic Imbalance Analysis by High-Density Single Nucleotide Polymorphic Allele (SNP) Array with Whole Genome Amplified DNA," Nucleic Acids Research, May 17, 2004, vol. 32, No. 9 (e69), 8 Pages.
Wright C., et al., "Cell-free Fetal Nucleic Acids for Noninvasive Prenatal Diagnosis," PHG Foundation, Jan. 1, 2009, pp. 1-64.
Wright C.F., et al., "Cell-Free Fetal DNA and RNA in Maternal Blood: Implications for Safer Antenatal Testing," BMJ, Jul. 18, 2009, vol. 339, b2451, pp. 161-165.
Wright C.F., et al., "The Use of Cell-free Fetal Nucleic Acids in Maternal Blood for Non-invasive Prenatal Diagnosis," Human Reproduction Update, 2009, vol. 15, No. 1, pp. 139-151.
Wu T-L., et al., "Cell-Free DNA: Measurement in Various Carcinomas and Establishment of Normal Reference Range," Clinica Chimica Acta, 2002, vol. 321, pp. 77-87.
Xia P., et al., "Simultaneous Quantitative Assessment of Circulating Cell-free Mitochondrial And Nuclear DNA By Multiplex Real-time PCR," Genetics and Molecular Biology, Mar. 1, 2009, vol. 32, No. 1, pp. 20-24.
Xie C., et al., "CNV-SEQ, A New Method to Detect Copy Number Variation Using High-throughput Sequencing," BMC Bioinformatics, Mar. 6, 2009, vol. 10 No. 80, pp. 1-9.
Xu W., et al., "A Novel Universal Primer-Multiplex-PCR Method with Sequencing Gel Electrophoresis Analysis," PLOS One, Jan. 17, 2012, vol. 7, No. 1, 10 Pages.
Xue X., et al., "Optimizing the Yield And Utility Of Circulating Cell-free DNA From Plasma And Serum," Clinica Chimica Acta, Jun. 27, 2009, vol. 404, No. 2, pp. 100-104.
Zachariah, R. et al., "Circulating Cell-free DNA As a Potential Biomarker for Minimal and Mild Endometriosis", Reproductive BioMedicine Online, Jan. 27, 2009, vol. 18, No. 3, pp. 407-411.
Zhang R., "Quantifying RNA Allelic Ratios by Microfluidic Multiplex PCR and Sequencing," Nature Methods, Jan. 2014, vol. 11, No. 1, pp. 51-56.
Zhang Z., et al., "Diagnosis of Acute Rejection by Analysis of Urinary DNA of Donor Origin in Renal Transplant Recipients," Transplantation Proceedings, Feb. 2001, vol. 33, No. 1-2, pp. 380-381.
Zhang Z., et al., "Use Of PCR And PCR-SSP For Detection Of Urinary Donor-Origin Dna In Renal Transplant Recipients With Acute Rejection," Chinese Medical Journal, Feb. 2003, vol. 116, No. 2, pp. 191-194, 5 Pages.
Zhao X., et al., An Integrated View of Copy Number and Allelic Alterations in the Cancer Genome Using Single Nucleotide Polymorphism Arrays, Cancer Research, May 1, 2004, vol. 64, pp. 3060-3071.
Zheng C-X., et al., "Whole-exome Sequencing to Identify Novel Somatic Mutations in Squamous Cell Lung Cancers," International Journal of Oncology, 2013, vol. 43, pp. 755-764, 2015.
Zheng Z., et al., "Anchored Multiplex PCR for Targeted Next-generation Sequencing," Nature Medicine, Dec. 2014, vol. 20, No. 12, pp. 1479-1486.
Zhong X.Y., et al., "Cell-free DNA in Urine: A Marker for Kidney Graft Rejection, but Not for Prenatal Diagnosis?," Annals New York Academy of Sciences, Sep. 1, 2001, vol. 945, pp. 250-257.
Zhong X.Y., et al., "Detection of Fetal Rhesus D and Sex Using Fetal DNA from Maternal Plasma by Multiplex Polymerase Chain Reaction," British Journal of Obstetrics and Gynaecology, Jun. 2000, vol. 107, pp. 766-769.
Zhong X.Y., et al., "Risk Free Simultaneous Prenatal Identification of Fetal Rhesus D Status and Sex by Multiplex Real-time PCR using Cell Free Fetal DNA in Maternal Plasma," Swiss Medical Weekly, Mar. 2001, vol. 131, pp. 70-74 (7 Pages).
Zimmermann B., et al., "Digital Pcr: A Powerful New Tool for Noninvasive Prenatal Diagnosis?," Prenatal Diagnosis, Nov. 10, 2008, vol. 28, pp. 1087-1093.
Zimmermann B., et al., "Novel Real-Time Quantitative PCR Test for Trisomy 21," Clinical Chemistry, 2002, vol. 48, No. 2, pp. 362-363.
Zimmermann B., et al., "Optimized Real-Time Quantitative PCR Measurement of Male Fetal DNA in Maternal Plasma," Clinical Chemistry, 2005, vol. 51, No. 9, pp. 1598-1604.
Zimmermann B., et al., "Real-Time Quantitative Polymerase Chain Reaction Measurement of Male Fetal DNA in Maternal Plasma," Methods in Molecular Medicine, 2007, vol. 132, pp. 43-49.
Zimmermann B. et al., "Use of Real-Time Polymerase Chain Reaction for the Detection of Fetal Aneuploidies," Methods in Molecular Biology, Feb. 2006, vol. 336, pp. 83-100.
Zimmermann B., et al., "Noninvasive Prenatal Aneuploidy Testing of Chromosomes 13, 18, 21, X, and Y, using Targeted Sequencing of Polymorphic Loci," Prenatal Diagnosis, Dec. 2012, vol. 32, No. 13, pp. 1233-1241, DOI: 10.1002/pd.3993, Epub Oct. 30, 2012.
Zimmermann B., "Noninvasive Prenatal Aneuploidy Testing of Chromosomes 13, 18, 21, X, and Y, using Targeted Sequencing of Polymorphic Loci, Supplemental Information," Prenatal Diagnosis, 2012, vol. 32, 7 Pages.

* cited by examiner

| Region | ID | 1 | 2 | 3 | 4 | 5 | 6 | 7 |
|---|---|---|---|---|---|---|---|---|
| 12:18959000-29050000 | 1 | **1.0000** | 0.0001 | 0.0058 | -0.0295 | 0.0374 | 0.0351 | -0.0037 |
| 16:60437000-89380000 | 2 | 0.0001 | **1.0000** | 0.0083 | 0.0227 | -0.0559 | -0.0241 | -0.0539 |
| 19:12042000-17796000 | 3 | 0.0058 | 0.0083 | **1.0000** | **0.1696** | **0.1402** | **0.0932** | 0.0407 |
| 19:28240000-33433000 | 4 | -0.0295 | 0.0227 | **0.1696** | **1.0000** | **0.3144** | **0.0765** | 0.0366 |
| 19:34341000-40857000 | 5 | 0.0374 | -0.0559 | **0.1402** | **0.3144** | **1.0000** | 0.0256 | 0.0676 |
| 22:42378000-49332000 | 6 | 0.0351 | -0.0241 | **0.0932** | **0.0765** | 0.0256 | **1.0000** | -0.0343 |
| 3:166356000-180256000 | 7 | -0.0037 | -0.0539 | 0.0407 | 0.0366 | **0.0676** | -0.0343 | 1.0000 |
| 8:617000-37343000 | 8 | 0.0278 | -0.0766 | 0.0134 | **0.0821** | **0.0797** | 0.0461 | -0.0074 |
| 8:115298000-145233000 | 9 | -0.0131 | -0.0066 | -0.0323 | -0.1370 | -0.1582 | -0.0688 | -0.0038 |
| 8:100758000-115298000 | 10 | -0.0339 | -0.0167 | -0.0145 | -0.0331 | -0.0847 | -0.0499 | 0.0019 |
| 20:1-26369569 | 11 | **0.0544** | -0.0275 | 0.0020 | -0.0079 | -0.0295 | -0.0446 | -0.0892 |
| 20:29369569-63025520 | 12 | **0.0790** | 0.0062 | **0.0732** | **0.0747** | -0.0435 | 0.0259 | **0.0530** |
| 17:25800001-31800000 | 13 | **0.0592** | 0.0199 | **0.0534** | **0.0518** | -0.0027 | 0.0115 | -0.0183 |
| 17:10700001-16000000 | 14 | **0.0829** | 0.0280 | -0.0124 | -0.0126 | -0.0633 | -0.0590 | 0.0049 |

FIG. 3A

| Region | I | 9 | 10 | 11 | 12 | 13 | 14 |
|---|---|---|---|---|---|---|---|
| 12:18959000-29050000 | 1 | -0.0131 | -0.0339 | **0.0544** | **0.0790** | **0.0592** | **0.0829** |
| 16:60437000-89380000 | 2 | 0.0066 | -0.0167 | -0.0275 | 0.0062 | 0.0199 | 0.0280 |
| 19:12042000-17796000 | 3 | -0.0323 | -0.0145 | 0.0020 | **0.0732** | **0.0534** | -0.0124 |
| 19:28240000-33433000 | 4 | -0.1370 | -0.0331 | -0.0079 | **0.0747** | **0.0518** | -0.0126 |
| 19:34341000-40857000 | 5 | -0.1582 | -0.0847 | -0.0295 | -0.0435 | -0.0027 | -0.0633 |
| 22:42378000-49332000 | 6 | -0.0688 | -0.0499 | -0.0446 | 0.0259 | 0.0115 | -0.0590 |
| 3:166356000-180256000 | 7 | -0.0038 | 0.0019 | -0.0892 | **0.0530** | -0.0183 | 0.0049 |
| 8:617000-37343000 | 8 | 0.0493 | -0.0221 | -0.0264 | 0.0304 | 0.0197 | 0.0091 |
| 8:115298000-145233000 | 9 | **1.0000** | **0.3285** | -0.0220 | 0.0271 | -0.0701 | -0.0733 |
| 8:100758000-115298000 | 10 | **0.3285** | **1.0000** | -0.0488 | 0.0481 | -0.0088 | -0.0487 |
| 20:1-26369569 | 11 | -0.0220 | -0.0488 | **1.0000** | -0.0156 | -0.0487 | 0.0117 |
| 20:29369569-63025520 | 12 | 0.0271 | 0.0481 | -0.0156 | **1.0000** | 0.0251 | **0.0513** |
| 17:25800001-31800000 | 13 | -0.0701 | -0.0088 | -0.0487 | 0.0251 | **1.0000** | 0.0396 |
| 17:10700001-16000000 | 14 | -0.0733 | -0.0487 | 0.0117 | **0.0513** | 0.0396 | **1.0000** |

FIG. 3B

| TCF | CN = 3 | CN = 4 | CN = 5 | CN = 6 |
|---|---|---|---|---|
| 1% | 0.50% | 0.99% | 1.48% | 1.96% |
| 2% | 0.99% | 1.96% | 2.91% | **3.85%** |
| 3% | 1.48% | 2.91% | **4.31%** | 5.66% |
| 5% | 2.44% | **4.76%** | 6.98% | **9.09%** |
| 7% | 3.38% | 6.54% | **9.50%** | 12.28% |
| 10% | **4.76%** | **9.09%** | 13.04% | 16.67% |
| 15% | 6.98% | 13.04% | 18.37% | 23.08% |
| 20% | **9.09%** | 16.67% | 23.08% | 28.57% |

FIG. 8

METHODS AND COMPOSITIONS FOR DETERMINING PLOIDY

CROSS-REFERENCE TO RELATED APPLICATIONS

This application is a continuation of U.S. application Ser. No. 17/845,169, filed on Jun. 21, 2022, which is a divisional of U.S. application Ser. No. 15/573,800, filed on Nov. 13, 2017 (now U.S. Pat. No. 11,479,812), which is a national phase filing under 35 U.S.C. of International Application of PCT/US2016/031686, filed on May 10, 2016, which claims the benefit of U.S. Provisional Application Ser. No. 62/159,958, filed May 11, 2015, which are hereby incorporated by reference in their entirety.

SEQUENCE LISTING

The instant application contains a Sequence Listing which has been submitted electronically in XML format and is hereby incorporated by reference in its entirety. Said XML copy, created on Feb. 14, 2024, is named NO15US03_Sequence_Listing.xml and is 4 kilobytes in size.

FIELD OF THE INVENTION

The disclosed invention relates generally to compositions and methods of genetic analysis for determining chromosomal ploidy.

BACKGROUND OF THE INVENTION

Copy number variation (CNV) has been identified as a major cause of structural variation in the genome, involving both duplications and deletions of sequences that typically range in length from 1,000 base pairs (1 kb) to 20 megabases (mb). Deletions and duplications of chromosome regions or entire chromosomes are associated with a variety of conditions, such as susceptibility or resistance to disease.

CNVs are often assigned to one of two main categories, based on the length of the affected sequence. The first category includes copy number polymorphisms (CNPs), which are common in the general population, occurring with an overall frequency of greater than 1%. CNPs are typically small (most are less than 10 kilobases in length), and they are often enriched for genes that encode proteins important in drug detoxification and immunity. A subset of these CNPs is highly variable with respect to copy number. As a result, different human chromosomes can have a wide range of copy numbers (e.g., 2, 3, 4, 5, etc.) for a particular set of genes. CNPs associated with immune response genes have recently been associated with susceptibility to complex genetic diseases, including psoriasis, Crohn's disease, and glomerulonephritis.

The second class of CNVs includes relatively rare variants that are much longer than CNPs, ranging in size from hundreds of thousands of base pairs to over 1 million base pairs in length. In some cases, these CNVs may have arisen during production of the sperm or egg that gave rise to a particular individual, or they may have been passed down for only a few generations within a family. These large and rare structural variants have been observed disproportionately in subjects with mental retardation, developmental delay, schizophrenia, and autism. Their appearance in such subjects has led to speculation that large and rare CNVs can be more important in neurocognitive diseases than other forms of inherited mutations, including single nucleotide substitutions.

Gene copy number can be altered in cancer cells. For instance, duplication of Chr1p is common in breast cancer, and the EGFR copy number can be higher than normal in non-small cell lung cancer. Cancer is one of the leading causes of death; thus, early diagnosis and treatment of cancer is important, since it can improve the patient's outcome (such as by increasing the probability of remission and the duration of remission). Early diagnosis can also allow the patient to undergo fewer or less drastic treatment alternatives. Many of the current treatments that destroy cancerous cells also affect normal cells, resulting in a variety of possible side-effects, such as nausea, vomiting, low blood cell counts, increased risk of infection, hair loss, and ulcers in mucous membranes. Thus, early detection of cancer is desirable since it can reduce the amount and/or number of treatments (such as chemotherapeutic agents or radiation) needed to eliminate the cancer.

Copy number variation has also been associated with severe mental and physical handicaps, and idiopathic learning disability. Non-invasive prenatal testing (NIPT) using cell-free DNA (cfDNA) can be used to detect abnormalities, such as fetal trisomies 13, 18, and 21, triploidy, and sex chromosome aneuploidies. Subchromosomal microdeletions, which can also result in severe mental and physical handicaps, are more challenging to detect due to their smaller size. Eight of the microdeletion syndromes have an aggregate incidence of more than 1 in 1000, making them nearly as common as fetal autosomal trisomies.

In addition, a higher copy number of CCL3L1 has been associated with lower susceptibility to HIV infection, and a low copy number of FCGR3B (the CD16 cell surface immunoglobulin receptor) can increase susceptibility to systemic lupus erythematosus and similar inflammatory autoimmune disorders.

Thus, improved methods are needed to detect deletions and duplications of chromosome regions or entire chromosomes. Preferably, these methods can be used to more accurately diagnose disease or an increased risk of disease, such as cancer or CNVs in a gestating fetus.

SUMMARY OF THE INVENTION

The invention provides improved methods, compositions, and kits for detecting ploidy of chromosome regions. In some aspects, the invention provides methods, compositions, and kits for detecting cancer or a chromosomal abnormality in a gestating fetus. The methods can utilize a set of SNPs that are found within haploblocks and can include analyzing a series of target chromosomal regions related to CNV in cancer or a chromosomal abnormality in a gestating fetus.

Accordingly, provided herein is a method for determining average allelic imbalance or ploidy (i.e. copy number) or for detecting copy number variation (CNV) or aneuploidy, of a chromosome or chromosomal region of interest (i.e. target chromosomal region) in a sample from an individual. The method can include the following steps:

a. making genotypic measurements for a plurality of polymorphic loci, such as a set of SNPs. The set of plurality of polymorphic loci can include at least 200, 250, 300, 400, 500, 1,000, 2,500, 5,000, or 10,000 loci (e.g. SNPs) on the chromosome or chromosome region of interest from a sample of blood, or a fraction thereof from the target individual, wherein at least 50, 60, 70, 75, 80, 90, 95, 96, 97, 97, 99, or 100% of the polymorphic loci of the plurality of polymorphic loci (or SNPs from the set of SNPs) have strong linkage disequilibrium with at least one other polymorphic loci of the plurality of polymorphic loci or SNP of the set of SNPs;

b. estimating the phase of the genotypic measurements; and c. determining on a computer, the likelihood of different ploidy states of the chromosome or chromosome region of interest by comparing the phased genotypic measurements to a set of joint distribution models of expected genotypic measurements for different ploidy states using identified chromosome crossover locations, thereby determining the ploidy state as the copy number of the chromosome or chromosome region with the highest likelihood. The determining can be performed by:

a. creating, on a computer, a set of ploidy state hypothesis where each ploidy state hypothesis is one possible ploidy state of the [target] chromosome or chromosome region of interest;

b. building a set of joint distribution models of expected genotypic measurements at the set of SNPs for each hypothesis given identified chromosome crossover locations;

c. determining, on the computer, the likelihood of each of the hypotheses given the estimated phase of the genotypic measurements and the joint distribution model.

The step of making genotypic measurements can be done by measuring genetic material using techniques selected from the group consisting of padlock probes, circularizing probes, genotyping microarrays, SNP genotyping assays, chip based microarrays, bead based microarrays, other SNP microarrays, other genotyping methods, Sanger DNA sequencing, pyrosequencing, high throughput sequencing, reversible dye terminator sequencing, sequencing by ligation, sequencing by hybridization, other methods of DNA sequencing, other high throughput genotyping platforms, fluorescent in situ hybridization (FISH), comparative genomic hybridization (CGH), array CGH, and multiples or combinations thereof. Genotypic measurements can be performed using high throughput sequencing or genotyping microarrays.

Also provided herein is a method for determining AAI or ploidy (i.e. copy number) or detecting copy number variation (CNV) or aneuploidy, of a chromosome or chromosomal region of interest (i.e. target chromosomal region) in a sample of an individual. The method includes the following steps:

a. measuring and/or receiving allele frequency data for each loci (e.g. SNP) of a plurality of polymorphic loci (e.g. set of SNPs) that includes at least 200, 250, 300, 400, 500, 1,000, 2,500, 5,000, or 10,000 loci (e.g. SNPs) on a plurality of segments within the chromosomal region, wherein each segment comprises loci with strong linkage disequilibrium (e.g. haploblocks), wherein the allele frequency data comprises the amount of each allele present in the sample at each loci;

b. estimating the phase of the allele frequency data taking into account an increased statistical correlation of polymorphic loci within the same segment;

c. generating individual likelihoods of allele frequencies for the polymorphic loci for different ploidy states using the allele frequency data;

d. generating joint likelihoods for the plurality of linked polymorphic loci using the individual likelihoods and the phased allele frequency data; and e. selecting, based on the joint likelihoods, a best fit model indicative of chromosomal copy number, thereby determining the copy number of the chromosome or chromosome region.

In the method for determining ploidy, set out above, at least 50, 60, 70, 75, 80, 90, 95, 96, 97, 97, 99, or 100% of the polymorphic loci of the plurality of polymorphic loci (or SNPs from the set of SNPs) can have strong linkage disequilibrium with at least one other loci (e.g. SNP) of the plurality of loci (e.g. set of SNPs). The method can detect CNV for example, by detecting an AAI above a sensitivity or cutoff value.

In the method for determining ploidy set out above, receiving allele frequency data can include receiving nucleic acid sequencing data for at least 200, 250, 300, 400, 500, 1,000, 2,500, 5,000, or 10,000 amplicons spanning each loci of the plurality of polymorphic loci and generating the allele frequency data from the sequencing data.

The method for determining ploidy set out above, can further include the following;

a. amplifying the plurality of polymorphic loci (e.g. set of SNPs) by an amplification method that includes the following:

i. forming a reaction mixture that includes circulating free nucleic acids derived from the sample, a polymerase and a pool of primers comprising at least 200, 250, 300, 400, 500, 1,000, 2,500, 5,000, or 10,000 primers or primer pairs that each specifically bind to a primer binding sequence located within an effective distance of one of the polymorphic loci; and ii. subjecting the reaction mixture to amplification conditions, thereby generating a plurality of amplicons; and subjecting each of the amplicons to a nucleic acid sequencing reaction to generate the nucleic acid sequencing data for the amplicons.

In addition to the above, methods of amplifying, reaction mixtures, and compositions comprising a set, pool, or plurality of primers or primer pairs are provided herein, that includes at least 200, 250, 500, 1000, or 2,500 primers or primer pairs, or between 100, 200, 250, 500, 1000, 2,500, 5,000, or 10,000 on the low end of the range, and 250, 500, 1000, 2,500, 5,000, or 10,000 on the high end of the range, that each specifically bind to a primer binding sequence located within one or more of a plurality of haploblocks, wherein each haploblock comprises at least 2, 3, 4, 5 or 10 of the primer binding sequences and wherein at least 50, 75, 90, 95, or 100% of the primer binding sequences are located within haploblocks.

A reaction mixture provided herein, can include:

a. a population of circulating free nucleic acids from an individual, or nucleic acid fragments derived therefrom, and b. a composition that includes at least 200, 250, 500, 1000, 2,500, 5,000, or 10,000 primers or primer pairs that each specifically bind to a primer binding sequence located within one or more of a plurality of haploblocks, wherein each haploblock comprises at least 2, 3, 4, 5 or 10 of the primer binding sequences and wherein at least 50, 75, 90, 95, or 100% of the primer binding sequences are located within haploblocks.

The primer binding sequences can be found within a chromosome region known to exhibit copy number variation (CNV) associated with a disorder or disease, such as cancer.

Further embodiments and aspects of the invention are provided in the detailed description section. It is understood that aspects and embodiments of the invention described herein include combinations of any two or more of the aspects or embodiments of the invention.

Definitions

Aneuploidy refers to the state where the wrong number of chromosomes (e.g., the wrong number of full chromosomes or the wrong number of chromosome regions, such as the presence of deletions or duplications of a chromosome region) is present in a cell. In the case of a somatic human cell it may refer to the case where a cell does not contain 22 pairs of autosomal chromosomes and one pair of sex chromosomes. In the case of a human gamete, it may refer to the case where a cell does not contain one of each of the 23 chromosomes. In the case of a single chromosome type, it may refer to the case where more or less than two homologous but non-identical chromosome copies are present, or where there are two chromosome copies present that originate from the same parent. In some embodiments, the deletion of a chromosome region is a microdeletion.

Allelic Data refers to a set of genotypic data for a set of one or more alleles. It may refer to the phased, haplotypic data. It may refer to SNP identities, and it may refer to the sequence data of the DNA, including insertions, deletions, repeats and mutations. It may include the parental origin of each allele.

Allele Count refers to the number of sequences that map to a particular locus, and if that locus is polymorphic, it refers to the number of sequences that map to each of the alleles thus providing allele frequency data. If each allele is counted in a binary fashion, then the allele count will be a whole number. If the alleles are counted probabilistically, then the allele count can be a fractional number.

Allelic Distribution, or "allele count distribution" refers to the relative amount of each allele that is present for each locus in a set of loci. An allelic distribution can refer to an individual, to a sample, or to a set of measurements made on a sample. In the context of digital allele measurements such as sequencing, the allelic distribution refers to the number or probable number of reads that map to a particular allele for each allele in a set of polymorphic loci. In the context of analog allele measurements such as SNP arrays, the allelic distribution refers to allele intensities and/or allele ratios. The allele measurements can be treated probabilistically, that is, the likelihood that a given allele is present for a give sequence read is a fraction between 0 and 1, or they can be treated in a binary fashion, that is, any given read is considered to be exactly zero or one copies of a particular allele.

Allelic imbalance for aneuploidy determinations, such as CNV determinations, refers to the difference between the frequencies of the alleles for a locus. It is an estimate of the difference in the copy of numbers of the homologs. Allelic imbalance can arise from the complete loss of an allele or from an increase in copy number of one allele relative to the other. Allelic imbalances can be detected by measuring the proportion of one allele relative to the other in cells from individuals that are constitutionally heterozygous at a given locus. (Mei et al, Genome Res, 2000). The proportion of abnormal DNA for a CNV can be measured by the average allelic imbalance (AAD, defined as $|(H1-H2)|/(H1+H2)$, where Hi is the average number of copies of homolog i in the sample and $Hi/(H1+H2)$ is the fractional abundance, or homolog ratio, of homolog i. The maximum homolog ratio is the homolog ratio of the more abundant homolog.

Haplotype refers to a combination of alleles at multiple loci that are typically inherited together on the same chromosome. Haplotype may refer to as few as two loci or to an entire chromosome depending on the number of recombination events that have occurred between a given set of loci.

Haplotype Data, also "Phased Data" or "Ordered Genetic Data," refers to data from a single chromosome or chromosome region in a diploid or polyploid genome, e.g., either the segregated maternal or paternal copy of a chromosome in a diploid genome.

Linkage Disequilibrium (LD) refers to the non-random association of alleles at two loci that can be measured by r2, |D|, |D'|. Two loci with high disequilibrium are said to be in "strong LD", or have "weak recombination". Haplotype blocks are sets of consecutive sites between which there is little or no evidence of historical recombination. Based on the default haplotype block definition (Gabriel et al, Science, 2002) a block is created by identifying a set of SNP loci on the same chromosome for which 95% of pairwise SNP comparisons between any 2 SNPs within that chromosome region have |D'|>95%. Therefore, for the purposes of the present disclosure, polymorphic loci (e.g. SNPs) are said to have strong linkage disequilibrium if 95% of pairwise SNP comparisons between any two SNPs within that chromosome/region have |D'| of >95%.

Phasing refers to the act of estimating the haplotypic genetic data of an individual. It may refer to the act of estimating which of the two alleles at a locus are associated with each of the two homologous chromosomes in an individual. "Perfect haplotyping" in discussions herein in the context of methods for analyzing a sample that includes ctDNA, is used to refer to molecular haplotyping through a supplementary tumor sample. Methods provided herein are especially well-suited for imperfectly phased data, especially data whose haplotype or phase has been estimated using an algorithm.

Phased Data refers to genetic data where one or more haplotypes have been estimated.

Copy Number Hypothesis, also "Ploidy State Hypothesis," refers to a hypothesis concerning the number of copies of a chromosome or chromosome region in an individual. It may also refer to a hypothesis concerning the identity of each of the chromosomes, including the parent of origin of each chromosome, and which of the parent's two chromosomes are present in the individual. It may also refer to a hypothesis concerning which chromosomes, or chromosome regions, if any, from a related individual correspond genetically to a given chromosome from an individual.

Primary Genetic Data refers to the analog intensity signals that are output by a genotyping platform. In the context of SNP arrays, primary genetic data refers to the intensity signals before any genotype calling has been done. In the context of sequencing, primary genetic data refers to the analog measurements, analogous to the chromatogram, that comes off the sequencer before the identity of any base pairs have been determined, and before the sequence has been mapped to the genome.

Secondary Genetic Data refers to processed genetic data that are output by a genotyping platform. In the context of a SNP array, the secondary genetic data refers to the allele calls made by software associated with the SNP array reader, wherein the software has made a call whether a given allele is present or not present in the sample. In the context of sequencing, the secondary genetic data refers to the base pair identities of the sequences have been determined, and possibly also where the sequences have been mapped to the genome.

Haploblocks or haplotype blocks refers to a segment of a chromosome that contains a set of consecutive loci between which there is little or no evidence of historical recombination. Based on the default haplotype block definition (Gabriel et al, Science, 2002) a block is created if 95% of pairwise SNP comparisons are "strong LD" using a 95% r2 cutoff. Publically available programs, such as plink (v1.90b3p 64-bit (10 Oct. 2014)), can be used to identify known or identified haploblocks for regions of interest based on this definition. It is noteworthy for considerations herein, that a series of consecutive SNPs that are amplified or deleted together are considered to be in the same haploblock, when haplotyping is done using a tumor sample.

Where ranges of values have been given in this disclosure, all intermediate values and end-points of the range form part of the disclosure.

Other features and advantages of the invention will be apparent from the following detailed description and from the claims.

BRIEF DESCRIPTION OF THE DRAWINGS

The present disclosure will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIGS. 3A-3B is a table of correlations of CNV events for 14 patients.

FIG. 4A PIK3CA, chromosome 3; FIG. 4B MYC, chromosome 8; FIG. 4C KRAS, chromosome 12; FIG. 4D RB1, chromosome 13, FIG. 4E CDH1, chromosome 16, FIG. 4F MAP2K4 and NF1, chromosome 17;

FIG. 4G AKT2, chromosome 19; and FIG. 4H, chromosome 20.

FIG. 8 provides a table of AAI as a function of TCF and tumor copy number, and detection limit of different technologies While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

Figure 1:
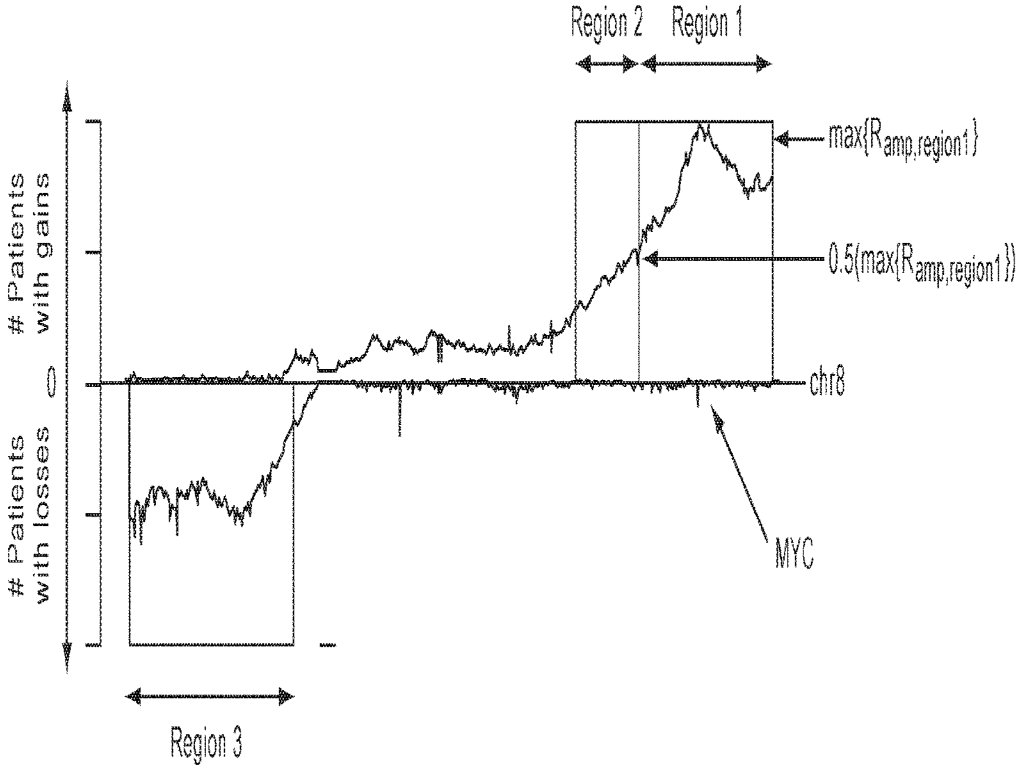
FIG. 1 is an example of CNV region identification. Illustrated is chromosome 8. The x-axis represents the genomic position on the chromosome. Both the x-axis range (0-250 Mb) and the y-axis range (0-453 patients) is consistent across plots.

The present invention provides, improved methods for determining the presence or absence of chromosomal aneuploidy such as copy number variations (CNVs), for example that result from deletions or duplications of chromosome regions or entire chromosomes. The present invention is especially well-suited for improving methods for detecting the presence or absence of CNV where haplotype information is estimated using analytical methods. According to the invention, by choosing polymorphic loci, and designing primers and assays for amplifying the same, that are within haplotype blocks, or haploblocks, informatics haplotyping can be improved. This can be especially beneficial when used as part of CNV detection methods, where the haploblocks are within chromosome regions known to exhibit CNV correlated with disease, such as cancer. Accordingly, for cfDNA samples by choosing polymorphic loci, and designing primers and assays for amplifying the same, additional sampling, such as from a buccal sample or from a tumor sample becomes unnecessary. It is noted that chromosomal regions that are deleted or duplicated in some diseases or disorders, such as cancer, can be referred to as chromosome segments. These chromosomal segments are typically made up of numerous segments of loci that share high linkage disequilibrium with neighboring loci.

The present invention generally relates to improved methods of determining the presence or absence of copy number variations, such as deletions or duplications of chromosome regions or entire chromosomes. The methods are particularly useful for detecting small deletions or duplications, which can be difficult to detect with high specificity and sensitivity using prior art methods due to the small amount of data available from the relevant chromosome region. The methods include improved analytical methods, improved bioassay methods, and combinations of improved analytical and bioassay methods. Methods of the invention are especially adapted to detect deletions or duplications that are only present in a small percentage of the cells or nucleic acid molecules that are tested. This allows deletions or duplications to be detected in circulating DNA fractions and/or prior to the occurrence of disease (such as at a precancerous stage) or in the early stages of disease, such as before a large number of diseased cells (such as cancer cells) with the deletion or duplication accumulate. The more accurate detection of deletions or duplications associated with a disease or disorder enable improved methods for diagnosing, prognosticating, preventing, delaying, stabilizing, or treating the disease or disorder. Several deletions or duplications are known to be associated with cancer or with severe mental or physical handicaps as well as with developmental disorders.

Successful treatment of a disease such as cancer often relies on early diagnosis, correct staging of the disease, selection of an effective therapeutic regimen, and close monitoring to prevent or detect relapse. For cancer diagnosis, histological evaluation of tumor material obtained from tissue biopsy is often considered the most reliable method. However, the invasive nature of biopsy-based sampling has rendered it impractical for mass screening and regular follow up. Furthermore, biopsies are limited to detecting mutations in the biopsy section sampled, not the entire tumor. Therefore, the present methods have the advantage of being able to be performed non-invasively if desired for relatively low cost with fast turnaround time. The targeted sequencing that can be used by the methods of the invention requires less reads than shotgun sequencing, such as a few million reads instead of 40 million reads, thereby decreasing cost. The multiplex PCR and next generation sequencing that can be used increase throughput and reduces costs.

The methods of the invention can be used to detect a deletion or duplication in an individual. A sample from the individual that contains cells or nucleic acids suspected of having a deletion or duplication can be analyzed. The sample can be from a tissue or organ suspected of having a deletion or duplication such as cells or a mass suspected of being cancerous. The methods of the invention can be used to detect deletion(s) or duplication(s) that are only present in one cell or a small number of cells in a mixture containing cells with the deletion(s) or duplication(s) and cells without the deletion(s) or duplication(s). In illustrative embodiments, cfDNA or cfRNA from a blood sample, or a fraction thereof, from the individual is analyzed according to methods provided herein. cfDNA or cfRNA can be secreted by cells, for example, cfDNA or cfRNA can be released by cells undergoing necrosis or apoptosis, such as cancer cells. The methods of the invention can be used to detect deletions or duplications that are only present in a small percentage of the cfDNA or cfRNA.

The methods can be used for non-invasive or invasive prenatal testing of a fetus by determining the presence or absence of deletions or duplications of a chromosome region or an entire chromosome, such as deletions or duplications known to be associated with severe mental or physical handicaps, learning disabilities, or cancer. For non-invasive prenatal testing (NIPT), cells, cfDNA or cfRNA from a blood sample, or a fraction thereof, from the pregnant mother can be tested. The methods allow the detection of a deletion or duplication in the cells, cfDNA, or cfRNA from the fetus despite the large amount of cells, cfDNA, or cfRNA from the mother that is also present. The Examples section herein, provides exemplary methods that focus on detecting CNV in cancer. However, a skilled artisan will understand that these methods as they relate to CNV in cancer, can be used for determining chromosomal ploidy in NIPT, where only imperfect haplotyping is performed, especially when haplotyping is not performed on a tumor sample. Chromosomes and chromosome regions that are duplicated or deleted in NIPT are known, and methods disclosed herein can be used to determine haploblocks, and design primers, primer pairs, and assays for determining alleles within polymorphic loci in those haploblocks.

In addition to determining the presence or absence of copy number variation, one or more other factors can be analyzed if desired. These factors can be used to increase the accuracy of the diagnosis (such a determining the presence or absence of cancer or an increased risk for cancer, classifying the cancer, or staging the cancer) or prognosis. These factors can also be used to select a particular therapy or treatment regimen that is likely to be effective in the subject. Exemplary factors include the presence or absence of polymorphisms or mutation; altered (increased or decreased) levels of total or particular cfDNA, cfRNA, microRNA (miRNA); altered (increased or decreased) tumor fraction; altered (increased or decreased) methylation levels, altered (increased or decreased) DNA integrity, altered (increased or decreased) or alternative mRNA splicing.

Methods for Determining Ploidy

The methods of the invention are based in part on the finding by the inventors that the ability to detect aneuploidy of a chromosome region(s) can be improved by selecting polymorphic loci within segments, called haploblocks or haplotype blocks, within the chromosome regions where neighboring SNPs demonstrate strong linkage disequilibrium. The improvements in AAI, copy number or ploidy determination and aneuploidy or CNV detection are especially pronounced when a pool of primers are selected for determining the allele frequency at a set of SNPs within a plurality of haploblocks within a target chromosome region, and the method includes a step where the phase of the allele frequency data within a chromosome region of interest is estimated to generate imperfect haplotype data that is used for the ploidy determination or aneuploidy detection.

Accordingly, provided herein is a method for AAI ploidy (i.e. copy number) or detecting copy number variation (CNV) or aneuploidy, of a chromosome or chromosomal region of interest (i.e. target chromosomal region) in a sample from an individual.

The method can include the following steps:

a. making genotypic measurements for a plurality of polymorphic loci, such as a set of SNPs. The set of plurality of polymorphic loci can include at least 200, 250, 300, 400, 500, 1,000, 2,500, 5,000, or 10,000 loci (e.g. SNPs) on the chromosome or chromosome region of interest from a sample of blood, or a fraction thereof from the target individual, wherein at least 50, 60, 70, 75, 80, 90, 95, 96, 97, 97, 99, or 100% of the polymorphic loci of the plurality of polymorphic loci (or SNPs from the set of SNPs) have strong linkage disequilibrium with at least one other polymorphic loci of the plurality of polymorphic loci or SNP of the set of SNPs;
b. estimating the phase of the genotypic measurements; and
c. determining on a computer, the likelihood of different ploidy states of the chromosome or chromosome region of interest by comparing the phased genotypic measurements to a set of joint distribution models of expected genotypic measurements for different ploidy states using identified chromosome crossover locations, thereby determining the ploidy state as the copy number of the chromosome or chromosome region with the highest likelihood.

The determining can be performed by:

a. creating, on a computer, a set of ploidy state hypothesis where each ploidy state hypothesis is one possible ploidy state of the [target] chromosome or chromosome region of interest;
b. building a set of joint distribution models of expected genotypic measurements at the set of SNPs for each hypothesis given identified chromosome crossover locations;
c. determining, on the computer, the likelihood of each of the hypotheses given the estimated phase of the genotypic measurements and the joint distribution model.

The step of making genotypic measurements can be done by measuring genetic material using techniques selected from the group consisting of padlock probes, circularizing probes, genotyping microarrays, SNP genotyping assays, chip based microarrays, bead based microarrays, other SNP microarrays, other genotyping methods, Sanger DNA sequencing, pyrosequencing, high throughput sequencing, reversible dye terminator sequencing, sequencing by ligation, sequencing by hybridization, other methods of DNA sequencing, other high throughput genotyping platforms, fluorescent in situ hybridization (FISH), comparative genomic hybridization (CGH), array CGH, and multiples or combinations thereof. Genotypic measurements can be performed using high throughput sequencing or genotyping microarrays.

, The step of measuring genetic material can be performed on genetic material that is amplified prior to being measured, using a technique that is selected from Polymerase Chain Reaction (PCR), ligand mediated PCR, degenerative oligonucleotide primer PCR, Multiple Displacement Amplification (MDA), allele-specific PCR, allele-specific amplification techniques, bridge amplification, padlock probes, circularizing probes, and combinations thereof. The amplification can be performed using multiplex PCR, including PCR using the sets of primers the pools, sets, pluralities, or libraries of primers set out herein.

Also provided herein is a method for determining AAI, ploidy (i.e. copy number) or detecting copy number variation (CNV) or aneuploidy, of a chromosome or chromosomal region of interest (i.e. target chromosomal region) in a sample of an individual. The method includes the following steps:

a. measuring and/or receiving allele frequency data for each loci (e.g. SNP) of a plurality of polymorphic loci (e.g. set of SNPs) that includes at least 200, 250, 300, 400, 500, 1,000, 2,500, 5,000, or 10,000 loci (e.g. SNPs) on a plurality of segments within the chromosomal region, wherein each segment comprises loci with strong linkage disequilibrium (e.g. haploblocks), wherein the allele frequency data comprises the amount of each allele present in the sample at each loci;
b. estimating the phase of the allele frequency data taking into account an increased statistical correlation of polymorphic loci within the same segment;
c. generating individual likelihoods of allele frequencies for the polymorphic loci for different ploidy states using the allele frequency data;
d. generating joint likelihoods for the plurality of linked polymorphic loci using the individual likelihoods and the phased allele frequency data; and
e. selecting, based on the joint likelihoods, a best fit model indicative of chromosomal copy number, thereby determining the copy number of the chromosome or chromosome region.

In the method for determining ploidy, set out above, at least 50, 60, 70, 75, 80, 90, 95, 96, 97, 97, 99, or 100% of the polymorphic loci of the plurality of polymorphic loci (or SNPs from the set of SNPs) can have strong linkage disequilibrium with at least one other loci (e.g. SNP) of the plurality of loci (e.g. set of SNPs).

In the method for determining ploidy set out above, receiving allele frequency data can include receiving nucleic acid sequencing data for at least 200, 250, 300, 400, 500, 1,000, 2,500, 5,000, or 10,000 amplicons spanning each loci of the plurality of polymorphic loci and generating the allele frequency data from the sequencing data.

The method for determining ploidy set out above, can further include the following;

a. amplifying the plurality of polymorphic loci (e.g. set of SNPs) by an amplification method that includes the following:
    i. forming a reaction mixture that includes circulating free nucleic acids derived from the sample, a polymerase and a pool of primers comprising at least 200, 250, 300, 400, 500, 1,000, 2,500, 5,000, or 10,000 primers or primer pairs that each specifically bind to a primer binding sequence located within an effective distance of one of the polymorphic loci; and
    ii. subjecting the reaction mixture to amplification conditions, thereby generating a plurality of amplicons; and
b. subjecting each of the amplicons to a nucleic acid sequencing reaction to generate the nucleic acid sequencing data for the amplicons.

For any of the quantitative, allelic methods provided herein, a confidence may be computed for the copy number determination. In combination with any 1 or more of the illustrative optional additional steps set out herein in this paragraph, or as a separate example, the method can further include obtaining prior likelihoods of each hypothesis from population data, and computing the confidence using Bayes Rule. In combination with any 1 or more of the illustrative embodiments set out herein in this paragraph, or as a separate example, the method can further include calculating a platform response to statistically correct for bias and/or increase the accuracy of the genotypic measurements, wherein the platform response is a mathematical characterization of the input/output characteristics of a genetic measurement platform. In combination with any 1 or more of the illustrative embodiments set out herein in this paragraph, or as a separate example, an average allelic imbalance can calculated and wherein the copy number determination is indicative of a copy number variation if the average allelic imbalance is equal to or greater than a cutoff value, which can be a sensitivity for an assay method, such as an AAI of 0.45%. In combination with any 1 or more of the illustrative embodiments set out herein in this paragraph, or as a separate example, a likelihood for each ploidy state can be determined based on a beta binomial distribution of expected and observed genetic or allelic frequency data at the plurality of SNP loci. In combination with any 1 or more of the illustrative embodiments set out herein in this paragraph, or as a separate example, the determining can include determining the ploidy state with the highest likelihood based on Bayesian estimation, as an indication of the number of copies of the chromosome or chromosome region of interest. In combination with any 1 or more of the illustrative embodiments set out herein in this paragraph, or as a separate example, the sample is the only sample whose phase is estimated for the individual. Thus, in these illustrative embodiments, for example wherein the subject is suspected of having cancer, the phase of genetic material in a tumor sample is not estimated. In these illustrative embodiments, for example wherein the subject is a pregnant mother, the phase of a genetic material from another sample from the mother besides a plasma sample, is not estimated.

Methods provided herein can include analysis of at least 2, 3, 4, 5, 10, 15, 20, 25, 50, 100, 200, 250, 300, 350, 400, 500, 600, 700, 750, 800, 900, 1000, 1250, 1500, 1750, 2000 polymorphic loci, such as SNPs, on the low end of the range, and 50, 100, 200, 250, 300, 350, 400, 500, 600, 700, 750, 800, 900, 1000, 1250, 1500, 1750, 2000, 2500, 5000, or 10,000 polymorphic loci, such as SNPs, on the high end of the range located within a plurality of haploblocks on a target chromosome region, each haploblock having between 2, 3, 4, 5, 6, 7, 8, 9, 10, 20, 25, or 50 SNP loci on the low end of the range, and 5, 6, 7, 8, 9, 10, 20, 25, 50 75, 100, 150, 200, or 250 SNP loci on the high end of the range. Furthermore, a plurality of haploblocks on the same chromosome region analyzed in such methods can include, for example, between 2, 3, 4, 5, 6, 7, 8, 9, or 10 haploblocks per target chromosome or chromosome region on the low end of the range, and 5, 6, 7, 8, 9, 10, 20, 25, 50 75, 100, 150, 200, or 250 haploblocks per chromosome or chromosome region on the high end of the range. A skilled artisan will understand that the size of the chromosome region will influence the number of haploblocks and SNPs within haploblocks, for that chromosome region. This is illustrated in the Examples herein, where the target chromosomal regions that were identified for lung cancer were small than those identified for ovarian cancer. Thus, less SNPs per chromosome region that occur within haploblocks of, for example at least 5 loci, were identified in the lung cancer regions than the ovarian cancer regions analyzed. This improvement in ancuploidy detection is especially valuable for samples in which only a small percentage of the nucleic acids in the sample exhibit aneuploidy, such as a plasma sample with circulating fetal or tumor DNA. The power of the analysis is further apparent when considering that aneuploidy occurs in fetal disorders and many cancers, such as ovarian or lung cancer, in targeted regions of the genome.

Accordingly, in certain embodiments, target segments are identified by identifying segments that include polymorphic loci with strong linkage disequilibrium using a 70, 75, 80, 85, 90, 95 or 99% |D'| cutoff where 75, 80, 90, 95, or 99% of pairwise SNP comparisons show a strong linkage disequilibrium. In illustrative embodiments, the segments are haploblocks (i.e. 95% of pairwise SNP comparisons are "strong LD" using a |D'|>95% cutoff). SNPs with minor allele frequency of less than 5.0, 10.0, 15.0 and 20.0% can be ignored in illustrative examples of the method. Haploblocks can include blocks of at least 2, 3, 4, 5, 6, 7, 8, 9, 10, 11, 12, 13, 14, 15, 20, 25, 30, 35, 40, 45, 50, 60, 70, 75, 80, 90, 100, 200, 250, 500, or 1000 neighboring SNPs that show a strong linkage disequilibrium.

Programs are known in the art for estimating haploblocks. For example, the program called plink (available on the Internet at pngu.mgh.harvard.edu) can be used to estimate haploblocks, as illustrated in the Examples section herein. The program estimates haploblocks for a given set of SNPs based on a given reference panel. Other programs are publicly available for estimating haploblocks, in addition to plink include LDHat (available on the Internet at ldhat.sourceforge.net/), Haploview (available on the Internet at www.broadinstitute.org/scientific-community/science/programs/medical-and-population-genetics/haploview/haploview), LdCompare (available on the Internet at www.affymetrix.com/support/developer/tools/devnettools.affx), TASSEL (available on the Internet at www.maizegenetics.net/?Itemid=119&id=89&option=com_content&task=view), and rAggr (available on the Internet at raggr.usc.edu).

This disclosure provides guidelines for assay design parameters for detecting polymorphic loci. For example, proper assay designs in illustrative examples are based on selecting non-interactive assays within chromosomal regions that show a high percentage of aneuploidy covering at least 50% of the chromosomal region. Furthermore, for cancer detection, recurrence profiles can be analyzed, such as that shown in FIG. 1. Finally, chromosomal regions that exhibit a minor allele frequency of 10-50% can be chosen. Guidelines for identifying amplicons and amplification parameters are provided herein. For example, in one embodiment amplicons can be identified that include SNPs, with lengths between 50 and 75 bp, with a Tm of between 53-59C with a GC content of 30-70 and with MAF of 10-50%.

Data generated by a method of the invention, for example a method for determining ploidy and/or detecting aneuploidy, that takes into account an increased probability of linkage for loci found in haploblocks located within a chromosome region, can be combined with any analytical method that uses imperfectly haplotyped allele data at polymorphic loci to determine ploidy to improve the accuracy and sensitivity of such ploidy analysis.

Accuracy can be increased by taking into account the linkage between SNPs, and the likelihood of crossovers having occurred during the meiosis that gave rise to the gametes that formed the embryo that grew into the fetus. Using linkage when creating the expected distribution of allele measurements for one or more hypotheses allows the creation of expected allele measurements distributions that correspond to reality considerably better than when linkage is not used. For example, imagine that there are two SNPs, 1 and 2 located nearby one another, and the mother is A at SNP 1 and A at SNP 2 on one homolog, and B at SNP 1 and B at SNP 2 on homolog two. If the father is A for both SNPs on both homologs, and a B is measured for the fetus SNP 1, this indicates that homolog two has been inherited by the fetus, and therefore that there is a much higher likelihood of a B being present in the fetus at SNP 2. A model that takes into account linkage can predict this, while a model that does not take linkage into account cannot. Alternately, if a mother is AB at SNP 1 and AB at nearby SNP 2, then two hypotheses corresponding to maternal trisomy at that location can be used-one involving a matching copy error (nondisjunction in meiosis II or mitosis in early fetal development), and one involving an unmatching copy error (nondisjunction in meiosis D. In the case of a matching copy error trisomy, if the fetus inherited an AA from the mother at SNP 1, then the fetus is much more likely to inherit either an AA or BB from the mother at SNP 2, but not AB. In the case of an unmatching copy error, the fetus inherits an AB from the mother at both SNPs. The allele distribution hypotheses made by a CNV calling method that takes into account linkage can make these predictions, and therefore correspond to the actual allele measurements to a considerably greater extent than a CNV calling method that does not take into account linkage. These predictions can be further improved by taking advantage of the increased statistical association for SNPs within haploblocks, by choosing SNP loci to analyze, that are within haploblocks.

Samples

In some embodiments of any of the aspects of the invention, the sample includes cellular and/or extracellular genetic material from cells suspected of having a deletion or duplication, such as cells suspected of being cancerous. In some embodiments, the sample comprises any tissue or bodily fluid suspected of containing cells, DNA, or RNA having a deletion or duplication, such as cancer cells, DNA, or RNA. The genetic measurements used as part of these methods can be made on any sample comprising DNA or RNA, for example but not limited to, tissue, blood, serum, plasma, urine, hair, tears, saliva, skin, fingernails, feces, bile, lymph, cervical mucus, semen, or other cells or materials comprising nucleic acids. Samples may include any cell type or DNA or RNA from any cell type can be used (such as cells from any organ or tissue suspected of being cancerous, or neurons). In some embodiments, the sample includes nuclear and/or mitochondrial DNA. In some embodiments, the sample is from any of the target individuals disclosed herein. In some embodiments, the target individual is a born individual, a gestating fetus, a non-gestating fetus such as a products of conception sample, an embryo, or any other individual.

Exemplary samples include those containing cfDNA or cfRNA. In some embodiments, cfDNA is available for analysis without requiring the step of lysing cells. Cell-free DNA can be obtained from a variety of tissues, such as tissues that are in liquid form, e.g., blood, plasma, lymph, ascites fluid, or cerebral spinal fluid. In some cases, cfDNA is comprised of DNA derived from fetal cells. In some cases, cfDNA is comprised of DNA derived from both fetal and maternal cells. In some cases, the cfDNA is isolated from plasma that has been isolated from whole blood that has been centrifuged to remove cellular material. The cfDNA can be a mixture of DNA derived from target cells (such as cancer cells) and non-target cells (such as non-cancer cells).

The sample can contain or can be suspected of containing a mixture of DNA (or RNA), such as mixture of cancer DNA (or RNA) and noncancerous DNA (or RNA). At least 0.5, 1, 3, 5, 7, 10, 15, 20, or 25% of the cells in the sample can be cancer cells. In other examples, at least 0.5, 1, 3, 5, 7, 10, 15, 20, or 25% of the DNA (such as cfDNA) or RNA (such as cfRNA) in the sample can be from cancer cell(s).

As indicated above, a sample analyzed in methods of the present invention, in certain illustrative embodiments, is a blood sample, or a fraction thereof. Methods and compositions provided herein, in certain embodiments, are specially adapted for amplifying DNA fragments, especially tumor DNA fragments that are found in circulating tumor DNA (ctDNA). Such fragments are typically about 160 nucleotides in length.

It is known in the art that cell-free nucleic acid (cfNA), e.g cfDNA, can be released into the circulation via various forms of cell death such as apoptosis, necrosis, autophagy and necroptosis. The cfDNA, is fragmented and the size distribution of the fragments varies from 150-350 bp to >10000 bp. (see Kalnina et al. *World J Gastroenterol.* 2015 Nov. 7; 21(41): 11636-11653). For example the size distributions of plasma DNA fragments in hepatocellular carcinoma (HCC) patients spanned a range of 100-220 bp in length with a peak in count frequency at about 166 bp and the highest tumor DNA concentration in fragments of 150-180 bp in length (see: Jiang et al. *Proc Natl Acad Sci* USA 112:E1317-E1325).

In an illustrative embodiment the circulating tumor DNA (ctDNA) is isolated from blood using EDTA-2Na tube after removal of cellular debris and platelets by centrifugation. The plasma samples can be stored at −80° C. until the DNA is extracted using, for example, QIAamp DNA Mini Kit (Qiagen, Hilden, Germany), (e.g. Hamakawa et al., *Br J Cancer.* 2015; 112:352-356). Hamakava et al. reported median concentration of extracted cell free DNA of all samples 43.1 ng per ml plasma (range 9.5-1338 ng ml/) and a mutant fraction range of 0.001-77.8%, with a median of 0.90%.

Methods provided herein are especially effective for samples where the copy number variation is present in a small percentage of nucleic acids that are from, or are derived from the same chromosomal region exhibiting the copy number variation. That is, samples where the copy number variation (CNV) is present for less than 20, 15, or 10% of the nucleic acids in the sample that are derived from the chromosomal region with the CNV. For example, ctDNA present in less than 20%, 15%, 10% or 5%, 4%, or 3% of a cfDNA sample, are illustrative embodiments. In other embodiments, ctDNA is present in between 0.5% or 1% of a cfDNA sample on the low end of the range and 20%, 15%, 10% or 5%, 4%, or 3% of a cfDNA sample on the high end of the range. In other illustrative embodiments, the sample has an average allelic imbalance of 20% or less, 15% or less, or 10% or less, or an average allelic imbalance of 0.45%, 0.5%, 1%, 2%, 3% or 4% on the low end of the range, and 4%, 5%, 10%, 12.5%, 15%, or 20% on the high end of the range.

In certain illustrative embodiments the sample is a tumor. Methods are known in the art for isolating nucleic acid from a tumor and for creating a nucleic acid library from such a DNA sample given the teachings here. Furthermore, given the teachings herein, a skilled artisan will recognize how to create a nucleic acid library appropriate for the methods herein from other samples such as other liquid samples where the DNA is free floating in addition to ctDNA samples.

Sample Preparation

Methods of the present invention in certain embodiments, typically include a step of generating and amplifying a nucleic acid library from the sample (i.e. library preparation). The nucleic acids from the sample during the library preparation step can have ligation adapters, often referred to as library tags or ligation adaptor tags (LTs), appended, where the ligation adapters contain a universal priming sequence, followed by a universal amplification. In an embodiment, this can be done using a standard protocol designed to create sequencing libraries after fragmentation. In an embodiment, the DNA sample can be blunt ended, and then an A can be added at the 3' end. A Y-adaptor with a T-overhang can be added and ligated. In some embodiments, other sticky ends can be used other than an A or T overhang. In some embodiments, other adaptors can be added, for example looped ligation adaptors.

Primer tails can improve the detection of fragmented DNA from universally tagged libraries. If the library tag and the primer-tails contain a homologous sequence, hybridization can be improved (for example, melting temperature ($T_m$) is lowered) and primers can be extended if only a portion of the primer target sequence is in the sample DNA fragment. In some embodiments, 13 or more target specific base pairs can be used. In some embodiments, 10 to 12 target specific base pairs can be used. In some embodiments, 8 to 9 target specific base pairs can be used. In some embodiments, 6 to 7 target specific base pairs can be used.

In one embodiment, libraries are generated from the samples above by ligating adaptors to the ends of DNA fragments in the samples, or to the ends of DNA fragments generated from DNA isolated from the samples. The adaptors in certain embodiments, include regions that are specifically designed to bind to downstream primers used in a sequencing workflow, especially a next generation sequencing workflow, and/or include regions that can be used for universal clonal amplification. The fragments can then be amplified using PCR, using standard conditions and protocols, including, for example, the following non-limiting exemplary protocol: 95° C., 2 min; 15×[95° C., 20 sec, 55° C., 20 sec, 68° C., 20 sec], 68° C. 2 min, 4° C. hold.

Many kits and methods are known in the art for generation of libraries of nucleic acids that include universal primer binding sites for subsequent amplification, for example clonal amplification, and for subsequence sequencing. To help facilitate ligation of adapters library preparation and amplification can include end repair and adenylation (i.e. A-tailing). Kits especially adapted for preparing libraries from small nucleic acid fragments, especially circulating free DNA, can be useful for practicing methods provided herein. For example, the NEXTflex Cell Free kits available from Bioo Scientific or the Natera Library Prep Kit (available from Natera, Inc. San Carlos, CA). However, such kits would typically be modified to include adaptors that are customized for the amplification and sequencing steps of the methods provided herein. Adaptor ligation can be performed using commercially available kits such as the ligation kit found in the AGILENT SURESELECT kit (Agilent, CA).

Reaction Mixtures of the Present Invention

A number of the embodiments provided herein, including, for example, methods for determining ploidy and/or detecting copy number variations in a ctDNA sample, include a step of receiving sequencing data for amplicons spanning each loci of a plurality or set of polymorphic loci. Such methods in illustrative embodiments, can further include an amplification step and/or a sequencing step (Sometimes referred to herein as a "ctDNA amplification/sequencing workflow) whose output is received according to a method of certain embodiments of the invention. In an illustrative example, a ctDNA amplification/sequencing workflow can include generating a set of amplicons by performing a multiplex amplification reaction on nucleic acids isolated from a sample of blood or a fraction thereof from an individual, such as an individual suspected of having a cancer, for example a lung cancer or an ovarian cancer, wherein each amplicon of the set of amplicons spans at least one polymorphic loci of a plurality or set of polymorphic loci, such as a SNP loci, known to be associated with cancer. The sequence of at least a portion of each amplicon of the plurality or set of amplicons can then be determined, wherein the portion includes a polymorphic loci.

Methods of the present invention, in certain embodiments, include forming an amplification reaction mixture. An amplification reaction mixture useful for the present invention includes some components known in the art for nucleic acid amplification, especially for PCR amplification. For example, the reaction mixture typically includes nucleotide triphosphates, a polymerase, magnesium, and primers, and optionally one or more template nucleic acids. The reaction mixture in certain embodiments, is formed by combining a polymerase, nucleotide triphosphates, nucleic acid fragments from a nucleic acid library generated from the sample, and a set of forward and/or reverse primers of the present invention.

The reaction mixtures provided herein are themselves illustrative embodiments of the invention. Furthermore, such reaction mixtures are used in numerous method embodiments provided herein, such as a method of determining copy number (i.e. ploidy) or detecting aneuoploidy or CNV, or methods for amplifying. Accordingly, in certain embodiments, provided herein is a reaction mixture that includes a population of circulating free nucleic acids from an individual, or nucleic acid fragments derived therefrom, and a pool of primers according to the present invention, at least some of which bind nucleic acids within the population of circulating free nucleic acids. The reaction mixture can include other components for an amplification reaction such as, but not limited to, a polymerase, nucleotide triphosphates, magnesium, and nucleic acid fragments from a nucleic acid library generated from the sample. The nucleic acid fragments can include adapter sequences, for example, for binding primers for sequencing reactions and/or universal amplification reactions, as discussed in more detail herein.

A composition that includes a set, plurality, library, or pool of primers or primer pairs is one embodiment of the present invention. Furthermore, such a composition can be part of numerous methods and other compositions provided herein. These methods include a step of amplifying nucleic acids from a sample, or for compositions, such compositions can be a reaction mixture. For any of these embodiments, the set, library, plurality or pool of primers or primer pairs can include between 25, 50, 100, 200, 250, 300, 400, 500, or 1000 primers or primer pairs on the low end of the range, and 100, 200, 250, 300, 400, 500, 1000, 1500, 2000, 2500, 5000, 10,000, or 25,000 primers or primer pairs on the high end of the range, that are each designed to amplify one or more polymorphic loci within a haploblock within a chromosomal region. For example, in one non-limiting embodiment, a set, library, plurality or pool of primers includes between 1000 and 10,000 primers of the invention each for amplifying an amplicon within a haploblock from a target chromosomal region that includes one or more polymorphic loci. Each primer of the set, plurality, or pool of primers binds an effective distance from one or more polymorphic loci, such as SNP loci, or a plurality of primer pairs in the set, library, plurality, or pool of primers, each define an amplicon that spans one or more polymorphic loci, such as a SNP loci.

The polymorphic loci, can be within genes known to be associated with cancer and are located within a haploblock. The haploblock can include 2, 3, 4, 5, 10, 20, 24, 50, 75, or 100 polymorphic loci on the low end and 4, 5, 10, 20, 24, 50, 75, 100, 150, 200 or 250 polymorphic loci on the high end of the range. One or more pools of primers of the invention can form a set of primer pools of the invention, which can include 1, 2, 3, 4, 5, 6, 7, 8, 9, 10, 15, 20, or 25 pools of primers of the invention on the low end of the range, and 2, 3, 4, 5, 6, 7, 8, 9, 10, 15, 20, 25, 50, or 100 pools of primers of the invention on the high end of the range, that are used to form a set of reaction mixtures that can include identical amplification components except for the pool of primers. For example, a set of primers can include between 10 and 100 primers or pairs of primers per haploblock, wherein the set of primers includes 1000 to 50,000 primers.

In certain embodiments, a composition according to the present invention, includes a set, library, plurality, or pool of primers, that includes 25, 50, 100, 200, 250, 300, 400, 500, 1,000, 2,500, 5,000, or 10,000 primers or primer pairs on the low end of the range, and 200, 250, 300, 400, 500, 1,000, 2,500, 5,000, 10,000, 20,000, 25,000, 50,000, or 100,000 primers or primer pairs on the high end of the range, that each specifically bind to a primer binding sequence located within one or more of a plurality of haploblocks found within a chromosome region known to exhibit copy number variation (CNV) associated with a disorder or disease, wherein each haploblock comprises at least 2 of the primer binding sequences and wherein at least 75, 80, 85, 90, 95, 96, 97, 98, 99%, or all of the primer binding sequences are located within haploblocks.

In certain embodiments, provided herein are methods for amplifying a set of target nucleic acids within a chromosome or chromosome region of interest (i.e. target chromosome or chromosome region of interest) of an individual. The method, in these embodiments, includes the following:

a. forming a reaction mixture that includes circulating free nucleic acids derived from a sample of blood or a fragment thereof of the individual, a polymerase and a pool of primers that includes at least 500 primers or primer pairs (or any of the primer pool examples set out above) wherein at least 50, 60, 70, 75, 80, 90, 95, 96, 97, 98, 99, or 100% of the primers or primer pairs in the reaction mixture specifically bind to a primer binding sequence located within one or more of a plurality of haploblocks found within the chromosome region, wherein the chromosome region is known to exhibit copy number variation (CNV) associated with a disorder or disease; and
b. subjecting the reaction mixture to amplification conditions, thereby amplifying the set of target nucleic acids.

In certain examples of this embodiment, each haploblock includes at least 2, 3, 4, 5, 10, 15, 20, or 25 loci that have strong linkage disequilibrium with at least 1, 2, 3, 4, 5, 10, 15, 20, or 25 other loci of the plurality of loci.

In certain embodiments of the method for amplifying provide herein, the primer or primer pairs are designed to amplify each loci of a plurality of polymorphic (e.g. SNP) loci fthat have a strong linkage disequilibrium with at least one other polymorphic loc, within one or more of a plurality of haploblocks (such as haploblocks identified based on linkage disequilibrium data from population data using publically available analysis tools (e.g. plink). In certain examples of the method for amplifying, at least 50, 60, 70, 75, 80, 90, 95, 96, 97, 98, 99, or 100% of the loci of the plurality of loci are found within the same haploblock as at least 1, 2, 3, 4, 5, 10, 15, 20, 25 other loci of the plurality of loci. In other examples, at least 50, 60, 70, 75, 80, 90, 95, 96, 97, 98, 99, or 100% of the loci of the plurality of loci have strong linkage disequilibrium with at least 1, 2, 3, 4, 5, 10, 15, 20, 25 other loci of the plurality of loci.

The size of a target chromosome region can affect the number of polymorphic loci and haploblocks selected for analysis. As illustrated in the Examples herein, for ovarian cancer using target chromosome regions greater than 50 Mb, in illustrative embodiments, haploblocks with at least 10 polymorphic loci (e.g. 10, 15, 20, or 25 polymorphic loci on the low end of the range and 15, 20, 25, 50, 100, 150, 200, 250, or 500 polymorphic loci on the high end of the range), and at least 500 or 1000 target polymorphic loci per chromosomal region and up to 1500, 2000, 2500, 5000, or 10,000 target polymorphic loci per chromosomal region, can be selected. These ranges are for finally selected polymorphic loci, which is a fraction of those available for analysis, as illustrated in the Examples herein. On the other hand, for focal chromosome regions (i.e. less than 50 Mb), minimum requirements can be relaxed. For example, for target chromosome regions that are less than 50 Mb, haploblocks with at least 2, 3, 4, or 5 polymorphic loci (e.g. 2, 3, 4, or 5 polymorphic loci on the low end of the range and 10, 15, 20, 25, 50, 100, 150, 200, or 250 on the high end of the range) and at least 100, 200, 250, 300, 400, or 500 total polymorphic loci per focused chromosome region, can be targeted. In some embodiments, depending on total number of SNPs desired for a chromosomal region, SNPs within haploblocks can be chosen starting from SNPs within the largest haploblocks. Haploblock minimum size can be determined when a minimum number of SNPs for the analysis is reached. Additional requirements or preferences for primers, loci, and amplicons can be relaxed as well, as will be apparent based on the large differences in size between large chromosome arm-level CNV in Example 1 and the focused chromosomal regions of Example 5 by comparing Example 1 and Example 5.

Exemplary primer design rules and primer selection methods are provided in Examples 1 and 5 herein. Primer designs can be generated with Primer3 (Untergrasser A, Cutcutache I, Koressaar T, Ye J, Faircloth B C, Remm M, Rozen S G (2012) "Primer3—new capabilities and interfaces." Nucleic Acids Research 40(15):e115 and Koressaar T, Remm M (2007) "Enhancements and modifications of primer design program Primer3." Bioinformatics 23(10): 1289-91) source code available at primer3.sourceforge.net). For example, primers can be designed using primer3 release 2.3.6 (Whitehead Institute for Biomedical Research, Steve Rozen (available on the Internet at primer3.sourceforge.net/releases.php) and then filtered in a reiterative fashion to check primer specificity. For each candidate SNP primer3 can be used to design left and right primers (two-sided) with an amplicon length within a range (as provided elsewhere herein, e.g. 25 to 150, 25 to 125, 25 to 100, or 50 to 75 bp) and a target melting temperature range and target temperature, for example between 50-65° C. or 53-60° C. A skilled artisan will understand that target Tm ranges can be changed depending on specific amplification temperatures (e.g. annealing temperature). Primer3 can be configured to use the SantaLucia salt correction and melting temperature formulae (SantaLucia JR (1998) "A unified view of polymer, dumbbell and oligonucleotide DNA nearest-neighbor thermodynamics", *Proc Natl Acad Sci* 95:1460-65).

Primer specificities can be determined using the BLASTn program from the ncbi-blast-2.2.29+ package. The task option "blastn-short" can be used to map the primers against hg19 human genome. Primer designs can be determined as "specific" if the primer has less than 100 hits to the genome and the top hit is the target complementary primer binding region of the genome and is at least two scores higher than other hits (score is defined by BLASTn program). This can be done in order to have a unique hit to the genome and to not have many other hits throughout the genome.

The final selected primers can be visualized in IGV (James T. Robinson, Helga Thorvaldsdottir, Wendy Winckler, Mitchell Guttman, Eric S. Lander, Gad Getz, Jill P. Mesirov. Integrative Genomics Viewer. Nature Biotechnology 29, 24-26 (2011)) and UCSC browser (Kent W J, Sugnet C W, Furey T S, Roskin K M, Pringle T H, Zahler A M, Haussler D. The human genome browser at UCSC. Genome Res. 2002 June; 12(6):996-1006) using bed files and coverage maps for validation.

Accordingly, in one embodiment, provided herein is a method for selecting a plurality or set of primers for determining ploidy of a chromosomal region in a sample of an individual, or a method for selecting a primer pool for determining ploidy of a chromosomal region in a sample of an individual, or a method for selecting a plurality or set of amplicons for determining ploidy of a chromosomal region in a sample of an individual, wherein any of these methods can includes the following:

- a. identifying target chromosomal regions, wherein the target chromosomal regions are known to exhibit ancuploidy associated with a disease or disorder;
- b. identifying target polymorphic loci within the target chromosomal regions;
- c. identifying candidate primers for amplifying the target polymorphic loci;
- d. filtering the candidate primers such that at least a minimum percent (e.g. 90%) of the candidate primers, and in illustrative embodiments 100% of the candidate primers bind to target loci within one of a plurality of known haploblocks; and
- e. selecting compatible primers from the candidate primers, thereby selecting the primer pool for determining ploidy.

Such methods are exemplified in Example 1 and Example 5 herein where the target disease or disorder is cancer, and in particular ovarian cancer (Example 1) and lung cancer (Example 5). Illustrative teachings for all of these steps are found in these examples. Details provided herein for the above steps, provide embodiments that can be used in any of the methods, compositions, or kits provided herein since such methods can be part of any of the methods herein, such as part of a method of determining ploidy or detecting aneuploidy, in certain embodiments.

Details regarding identifying target chromosomal regions are provided in a separate section herein. Polymorphic loci are identified, by identifying polymorphic loci (exemplified by SNPs), that are found in, and preferably are found throughout specific genes known to exhibit CNV in a disease or disorder of interest (e.g. cancer-related genes). In preferred embodiments, even for target focused chromosomal regions, at least 1,000 SNPs are identified per target region. However, for such focused chromosomal regions involved in CNV, requirements for total number of SNPs can be relaxed, such as at least 200, 250, 300, 400, or 500 SNPs. Furthermore, polymorphic loci with a minor allele frequency of at least 0.1 are preferred in certain embodiments, especially for chromosome regions greater than 50 Mb. However, for focused chromosome regions, an allele frequency of 0.01 can be used. Filtering can be employed to eliminate certain loci, if there is not sufficient evidence that a mutation in the loci recurs.

Candidate primers for amplifying the target polymorphic loci are selected using one or more or all of a number of design rules. As disclosed herein, Primer3 can be used in the primer design process. Preferably, a SNP target loci is within the first 100, 75, and most preferably 50 nucleotides (e.g. bases) of an amplicon. Therefore, primers can be selected accordingly. Primer designs compatible with massively multiplex PCR (e.g. multiplex PCR with greater than 1000 primer pairs) in one pool with deltaG higher than −4 kcal/mol are selected in illustrative embodiments. In certain embodiments, primers are selected that yield amplicons that are compatible with a downstream analysis technology, such as a high throughput sequencing technology. Preferably, primer pairs are selected such that one primer pair is selected as a left and right primer for amplifying a SNP. Primers with a Tm within a range, for example, from 50C-60C or 53C-59C can be selected, in particularly embodiments, associated with an annealing temperature that is at least 2, 3, 4, 5, 6, 7, 8, 9, or 10 degrees higher than the median Tm of the primers in a primer pool, or higher than the highest Tm of the primers in the primer pool. For example, an annealing temperature of 60-65C, such as 61-63C or 62C can be selected.

The effective distance of binding of the primers can be within 1, but in preferred embodiments, is between 2, 3, 4, 5, 6, 7, 8, 9, 10, 11, 12, 13, 14, 15, 20, 25, 30, 35, 40, 45, 50, 75, 100, 125, or 150 base pairs of a polymorphic loci on the low end of the range and 3, 4, 5, 6, 7, 8, 9, 10, 11, 12, 13, 14, 15, 20, 25, 30, 35, 40, 45, 50, 75, 100, 125, or 150 base pairs of a polymorphic loci on the high end of the range. In some embodiments, primers bind 2-5 nucleotides from a polymorphic loci. The effective range that a pair of primers spans typically includes a polymorphic loci and is typically 160 base pairs or less, and can be 150, 140, 130, 125, 100, 75, 50 or 25 base pairs or less. In other embodiments, the effective range that a pair of primers spans is 20, 25, 30, 40, 50, 60, 70, 75, 100, 110, 120, 125, 130, 140, or 150 nucleotides within a polymorphic loci on the low end of the range, and 25, 30, 40, 50, 60, 70, 75, 100, 110, 120, 125, 130, 140, or 150, 160, 170, 175, or 200 nucleotides from a polymorphic loci on the high end of the range. Amplicons formed using primer pairs of the invention include polymorphic loci.

An important improvement provided herein, is that by selecting primers that can be used to amplify target loci within haploblocks having a minimum number of SNP loci within a chromosome region known to exhibit aneuploidy associated with a disease or disorder, as disclosed in more detail herein, methods for determining ploidy and detecting CNV are more robust to imperfect haplotyping. Therefore, candidate primers are filtered such that at least 75, 80, 85, 90, 95, 96, 97, 98, 99 or in certain particularly illustrative embodiments 100% of the candidate primers bind to target loci within one of a plurality or set of haploblocks within the target chromosome region.

Further embodiments of the present invention that relate to the improvement of selecting polymorphic loci within haploblocks within target regions known to exhibit aneuploidy associated with a disease or disorder, can be input, used, and/or included in any of the methods, compositions, or kits provided herein. For example, in certain embodiments, a plurality, pool and/or set of primers includes at least 250, 300, 400, 500, or 1000 primers, and less than 100, 75, 50, 25, 10, 5, 4, 3, 2, or 1 of the primers of the plurality, pool, and/or set of primers each bind to a different target binding site that is not found in a haploblock within a target chromosome region associated with a disease or disorder, and in further exemplary embodiments, not found in a haploblock with at least 2, 3, 4, 5, or 10 polymorphic loci. Accordingly, in certain embodiments, a plurality, pool and/or set of primers includes at least 250, 300, 400, 500, or 1000 primers, and 75, 80, 85, 90, 95, 96, 97, 98, 99 or 100% of the primers of the plurality, pool, and/or set of primers each bind to a different primer binding site that is found within one of a plurality of haploblocks within a target chromosome region associated with a disease or disorder, or that binds within 2, 3, 4, 5, 6, 7, 8, 9, or 10 nucleotides from a polymorphic loci that is found within a haploblock and in further exemplary embodiments, a haploblock with at least 2, 3, 4, 5, 10 polymorphic loci. In related embodiments, amplicons generated and/or analyzed in methods provided herein include amplicons that map to the human genome and amplicons that do not map to the human genome, for example because that are formed by non-specific reactions. In illustrative embodiments, a plurality, pool and/or set of primers includes at least 250, 300, 400, 500, or 1000 amplicons, and at least 75, 80, 85, 90, 95, 96, 97, 98, 99 or 100% of total amplicons generated or input into a method provided herein that map to a human genome, are complementary to nucleic acid segments found within haploblocks, and in especially illustrative embodiments, haploblocks that include at least 2, 3, 4, 5, 6, 7, 8, 9, or 10 polymorphic loci.

In one aspect, the invention features a reaction mixture or a set of reaction mixtures or primer pools, that include a plurality, set, or library of primers or primer pairs, such as primers selected from a library of candidate primers using any of the methods of the invention. In some embodiments, the plurality, set, or library in the reaction mixture includes primers or primer pairs that simultaneously hybridize (or are capable of simultaneously hybridizing) to or that simultaneously amplify (or are capable of simultaneously amplifying) between 100; 200; 500; 750; 1,000; 2,000; 5,000; 7,500; 10,000; 20,000; or 25,000 different target loci on the low end of the range and 250; 500; 750; 1,000; 2,000; 5,000; 7,500; 10,000; 20,000; 25,000; 30,000; 40,000; 50,000; 75,000; or 100,000 different target loci on the high end of the range, in one reaction volume. In illustrative embodiments, at least 50, 60, 70, 75, 80, 90, 95, 96, 97, 98, 99, or 100% of the target loci hybridized or amplified by the primers, are within haploblocks, for example haploblocks having at least 2, 3, 4, 5, 6, 7, 8, 9, 10, 15, 20, or 15 polymorphic loci each. In various embodiments, the pool, plurality, set, or library includes primers that simultaneously amplify (or are capable of simultaneously amplifying) between 100 to 500; 500 to 1,000; 1,000 to 2,000; 2,000 to 5,000; 5,000 to 7,500; 5,000 to 10,000; 5,000 to 20,000; 5,000 to 25,000; 5,000 to 30,000; 5,000 to 40,000; 5,000 to 50,000; 5,000 to 75,000; or 5,000 to 100,000 different target loci in one reaction volume, inclusive. In various embodiments, the pool, plurality, set, or library in a reaction mixture, includes primers that simultaneously amplify (or are capable of simultaneously amplifying) between 1,000 to 100,000 different target loci in one reaction volume, such as between 1,000 to 50,000; 1,000 to 30,000; 1,000 to 20,000; 1,000 to 10,000; 2,000 to 30,000; 2,000 to 20,000; 2,000 to 10,000; 5,000 to 30,000; 5,000 to 20,000; or 5,000 to 10,000 different target loci, inclusive. In some embodiments, the pool, set, plurality, or library includes primers that simultaneously amplify (or are capable of simultaneously amplifying) the target loci in one reaction volume such that less than 60, 40, 30, 20, 10, 5, 4, 3, 2, 1, 0.5, 0.25, 0.1, or 0.5% of the amplified products are primer dimers. The various embodiments, the amount of amplified products that are primer dimers is between 0.5 to 60%, such as between 0.1 to 40%, 0.1 to 20%, 0.25 to 20%, 0.25 to 10%, 0.5 to 20%, 0.5 to 10%, 1 to 20%, or 1 to 10%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the amplified products are target amplicons. In various embodiments, the amount of amplified products that are target amplicons is between 50 to 99.5%, such as between 60 to 99%, 70 to 98%, 80 to 98%, 90 to 99.5%, or 95 to 99.5%, inclusive. In some embodiments, the primers simultaneously amplify (or are capable of simultaneously amplifying) the target loci in one reaction volume such that at least 50, 60, 70, 80, 90, 95, 96, 97, 98, 99, or 99.5% of the targeted loci are amplified (e.g, amplified at least 5, 10, 20, 30, 50, or 100-fold compared to the amount prior to amplification). In various embodiments, the amount target loci that are amplified (e.g, amplified at least 5, 10, 20, 30, 50, or 100-fold compared to the amount prior to amplification) is between 50 to 99.5%, such as between 60 to 99%, 70 to 98%, 80 to 99%, 90 to 99.5%, 95 to 99.9%, or 98 to 99.99% inclusive. In some embodiments, the library of primers includes at least 100; 200; 500; 750; 1,000; 2,000; 5,000; 7,500; 10,000; 20,000; 25,000; 30,000; 40,000; 50,000; 75,000; or 100,000 primer pairs, wherein each pair of primers includes a forward test primer and a reverse test primer where each pair of test primers hybridize to a target locus. In some embodiments, the library of primers includes at least 100; 200; 500; 750; 1,000; 2,000; 5,000; 7,500; 10,000; 20,000; 25,000; 30,000; 40,000; 50,000; 75,000; or 100,000 individual primers that each hybridize to a different target locus, wherein the individual primers are not part of primer pairs.

In various embodiments, the concentration of each primer is less than 100, 75, 50, 25, 20, 10, 5, 2, or 1 nM, or less than 500, 100, 10, or 1 uM. In various embodiments, the concentration of each primer is between 1 uM to 100 nM, such as between 1 uM to 1 nM, 1 to 75 nM, 2 to 50 nM or 5 to 50 nM, inclusive. In various embodiments, the GC content of the primers is between 30 to 80%, such as between 40 to 70%, or 50 to 60%, inclusive. In some embodiments, the range of GC content of the primers is less than 30, 20, 10, or 5%. In some embodiments, the range of GC content of the primers is between 5 to 30%, such as 5 to 20% or 5 to 10%, inclusive. In some embodiments, the melting temperature ($T_m$) of the test primers is between 40 to 80° C., such as 50 to 70° C., 55 to 65° C., or 57 to 60.5° C., inclusive. In some embodiments, the $T_m$ is calculated using the Primer3 program (libprimer3 release 2.2.3) using the built-in SantaLucia parameters (the world wide web at primer3.sourceforge.net) (SantaLucia JR (1998) "A unified view of polymer, dumbbell and oligonucleotide DNA nearest-neighbor thermodynamics", Proc Natl Acad Sci 95:1460-65). In some embodiments, the range of melting temperature of the primers is less than 15, 10, 5, 3, or 1° C. In some embodiments, the range of melting temperature of the primers is between 1 to 15° C., such as between 1 to 10° C., 1 to 5° C., or 1 to 3° C., inclusive. In some embodiments, the length of the primers is between 15 to 100 nucleotides, such as between 15 to 75 nucleotides, 15 to 40 nucleotides, 17 to 35 nucleotides, 18 to 30 nucleotides, or 20 to 65 nucleotides, inclusive. In some embodiments, the range of the length of the primers is less than 50, 40, 30, 20, 10, or 5 nucleotides. In some embodiments, the range of the length of the primers is between 5 to 50 nucleotides, such as 5 to 40 nucleotides, 5 to 20 nucleotides, or 5 to 10 nucleotides, inclusive. In some embodiments, the length of the target amplicons is between 50 and 100 nucleotides, such as between 60 and 80 nucleotides, or 60 to 75 nucleotides, inclusive. In some embodiments, the range of the length of the target amplicons is less than 50, 25, 15, 10, or 5 nucleotides. In some embodiments, the range of the length of the target amplicons is between 5 to 50 nucleotides, such as 5 to 25 nucleotides, 5 to 15 nucleotides, or 5 to 10 nucleotides, inclusive. In some embodiments, the set, plurality, pool, or library does not comprise a microarray. In some embodiments, the set, plurality, pool, or library comprises a microarray.

Some non-limiting exemplary embodiments of any of the compositions, kits, and methods provided herein, such as, but not limited to, for selecting a set of primers or primer pools, for determining ploidy, for detecting aneuploidy such as CNV, for detecting circulating tumor DNA, provided herein, include the following:

- at least 1000 amplicons are formed and/or input, and wthe amplicons represent at least 95% of total amplicons that map to a human genome.
- at least 1000 amplicons are formed and/or input, and represent at least 99% of total amplicons that map to a human genome.
- at least 1000 amplicons are formed and/or input, and represent all of the total amplicons that map to a human genome.
- at least 500 primers or primer pairs are selected and/or used, wherein at least 95% of the primer or primer pairs that specifically bind to a nucleic acid in the circulating free nucleic acids and/or or that specifically bind to a genome of the individual, bind to a haploblock of a plurality or set of haploblocks, wherein the plurality of haploblocks are found within a chromosome region known to exhibit copy number variation (CNV) associated with a disorder or disease.
- at least 10 polymorphic loci and at least 10 candidate primers are identified for each haploblock, and wherein at least 1000 candidate primers are identified for the primer pool and/or on a target chromosome region.
- at least 10 candidate primer pairs are identified for each segment and optionally a maximum of 100 polymorphic loci and primer pairs are identified for each segment.
- candidate primers are selected such that their 3' end is between 2 and 5 nucleotides away from
- a polymorphic loci of interest.
- candidate primers are selected that form a primer pair for amplifying a segment between 50 and 75 nucleotides in length, wherein the primers are between 18 and 30 nucleotides in length and having a Tm between 50 and 60C.
- candidate primers have a GC content between 30 and 70%.
- polymorphic loci have a minor allele frequency of at least 10%.

The disease or disorder that the compositions and methods provided herein relate to, can include any disease or disorder correlated to allelic imbalance, copy number variation, or ploidy, especially where samples that can be used to detect, monitor, or diagnose such disease or disorder include a relatively small percentage of the total nucleic acids in a nucleic acid sample (for non-limiting example, between 1% and 25%), as set out in detail herein. For example, the disease or disorder in illustrative embodiments, is cancer, especially cancers known to involve a relative high percentage of CNVs in cancerous cells and a relatively high percentage of ctDNA.

In some embodiments, the chromosome or chromosome region is all or a part of a chromosome known to be associated with a developmental disorder in non-invasive prenatal testing. Accordingly, in some embodiments, the method involves determining from a plasma sample of a mother, whether a fetus has one or more of the following conditions: cystic fibrosis, Huntington's disease, Fragile X, thallasemia, muscular dystrophy (such as Duchenne's muscular dystrophy), Alzheimer, Fanconi Anemia, Gaucher Disease, Mucolipidosis IV, Niemann-Pick Disease, Tay-Sachs disease, Sickle cell anemia, Parkinson disease, Torsion Dystonia, and cancer. In some embodiments, a target chromosome is one or more chromosomes taken from the group consisting of chromosomes 13, 18, 21, X, and Y. In some embodiments, a fetal haplotype is determined for all of the fetal chromosomes.

After the reaction mixture is formed it is subjected to amplification conditions to generate a set of amplicons each comprising at least one polymorphic loci of a plurality of polymorphic loci located within haploblocks, preferably known to be associated with cancer. Amplification (e.g. temperature cycling) conditions for PCR are well known in the art. The methods provided herein can include any PCR cycling conditions that result in amplification of target nucleic acids such as target nucleic acids from a library. Non-limiting exemplary cycling conditions are provided in the Examples section herein.

There are many workflows that are possible when conducting PCR; some workflows typical to the methods disclosed herein are provided herein. The steps outlined herein are not meant to exclude other possible steps nor does it imply that any of the steps described herein are required for the method to work properly. A large number of parameter variations or other modifications are known in the literature, and can be made without affecting the essence of the invention.

Following amplification (whether as part of a method of the invention or as a separate step performed outside of a method of the invention), in methods provided herein for determining ploidy that include a step of determining the sequence of an amplicon and/or haploblock, the sequence is determined for at least a portion of each amplicon of a plurality or set of amplicons, wherein the sequenced portion includes a polymorphic loci. In illustrative embodiments, the sequencing data that is generated and that is received in certain embodiments of methods provided herein, includes sequencing data that maps to the genome of the individual whose ploidy is being determined, such as the human genome, and optionally sequencing data that does not map to the genome of the individual (e.g. human genome), such as from non-specific amplicons (e.g. primer dimers). Amplicons according to illustrative embodiments, are within haploblocks that map to the human genome, since as discussed herein, primers in these illustrative embodiments are selected to amplify polymorphic loci within haploblocks. Accordingly, in illustrative embodiments over 75, 80, 90, 95, 98, 99, 99.5, 99.9, or 100% of the sequencing data generated in a method for determining ploidy herein, maps to the human genome, and over 75, 80, 90, 95, 98, 99, 99.5, 99.9, or 100% of the sequencing data that maps to the human genome is from polymorphic loci within haploblocks. The haploblocks, in certain examples, are segments that include at least 5, 10, 15, 20, 25, 50, or 100 polymorphic loci on the low end of the range, and 10, 15, 20, 25, 50, 100, 200, or 250 polymorphic loci on the high end, at least 95% of which exhibit strong linkage disequilibrium with a neighbor loci. Further disclosure regarding the size in nucleotide length and number of polymorphic loci within haplotypes of the invention are provided in other sections herein. It will be understood that the fact that at least 75% and up to 100% of sequencing data in a sequencing reaction that maps to a genome is from within haploblocks, is an important advancement over prior methods for determining ploidy using allele data from polymorphic sites, that did not utilize primer selection for targeted amplification for ploidy determination, especially from cfDNA, before sequencing, that focused on primers that amplify across polymorphic loci found within haploblocks. By selecting a primer pool that amplifies across polymorphic loci within haploblocks, methods for ploidy determination that utilize allele counts at polymorphic loci, become more robust to haplotype determination, such that the methods yield improved results when imperfect haplotype data is used.

In certain embodiments of the method provided herein, the nucleic acid sequence of at least a portion of a nucleic acid segment that includes a polymorphic loci, and in illustrative examples the entire sequence of an amplicon, is determined. Methods for determining the sequence of an amplicon are known in the art. Any of the sequencing methods known in the art, e.g. Sanger sequencing, can be used for such sequence determination. In illustrative embodiments high throughput next-generation sequencing techniques (also referred to herein as massively parallel sequencing techniques) such as, but not limited to, those employed in MYSEQ (Illumina), HISEQ (Illumina), ION TORRENT (Life Technologies), GENOME ANALYZER ILX (Illumina), GS FLEX+(Roche 454), can be used for sequencing the amplicons produced by the methods provided herein. In addition, the sequence of a plurality of polymorphic loci can be determined using microarrays.

In some embodiments, the amplified products are detected using an array, such as an array especially a microarray with probes to one or more chromosomes of interest (e.g., chromosome 13, 18, 21, X, Y, or any combination thereof, or chromosome regions associated with cancer). It will be understood for example, that a commercially available SNP detection microarray could be used such as, for example, the Illumina (San Diego, CA) GoldenGate, DASL, Infinium, or CytoSNP-12 genotyping assay, or a SNP detection microarray product from Affymetrix, such as the OncoScan microarray. In some embodiments, phased genetic data for one or both biological parents of the embryo or fetus is used to increase the accuracy of analysis of array data from a single cell.

In some embodiments involving sequencing, the depth of read is the number of sequencing reads that map to a given locus. The depth of read can be normalized over the total number of reads. In some embodiments for depth of read of a sample, the depth of read is the average depth of read over the targeted loci. In some embodiments for the depth of read of a locus, the depth of read is the number of reads measured by the sequencer mapping to that locus. In general, the greater the depth of read of a locus, the closer the ratio of alleles at the locus tend to be to the ratio of alleles in the original sample of DNA. Depth of read can be expressed in variety of different ways, including but not limited to the percentage or proportion. Thus, for example in a highly parallel DNA sequencer such as an Illumina HISEQ, which, e.g., produces a sequence of 1 million clones, the sequencing of one locus 3,000 times results in a depth of read of 3,000 reads at that locus. The proportion of reads at that locus is 3,000 divided by 1 million total reads, or 0.3% of the total reads.

In some embodiments, allelic data is obtained, wherein the allelic data includes quantitative measurement(s) indicative of the number of copies of a specific allele of a polymorphic locus. In some embodiments, the allelic data includes quantitative measurement(s) indicative of the number of copies of each of the alleles observed at a polymorphic locus. Typically, quantitative measurements are obtained for all possible alleles of the polymorphic locus of interest. For example, any of the methods discussed in the preceding paragraphs for determining the allele for a SNP locus, such as for example, microarrays, qPCR, DNA sequencing, such as high throughput DNA sequencing, can be used to generate quantitative measurements of the number of copies of a specific allele of a polymorphic locus. This quantitative measurement is referred to herein as allelic frequency data or measured genetic allelic data. Methods using allelic data are sometimes referred to as quantitative allelic methods; this is in contrast to quantitative methods which exclusively use quantitative data from non-polymorphic loci, or from polymorphic loci but without regard to allelic identity. When the allelic data is measured using high-throughput sequencing, the allelic data typically include the number of reads of each allele mapping to the locus of interest.

In some embodiments obtaining genetic data includes (i) acquiring DNA sequence information by laboratory techniques, e.g., by the use of an automated high throughput DNA sequencer, or (ii) acquiring information that had been previously obtained by laboratory techniques, wherein the information is electronically transmitted, e.g., by a computer over the internet or by electronic transfer from the sequencing device.

High throughput genetic sequencers are amenable to the use of barcoding (i.e., sample tagging with distinctive nucleic acid sequences) so as to identify specific samples from individuals thereby permitting the simultaneous analysis of multiple samples in a single run of the DNA sequencer. The number of times a given region of the genome in a library preparation (or other nucleic preparation of interest) is sequenced (number of reads) will be proportional to the number of copies of that sequence in the genome of interest. Biases in amplification efficiency can be taken into account in such quantitative determination.

Further details regarding methods of amplification that can be used in a ctDNA amplification/sequencing workflow to determine ploidy for use in methods of the invention are provided in other sections of this specification.

Target Chromosome Regions

Target regions of a gene of interest known to exhibit aneuploidy associated with a disease or disorder are first identified in illustrative embodiments. Non-limiting exemplary methods for identifying such target regions are provided herein for identifying target chromosomal regions associated with cancer and CNV. Although the examples are set out in the context of lung cancer (Example 5) and ovarian cancer, a skilled artisan will understand that such methods can be applied to any cancer where CNV is involved. In some embodiments, the selection of the CNV regions into gain/loss enriched regions can be based on selection of CNV recurrence. In one embodiment, the selection was based on 453 ovarian patient profiles in the TCGA Ovarian Cancer Cohort. As illustrated in FIG. 1.

In some embodiments, the selection of the CNV regions into gain/loss enriched regions can be based on selection of CNV recurrence. In one embodiment, the selection was based on 453 ovarian patient profiles in the TCGA Ovarian Cancer Cohort. As illustrated in FIG. 1, three regions, Regions 1-3 were identified on chromosome 8 as regions having CNVs within 50% of peak recurrence. Regions 1 and 2 were gain regions and were split according to recurrence profile and Region 3 was a loss region. Regions 1 and 2 were split from Region 3 to maximize partitioning of amplifications versus deletions. Further, incorporated were reported amplifications and deletions identified through significance testing by TCGA, arm-level and focal events (focal events represented by vertical lines). As used herein an "arm-level" can be a CNV that spans a chromosome arm p or q. As used herein a "focal event" can be a CNV that spans a region smaller than an arm-level event. The regions were validated by interrogating COSMIC's CNV calls for the same samples (COSMIC was more conservative for calling deletions).

Figure 2:
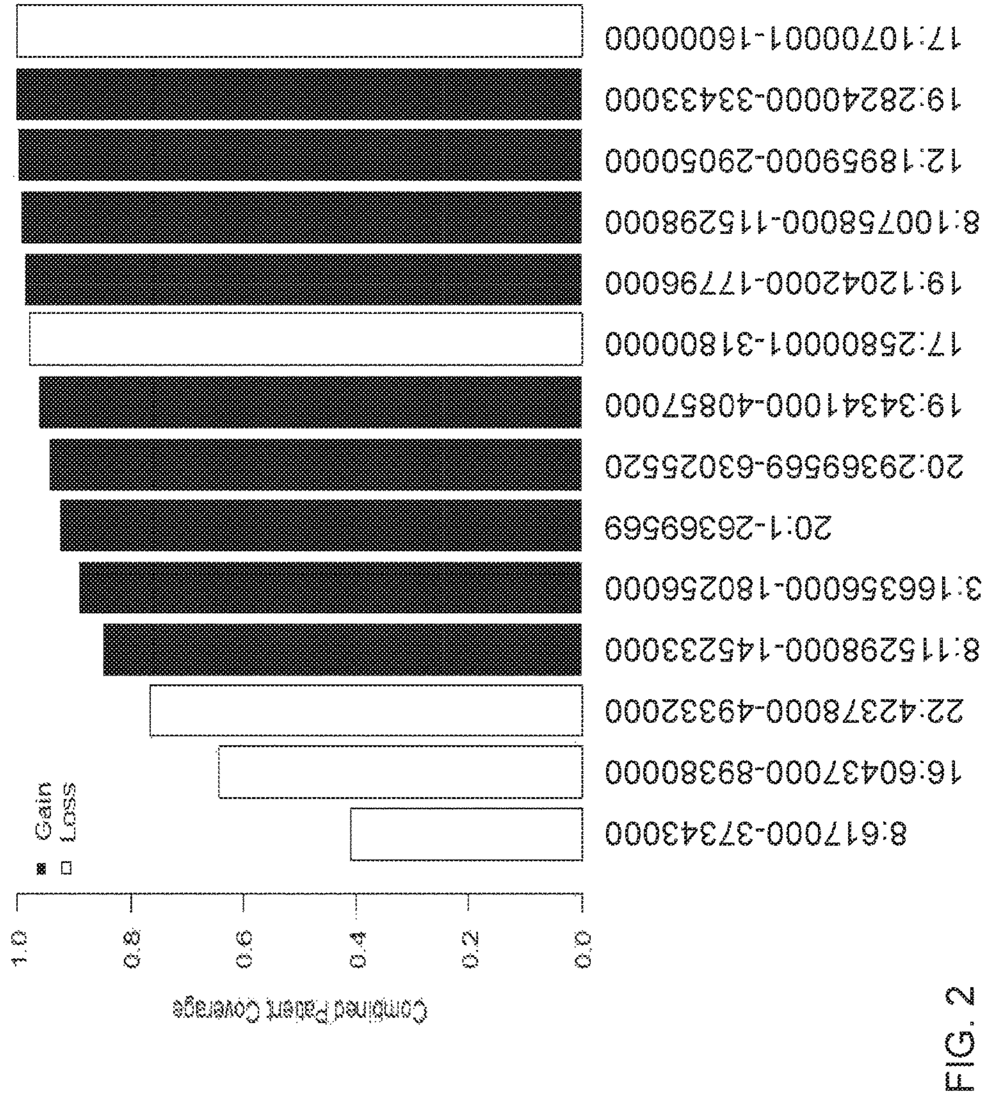
FIG. 2 is a bar chart of 14 prioritized candidate regions with chromosome number and positions labeled on the x-axis and cumulative patient coverage on the y-axis.

The identified gain/loss enriched regions were then prioritized by candidate regions based on the number of ovarian patients that have a CNV in the region. FIG. 2 illustrates the identification of 14 regions, nine gain regions and five loss region. There is a correlation in that CNV events co-occur within and between patients (FIGS. 3A-3B). The table represents the pairwise Pearson correlation between the 14 regions based on the presence or absence of events across those patients captured by each of the 14 regions. Reported values are Pearson R-squared values. Bold entries indicate positive correlation, boxed entries indicate correlation <0.1. The genomic coordinates of each of the locations is reported in GRCh37 coordinates.

If the deletion regions are excluded, patient coverage is reduced by 7-8% while if the regions are ranked using COSMIC call, nine of the top ranking regions are amplifications. When removing deletions at most two copies can be lost as deletions have a limited signal whereas amplifications can have more than two copies gained. Thus, amplifications can provide a better signal for CNV calling. Chromosome number and locations are listed on the x-axis and cumulative patient coverage is listed on the y-axis.

In some embodiments, the selection of the CNV chromosome target regions can be based on CNV recurrence analysis in a population of cancer patients. In one embodiment, the selection was based on 453 ovarian patient profiles in the TCGA Ovarian Cancer Cohort. As illustrated in FIG. 1, three regions, Regions 1-3 were identified on chromosome 8 as regions having CNVs within 50% peak recurrence. Regions 1 and 2 were gain regions and were split according to recurrence profile and Region 3 was a loss region. Regions 1 and 2 were split from Region 3 to maximize portioning of amplifications versus deletions. Further, incorporated were reported amplifications and deletions identified through significance testing by TCGA, arm-level and focal events (vertical lines). The regions were validated by interrogating COSMIC's CNV calls for the same samples (COSMIC was more conservative for calling deletions).

In some embodiments, a pooling algorithm is created for analyzing the haploblock data. The chromosomal segments/regions used to form a haploblock can have candidate SNPs selected from the 1000GP database with MAF >10%. These blocks were identified using the 1000GP reference panel. PCR assays for the selected SNPs are designed in a reiterative process to allow for massive multiplexing PCR. Assays within small haploblocks, i.e., haploblocks having <10 CNVs, are filtered. The resulting optimized set of non-interactive assays are selected and can be further optimized by evaluating: The total number of patients with CNVs covering at least 50% of the region; the recurrence profile of each patient; the size of the haploblock; the MAF, population diversity and heterozygosity rate for each SNP; the type of mutation, transversion or transition; and the length of the amplicon, Tm and GC-content.

In some embodiments, an in silico simulation of the use of designed assays can be run to refine use of haploblocks for detection. To illustrate, an in silico experiment simulates use of HCC1954 and HCC2218 in a titration experiment using the blocks from the described design criteria above. It is assumed that there is perfect information within the blocks and no information between the blocks. Blocks of a minimum size of CNVs are tested with sizes of 1, 10, 15 and 20 CNVs. It was found that performance stabilizes around a minimum block size of 10-15 as too many false positives resulted from not having a minimum block requirement. Using a minimum block size of 10 it was found that performance was similar to perfect haplotypes in regions with >1000 SNPs (down to 0.5% allelic imbalance detection with some false positives). A poor region (having approximately 300 SNPs in blocks) had detection around 2% allelic imbalance. Tables 1A-1B illustrate in silico results in single pools for the designed regions.

TABLE 1A

| Chrom | Start | End | Patients | Number of Assays |
|---|---|---|---|---|
| 8* | 115,298,000 | 145,233,000 | 173 | 1451 |
| 3* | 166,356,000 | 180,256,000 | 108 | 1364 |
| 8* | 100,758,000 | 115,298,000 | 101 | 1490 |
| 8* | 617,000 | 37,343,000 | 99 | 1452 |
| 19* | 28,240,000 | 33,433,000 | 82 | 1376 |
| 20* | 29,369,569 | 63,025,520 | 82 | 1483 |
| 20* | 1 | 26,369,569 | 67 | 1568 |
| 12* | 18,959,000 | 29,050,000 | 65 | 1186 |
| 19* | 34,341,000 | 40,857,000 | 55 | 1225 |
| 19 | 12,042,000 | 17,796,000 | 54 | 903 |
| 16* | 60,437,000 | 89,380,000 | 50 | 1480 |
| 17 | 25,800,001 | 31,800,000 | 30 | 841 |
| 22* | 42,378,000 | 49,332,000 | 21 | 1574 |
| 17 | 10,700,001 | 16,000,000 | 16 | 535 |

*covering 436 patients out of 453

TABLE 1B

| Chrom | Expected Number of hets | SNPs in blocks >10 | Yield | Longest block | Haplotyping error rate |
|---|---|---|---|---|---|
| 8* | 568 | 1381 | 95% | 66 | 3.00% |
| 3* | 496 | 1202 | 88% | 49 | 3.60% |
| 8* | 554 | 1464 | 98% | 68 | 2.40% |
| 8* | 538 | 1406 | 97% | 65 | 3.20% |
| 19* | 520 | 1237 | 90% | 64 | 2.10% |
| 20* | 553 | 1420 | 96% | 65 | 3.10% |
| 20* | 593 | 1537 | 98% | 93 | 3.00% |
| 12* | 414 | 1035 | 87% | 62 | 3.20% |
| 19* | 455 | 1105 | 90% | 57 | 2.70% |
| 19 | 330 | 731 | 81% | 37 | 3.80% |
| 16* | 534 | 1398 | 94% | 53 | 3.20% |
| 17 | 321 | 749 | 89% | 35 | 2.80% |
| 22* | 612 | 1168 | 74% | 66 | 3.40% |
| 17 | 195 | 429 | 80% | 21 | 5.30% |

*covering 436 patients out of 453

Figure 4A:
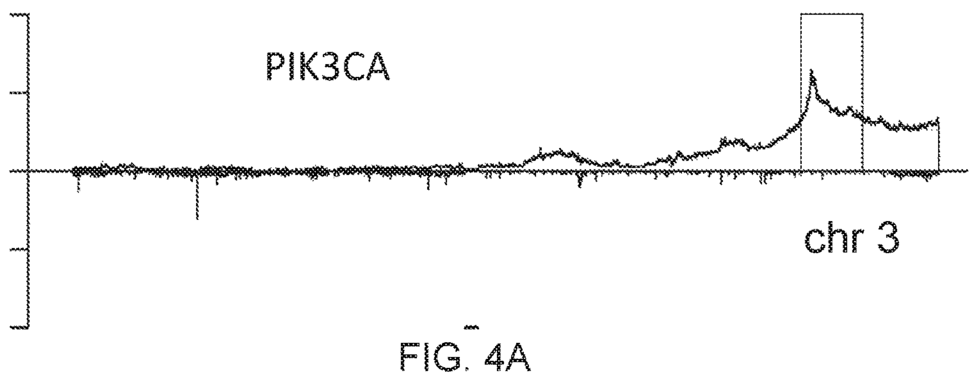
FIGS. 4A-4H are graphs of exemplary CNV region identification.
Figure 4B:
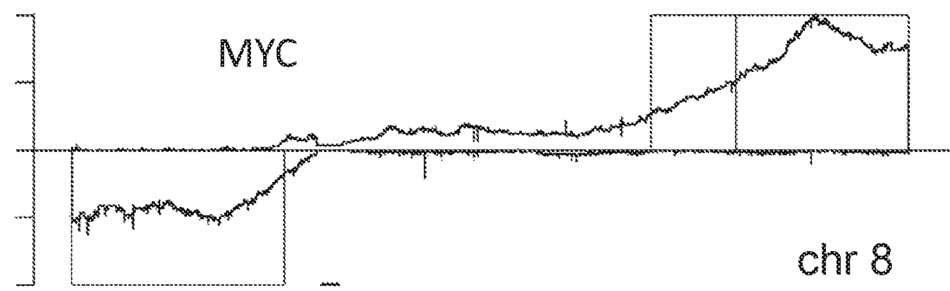
Figure 4C:
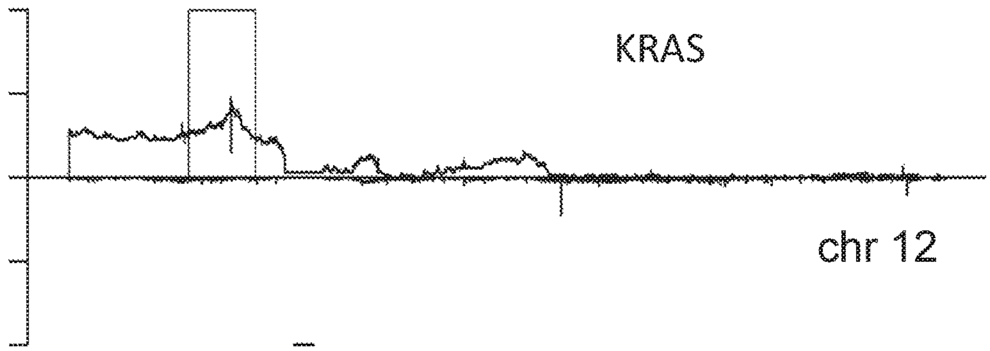
Figure 4D:
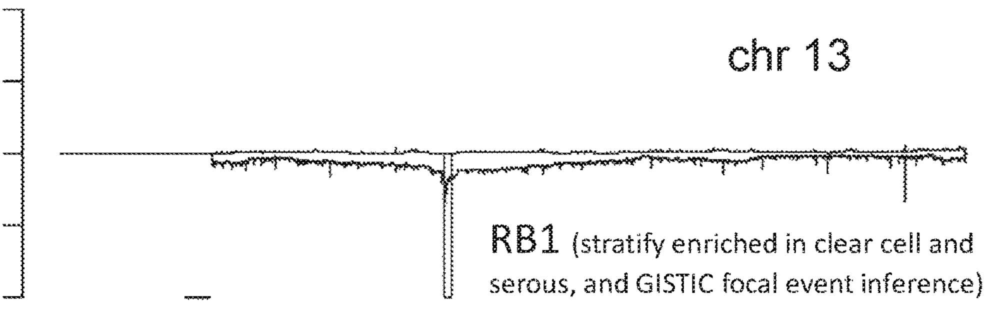
Figure 4E:
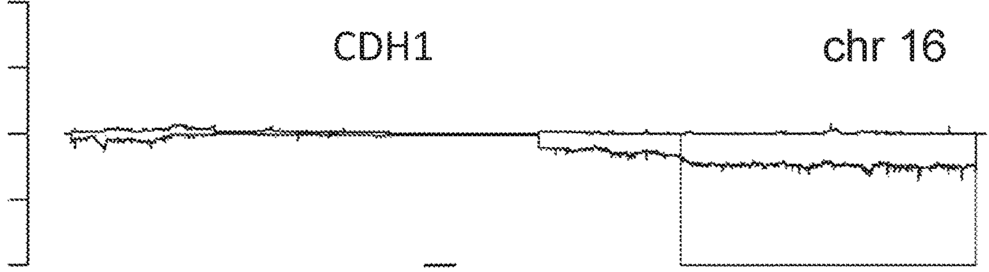
Figure 4F:
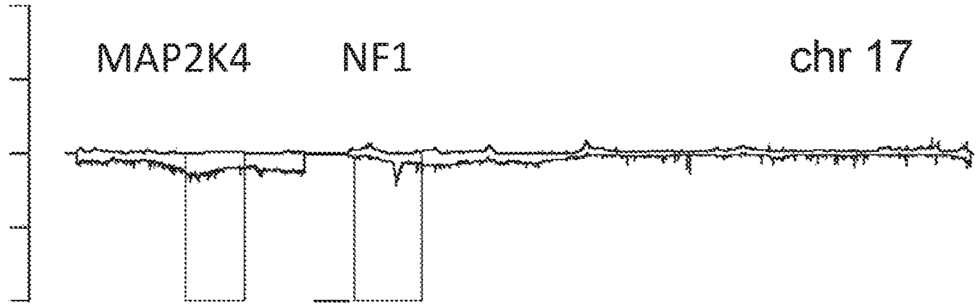
Figure 4G:
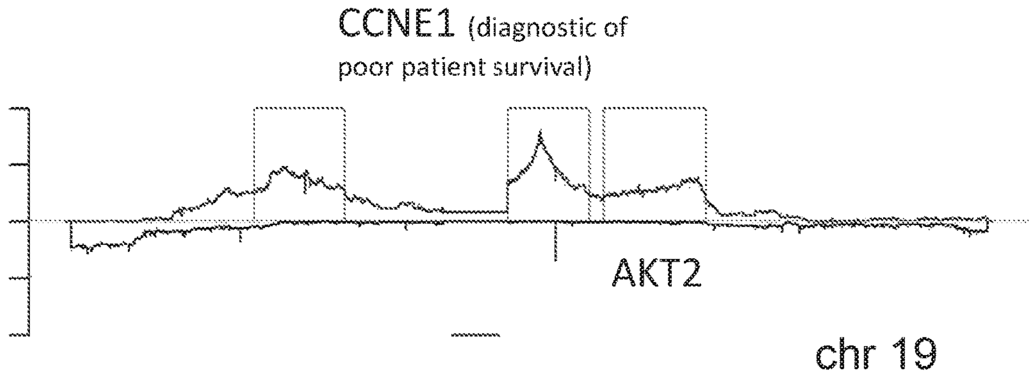
Figure 4H:
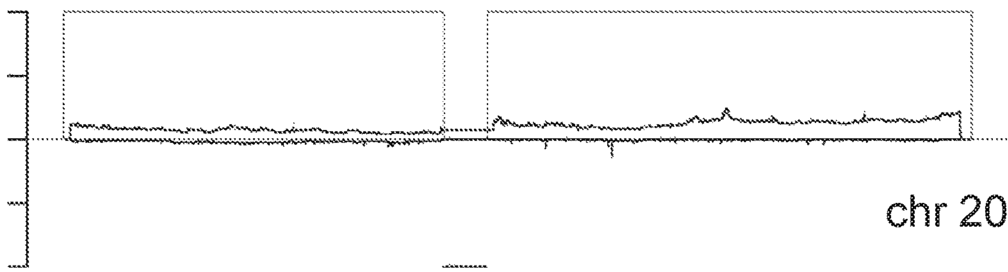

In some embodiments, the regions can be enriched for gain (amplification) or loss (deletion). FIGS. 4A-4H illustrate gain/loss enriched regions for selected chromosomes. The graphs illustrate the gain/loss enriched regions as a lined box: above the x-axis is a gain, below the x-axis is a loss, and the solid dashed line below the x-axis indicates the centromere position between the chromosome arms. Specifically known cancer genes are also identified. There were 15 candidate gain/loss enriched regions identified, nine regions were enriched for amplifications (gains) and six regions were enriched for deletions (loss). A deletion was included because the region spans cancer census genes and/or was reported to distinguish between ovarian subtypes. Chromosome number and locations are listed on the x-axis and cumulative patient coverage is listed on the y-axis. FIG. 4A, chromosome 3, one gain enriched region is illustrated, the region spans PIK3CA gene. FIG. 4B, chromosome 8, two gain and one loss enriched regions are illustrated, the region spans MYC gene. FIG. 4C, chromosome 12, one gain enriched region is illustrated, the region spans KRAS gene. FIG. 4D, chromosome 13, one loss enriched region is illustrated, the region spans RB1 gene, whose CNV status in patients has been reported to stratify clear cell and serous and ovarian cancer subtypes and GISTIC focal event inference. FIG. 4E, chromosome 16, one loss enriched region is illustrated, the region spans CDH1 gene. FIG. 4F, chromosome 17, two loss enriched regions are illustrated, the region spans MAP2K4 AND NF1 genes. Chromosome 17 was included based on GISTIC arm-level inference. FIG. 4G, chromosome 19, three gain enriched regions are illustrated, the region spans CCNE1, which is diagnostic of poor patient survival, and AKT2 genes. FIG. 4H, chromosome 20, two gain enriched regions are illustrated. Inclusion of chromosome 20 was based on GISTIC arm-level inference. GISTIC refers to an algorithm that infers the statistical significance of either gain or loss recurrence within a patient cohort. GISTIC was applied to the TCGA data and published in the TCGA Ovarian Cancer publication ("Integrated genomic analysis of ovarian carcinoma" Nature 474:609-616. 2011).

Chromosome regions exhibiting CNV can be either arm-level CNVs or focal (<50 Mb) events, and methods provided herein can analyze either type of CNV. Example 1 provides an example of arm-length CNV detection. Example 5 provides an example of focal CNV detection. Accordingly, in certain embodiments, the target chromosome region is greater than 50 Mb and in other embodiments, the target chromosome region 50 Mb or less or is less than 50 Mb, or for example 10 Mb, 15 Mb, 20 Mb, 25 Mb, 30 Mb, 40 Mb, on the low end of the range and 15 Mb, 20 Mb, 25 Mb, 30 Mb, 40 Mb, 45 Mb, or 50 Mb on the high end of the range.

George et. Al. 2015 provides an algorithm for copy number analyses called CGRAS, which uses Rank sums and smoothing procedures. Statistics of smoothed rank sum profiles are computed to determine significant copy-number alterations. Additional processes can then be applied, such as those shown in Example 5, to assist in a final determination of target chromosome region(s). Chromosome regions that show CNV in at least 50, 60, 70, 80, or 90% of samples from individuals with a target disease or disorder are selected, in illustrative embodiments. In embodiments, chromosome regions that include driver genes are selected.

Target regions of the nucleic acid library generated from DNA isolated from the sample, especially a circulating free DNA sample for the methods of the present invention, are then amplified. For this amplification, a series of primers or primer pairs, which can include between 5, 10, 15, 20, 25, 50, 100, 125, 150, 250, 500, 1000, 2500, 5000, 10,000, 20,000, 25,000, or 50,000 on the low end of the range and 15, 20, 25, 50, 100, 125, 150, 250, 500, 1000, 2500, 5000, 10,000, 20,000, 25,000, 50,000, 60,000, 75,000, or 100,000 primers on the upper end of the range, that each bind to one of a series of primer binding sites.

A plurality of chromosome regions have been identified, as illustrated in the Examples section herein, that are particularly effective when detecting, diagnosing, and/or determining an effective treatment plan or identifying an effective therapeutic for ovarian cancer (Examples 1-4; See Example 1 for target chromosome regions) and a plurality of chromosome regions have been identified that are particularly effective when detecting, diagnosing, and/or determining a effective treatment plan or identifying an effective therapeutic, for lung cancer (Example 5; lung cancer therapeutic target chromosome regions provided in Example 5). The exemplary target chromosome regions for ovarian cancer include chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, and chromosome 17 nucleotides 10700001-16000000. In certain embodiments, methods of the present invention, include determining or estimating a phase of a plurality of polymorphic loci within a set of chromosomes that includes 1, 2, 3, 4, 5, 6, 7, 8, 9, 10, 11, 12, 13, or all 14 of the above target chromosome regions.

The exemplary target chromosome regions for lung cancer that have been identified, as illustrated in the Examples herein, are regions that are particularly well-suited for targeted therapy and include chromosome 7 nucleotides 140433813-140624564 (BRAF), chromosome 7 nucleotides 55086725-55275031 (EGFR), chromosome 17 nucleotides 37856231-37884915 (ERBB2), chromosome 8 nucleotides 38268656-38325363 (FGFR1), chromosome 12 nucleotides 25358180-25403854 (KRAS), chromosome 7 nucleotides 116312459-116438440 (MET), chromosome 8 nucleotides 128748315-128753680 (MYC), and chromosome 3 nucleotides 178866311-178952497 (PIK3CA). In certain embodiments, methods of the present invention, include determining or estimating a phase of a plurality of polymorphic loci within a set of chromosome regions that includes 1, 2, 3, 4, 5, 6, 7, or all 8 of the above target chromosome regions.

It will be understood that the above chromosome regions identified for ovarian and lung CNV provide guideposts and that regions that include at least 50, 60, 70, 75, 80, 90, 95, 98, 99, or 100% of the contiguous nucleic acids of the above regions could be useful in the methods of the invention, or regions that include 50, 60, 70, 75, 80, 90, 95, 98, 99, or 100% of the polymorphic loci within the target chromosome regions. Accordingly, in some embodiments, methods of the invention include analyzing between: 50%-100% of the contiguous nucleic acids of the exemplary target chromosome regions, 60%-99% of the contiguous nucleic acids of the target chromosome regions, 65%-95% of the contiguous nucleic acids of the target chromosome regions, 70%-90% of the contiguous nucleic acids of the target chromosome regions, and 75%-85% of the contiguous nucleic acids of the target chromosome regions. In some embodiments, at least 75, 80, 85, 90, 95, 98, or 99%, or all of the contiguous nucleic acids of each chromosome region of the set of chromosome regions are analyzed. In some embodiments, the target chromosome region includes 5, 10, 15, 20, 25, 50, 75, or 100% more of a chromosomal region than includes the exemplary target chromosome regions. In some embodiments, the analysis is nucleic acid sequencing of the entire region. However, in illustrative embodiments, the analyzing is determining the nucleic acid sequence of polymorphic loci within haploblocks within the chromosome regions using targeted amplification and sequencing.

Exemplary Methods for Determining Whether ctDNA is Present

In one aspect of the present invention, chromosomal regions are employed in a method for determining whether circulating tumor nucleic acids from a cancer, such as an Ovarian cancer or lung cancer, are present in a liquid sample from an individual, comprising: analyzing the sample to determine a ploidy at a plurality of chromosome regions in the individual, wherein the analyzing comprises separately analyzing SNP allelic data for between 10 and 100 SNP loci within a set of chromosome segments from each of the plurality of chromosome regions, and then combining the separate SNP allelic data to determine a segment allele for each of the set of chromosome segments, and then combining segment allelic data for segments on the same chromosome region to determine ploidy of each of the chromosome regions; and determining the level of allelic imbalance present for each chromosome region of the plurality of chromosome regions based on the ploidy determination, whereby an allelic imbalance above a cutoff value is indicative of the presence of circulating tumor nucleic acids. As illustrated in Tables 1A-1B, the number of SNPs in a chromosomal region and the number of SNP and haplotype blocks in a given chromosome region can provide information for detecting chromosomal aneuploidy.

In certain embodiments, the method further includes detecting a single nucleotide variant at a single nucleotide variance site in a set of single nucleotide variance locations, wherein detecting either an allelic imbalance equal to or greater than 0.45% or detecting the single nucleotide variant, or both, is indicative of the presence of circulating tumor nucleic acids in the sample. Accordingly, such methods have the advantage of analyzing for either or both SNVs and CNVs, to increase the performance of the test method.

In one embodiment of the method for determining whether circulating tumor nucleic acids from an Ovarian cancer are present in the liquid sample comprises analyzing a plurality of chromosome regions comprise at least two segments selected from the group of chromosome regions consisting of at least 70%, at least 80%, at least 85%, at least 90%, at least 95% and at least 99% of the contiguous nucleotides of the following plurality of chromosome regions: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, chromosome 17 nucleotides 10700001-16000000. In one embodiment, the group of chromosome regions consists of at least 70%, at least 80%, at least 85%, at least 90%, at least 95% and at least 99% of the contiguous nucleotides of the plurality of chromosome regions. In one embodiment, each chromosome region in the plurality of chromosome regions comprises a plurality of segments of between: 20 and 600 segments, 30 and 550 segments, 75 and 500 segments, and 100 and 350 segments.

In one embodiment, each chromosome region in the plurality of chromosome regions comprises at least two chromosome regions from at least two chromosomes selected from the group consisting of chromosome 3, chromosome 8, chromosome 12, chromosome 13, chromosome 16, chromosome 19, chromosome 20, and chromosome 22. In one embodiment, the plurality of chromosome regions comprise at least 2, 3, 4, 5, 6, 7, 8, 9, 10, 11, 12, or 13 or all 14 segments selected from the group of chromosome regions consisting of at least the following plurality of chromosome regions: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, chromosome 17 nucleotides 10700001-16000000. In one embodiment, the set of chromosome segments from each of the plurality of chromosome regions a plurality of segments comprise between: 50%-100% of the chromosome segments, 60%-99% of the chromosome segments, 65%-95% of the chromosome segments, 70%-90% of the chromosome segments, and 75%-85% of the chromosome segments. In one embodiment, the analyzing is performed using high throughput nucleic acid sequencing by determining the nucleic acid sequence of less than 10% of the nucleotides within each segment of the plurality of chromosome regions.

In one embodiments, disclosed is a method for determining whether circulating tumor nucleic acids from an Ovarian cancer are present in a liquid sample from an individual, comprising analyzing the sample to determine a ploidy at a plurality of chromosome regions in the individual, wherein the chromosome regions comprise at least two segments that exhibit copy number variation in at least 50% of Ovarian cancer patients; and determining the level of allelic imbalance present for each chromosome region of the set of chromosome regions based on the ploidy determination, wherein an allelic imbalance equal to or greater than 0.45% for any of the chromosome regions is indicative of the presence of circulating tumor nucleic acids in the sample. I some embodiments, the analyzing comprises separately analyzing SNP allelic data for between 10 and 100 SNP loci with strong linkage disequilibrium within each segment of a set of chromosome segments from each of the plurality of chromosome regions, and then combining the separate SNP allelic data to determine a segment allele for each of the set of chromosome segments, and then combining segment allelic data for segments on the same chromosome region to determine ploidy of each of the chromosome regions. In some embodiments, the analyzing comprises analyzing at least two chromosome segments selected from the group of chromosome regions consisting of the following plurality of chromosome regions: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, and chromosome 17 nucleotides 10700001-16000000 for an average allelic imbalance indicative of a deletion of the segment.

In one embodiment, the method for determining whether circulating tumor nucleic acids from an Ovarian cancer are present in a liquid sample from an individual, comprises detecting a single nucleotide variant at a single nucleotide variance site in a set of single nucleotide variance locations, wherein detecting either an allelic imbalance equal to or greater than 0.45% or detecting the single nucleotide variant, or both, is indicative of the presence of circulating tumor nucleic acids in the sample. In one embodiment, the method comprises performing the method on an Ovarian cancer control nucleic acid sample with a known average allelic imbalance ratio and the control can be a chromosomal region sample from the tumor of the individual. In some embodiments, the analyzing of the sample comprises performing a multiplex PCR to amplify amplicons across 1000 to 50,000 polymeric loci on the set of chromosome regions.

Target Genes

Target genes of the present invention in exemplary embodiments, are cancer-related genes. A cancer-related gene (for example, an ovarian cancer-related gene, a lung cancer-related gene or a lung SCC-related gene or a lung ADC-related gene) refers to a gene associated with an altered risk for a cancer (e.g. ovarian cancer, lung cancer or lung SCC or lung ADC, respectively) or an altered prognosis for a cancer. or a target for a cancer therapy. Exemplary cancer-related genes that promote cancer include oncogenes; genes that enhance cell proliferation, invasion, or metastasis; genes that inhibit apoptosis; and pro-angiogenesis genes. Cancer-related genes that inhibit cancer include, but are not limited to, tumor suppressor genes; genes that inhibit cell proliferation, invasion, or metastasis; genes that promote apoptosis; and anti-angiogenesis genes.

Exemplary polymorphisms or mutations (such as deletions or duplications) detected by methods provided herein are in one or more of the following genes: TP53, PTEN, PIK3CA, APC, EGFR, NRAS, NF2, FBXW7, ERBBs, ATAD5, KRAS, BRAF, VEGF, EGFR, HER2, ALK, p53, BRCA, BRCA1, BRCA2, SETD2, LRP1B, PBRM, SPTA1, DNMT3A, ARID1A, GRIN2A, TRRAP, STAG2, EPHA3/5/7, POLE, SYNE1, C20orf80, CSMD1, CTNNB1, ERBB2. FBXW7, KIT, MUC4, ATM, CDH1, DDX11, DDX12, DSPP, EPPK1, FAM186A, GNAS, HRNR, KRTAP4-11, MAP2K4, MLL3, NRAS, RB1, SMAD4, TTN, ABCC9, ACVR1B, ADAM29, ADAMTS19, AGAP10, AKT1, AMBN, AMPD2, ANkRD30A, ANkRD40, APOBR, AR, BIRC6, BMP2, BRAT1, BTNL8, C12orf4, C1QTNF7, C20orf186, CAPRIN2, CBWD1, CCDC30, CCDC93, CD5L, CDC27, CDC42BPA, CDH9, CDKN2A, CHD8, CHEK2, CHRNA9, CIZ1, CLSPN, CNTN6, COL14A1, CREBBP, CROCC, CTSF, CYP1A2, DCLK1, DHDDS, DHX32, DKK2, DLEC1, DNAH14, DNAH5, DNAH9, DNASE1L3, DUSP16, DYNC2H1, ECT2, EFHB, RRN3P2, TRIM49B, TUBB8P5, EPHA7, ERBB3, ERCC6, FAM21A, FAM21C, FCGBP, FGFR2, FLG2, FLT1, FOLR2, FRYL, FSCB, GAB1, GABRA4, GABRP, GH2, GOLGA6L1, GPHB5, GPR32, GPX5, GTF3C3, HECW1, HIST1H3B, HLA-A, HRAS, HS3ST1, HS6ST1, HSPD1, IDH1, JAK2, KDM5B, KIAA0528, KRT15, KRT38, KRTAP21-1, KRTAP4-5, KRTAP4-7, KRTAP5-4, KRTAP5-5, LAMA4, LATS1, LMF1, LPAR4, LPPR4, LRRFIP1, LUM, LYST, MAP2K1, MARCH1, MARCO, MB21D2, MEGF10, MMP16, MORC1, MRE11A, MTMR3, MUC12, MUC17, MUC2, MUC20, NBPF10, NBPF20, NEK1, NFE2L2, NLRP4, NOTCH2, NRK, NUP93, OBSCN, OR11H1, OR2B11, OR2M4, OR4Q3, OR5D13, OR812, OXSM, PIK3R1, PPP2R5C, PRAME, PRF1, PRG4, PRPF19, PTH2, PTPRC, PTPRJ, RAC1, RAD50, RBM12, RGPD3, RGS22, ROR1, RP11-671M22.1, RP13-996F3.4, RP1L1, RSBN1L, RYR3, SAMD3, SCN3A, SEC31A, SF1, SF3B1, SLC25A2, SLC44A1, SLC4A11, SMAD2, SPTA1, ST6GAL2, STK11, SZT2, TAF1L, TAX1BP1, TBP, TGFB1, TIF1, TMEM14B, TMEM74, TPTE, TRAPPC8, TRPS1, TXNDC6, USP32, UTP20, VASN, VPS72, WASH3P, WWTR1, XPO1, ZFHX4, ZMIZ1, ZNF167, ZNF436, ZNF492, ZNF598, ZRSR2, ABL1, AKT2, AKT3, ARAF, ARFRP1, ARID2, ASXL1, ATR, ATRX, AURKA, AURKB, AXL, BAP1, BARD1, BCL2, BCL2L2, BCL6, BCOR, BCORL1, BLM, BRIP1, BTK, CARD11, CBFB, CBL, CCND1, CCND2, CCND3, CCNE1, CD79A, CD79B, CDC73, CDK12, CDK4, CDK6, CDK8, CDKN1B, CDKN2B, CDKN2C, CEBPA, CHEK1, CIC, CRKL, CRLF2, CSF1R, CTCF, CTNNA1, DAXX, DDR2, DOTIL, EMSY (C11orf30), EP300, EPHA3, EPHA5, EPHB1, ERBB4, ERG, ESR1, EZH2, FAM123B (WTX), FAM46C, FANCA, FANCC, FANCD2, FANCE, FANCF, FANCG, FANCL, FGF10, FGF14, FGF19, FGF23, FGF3, FGF4, FGF6, FGFR1, FGFR2, FGFR3, FGFR4, FLT3, FLT4, FOXL2, GATA1, GATA2, GATA3, GID4 (C17orf39), GNA11, GNA13, GNAQ, GNAS, GPR124, GSK3B, HGF, IDH1, IDH2, IGF1R, IKBKE, IKZF1, IL7R, INHBA, IRF4, IRS2, JAK1, JAK3, JUN, KAT6A (MYST3), KDM5A, KDM5C, KDM6A, KDR, KEAP1, KLHL6, MAP2K2, MAP2K4, MAP3K1, MCL1, MDM2, MDM4, MED12, MEF2B, MEN1, MET, MITF, MLH1, MLL, MLL2, MPL, MSH2, MSH6, MTOR, MUTYH, MYC, MYCL1, MYCN, MYD88, NF1, NFKBIA, NkX2-1, NOTCH1, NPM1, NRAS, NTRK1, NTRK2, NTRK3, PAK3, PALB2, PAX5, PBRM1, PDGFRA, PDGFRB, PDK1, PIK3CG, PIK3R2, PPP2RIA, PRDM1, PRKAR1A, PRKDC, PTCH1, PTPN11, RAD51, RAF1, RARA, RET, RICTOR, RNF43, RPTOR, RUNX1, SMARCA4, SMARCB1, SMO, SOCS1, SOX10, SOX2, SPEN, SPOP, SRC, STAT4, SUFU, TET2, TGFBR2, TNFAIP3, TNFRSF14, TOP1, TP53, TSC1, TSC2, TSHR, VHL, WISP3, WT1, ZNF217, ZNF703, and combinations thereof (Su et al., J Mol Diagn 2011, 13:74-84; DOI: 10.1016/j.jmoldx.2010.11.010; and Abaan et al., "The Exomes of the NCI-60 Panel: A Genomic Resource for Cancer Biology and Systems Pharmacology", Cancer Research, Jul. 15, 2013). In some embodiments, the duplication is a chromosome 1p ("Chr1p") duplication associated with breast cancer. In some embodiments, one or more polymorphisms or mutations are in BRAF, such as the V600E mutation. In some embodiments, one or more polymorphisms or mutations are in K-ras. In some embodiments, there is a combination of one or more polymorphisms or mutations in K-ras and APC. In some embodiments, there is a combination of one or more polymorphisms or mutations in K-ras and p53. In some embodiments, there is a combination of one or more polymorphisms or mutations in APC and p53. In some embodiments, there is a combination of one or more polymorphisms or mutations in K-ras, APC, and p53. In some embodiments, there is a combination of one or more polymorphisms or mutations in K-ras and EGFR. Exemplary polymorphisms or mutations are in one or more of the following microRNAs: miR-15a, miR-16-1, miR-23a, miR-23b, miR-24-1, miR-24-2, miR-27a, miR-27b, miR-29b-2, miR-29c, miR-146, miR-155, miR-221, miR-222, and miR-223 (Calin et al. "A microRNA signature associated with prognosis and progression in chronic lymphocytic leukemia." N Engl J Med 353:1793-801, 2005, which is hereby incorporated by reference in its entirety).

In some embodiments, the deletion is a deletion of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the deletion is a deletion of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive.

In some embodiments, the duplication is a duplication of at least 0.01 kb, 0.1 kb, 1 kb, 10 kb, 100 kb, 1 mb, 2 mb, 3 mb, 5 mb, 10 mb, 15 mb, 20 mb, 30 mb, or 40 mb. In some embodiments, the duplication is a duplication of between 1 kb to 40 mb, such as between 1 kb to 100 kb, 100 kb to 1 mb, 1 to 5 mb, 5 to 10 mb, 10 to 15 mb, 15 to 20 mb, 20 to 25 mb, 25 to 30 mb, or 30 to 40 mb, inclusive.

In some embodiments, the tandem repeat is a repeat of between 2 and 60 nucleotides, such as 2 to 6, 7 to 10, 10 to 20, 20 to 30, 30 to 40, 40 to 50, or 50 to 60 nucleotides, inclusive. In some embodiments, the tandem repeat is a repeat of 2 nucleotides (dinucleotide repeat). In some embodiments, the tandem repeat is a repeat of 3 nucleotides (trinucleotide repeat).

In some embodiments, the polymorphism or mutation is prognostic. Exemplary prognostic mutations include K-ras mutations, such as K-ras mutations that are indicators of post-operative disease recurrence in colorectal cancer (Ryan et al. "A prospective study of circulating mutant KRAS2 in the serum of patients with colorectal neoplasia: strong prognostic indicator in postoperative follow up," Gut 52: 101-108, 2003; and Lecomte T et al. Detection of free-circulating tumor-associated DNA in plasma of colorectal cancer patients and its association with prognosis," Int J Cancer 100:542-548, 2002.

Methods provided herein can be used to detect CNVs known to be associated with lung cancer. Exemplary lung cancer CNVs can be in one or more of the following genes: EGFR, FGFR1, FGFR2, ALK, MET, ROS1, NTRK1, RET, HER2, DDR2, PDGFRA, KRAS, NF1, BRAF, PIK3CA, MEK1, NOTCH1, MLL2, EZH2, TET2, DNMT3A, SOX2, MYC, KEAP1, CDKN2A, NRG1, TP53, LKB1, and PTEN, which have been identified in various lung cancer samples as being mutated, having increased copy numbers, or being fused to other genes and combinations thereof (Non-small-cell lung cancers: a heterogeneous set of diseases. Chen et al. Nat. Rev. Cancer. 2014 Aug. 14(8):535-551). In illustrative embodiments, a method or composition of the invention is directed to determining ploidy in an individual that is screened for, or suspected of having Ovarian cancer, and the target chromosome regions are found in the MYC, PIK3CA, CCNE1, KRAS, AKT2, CDH1, NF1, RB1, and/or MAP2K4 genes, as illustrated in Example 1. In other illustrative embodiments, a method or composition of the invention is directed to determining ploidy in an individual that is screened for, or suspected of having lung cancer, and the target chromosome regions are found in the BRAF, EGFR, ERBB2, FGFR1, KRAS, MET, MYC and/or PIK3CA genes. Such methods can further include recommending administration or, or administering a targeted therapeutic agent, such as those identified in Example 5 herein.

Exemplary Cancers

Exemplary diseases or disorders for the methods, compositions, and kits herein include cancers that can be diagnosed, prognosed, stabilized, treated, or prevented using any of the methods of the invention including solid tumors, carcinomas, sarcomas, lymphomas, leukemias, germ cell tumors, or blastomas. In various embodiments, the cancer is an acute lymphoblastic leukemia, acute myeloid leukemia, adrenocortical carcinoma, AIDS-related cancer, AIDS-related lymphoma, anal cancer, appendix cancer, astrocytoma (such as childhood cerebellar or cerebral astrocytoma), basal-cell carcinoma, bile duct cancer (such as extrahepatic bile duct cancer) bladder cancer, bone tumor (such as osteosarcoma or malignant fibrous histiocytoma), brainstem glioma, brain cancer (such as cerebellar astrocytoma, cerebral astrocytoma/malignant glioma, ependymo, medulloblastoma, supratentorial primitive neuroectodermal tumors, or visual pathway and hypothalamic glioma), glioblastoma, breast cancer, bronchial adenoma or carcinoid, burkitt's lymphoma, carcinoid tumor (such as a childhood or gastrointestinal carcinoid tumor), carcinoma central nervous system lymphoma, cerebellar astrocytoma or malignant glioma (such as childhood cerebellar astrocytoma or malignant glioma), cervical cancer, childhood cancer, chronic lymphocytic leukemia, chronic myelogenous leukemia, chronic myeloproliferative disorders, colon cancer, cutaneous t-cell lymphoma, desmoplastic small round cell tumor, endometrial cancer, ependymoma, esophageal cancer, ewing's sarcoma, tumor in the ewing family of tumors, extracranial germ cell tumor (such as a childhood extracranial germ cell tumor), extragonadal germ cell tumor, eye cancer (such as intraocular melanoma or retinoblastoma eye cancer), gallbladder cancer, gastric cancer, gastrointestinal carcinoid tumor, gastrointestinal stromal tumor, germ cell tumor (such as extracranial, extragonadal, or ovarian germ cell tumor), gestational trophoblastic tumor, glioma (such as brain stem, childhood cerebral astrocytoma, or childhood visual pathway and hypothalamic glioma), gastric carcinoid, hairy cell leukemia, head and neck cancer, heart cancer, hepatocellular (liver) cancer, hodgkin lymphoma, hypopharyngeal cancer, hypothalamic and visual pathway glioma (such as childhood visual pathway glioma), islet cell carcinoma (such as endocrine or pancreas islet cell carcinoma), kaposi sarcoma, kidney cancer, laryngeal cancer, leukemia (such as acute lymphoblastic, acute myeloid, chronic lymphocytic, chronic myelogenous, or hairy cell leukemia), lip or oral cavity cancer, liposarcoma, liver cancer (such as non-small cell or small cell cancer), lung cancer, lymphoma (such as AIDS-related, burkitt, cutaneous T cell, Hodgkin, non-hodgkin, or central nervous system lymphoma), macroglobulinemia (such as waldenström macroglobulinemia, malignant fibrous histiocytoma of bone or osteosarcoma, medulloblastoma (such as childhood medulloblastoma), melanoma, merkel cell carcinoma, mesothelioma (such as adult or childhood mesothelioma), metastatic squamous neck cancer with occult, mouth cancer, multiple endocrine neoplasia syndrome (such as childhood multiple endocrine neoplasia syndrome), multiple myeloma or plasma cell neoplasm. mycosis fungoides, myelodysplastic syndrome, myelodysplastic or myeloproliferative disease, myelogenous leukemia (such as chronic myelogenous leukemia), myeloid leukemia (such as adult acute or childhood acute myeloid leukemia), myeloproliferative disorder (such as chronic myeloproliferative disorder), nasal cavity or paranasal sinus cancer, nasopharyngeal carcinoma, neuroblastoma, oral cancer, oropharyngeal cancer, osteosarcoma or malignant fibrous histiocytoma of bone, ovarian cancer, ovarian epithelial cancer, ovarian germ cell tumor, ovarian low malignant potential tumor, pancreatic cancer (such as islet cell pancreatic cancer), paranasal sinus or nasal cavity cancer, parathyroid cancer, penile cancer, pharyngeal cancer, pheochromocytoma, pineal astrocytoma, pineal germinoma. pincoblastoma or supratentorial primitive neuroectodermal tumor (such as childhood pineoblastoma or supratentorial primitive neuroectodermal tumor), pituitary adenoma, plasma cell neoplasia, pleuropulmonary blastoma, primary central nervous system lymphoma, cancer, rectal cancer, renal cell carcinoma, renal pelvis or ureter cancer (such as renal pelvis or ureter transitional cell cancer, retinoblastoma, rhabdomyosarcoma (such as childhood rhabdomyosarcoma), salivary gland cancer, sarcoma (such as sarcoma in the ewing family of tumors, Kaposi, soft tissue, or uterine sarcoma), sézary syndrome, skin cancer (such as nonmelanoma, melanoma, or merkel cell skin cancer), small intestine cancer, squamous cell carcinoma, supratentorial primitive neuroectodermal tumor (such as childhood supratentorial primitive neuroectodermal tumor), T-cell lymphoma (such as cutaneous T-cell lymphoma), testicular cancer, throat cancer, thymoma (such as childhood thymoma), thymoma or thymic carcinoma, thyroid cancer (such as childhood thyroid cancer), trophoblastic tumor (such as gestational trophoblastic tumor), unknown primary site carcinoma (such as adult or childhood unknown primary site carcinoma), urethral cancer (such as endometrial uterine cancer), uterine sarcoma, vaginal cancer, visual pathway or hypothalamic glioma (such as childhood visual pathway or hypothalamic glioma), vulvar cancer, waldenström macroglobulinemia, or wilms tumor (such as childhood wilms tumor). In various embodiments, the cancer has metastasized or has not metastasized.

The cancer may or may not be a hormone related or dependent cancer (e.g., an estrogen or androgen related cancer). Benign tumors or malignant tumors can be diagnosed, prognosed, stabilized, treated, or prevented using the methods and/or compositions of the present invention.

In some embodiments, the subject has a cancer syndrome. A cancer syndrome is a genetic disorder in which genetic mutations in one or more genes predispose the affected individuals to the development of cancers and may also cause the early onset of these cancers. Cancer syndromes often show not only a high lifetime risk of developing cancer, but also the development of multiple independent primary tumors. Many of these syndromes are caused by mutations in tumor suppressor genes, genes that are involved in protecting the cell from turning cancerous. Other genes that can be affected are DNA repair genes, oncogenes and genes involved in the production of blood vessels (angiogenesis). Common examples of inherited cancer syndromes are hereditary breast-ovarian cancer syndrome and hereditary non-polyposis colon cancer (Lynch syndrome).

In some embodiments, a subject with one or more polymorphisms or mutations n K-ras, p53, BRA, EGFR, or HER2 is administered a treatment that targets K-ras, p53, BRA, EGFR, or HER2, respectively.

In certain embodiments, methods provided herein can be used to direct a therapeutic regimen. In some embodiments, the polymorphism or mutation is associated with altered response to a particular treatment (such as increased or decreased efficacy or side-effects). Therapies are available and under development that target specific mutations associated with various cancers, including lung cancer and ovarian cancer. It is known that therapeutics can be effective against targeted mutations such as CNVs. Example 5 herein, provides a Table of targeted therapeutics indicated by CNVs in particular genes, (see Table 20).

Analytical Methods

Methods for determining ploidy herein, typically include an analytical method that analyzes allelic data, such as allelic count sequencing data, regarding a plurality of SNPs, receives or generates imperfectly phased allelic information, and generates individual and joint probabilities for different ploidy states, to determine a ploidy state of a chromosomal region. Such analytical methods have been reported (See e.g. WO 2007/062164, WO 2012/108920, and WO 2015/164432) and can be used in methods provided herein. Surprisingly, presented herein is data that shows that by choosing SNPs that are found within haploblocks, increased performance of such SNP-based analytical methods, can be achieved.

In such analytical methods, individual probabilities can be generated using a set of models or hypothesis of both different ploidy states and average allelic imbalance fractions for the set of polymorphic loci. For example, in a particularly illustrative example, individual probabilities are generated by modeling ploidy states of a first homolog of the chromosome region and a second homolog of the chromosome region. The ploidy states that are modeled include the following:

(1) all cells have no deletion or amplification of the first homolog or the second homolog of the chromosome region;

(2) at least some cells have a deletion of the first homolog or an amplification of the second homolog of the chromosome region; and (3) at least some cells have a deletion of the second homolog or an amplification of the first homolog of the chromosome region.

It will be understood that the above models can also be referred to as hypothesis that are used to constrain a model. Therefore, demonstrated above are 3 hypothesis that can be used.

The average allelic imbalance fractions modeled can include any range of average allelic imbalance that includes the actual average allelic imbalance of the chromosomal region. For example, in certain illustrative embodiments, the range of average allelic imbalance that is modeled can be between 0, 0.1, 0.2, 0.25, 0.3, 0.4, 0.5, 0.6, 0.75, 1, 2, 2.5, 3, 4, and 5% on the low end, and 1, 2, 2.5, 3, 4, 5, 10, 15, 20, 25, 30, 40, 50, 60, 70 80 90, 95, and 99% on the high end. The intervals for the modeling with the range can be any interval depending on the computing power used and the time allowed for the analysis. For example, 0.01, 0.05, 0.02, or 0.1 intervals can be modeled.

In certain illustrative embodiments, the sample has an average allelic imbalance for the chromosomal region of between 0.4% and 5%. In certain embodiments, the average allelic imbalance is low. In these embodiments, average allelic imbalance is typically less than 10%. In certain illustrative embodiments, the allelic imbalance is between 0.25, 0.3, 0.4, 0.5, 0.6, 0.75, 1, 2, 2.5, 3, 4, and 5% on the low end, and 1, 2, 2.5, 3, 4, and 5% on the high end. In other exemplary embodiments, the average allelic imbalance is between 0.4, 0.45, 0.5, 0.6, 0.7, 0.8, 0.9, or 1.0 on the low end and 0.5, 0.6, 0.7, 0.8, 0.9, 1.0, 1.5, 2.0, 3.0, 4.0, or 5.0 on the high end. For example, the average allelic imbalance of the sample in an illustrative example is between 0.45 and 2.5%. In another example, the average allelic imbalance is detected with a sensitivity of 0.45, 0.5, 0.6, 0.8, 0.8, 0.9, or 1.0. In An exemplary sample with low allelic imbalance in methods of the present invention include plasma samples from individuals with cancer having circulating tumor DNA or plasma samples from pregnant females having circulating fetal DNA.

It will be understood that for SNVs, the proportion of abnormal DNA is typically measured using mutant allele frequency (number of mutant alleles at a locus/total number of alleles at that locus). Since the difference between the amounts of two homologs in tumours is analogous, we measure the proportion of abnormal DNA for a CNV by the average allelic imbalance (AAD, defined as $|(H1-H2)|/(H1+H2)$, where Hi is the average number of copies of homolog i in the sample and $Hi/(H1+H2)$ is the fractional abundance, or homolog ratio, of homolog i. The maximum homolog ratio is the homolog ratio of the more abundant homolog.

Assay drop-out rate is the percentage of SNPs with no reads, estimated using all SNPs. Single allele drop-out (ADO) rate is the percentage of SNPs with only one allele present, estimated using only heterozygous SNPs. Genotype confidence can be determined by fitting a binomial distribution to the number of reads at each SNP that were B-allele reads, and using the ploidy status of the focal region of the SNP to estimate the probability of each genotype.

Genotypic measurements are made during methods provided herein. Such measurements can be obtained by measuring signal intensities for different alleles for each of the SNPs using a SNP microarray or by allele frequency measurements using sequencing reactions, especially high throughput sequencing. Accordingly, genotypic measurements include allele frequency data and allele counts, for example. Genotypic measurements can be made by amplifying genetic material in the sample and then analyzing amplicons using SNP microarrays and/or high throughput sequencing.

In certain illustrative examples, the allele frequency data is corrected for errors before it is used to generate individual probabilities. In specific illustrative embodiments, the errors that are corrected include allele amplification efficiency bias. In other embodiments, the errors that are corrected include ambient contamination and genotyped contamination. In some embodiments, errors that are corrected include allele amplification bias, ambient contamination and genotype contamination. Analytical methods are provided herein, for correcting for such errors.

In certain embodiments, the individual probabilities are generated using a set of models of both different ploidy states and allelic imbalance fractions for the set of polymorphic loci. In these embodiments, and other embodiments, the joint probabilities are generated by considering the linkage between polymorphic loci on the chromosome region.

For tumor tissue samples, chromosomal aneuploidy (exemplified in this paragraph by CNVs) can be delineated by transitions between allele frequency distributions. In plasma samples, CNVs can be identified by a maximum likelihood algorithm that searches for plasma CNVs in regions where the tumor sample from the same individual also has CNVs, using haplotype information deduced from the tumor sample. This algorithm can model expected allelic frequencies across all allelic imbalance ratios at 0.025% intervals for three sets of hypotheses: (1) all cells are normal (no allelic imbalance), (2) some/all cells have a homolog 1 deletion or homolog 2 amplification, or (3) some/all cells have a homolog 2 deletion or homolog 1 amplification. The likelihood of each hypothesis can be determined at each SNP using a Bayesian classifier based on a beta binomial model of expected and observed allele frequencies at all heterozygous SNPs, and then the joint likelihood across multiple SNPs can be calculated, in certain illustrative embodiments taking linkage of the SNP loci into consideration, as exemplified herein. The maximum likelihood hypothesis can then be selected.

Consider a chromosomal region with an average of N copies in the tumor, and let c denote the fraction of DNA in plasma derived from the mixture of normal and tumor cells in a disomic region. AAI is calculated as:

$$AAI = \frac{c|N2|}{2 + c(N2)}$$

In certain illustrative examples, the allele frequency data is corrected for errors before it is used to generate individual probabilities. Different types of error and/or bias correction are disclosed herein. In specific illustrative embodiments, the errors that are corrected are allele amplification efficiency bias. In other embodiments, the errors that are corrected include ambient contamination and genotype contamination. In some embodiments, errors that are corrected include allele amplification bias, ambient contamination and genotype contamination.

It will be understood that allele amplification efficiency bias can be determined for an allele as part of an experiment or laboratory determination that includes an on test sample, or it can be determined at a different time using a set of samples that include the allele whose efficiency is being calculated. Ambient contamination and genotype contamination are typically determined on the same run as the on-test sample analysis.

In certain embodiments, ambient contamination and genotype contamination are determined for homozygous alleles in the sample. It will be understood that for any given sample from an individual some loci in the sample, will be heterozygous and others will be homozygous, even if a locus is selected for analysis because it has a relatively high heterozygosity in the population. It is advantageous in some embodiments, although ploidy of a chromosomal region can be determined using heterozygous loci for an individual. Homozygous loci can be used to calculate ambient and genotype contamination.

In certain illustrative examples, the selecting is performed by analyzing a magnitude of a difference between the phased allelic information and estimated allelic frequencies generated for the models.

In illustrative examples, the individual probabilities of allele frequencies are generated based on a beta binomial model of expected and observed allele frequencies at the set of polymorphic loci. In illustrative examples, the individual probabilities are generated using a Bayesian classifier.

In certain illustrative embodiments, the nucleic acid sequence data is generated by performing high throughput DNA sequencing of a plurality of copies of a series of amplicons generated using a multiplex amplification reaction, wherein each amplicon of the series of amplicons spans at least one polymorphic loci of the set of polymorphic loci and wherein each of the polymeric loci of the set is amplified. In certain embodiments, the multiplex amplification reaction is performed under limiting primer conditions for at least ½ of the reactions. In some embodiments, limiting primer concentrations are used in 1/10, 1/5, 1/4, 1/3, ½, or all of the reactions of the multiplex reaction. Provided herein are factors to consider to achieve limiting primer conditions in an amplification reaction such as PCR.

In certain embodiments, methods provided herein detect ploidy for multiple chromosomal regions across multiple chromosomes. Accordingly, the chromosomal ploidy in these embodiments is determined for a set of chromosome regions in the sample. For these embodiments, higher multiplex amplification reactions are needed. Accordingly, for these embodiments the multiplex amplification reaction can include, for example, between 2,500 and 50,000 multiplex reactions. In certain embodiments, the following ranges of multiplex reactions are performed: between 100, 200, 250, 500, 1000, 2500, 5000, 10,000, 20,000, 25000, 50000 on the low end of the range and between 200, 250, 500, 1000, 2500, 5000, 10,000, 20,000, 25000, 50000, and 100,000 on the high end of the range.

In illustrative embodiments, the set of polymorphic loci is a set of loci that are known to exhibit high heterozygosity. However, it is expected that for any given individual, some of those loci will be homozygous. In certain illustrative embodiments, methods of the invention utilize nucleic acid sequence information for both homozygous and heterozygous loci for an individual. The homozygous loci of an individual are used, for example, for error correction, whereas heterozygous loci are used for the determination of allelic imbalance of the sample. In certain embodiments, at least 10% of the polymorphic loci are heterozygous loci for the individual.

As disclosed herein, preference is given for analyzing target SNP loci that are known to be heterozygous in the population. Accordingly, in certain embodiments, polymorphic loci are chosen wherein at least 10, 20, 25, 50, 75, 80, 90, 95, 99, or 100% of the polymorphic loci are known to be heterozygous in the population.

In some examples, the method further comprises performing the method on a control sample with a known average allelic imbalance ratio. The control can have an average allelic imbalance ratio for a particular allelic state indicative of aneuploidy of the chromosome region, of between 0.4 and 10% to mimic an average allelic imbalance of an allele in a sample that is present in low concentrations, such as would be expected for a circulating free DNA from a fetus or from a tumor.

In certain embodiments of the methods of determining ploidy, the sample is a plasma sample from an individual suspected of having cancer. In these embodiments, the method further comprises determining based on the selecting whether copy number variation is present in cells of a tumor of the individual. For these embodiments, the sample can be a plasma sample from an individual. For these embodiments, the method can further include determining, based on the selecting, whether cancer is present in the individual.

These embodiments for determining ploidy of a chromosomal region, can further include detecting a single nucleotide variant at a single nucleotide variance location in a set of single nucleotide variance locations, wherein detecting either a chromosomal aneuploidy or the single nucleotide variant or both, indicates the presence of circulating tumor nucleic acids in the sample.

As disclosed herein, certain embodiments of the methods of determining ploidy can further include removing outliers from the initial or corrected allele frequency data before comparing the initial or the corrected allele frequencies to the set of models. For example, in certain embodiments, loci allele frequencies that are at least 2 or 3 standard deviations above or below the mean value for other loci on the chromosome region, are removed from the data before being used for the modeling.

As mentioned herein, it will be understood that for illustrative embodiments provided herein, including those for determining ploidy of a chromosomal region, imperfectly phased data is generated. It will also be understood, that provided herein are a number of features that provide improvements over prior methods for detecting ploidy, and that many different combinations of these features could be used. Furthermore, it will be understood that the plurality of polymorphic loci on a chromosome region can be linked loci since they are on the same chromosome region, and therefore have some statistical correlation for phasing estimates. However, within haploblocks, there is an increased statistical correlation of polymorphic loci with respect to phase estimation, because the loci exhibit a strong linkage disequilibrium, as disclosed herein.

In various embodiments, the phase of an individual's genetic data is estimated using data about the probability of chromosomes crossing over at different locations in a chromosome or chromosome region (such as using recombination data such as can be found in the HapMap database to create a recombination risk score for any interval) to model dependence between polymorphic alleles on the chromosome or chromosome region. In some embodiments, allele counts at the polymorphic loci are calculated on a computer based on sequencing data or SNP array data. A plurality of hypotheses each pertaining to a different possible state of the chromosome or chromosome region (such as an overrepresentation of the number of copies of a first homologous chromosome region as compared to a second homologous chromosome region in the genome of one or more cells from an individual, a duplication of the first homologous chromosome region, a deletion of the second homologous chromosome region, or an equal representation of the first and second homologous chromosome regions) can be created (such as creation on a computer); a model (such as a joint distribution model) for the expected allele counts at the polymorphic loci on the chromosome can be built (such as building on a computer) for each hypothesis; a relative probability of each of the hypotheses can be determined (such as determination on a computer) using the joint distribution model and the allele counts; and the hypothesis with the greatest probability can be selected. In some embodiments, building a joint distribution model for allele counts and the step of determining the relative probability of each hypothesis are done using a method that does not require the use of a reference chromosome.

In some embodiments, the analytical methods utilize a statistical technique selected from the group consisting of maximum likelihood estimation, maximum a-posteriori estimation, Bayesian estimation, dynamic estimation (such as dynamic Bayesian estimation), and expectation-maximization estimation. In some embodiments, the analytical methods estimate the ratio of DNA or RNA from the one or more target cells to the total DNA or RNA in the sample. In some embodiments, the ratio of DNA or RNA from the one or more target cells to the total DNA or RNA in the sample is assumed to be the same for two or more (or all) of the CNVs of interest. In some embodiments, the ratio of DNA or RNA from the one or more target cells to the total DNA or RNA in the sample is calculated for each CNV of interest. In some embodiments, the ratio of target DNA to total DNA in the sample utilizes maximum likelihood estimation, maximum a-posteriori estimation, Bayesian estimation, dynamic estimation (such as dynamic Bayesian estimation), and/or expectation-maximization estimation.

In some embodiments, phased genetic data is used to determine if there is an overrepresentation of the number of copies of a first homologous chromosome region as compared to a second homologous chromosome region in the genome of an individual (such as in the genome of one or more cells or in cfDNA or cfRNA). Exemplary overrepresentations include the duplication of the first homologous chromosome region or the deletion of the second homologous chromosome region. In some embodiments, there is not an overrepresentation since the first and homologous chromosome regions are present in equal proportions (such as one copy of each segment in a diploid sample). In some embodiments, calculated allele ratios in a nucleic acid sample are compared to expected allele ratios to determine if there is an overrepresentation as described further below. In this specification the phrase "a first homologous chromosome region as compared to a second homologous chromosome region" means a first homolog of a chromosome region and a second homolog of the chromosome region.

In some embodiments, the method involves calculating allele ratios for one or more loci in the set of polymorphic loci that are heterozygous in at least one cell from which the sample was derived (such as the loci that are heterozygous in the fetus and/or heterozygous in the mother). In some embodiments, the calculated allele ratio for a particular locus is the measured quantity of one of the alleles divided by the total measured quantity of all the alleles for the locus. In some embodiments, the calculated allele ratio for a particular locus is the measured quantity of one of the alleles (such as the allele on the first homologous chromosome region) divided by the measured quantity of one or more other alleles (such as the allele on the second homologous chromosome region) for the locus. The calculated allele ratios can be calculated using any of the methods described herein or any standard method (such as any mathematical transformation of the calculated allele ratios described herein).

In illustrative embodiments of the methods herein, the phase of genetic data generated from a sample, such as allele frequency data, are imperfectly estimated. In one embodiment, an individual's genetic data is phased using a computer program that uses population based haplotype frequencies to infer the most likely phase, such as HapMap-based phasing. For example, haploid data sets can be deduced directly from diploid data using statistical methods that utilize known haplotype blocks in the general population (such as those created for the public HapMap Project and for the Perlegen Human Haplotype Project). A haplotype block is essentially a series of correlated alleles that occur repeatedly in a variety of populations. Since these haplotype blocks are often ancient and common, they can be used to predict haplotypes from diploid genotypes. Publicly available algorithms that accomplish this task include an imperfect phylogeny approach, Bayesian approaches based on conjugate priors, and priors from population genetics. Some of these algorithms use a hidden Markov model.

In one embodiment, an individual's genetic data is phased using an algorithm that estimates haplotypes from genotype data, such as an algorithm that uses localized haplotype clustering (sec, e.g., Browning and Browning, "Rapid and Accurate Haplotype Phasing and Missing-Data Inference for Whole-Genome Association Studies By Use of Localized Haplotype Clustering" Am J Hum Genet. November 2007; 81(5): 1084-1097, which is hereby incorporated by reference in its entirety). An exemplary program is Beagle version: 3.3.2 or version 4 (available at the world wide web at hfaculty.washington.edu/browning/beagle/beagle.html, which is hereby incorporated by reference in its entirety).

In one embodiment, an individual's genetic data is phased using an algorithm that estimates haplotypes from genotype data, such as an algorithm that uses the decay of linkage disequilibrium with distance, the order and spacing of genotyped markers, missing-data imputation, recombination rate estimates, or a combination thereof (sec, e.g., Stephens and Scheet, "Accounting for Decay of Linkage Disequilibrium in Haplotype Inference and Missing-Data Imputation" Am. J. Hum. Genet. 76:449-462, 2005, which is hereby incorporated by reference in its entirety). An exemplary program is PHASE v.2.1 or v2.1.1. (available at the world wide web at stephenslab.uchicago.edu/software.html, which is hereby incorporated by reference in its entirety).

In one embodiment, an individual's genetic data is phased using an algorithm that estimates haplotypes from population genotype data, such as an algorithm that allows cluster memberships to change continuously along the chromosome according to a hidden Markov model. This approach is flexible, allowing for both "block-like" patterns of linkage disequilibrium and gradual decline in linkage disequilibrium with distance (sec, e.g., Scheet and Stephens, "A fast and flexible statistical model for large-scale population genotype data: applications to inferring missing genotypes and haplotypic phase." Am J Hum Genet, 78:629-644, 2006, which is hereby incorporated by reference in its entirety). An exemplary program is fastPHASE (available at the world wide web at stephenslab.uchicago.edu/software.html, which is hereby incorporated by reference in its entirety).

In one embodiment, an individual's genetic data is phased using a genotype imputation method, such as a method that uses one or more of the following reference datasets: HapMap dataset, datasets of controls genotyped on multiple SNP chips, and densely typed samples from the 1,000 Genomes Project. An exemplary approach is a flexible modelling framework that increases accuracy and combines information across multiple reference panels (sec, e.g., Howie, Donnelly, and Marchini (2009) "A flexible and accurate genotype imputation method for the next generation of genome-wide association studies." *PLoS Genetics* 5(6): e1000529, 2009, which is hereby incorporated by reference in its entirety). Exemplary programs are IMPUTE or IMPUTE version 2 (also known as IMPUTE2) (available at the world wide web at mathgen.stats.ox.ac.uk/impute/impute_v2.html, which is hereby incorporated by reference in its entirety).

In one embodiment, an individual's genetic data is phased using an algorithm that infers haplotypes, such as an algorithm that infers haplotypes under the genetic model of coalescence with recombination, such as that developed by Stephens in PHASE v2.1. The major algorithmic improvements rely on the use of binary trees to represent the sets of candidate haplotypes for each individual. These binary tree representations: (1) speed up the computations of posterior probabilities of the haplotypes by avoiding the redundant operations made in PHASE v2.1, and (2) overcome the exponential aspect of the haplotypes inference problem by the smart exploration of the most plausible pathways (i.e., haplotypes) in the binary trees (sec, e.g., Delancau, Coulonges and Zagury, "Shape-IT: new rapid and accurate algorithm for haplotype inference," BMC Bioinformatics 9:540, 2008 doi: 10.1186/1471-2105-9-540, which is hereby incorporated by reference in its entirety). An exemplary program is SHAPEIT (available at the world wide web at mathgen.stats.ox.ac.uk/genetics_software/shapeit/shapeit.html, which is hereby incorporated by reference in its entirety).

In one embodiment, an individual's genetic data is phased using an algorithm that estimates haplotypes from population genotype data, such as an algorithm that uses haplotype-fragment frequencies to obtain empirically based probabilities for longer haplotypes. In some embodiments, the algorithm reconstructs haplotypes so that they have maximal local coherence (sec, e.g., Eronen, Geerts, and Toivonen, "HaploRec: Efficient and accurate large-scale reconstruction of haplotypes," *BMC Bioinformatics* 7:542, 2006, which is hereby incorporated by reference in its entirety). An exemplary program is HaploRec, such as HaploRec version 2.3. (available at the world wide web at cs.helsinki.fi/group/genetics/haplotyping.html, which is hereby incorporated by reference in its entirety).

In one embodiment, an individual's genetic data is phased using an algorithm that estimates haplotypes from population genotype data, such as an algorithm that uses a partition-ligation strategy and an expectation-maximization-based algorithm (sec, e.g., Qin, Niu, and Liu, "Partition-Ligation-Expectation-Maximization Algorithm for Haplotype Inference with Single-Nucleotide Polymorphisms," Am J Hum Genet. 71(5): 1242-1247, 2002, which is hereby incorporated by reference in its entirety). An exemplary program is PL-EM (available at the world wide web at people.fas.harvard.edu/~junliu/plem/click.html, which is hereby incorporated by reference in its entirety).

In one embodiment, an individual's genetic data is phased using an algorithm that estimates haplotypes from population genotype data, such as an algorithm for simultaneously phasing genotypes into haplotypes and block partitioning. In some embodiments, an expectation-maximization algorithm is used (sec, e.g., Kimmel and Shamir, "GERBIL: Genotype Resolution and Block Identification Using Likelihood," Proceedings of the National Academy of Sciences of the United States of America (PNAS) 102: 158-162, 2005, which is hereby incorporated by reference in its entirety). An exemplary program is GERBIL, which is available as part of the GEVALT version 2 program (available at the world wide web at acgt.cs.tau.ac.il/gevalt/, which is hereby incorporated by reference in its entirety).

In one embodiment, an individual's genetic data is phased using an algorithm that estimates haplotypes from population genotype data, such as an algorithm that uses an EM algorithm to calculate ML estimates of haplotype frequencies given genotype measurements which do not specify phase. The algorithm also allows for some genotype measurements to be missing (due, for example, to PCR failure). It also allows multiple imputation of individual haplotypes (sec, e.g., Clayton, D. (2002), "SNPHAP: A Program for Estimating Frequencies of Large Haplotypes of SNPs", which is hereby incorporated by reference in its entirety). An exemplary program is SNPHAP (available at the world wide web at gene.cimr.cam.ac.uk/clayton/software/snphap.txt, which is hereby incorporated by reference in its entirety).

In one embodiment, an individual's genetic data is phased using an algorithm that estimates haplotypes from population genotype data, such as an algorithm for haplotype inference based on genotype statistics collected for pairs of SNPs. This software can be used for comparatively accurate phasing of large number of long genome sequences, e.g. obtained from DNA arrays. An exemplary program takes genotype matrix as an input, and outputs the corresponding haplotype matrix (sec, e.g., Brinza and Zelikovsky, "2SNP: scalable phasing based on 2-SNP haplotypes," Bioinformatics.22(3):371-3, 2006, which is hereby incorporated by reference in its entirety). An exemplary program is 2SNP (available at the world wide web at alla.cs.gsu.edu/~software/2SNP, which is hereby incorporated by reference in its entirety).

Accordingly, in certain embodiments, publicly available programs, such as those disclosed above, can be utilized to estimate the phase genetic data such as allele frequency data from the sample. The Examples provided herein utilize imperfect haplotyping and demonstrate that haplotyping is more accurate within haploblocks. Therefore, by choosing loci within haploblocks for analysis of ploidy (e.g. CNV detection, ploidy determination, or AAI determination), improved results are obtained from those using imperfectly phased information that is from outside haploblocks. These methods for estimating phase of genetic data provided by the various methods disclosed herein, when used in illustrative embodiments, provide the value for c that is used in the Combined_Likelihoods equation provided herein.

In some embodiments, the method involves determining if there is an overrepresentation of the number of copies of the first homologous chromosome region by comparing one or more calculated allele ratios for a locus to an allele ratio that is expected for that locus if the first and second homologous chromosome regions are present in equal proportions. In some embodiments, the expected allele ratio assumes the possible alleles for a locus have an equal likelihood of being present. In some embodiments in which the calculated allele ratio for a particular locus is the measured quantity of one of the alleles divided by the total measured quantity of all the alleles for the locus, the corresponding expected allele ratio is 0.5 for a biallelic locus, or ⅓ for a triallelic locus. In some embodiments, the expected allele ratio is the same for all the loci, such as 0.5 for all loci. In some embodiments, the expected allele ratio assumes that the possible alleles for a locus can have a different likelihood of being present, such as the likelihood based on the frequency of each of the alleles in a particular population that the subject belongs in, such as a population based on the ancestry of the subject. Such allele frequencies are publicly available (sec, e.g., HapMap Project; Perlegen Human Haplotype Project; web at ncbi.nlm.nih.gov/projects/SNP/; Sherry S T, Ward M H, Kholodov M, et al. dbSNP: the NCBI database of genetic variation. Nucleic Acids Res. 2001 Jan. 1; 29(1):308-11, which are each incorporated by reference in its entirety). In some embodiments, the expected allele ratio is the allele ratio that is expected for the particular individual being tested for a particular hypothesis specifying the degree of overrepresentation of the first homologous chromosome region. For example, the expected allele ratio for a particular individual can be determined based on phased or unphased genetic data from the individual (such as from a sample from the individual that is unlikely to have a deletion or duplication such as a noncancerous sample) or data from one or more relatives from the individual. In some embodiments for prenatal testing, the expected allele ratio is the allele ratio that is expected for a mixed sample that includes DNA or RNA from the pregnant mother and the fetus (such as a maternal plasma or serum sample that includes cfDNA from the mother and cfDNA from the fetus) for a particular hypothesis specifying the degree of overrepresentation of the first homologous chromosome region. For example, the expected allele ratio for the mixed sample can be determined based on genetic data from the mother and predicted genetic data for the fetus (such as predictions for alleles that the fetus may have inherited from the mother and/or father). The expected allele ratios can be calculated using any of the methods described herein or any standard method (such as any mathematical transformation of the expected allele ratios described herein) or methods provided in U.S. Publication No 2012/0270212, filed Nov. 18, 2011.

In some embodiments, a calculated allele ratio is indicative of an overrepresentation of the number of copies of the first homologous chromosome region if either (i) the allele ratio for the measured quantity of the allele present at that locus on the first homologous chromosome divided by the total measured quantity of all the alleles for the locus is greater than the expected allele ratio for that locus, or (ii) the allele ratio for the measured quantity of the allele present at that locus on the second homologous chromosome divided by the total measured quantity of all the alleles for the locus is less than the expected allele ratio for that locus. In some embodiments, a calculated allele ratio is only considered indicative of overrepresentation if it is significantly greater or lower than the expected ratio for that locus. In some embodiments, a calculated allele ratio is indicative of no overrepresentation of the number of copies of the first homologous chromosome region if either (i) the allele ratio for the measured quantity of the allele present at that locus on the first homologous chromosome divided by the total measured quantity of all the alleles for the locus is less than or equal to the expected allele ratio for that locus, or (ii) the allele ratio for the measured quantity of the allele present at that locus on the second homologous chromosome divided by the total measured quantity of all the alleles for the locus is greater than or equal to the expected allele ratio for that locus. In some embodiments, calculated ratios equal to the corresponding expected ratio are ignored (since they are indicative of no overrepresentation).

In various embodiments, one or more of the following methods is used to compare one or more of the calculated allele ratios to the corresponding expected allele ratio(s). In some embodiments, one determines whether the calculated allele ratio is above or below the expected allele ratio for a particular locus irrespective of the magnitude of the difference. In some embodiments, one determines the magnitude of the difference between the calculated allele ratio and the expected allele ratio for a particular locus irrespective of whether the calculated allele ratio is above or below the expected allele ratio. In some embodiments, one determines whether the calculated allele ratio is above or below the expected allele ratio and the magnitude of the difference for a particular locus. In some embodiments, one determines whether the average or weighted average value of the calculated allele ratios is above or below the average or weighted average value of the expected allele ratios irrespective of the magnitude of the difference. In some embodiments, one determines the magnitude of the difference between the average or weighted average value of the calculated allele ratios and the average or weighted average value of the expected allele ratios irrespective of whether the average or weighted average of the calculated allele ratio is above or below the average or weighted average value of the expected allele ratio. In some embodiments, one determines whether the average or weighted average value of the calculated allele ratios is above or below the average or weighted average value of the expected allele ratios and the magnitude of the difference. In some embodiments, one determines an average or weighted average value of the magnitude of the difference between the calculated allele ratios and the expected allele ratios.

In some embodiments, the magnitude of the difference between the calculated allele ratio and the expected allele ratio for one or more loci is used to determine whether the overrepresentation of the number of copies of the first homologous chromosome region is due to a duplication of the first homologous chromosome region or a deletion of the second homologous chromosome region in the genome of one or more of the cells.

In some embodiments, an overrepresentation of the number of copies of the first homologous chromosome region is determined to be present if one or more of following conditions is met. In some embodiments, the number of calculated allele ratios that are indicative of an overrepresentation of the number of copies of the first homologous chromosome region is above a threshold value. In some embodiments, the number of calculated allele ratios that are indicative of no overrepresentation of the number of copies of the first homologous chromosome region is below a threshold value. In some embodiments, the magnitude of the difference between the calculated allele ratios that are indicative of an overrepresentation of the number of copies of the first homologous chromosome region and the corresponding expected allele ratios is above a threshold value. In some embodiments, for all calculated allele ratios that are indicative of overrepresentation, the sum of the magnitude of the difference between a calculated allele ratio and the corresponding expected allele ratio is above a threshold value. In some embodiments, the magnitude of the difference between the calculated allele ratios that are indicative of no overrepresentation of the number of copies of the first homologous chromosome region and the corresponding expected allele ratios is below a threshold value. In some embodiments, the average or weighted average value of the calculated allele ratios for the measured quantity of the allele present on the first homologous chromosome divided by the total measured quantity of all the alleles for the locus is greater than the average or weighted average value of the expected allele ratios by at least a threshold value. In some embodiments, the average or weighted average value of the calculated allele ratios for the measured quantity of the allele present on the second homologous chromosome divided by the total measured quantity of all the alleles for the locus is less than the average or weighted average value of the expected allele ratios by at least a threshold value. In some embodiments, the data fit between the calculated allele ratios and allele ratios that are predicted for an overrepresentation of the number of copies of the first homologous chromosome region is below a threshold value (indicative of a good data fit). In some embodiments, the data fit between the calculated allele ratios and allele ratios that are predicted for no overrepresentation of the number of copies of the first homologous chromosome region is above a threshold value (indicative of a poor data fit).

In some embodiments, an overrepresentation of the number of copies of the first homologous chromosome region is determined to be absent if one or more of following conditions is met. In some embodiments, the number of calculated allele ratios that are indicative of an overrepresentation of the number of copies of the first homologous chromosome region is below a threshold value. In some embodiments, the number of calculated allele ratios that are indicative of no overrepresentation of the number of copies of the first homologous chromosome region is above a threshold value. In some embodiments, the magnitude of the difference between the calculated allele ratios that are indicative of an overrepresentation of the number of copies of the first homologous chromosome region and the corresponding expected allele ratios is below a threshold value. In some embodiments, the magnitude of the difference between the calculated allele ratios that are indicative of no overrepresentation of the number of copies of the first homologous chromosome region and the corresponding expected allele ratios is above a threshold value. In some embodiments, the average or weighted average value of the calculated allele ratios for the measured quantity of the allele present on the first homologous chromosome divided by the total measured quantity of all the alleles for the locus minus the average or weighted average value of the expected allele ratios is less than a threshold value. In some embodiments, the average or weighted average value of the expected allele ratios minus the average or weighted average value of the calculated allele ratios for the measured quantity of the allele present on the second homologous chromosome divided by the total measured quantity of all the alleles for the locus is less than a threshold value. In some embodiments, the data fit between the calculated allele ratios and allele ratios that are predicted for an overrepresentation of the number of copies of the first homologous chromosome region is above a threshold value. In some embodiments, the data fit between the calculated allele ratios and allele ratios that are predicted for no overrepresentation of the number of copies of the first homologous chromosome region is below a threshold value. In some embodiments, the threshold is determined from empirical testing of samples known to have a CNV of interest and/or samples known to lack the CNV.

In some embodiments, determining if there is an overrepresentation of the number of copies of the first homologous chromosome region includes enumerating a set of one or more hypotheses specifying the degree of overrepresentation of the first homologous chromosome region. On exemplary hypothesis is the absence of an overrepresentation since the first and homologous chromosome regions are present in equal proportions (such as one copy of each segment in a diploid sample). Other exemplary hypotheses include the first homologous chromosome region being duplicated one or more times (such as 1, 2, 3, 4, 5, or more extra copies of the first homologous chromosome compared to the number of copies of the second homologous chromosome region). Another exemplary hypothesis includes the deletion of the second homologous chromosome region. Yet another exemplary hypothesis is the deletion of both the first and the second homologous chromosome regions. In some embodiments, predicted allele ratios for the loci that are heterozygous in at least one cell (such as the loci that are heterozygous in the fetus and/or heterozygous in the mother) are estimated for each hypothesis given the degree of overrepresentation specified by that hypothesis. In some embodiments, the likelihood that the hypothesis is correct is calculated by comparing the calculated allele ratios to the predicted allele ratios, and the hypothesis with the greatest likelihood is selected.

Exemplary Methods for Predicting Allele Ratios

Exemplary methods are discussed below for calculating expected allele ratios for a sample. Table 3 shows expected allele ratios for a mixed sample (such as a maternal blood sample) containing nucleic acids from both the mother and the fetus. These expected allele ratios indicate what is expected for measurement of the total amount of each allele, including the amount of the allele from both maternal nucleic acids and fetal nucleic acids in the mixed sample. In an example, the mother is heterozygous at two neighboring loci that are expected to cosegregate (e.g., two loci for which no chromosome crossovers are expected between the loci). Thus, the mother is (AB, AB). Now imagine that the phased data for the mother indicates that for one haplotype she is (A, A); thus, for the other haplotype one can infer that she is (B, B). Table 3 gives the expected allele ratios for different hypotheses where the fetal fraction is 20%. For this example, no knowledge of the paternal data is assumed, and the heterozygosity rate is assumed to be 50%. The expected allele ratios are given in terms of (expected proportion of A reads/total number of reads) for each of the two SNPs. These ratios are calculated both using maternal phased data (the knowledge that one haplotype is (A, A) and one is (B, B)) and without using the maternal phased data. Table 3 includes different hypotheses for the number of copies of the chromosome region in the fetus from each parent.

TABLE 3

Expected Genetic Data for Mixed Sample of Maternal and Fetal Nucleic Acids

| Copy Number Hypothesis | Expected allele ratios when using maternal phased data | | Expected allele ratios when not using maternal phased data | |
|---|---|---|---|---|
| Monosomy (maternal copy missing) | (0.444; 0.444) | | (0.444; 0.444) | |
| | (0.444; 0.555) | | (0.444; 0.555) | |
| | (0.555; 0.444) | | (0.555; 0.444) | |
| | (0.555; 0.555) | | (0.555; 0.555) | |
| Monosomy (paternal copy missing) | (0.444; 0.444) | | (0.444; 0.444) | |
| | (0.555; 0.555) | | (0.444; 0.555) | |
| | | | (0.555; 0.444) | |
| | | | (0.555; 0.555) | |
| Disomy | (0.40; 0.40) | | (0.40; 0.40) | (0.50; 0.60) |
| | (0.40; 0.50) | | (0.40; 0.50) | (0.60; 0.40) |
| | (0.50; 0.40) | | (0.40; 0.60) | (0.60; 0.50) |
| | (0.50; 0.50) | | (0.50; 0.40) | (0.60; 0.60) |
| | (0.50; 0.60) | | (0.50; 0.50) | |
| | (0.60; 0.50) | | | |
| | (0.60; 0.60) | | | |
| Trisomy (extra matching maternal copy) | (0.36; 0.36) | | (0.36; 0.36) | (0.54; 0.36) |
| | (0.36; 0.45) | | (0.36; 0.45) | (0.54; 0.45) |
| | (0.45; 0.36) | | (0.36; 0.54) | (0.54; 0.54) |
| | (0.45; 0.45) | | (0.36; 0.63) | (0.54; 0.63) |
| | (0.54; 0.54) | | (0.45; 0.36) | (0.63; 0.36) |
| | (0.54; 0.63) | | (0.45; 0.45) | (0.63; 0.45) |
| | (0.63; 0.54) | | (0.45; 0.54) | (0.63; 0.54) |
| | (0.63; 0.63) | | (0.45; 0.63) | (0.63; 0.63) |
| Trisomy (extra unmatching maternal copy) | (0.45, 0.45) | | (0.36; 0.36) | (0.54; 0.36) |
| | (0.45; 0.54) | | (0.36; 0.45) | (0.54; 0.45) |
| | (0.54; 0.45) | | (0.36; 0.54) | (0.54; 0.54) |
| | (0.54; 0.54) | | (0.36; 0.63) | (0.54; 0.63) |
| | | | (0.45; 0.36) | (0.63; 0.36) |
| | | | (0.45; 0.45) | (0.63; 0.45) |
| | | | (0.45; 0.54) | (0.63; 0.54) |
| | | | (0.45; 0.63) | (0.63; 0.63) |
| Trisomy (extra matching paternal copy) | (0.36; 0.36) | | (0.36; 0.36) | (0.54; 0.36) |
| | (0.36; 0.54) | | (0.36; 0.45) | (0.54; 0.45) |
| | (0.54; 0.36) | | (0.36; 0.54) | (0.54; 0.54) |
| | (0.54; 0.54) | | (0.36; 0.63) | (0.54; 0.63) |
| | (0.45; 0.45) | | (0.45; 0.36) | (0.63; 0.36) |
| | (0.45; 0.63) | | (0.45; 0.45) | (0.63; 0.45) |
| | (0.63; 0.45) | | (0.45; 0.54) | (0.63; 0.54) |
| | (0.63; 0.63) | | (0.45; 0.63) | (0.63; 0.63) |
| Trisomy (extra unmatching paternal copy) | (0.36; 0.36) | (0.54; 0.36) | (0.36; 0.36) | (0.54; 0.36) |
| | (0.36; 0.45) | (0.54; 0.45) | (0.36; 0.45) | (0.54; 0.45) |
| | (0.36; 0.54) | (0.54; 0.54) | (0.36; 0.54) | (0.54; 0.54) |
| | (0.36; 0.63) | (0.54; 0.63) | (0.36; 0.63) | (0.54; 0.63) |
| | (0.45; 0.36) | (0.63; 0.36) | (0.45; 0.36) | (0.63; 0.36) |
| | (0.45; 0.45) | (0.63; 0.45) | (0.45; 0.45) | (0.63; 0.45) |
| | (0.45; 0.54) | (0.63; 0.54) | (0.45; 0.54) | (0.63; 0.54) |
| | (0.45; 0.63) | (0.63; 0.63) | (0.45; 0.63) | (0.63; 0.63) |

In addition to the fact that using phased data reduces the number of possible expected allele ratios, it also changes the prior likelihood of each of the expected allele ratios, such that the maximum likelihood result is more likely to be correct. Eliminating expected allele ratios or hypotheses that are not possible increases the likelihood that the correct hypothesis will be chosen. As an example, suppose the measured allele ratios are (0.41, 0.59). Without using phased data, one might assume that the hypothesis with maximum likelihood is a disomy hypothesis (given the similarity of the measured allele ratios to expected allele ratios of (0.40, 0.60) for disomy). However, using phased data, one can exclude (0.40, 0.60) as expected allele ratios for the disomy hypothesis, and one can select a trisomy hypothesis as more likely.

Assume the measured allele ratios are (0.4, 0.4). Without any haplotype information, the probability of a maternal deletion at each SNP would be 0.5×P(A deleted)+0.5×P(B deleted). Therefore, although it looks like A is deleted (missing in the fetus), the likelihood of deletion would be the average of the two. For high enough fetal fraction, one can still determine the most likely hypothesis. For low enough fetal fraction, averaging may work in disfavor of the deletion hypothesis. However, with haplotype information, the probability of homolog 1 being deleted, P(A deleted), is greater and will fit the measured data better. If desired, crossover probabilities between the two loci can also be considered.

Further Detailed Exemplary Embodiments of Analytical Methods

Exemplary Test Statistic for Analysis of Phased Data

An exemplary test statistic is described below for analysis of phased data from a sample known or suspected of being a mixed sample containing DNA or RNA that originated from two or more cells that are not genetically identical. Let f denote the fraction of DNA or RNA of interest, for example the fraction of DNA or RNA with a CNV of interest, or the fraction of DNA or RNA from cells of interest, such as cancer cells. In some embodiments for prenatal testing, f denotes the fraction of fetal DNA, RNA, or cells in a mixture of fetal and maternal DNA, RNA, or cells. In other embodiments, f denotes the fraction of ctDNA DNA, RNA, or cells in a mixture of ctDNA and DNA, RNA, or cells from non-cancerous cells of the individual. Note that this refers to the fraction of DNA from cells of interest assuming two copies of DNA are given by each cell of interest. This differs from the DNA fraction from cells of interest at a segment that is deleted or duplicated.

The possible allelic values of each SNP are denoted A and B. AA, AB, BA, and BB are used to denote all possible ordered allele pairs. In some embodiments, SNPs with ordered alleles AB or BA are analyzed. Let $N_i$ denote the number of sequence reads of the ith SNP, and $A_i$ and $B_i$ denote the number of reads of the ith SNP that indicate allele A and B, respectively. It is assumed:

$$N_i = A_i + B_i.$$

The allele ratio $R_i$ is defined:

$$R_i \triangleq \frac{A_i}{N_i}.$$

Let T denote the number of SNPs targeted.

Without loss of generality, some embodiments focus on a single chromosome region. As a matter of further clarity, in this specification the phrase "a first homologous chromosome region as compared to a second homologous chromosome region" means a first homolog of a chromosome region and a second homolog of the chromosome region. In some such embodiments, all of the target SNPs are contained in the segment chromosome of interest. In other embodiments, multiple chromosome regions are analyzed for possible copy number variations.

Map Estimation

This method leverages the knowledge of phasing via ordered alleles to detect the deletion or duplication of the target segment. For each SNP i, define $$X_i \triangleq \begin{cases} 1 & R_i < 0.5 \text{ and } SNP\ i\ AB \\ 0 & R_i \geq 0.5 \text{ and } SNP\ i\ AB \\ 0 & R_i < 0.5 \text{ and } SNP\ i\ BA \\ 1 & R_i \geq 0.5 \text{ and } SNP\ i\ BA \end{cases}$$

Then define $$S \triangleq \sum_{All\ SNPs} X_i.$$

The distributions of the $X_i$ and S under various copy number hypotheses (such as hypotheses for disomy, deletion of the first or second homolog, or duplication of the first or second homolog) are described below.

Disomy Hypothesis

Under the hypothesis that the target segment is not deleted or duplicated, $$X_i = \begin{cases} 0 & wp\ 1 - p\left(\frac{1}{2}, N_i\right) \\ 1 & wp\ p\left(\frac{1}{2}, N_i\right) \end{cases}$$

where $$p(b, n) \triangleq Pr\left\{X \sim Bino(b, n) \geq \frac{n}{2}\right\}.$$

If we assume a constant depth of read N, this gives us a Binomial distribution S with parameters $$p\left(\frac{1}{2}, N\right)$$

and T.

Deletion Hypotheses

Under the hypothesis that the first homolog is deleted (i.e., an AB SNP becomes B, and a BA SNP becomes A), then $R_i$ has a Binomial distribution with parameters $$1 - \frac{1}{2 - f}$$

and T for AB SNPs, and $$\frac{1}{2 - f}$$

and T for BA SNPs. Therefore, $$X_i = \begin{cases} 0 & wp\ 1 - p\left(\frac{1}{2 - f}, N_i\right) \\ 1 & wp\ p\left(\frac{1}{2 - f}, N_i\right) \end{cases}$$

If we assume a constant depth of read N, this gives a Binomial distribution S with parameters $$p\left(\frac{1}{2 - f}, N\right)$$

and T.

Under the hypothesis that the second homolog is deleted (i.e., an AB SNP becomes A, and a BA SNP becomes B), then $R_i$ has a Binomial distribution with parameters $$\frac{1}{2 - f}$$

and T for AB SNPs, and $$1 - \frac{1}{2 - f}$$

and T for BA SNPs. Therefore, $$X_i = \begin{cases} 0 & wp\ p\left(\frac{1}{2 - f}, N_i\right) \\ 1 & wp\ 1 - p\left(\frac{1}{2 - f}, N_i\right) \end{cases}$$

If we assume a constant depth of read N, this gives a Binomial distribution S with parameters $$1 - p\left(\frac{1}{2 - f}, N\right)$$

and T.

Duplication Hypotheses

Under the hypothesis that the first homolog is duplicated (i.e., an AB SNP becomes AAB, and a BA SNP becomes BBA), then $R_i$ has a Binomial distribution with parameters $$\frac{1 + f}{2 + f}$$

and T for AB SNPs, and $$1 - \frac{1 + f}{2 + f}$$

and T for BA SNPs. Therefore, $$X_i = \begin{cases} 0 & wp\ p\left(\frac{1+f}{2+f}, N_i\right) \\ 1 & wp\ 1 - p\left(\frac{1+F}{2+f}, N_i\right) \end{cases}$$

If we assume a constant depth of read N, this gives us a Binomial distribution S with parameters $$1 - p\left(\frac{1+f}{2+f}, N\right)$$

and T.

Under the hypothesis that the second homolog is duplicated (i.e., an AB SNP becomes ABB, and a BA SNP becomes BAA), then $R_i$ has a Binomial distribution with parameters $$1 - \frac{1+f}{2+f}$$

and T for AB SNPs, and $$\frac{1+f}{2+f}$$

and T for BA SNPs. Therefore, $$X_i = \begin{cases} 0 & wp\ 1 - p\left(\frac{1+f}{2+f}, N_i\right) \\ 1 & wp\ p\left(\frac{1+f}{2+f}, N_i\right) \end{cases}$$

If we assume a constant depth of read N, this gives a Binomial distribution S with parameters $$p\left(\frac{1+f}{2+f}, N\right)$$

and T.

Classification

As demonstrated in the sections above, $X_i$ is a binary random variable with $$Pr\{X_1 = 1\} = \begin{cases} p\left(\frac{1}{2}, N_i\right) & \text{given disomy} \\ p\left(\frac{1}{2-f}, N_i\right) & \text{homolog 1 deletion} \\ 1 - p\left(\frac{1}{2-f}, N_i\right) & \text{homolog 2 deletion} \\ 1 - p\left(\frac{1+f}{2+f}, N_i\right) & \text{homolog 1 duplication} \\ p\left(\frac{1+f}{2+f}, N_i\right) & \text{homolog 2 duplication} \end{cases}$$

This allows one to calculate the probability of the test statistic S under each hypothesis. The probability of each hypothesis given the measured data can be calculated. In some embodiments, the hypothesis with the greatest probability is selected. If desired, the distribution on S can be simplified by either approximating each $N_i$ with a constant depth of reach N or by truncating the depth of reads to a constant N. This simplification gives $$S \sim \begin{cases} Bino\left(p\left(\frac{1}{2}, N\right), T\right) & \text{given disomy} \\ Bino\left(p\left(\frac{1}{2-f}, N\right), T\right) & \text{homolog 1 deletion} \\ Bino\left(1 - p\left(\frac{1}{2-f}, N\right), T\right) & \text{homolog 2 deletion} \\ Bino\left(1 - p\left(\frac{1+f}{2+f}, N\right), T\right) & \text{homolog 1 duplication} \\ Bino\left(p\left(\frac{1+f}{2+f}, N\right), T\right) & \text{homolog 2 duplication} \end{cases}$$

The value for f can be estimate by selecting the most likely value of f given the measured data, such as the value of f that generates the best data fit using an algorithm (e.g., a search algorithm) such as maximum likelihood estimation, maximum a-posteriori estimation, or Bayesian estimation. In some embodiments, multiple chromosome regions are analyzed and a value for f is estimated based on the data for each segment. If all the target cells have these duplications or deletions, the estimated values for f based on data for these different segments are similar. In some embodiments, f is experimentally measured such as by determining the fraction of DNA or RNA from cancer cells based on methylation differences (hypomethylation or hypermethylation) between cancer and non-cancerous DNA or RNA.

In some embodiments for mixed samples of fetal and maternal nucleic acids, the value of f is the fetal fraction, that is the fraction of fetal DNA (or RNA) out of the total amount of DNA (or RNA) in the sample. In some embodiments, the fetal fraction is determined by obtaining genotypic data from a maternal blood sample (or fraction thereof) for a set of polymorphic loci on at least one chromosome that is expected to be disomic in both the mother and the fetus; creating a plurality of hypotheses each corresponding to different possible fetal fractions at the chromosome; building a model for the expected allele measurements in the blood sample at the set of polymorphic loci on the chromosome for possible fetal fractions; calculating a relative probability of each of the fetal fractions hypotheses using the model and the allele measurements from the blood sample or fraction thereof; and determining the fetal fraction in the blood sample by selecting the fetal fraction corresponding to the hypothesis with the greatest probability. In some embodiments, the fetal fraction is determined by identifying those polymorphic loci where the mother is homozygous for a first allele at the polymorphic locus, and the father is (i) heterozygous for the first allele and a second allele or (ii) homozygous for a second allele at the polymorphic locus; and using the amount of the second allele detected in the blood sample for each of the identified polymorphic loci to determine the fetal fraction in the blood sample (sec, e.g., US Publ. No. 2012/0185176, filed Mar. 29, 2012, and US Pub. No. 2014/0065621, filed Mar. 13, 2013 which are each incorporated herein by reference in their entirety).

Another method for determining fetal fraction includes using a high throughput DNA sequencer to count alleles at a large number of polymorphic (such as SNP) genetic loci and modeling the likely fetal fraction (sec, for example, US Publ. No. 2012/0264121, which is incorporated herein by reference in its entirety). Another method for calculating fetal fraction can be found in Sparks et al., "Noninvasive prenatal detection and selective analysis of cell-free DNA obtained from maternal blood: evaluation for trisomy 21 and trisomy 18," Am J Obstet Gynecol 2012; 206:319.el-9, which is incorporated herein by reference in its entirety. In some embodiments, fetal fraction is determined using a methylation assay (sec, e.g., U.S. Pat. Nos. 7,754,428; 7,901,884; and 8,166,382, which are each incorporated herein by reference in their entirety) that assumes certain loci are methylated or preferentially methylated in the fetus, and those same loci are unmethylated or preferentially unmethylated in the mother.

FIGS. 1A-13D are graphs showing the distribution of the test statistic S divided by T (the number of SNPs) ("S/T") for various copy number hypotheses for various depth of reads and tumor fractions (where f is the fraction of tumor DNA out of total DNA) for an increasing number of SNPs.

Single Hypothesis Rejection

The distribution of S for the disomy hypothesis does not depend on f. Thus, the probability of the measured data can be calculated for the disomy hypothesis without calculating f. A single hypothesis rejection test can be used for the null hypothesis of disomy. In some embodiments, the probability of S under the disomy hypothesis is calculated, and the hypothesis of disomy is rejected if the probability is below a given threshold value (such as less than 1 in 1,000). This indicates that a duplication or deletion of the chromosome region is present. If desired, the false positive rate can be altered by adjusting the threshold value.

Illustrative Methods for Analysis of Phased Data

Exemplary methods are described below for analysis of data from a sample known or suspected of being a mixed sample containing DNA or RNA that originated from two or more cells that are not genetically identical. In some embodiments, phased data is used. In some embodiments, the method involves determining, for each calculated allele ratio, whether the calculated allele ratio is above or below the expected allele ratio and the magnitude of the difference for a particular locus. In some embodiments, a likelihood distribution is determined for the allele ratio at a locus for a particular hypothesis and the closer the calculated allele ratio is to the center of the likelihood distribution, the more likely the hypothesis is correct. In some embodiments, the method involves determining the likelihood that a hypothesis is correct for each locus. In some embodiments, the method involves determining the likelihood that a hypothesis is correct for each locus, and combining the probabilities of that hypothesis for each locus, and the hypothesis with the greatest combined probability is selected. In some embodiments, the method involves determining the likelihood that a hypothesis is correct for each locus and for each possible ratio of DNA or RNA from the one or more target cells to the total DNA or RNA in the sample. In some embodiments, a combined probability for each hypothesis is determined by combining the probabilities of that hypothesis for each locus and each possible ratio, and the hypothesis with the greatest combined probability is selected.

The following paragraphs set out a specific non-limiting example of specific analytical considerations for practicing a quantitative, allelic method of the present invention, for determining copy number, ploidy, AAI and/or detecting aneuploidy and/or CNV, referred to herein as the Allelic_Analysis_Example. The following hypotheses are considered: $H_{11}$ (all cells are normal), $H_{10}$ (presence of cells with only homolog 1, hence homolog 2 deletion), $H_{01}$ (presence of cells with only homolog 2, hence homolog 1 deletion), $H_{21}$ (presence of cells with homolog 1 duplication), $H_{12}$ (presence of cells with homolog 2 duplication). For a fraction f of target cells such as cancer cells or mosaic cells (or the fraction of DNA or RNA from the target cells), the expected allele ratio for heterozygous (AB or BA) SNPs can be found as follows:

$$r(AB, H_{11}) = r(BA, H_{11}) = 0.5, \qquad \text{Equation (1)}$$

$$r(AB, H_{10}) = r(BA, H_{01}) = \frac{1}{2-f},$$

$$r(AB, H_{01}) = r(BA, H_{10}) = \frac{1-f}{2-f},$$

$$r(AB, H_{21}) = r(BA, H_{12}) = \frac{1+f}{2+f},$$

$$r(AB, H_{12}) = r(BA, H_{21}) = \frac{1}{2+f}.$$

Bias, Contamination, and Sequencing Error Correction:

A method of the invention, such as the exemplary Allelic_Analysis_Example, can then consider bias, contamination and sequencing error correction. For example, the observation that $D_s$ at the SNP can include the number of original mapped reads with each allele present, $n_A^0$ and $n_0^B$. Then, one can find the corrected reads $n_A$ and $n_B$ using the expected bias in the amplification of A and B alleles.

Let $c_a$ denote the ambient contamination (such as contamination from DNA in the air or environment) and $r(c_a)$ to denote the allele ratio for the ambient contaminant (which is taken to be 0.5 initially). Moreover, $c_g$ denotes the genotyped contamination rate (such as the contamination from another sample), and $r(c_g)$ is the allele ratio for the contaminant. Let $s_e(A,B)$ and $s_e(B,A)$ denote the sequencing errors for calling one allele a different allele (such as by erroneously detecting an A allele when a B allele is present).

One can find the observed allele ratio $q(r, c_a, r(c_a), c_g, r(c_g), s_e(A,B), s_e(B,A))$ for a given expected allele ratio r by correcting for ambient contamination, genotyped contamination, and sequencing error.

Since the contaminant genotypes are unknown, population frequencies can be used to find $P(r(c_g))$. More specifically, let p be the population frequency for one of the alleles (which can be referred to as a reference allele). Then, we have $P(r(c_g)=0)=(1-p)^2$, $P(r(c_g)=0)=2p(1-p)$, and $P(r(c_g)=0)=p^2$. The conditional expectation over $r(c_g)$ can be used to determine the $E[q(r, c_a, r(c_a), c_g, r(c_g), s_e(A,B), s_e(B,A))]$. Note that the ambient and genotyped contamination are determined using the homozygous SNPs, hence they are not affected by the absence or presence of deletions or duplications. Moreover, it is possible to measure the ambient and genotyped contamination using a reference chromosome if desired.

Likelihood at each SNP:

In the methods provided herein, a likelihood at each SNP can be determined. The equation below, Equation (2), gives the probability using a binomial analysis of observing $n_A$ and $n_B$ given an allele ratio r:

$$P(n_A, n_B \mid r) = p_{bino}(n_A; n_A + n_B, r) = \binom{n_A + n_B}{n_A} r^{n_A}(1-r)^{n_B}. \qquad (2)$$

Let $D_s$ denote the data for SNP s. For each hypothesis $h \in \{H_{11}, H_{01}, H_{10}, H_{21}, H_{12}\}$, one can let r=r(AB,h) or r=r(BA,h) in the equation (1) and find the conditional expectation over $r(c_g)$ to determine the observed allele ratio $E[q(r, c_a, r(c_a), c_g, r(c_g))]$. Then, letting $r=E[q(r, c_a, r(c_a), c_g, r(c_g), s_e(A,B), s_e(B,A))]$ in equation (2) one can determine $P(D_s|h,f)$.

Methods of the present invention, such as the Allelic_Analysis_Example, can use a beta-binomial distribution. Equation (3) gives the likelihood of observing $n_A$ and $n_B$ given an expected allele ratio r following a beta distribution with parameters α and β. α and β are estimated from the training data.

$$Lik(n_A, n_B \mid r) = \binom{n_A + n_B}{n_A} \frac{\Gamma(n_A+\alpha)\Gamma(n_B+\beta)}{\Gamma(n_A+n_B+\alpha+\beta)} \frac{\Gamma(\alpha)\Gamma(\beta)}{\Gamma(\alpha+\beta)} \quad (3)$$

Search Algorithm:

Methods of the present invention can then use a search algorithm to search for the average allelic imbalance value that has the highest likelihood of being correct. In some examples of methods provided herein, such as the Allelic_Analysis_Example, SNPs with allele ratios that seem to be outliers can be ignored (such as by ignoring or eliminating SNPs with allele ratios that are at least 2 or 3 standard deviations above or below the mean value). Note that an advantage identified for this approach is that in the presence of higher mosaicism percentage, the variability in the allele ratios can be high, hence this ensures that SNPs will not be trimmed due to mosaicism.

In methods of the present invention, such as such as the Allelic_Analysis_Example method, $F=\{f_1, \ldots, f_N\}$ can denote the search space for the mosaicism percentage (such as the tumor fraction). The method can determine $P(D_s|h,f)$ at each SNP s and f∈F, and combine the likelihood over all SNPs.

The algorithm goes over each f for each hypothesis. Using a search method, one concludes that mosaicism exists if there is a range F* off where the confidence of the deletion or duplication hypothesis is higher than the confidence of the no deletion and no duplication hypotheses. In some embodiments, the maximum likelihood estimate for $P(D_s|h,f)$ in F* is determined. If desired, the conditional expectation over f∈F* can be determined. If desired, the confidence for each hypothesis can be determined.

Combining Likelihoods

Methods provided herein can combine likelihoods using phased date. For example, in the Allelic_Analysis_Example method, likelihoods using phased data, consider two consecutive SNPs s1 and s2, and use D1 and D2 to denote the allele data in these SNPs. Provided herein is an example on how, as incorporated into the Allelic_Analysis_Example, to combine the likelihoods for these two SNPs. Let c denote the probability that two consecutive heterozygous SNPs have the same allele in the same homolog (i.e., both SNPs are AB or both SNPs are BA). Hence 1-c is the probability that one SNP is AB and the other one is BA. For example, consider the hypothesis H10 and allelic imbalance value f. First, assume that all likelihoods are computed assuming that all SNPs are either AB or BA. Then, we can combine the likelihoods in two consecutive SNPs in the following formula (Combined_Likelihoods):

$$Lik(D_1, D_2 \mid H_{10}, f) = Lik(D_1 \mid H_{10}, f) \times c \times Lik(D_2 \mid H_{10}, f) + Lik(D_1 \mid H_{10}, f) \times (1-c) \times Lik(D_2 \mid H_{01}, f).$$

The above can be done recursively to determine the joint likelihood $Lik(D_1, \ldots, D_N|H_{10}, f)$ for all SNPs.

It is noteworthy that c values can be obtained as outputs from informatics haplotyping programs, as disclosed herein. In the presence of perfect haplotype information, we have c=0 or c=1 for individual haploblocks. In the absence of perfect haplotype information, but where target polymorphic loci are selected within haploblocks, estimates of haplotyping are improved, and therefore c values are closer to 0 or 1 than when polymorphic loci are analyzed that are not within haploblocks. Therefore, it is believed, and demonstrated in the Examples herein both in computer simulation and actual wet lab data, that by choosing loci within haploblocks, combined likelihoods can yield sufficiently accurate estimates of average allelic imbalance, chromosome copy number, and CNV, even with using estimated phase information that is not perfect. This accuracy is improved as more polymorphic loci within a chromosome region of interest are analyzed. This improved accuracy of determining and/or detecting average allelic imbalance, chromosome copy number, and/or CNV is especially useful in embodiments where average allelic imbalance in a sample is between 1, 2, or 3% on the low end of the range and 40, 30, 25 or 20% on high end of the range.

Theoretical Performance Using Simulations:

If desired, one can evaluate the theoretical performance of a method provided herein by randomly assigning number of reference reads to a SNP with given depth of read (DOR). For the normal case, use p=0.5 for the binomial probability parameter, and for deletions or duplications, p is revised accordingly. Exemplary input parameters for each simulation are as follows: (1) number of SNPs S (2) constant DOR D per SNP, (3) p, and (4) number of experiments.

First Simulation Experiment:

Accordingly, we evaluated performance of the theoretical Allelic_Analysis_Example method. The experiment focused on S∈{500, 1000}, D∈{500, 1000} and p∈{0%, 1%, 2%, 3%, 4%, 5%}. We performed 1,000 simulation experiments in each setting (hence 24,000 experiments with phase, and 24,000 without phase). We simulated the number of reads from a binomial distribution (if desired, other distributions can be used). The false positive rate (in the case of p=0%) and false negative rate (in the case of p>0%) were determined both with or without phase information. Including phase information was very helpful in reducing false positive rates, especially for S=1000, D=1000. Although for S=500, D=500, the algorithm has the highest false positive rates with or without phase out of the conditions tested.

Phase information is particularly useful for low mosaicism percentages (≤3%). Without phase information, a high level of false negatives were observed for p=1% because the confidence on deletion is determined by assigning equal chance to $H_{10}$ and $H_{01}$, and a small deviation in favor of one hypothesis is not sufficient to compensate for the low likelihood from the other hypothesis. This applies to duplications as well. Note also that the algorithm seems to be more sensitive to depth of read compared to number of SNPs. For the results with phase information, we assume that perfect phase information is available for a high number of consecutive heterozygous SNPs. If desired, haplotype information can be obtained by probabilistically combining haplotypes on smaller segments.

Second Simulation Experiment:

We then evaluated the theoretical performance of the Allelic_Analysis_Example method in a second simulation. This experiment focused on S∈{100, 200, 300, 400, 500}, D∈{1000, 2000, 3000, 4000, 5000} and p∈{0%, 1%, 1.5%, 2%, 2.5%, 3%} and 10000 random experiments at each setting. The false positive rate (in the case of p=0%) and false negative rate (in the case of p>0%) were determined both with or without phase information. The false negative rate is below 10% for D≥3000 and N≥200 using haplotype information, whereas the same performance is reached for D=5000 and N≥400. The difference between the false negative rate was particularly stark for small mosaicism percentages. For example, when p=1%, a less than 20% false negative rate is never reached without haplotype data, whereas it is close to 0% for N≥300 and D≥3000. For p=3%, a 0% false negative rate is observed with haplotype data, while N≥300 and D≥3000 is needed to reach the same performance without haplotype data.

Additional Analytical Method Considerations:

In some embodiments, a beta binomial distribution is used instead of binomial distribution. In some embodiments, a reference chromosome or chromosome region is used to determine the sample specific parameters of beta binomial.

Exemplary Reference Chromosomes or Chromosome Segments

In some embodiments, the one or more loci used to determine the tumor fraction are on a reference chromosome or chromosomes segment, such as a chromosome or chromosome region known or expected to be disomic, a chromosome or chromosome region that is rarely duplicated or deleted in cancer cells in general or in a particular type of cancer that an individual is known to have or is at increased risk of having, or a chromosome or chromosome region that is unlikely to be aneuploid (such segment that is expected to lead to cell death if deleted or duplicated). In some embodiments, any of the methods of the invention are used to confirm that the reference chromosome or chromosome region is disomic in both the cancer cells and noncancerous cells. In some embodiments, one or more chromosomes or chromosomes segments for which the confidence for a disomy call is high are used.

Exemplary loci that can be used to determine the tumor fraction include polymorphisms or mutations (such as SNPs) in a cancer cell (or DNA or RNA such as cfDNA or cfRNA from a cancer cell) that aren't present in a noncancerous cell (or DNA or RNA from a noncancerous cell) in the individual. In some embodiments, the tumor fraction is determined by identifying those polymorphic loci where a cancer cell (or DNA or RNA from a cancer cell) has an allele that is absent in noncancerous cells (or DNA or RNA from a noncancerous cell) in a sample (such as a plasma sample or tumor biopsy) from an individual; and using the amount of the allele unique to the cancer cell at one or more of the identified polymorphic loci to determine the tumor fraction in the sample. In some embodiments, a noncancerous cell is homozygous for a first allele at the polymorphic locus, and a cancer cell is (i) heterozygous for the first allele and a second allele or (ii) homozygous for a second allele at the polymorphic locus. In some embodiments, a noncancerous cell is heterozygous for a first allele and a second allele at the polymorphic locus, and a cancer cell is (i) has one or two copies of a third allele at the polymorphic locus. In some embodiments, the cancer cells are assumed or known to only have one copy of the allele that is not present in the noncancerous cells. For example, if the genotype of the noncancerous cells is AA and the cancer cells is AB and 5% of the signal at that locus in a sample is from the B allele and 95% is from the A allele, then the tumor fraction of the sample is 10%. In some embodiments, the cancer cells are assumed or known to have two copies of the allele that is not present in the noncancerous cells. For example, if the genotype of the noncancerous cells is AA and the cancer cells is BB and 5% of the signal at that locus in a sample is from the B allele and 95% is from the A allele, the tumor fraction of the sample is 5%. In some embodiments, multiple loci for which the cancer cells have an allele not in the noncancerous cells are analyzed to determine which of the loci in the cancer cells are heterozygous and which are homozygous. For example for loci in which the noncancerous cells are AA, if the signal from the B allele is ~5% at some loci and ~10% at some loci, then the cancer cells are assumed to be heterozygous at loci with ~5% B allele, and homozygous at loci with ~10% B allele (indicating the tumor fraction is ~10%).

Exemplary loci that can be used to determine the tumor fraction include loci for which a cancer cell and noncancerous cell have one allele in common (such as loci in which the cancer cell is AB and the noncancerous cell is BB, or the cancer cell is BB and the noncancerous cell is AB). The amount of A signal, the amount of B signal, or the ratio of A to B signal in a mixed sample (containing DNA or RNA from a cancer cell and a noncancerous cell) is compared to the corresponding value for (i) a sample containing DNA or RNA from only cancer cells or (ii) a sample containing DNA or RNA from only noncancerous cells. The difference in values is used to determine the tumor fraction of the mixed sample.

In some embodiments, loci that can be used to determine the tumor fraction are selected based on the genotype of (i) a sample containing DNA or RNA from only cancer cells, and/or (ii) a sample containing DNA or RNA from only noncancerous cells. In some embodiments, the loci are selected based on analysis of the mixed sample, such as loci for which the absolute or relative amounts of each allele differs from what would be expected if both the cancer and noncancerous cells have the same genotype at a particular locus. For example, if the cancer and noncancerous cells have the same genotype, the loci would be expected to produce 0% B signal if all the cells are AA, 50% B signal if all the cells are AB, or 100% B signal if all the cells are BB. Other values for the B signal indicate that the genotype of the cancer and noncancerous cells are different at that locus and thus that locus can be used to determine the tumor fraction.

In some embodiments, the tumor fraction calculated based on the alleles at one or more loci is compared to the tumor fraction calculated using one or more of the counting methods disclosed herein.

Exemplary Counting Methods/Quantitative Methods

In some embodiments, one or more counting methods (also referred to as quantitative methods) are used to detect one or more CNVs, such as deletions or duplications of chromosome segments or entire chromosomes. In some embodiments, one or more counting methods are used to determine whether the overrepresentation of the number of copies of the first homologous chromosome segment is due to a duplication of the first homologous chromosome segment or a deletion of the second homologous chromosome segment. In some embodiments, one or more counting methods are used to determine the number of extra copies of a chromosome segment or chromosome that is duplicated (such as whether there are 1, 2, 3, 4, or more extra copies). In some embodiments, one or more counting methods are used to differentiate a sample has many duplications and a smaller tumor fraction from a sample with fewer duplications and a larger tumor fraction. For example, one or more counting methods can be used to differentiate a sample with four extra chromosome copies and a tumor fraction of 10% from a sample with two extra chromosome copies and a tumor fraction of 20%. Exemplary methods are disclosed, e.g. U.S. Publication Nos. 2007/0184467; 2013/0172211; and 2012/0003637; U.S. Pat. Nos. 8,467,976; 7,888,017; 8,008,018; 8,296,076; and 8,195,415; U.S. Ser. No. 62/008, 235, filed Jun. 5, 2014, and U.S. Ser. No. 62/032,785, filed Aug. 4, 2014, which are each hereby incorporated by reference in their entirety.

In some embodiment, the counting method includes counting the number of DNA sequence-based reads that map to one or more given chromosomes or chromosome segments. Some such methods involve creation of a reference value (cut-off value) for the number of DNA sequence reads mapping to a specific chromosome or chromosome segment, wherein a number of reads in excess of the value is indicative of a specific genetic abnormality.

In some embodiments, the total measured quantity of all the alleles for one or more loci (such as the total amount of a polymorphic or non-polymorphic locus) is compared to a reference amount. In some embodiments, the reference amount is (i) a threshold value or (ii) an expected amount for a particular copy number hypothesis. In some embodiments, the reference amount (for the absence of a CNV) is the total measured quantity of all the alleles for one or more loci for one or more chromosomes or chromosomes segments known or expected to not have a deletion or duplication. In some embodiments, the reference amount (for the presence of a CNV) is the total measured quantity of all the alleles for one or more loci for one or more chromosomes or chromosomes segments known or expected to have a deletion or duplication. In some embodiments, the reference amount is the total measured quantity of all the alleles for one or more loci for one or more reference chromosomes or chromosome segments. In some embodiments, the reference amount is the mean or median of the values determined for two or more different chromosomes, chromosome segments, or different samples. In some embodiments, random (e.g., massively parallel shotgun sequencing) or targeted sequencing is used to determine the amount of one or more polymorphic or non-polymorphic loci.

In some embodiments utilizing a reference amount, the method includes (a) measuring the amount of genetic material on a chromosome or chromosome segment of interest; (b) comparing the amount from step (a) to a reference amount; and (c) identifying the presence or absence of a deletion or duplication based on the comparison.

In some embodiments utilizing a reference chromosome or chromosome segment, the method includes sequencing DNA or RNA from a sample to obtain a plurality of sequence tags aligning to target loci. In some embodiments, the sequence tags are of sufficient length to be assigned to a specific target locus (e.g., 15-100 nucleotides in length); the target loci are from a plurality of different chromosomes or chromosome segments that include at least one first chromosome or chromosome segment suspected of having an abnormal distribution in the sample and at least one second chromosome or chromosome segment presumed to be normally distributed in the sample. In some embodiments, the plurality of sequence tags are assigned to their corresponding target loci. In some embodiments, the number of sequence tags aligning to the target loci of the first chromosome or chromosome segment and the number of sequence tags aligning to the target loci of the second chromosome or chromosome segment are determined. In some embodiments, these numbers are compared to determine the presence or absence of an abnormal distribution (such as a deletion or duplication) of the first chromosome or chromosome segment.

In some embodiments, the value of f (such as the fetal fraction or tumor fraction) is used in the CNV determination, such as to compare the observed difference between the amount of two chromosomes or chromosome segments to the difference that would be expected for a particular type of CNV given the value of f (sec, e.g., US Publication No 2012/0190020; US Publication No 2012/0190021; US Publication No 2012/0190557; US Publication No 2012/0191358, which are each hereby incorporated by reference in its entirety). For example, the difference in the amount of a chromosome segment that is duplicated in a fetus compared to a disomic reference chromosome segment in a blood sample from a mother carrying the fetus increases as the fetal fraction increases. Additionally, the difference in the amount of a chromosome segment that is duplicated in a tumor compared to a disomic reference chromosome segment increases as the tumor fraction increases. In some embodiments, the method includes comparing the relative frequency of a chromosome or chromosome segment of interest to a reference chromosomes or chromosome segment (such as a chromosome or chromosome segment expected or known to be disomic) to the value of f to determine the likelihood of the CNV. For example, the difference in amounts between the first chromosomes or chromosome segment to the reference chromosome or chromosome segment can be compared to what would be expected given the value of f for various possible CNVs (such as one or two extra copies of a chromosome segment of interest).

The following prophetic examples illustrate the use of a counting method/quantitative method to differentiate between a duplication of the first homologous chromosome segment and a deletion of the second homologous chromosome segment. If one considers the normal disomic genome of the host to be the baseline, then analysis of a mixture of normal and cancer cells yields the average difference between the baseline and the cancer DNA in the mixture. For example, imagine a case where 10% of the DNA in the sample originated from cells with a deletion over a region of a chromosome that is targeted by the assay. In some embodiments, a quantitative approach shows that the quantity of reads corresponding to that region is expected to be 95% of what is expected for a normal sample. This is because one of the two target chromosomal regions in each of the tumor cells with a deletion of the targeted region is missing, and thus the total amount of DNA mapping to that region is 90% (for the normal cells) plus ½×10% (for the tumor cells) =95%. Alternately in some embodiments, an allelic approach shows that the ratio of alleles at heterozygous loci averaged 19:20. Now imagine a case where 10% of the DNA in the sample originated from cells with a five-fold focal amplification of a region of a chromosome that is targeted by the assay. In some embodiments, a quantitative approach shows that the quantity of reads corresponding to that region is expected to be 125% of what is expected for a normal sample. This is because one of the two target chromosomal regions in each of the tumor cells with a five-fold focal amplification is copied an extra five times over the targeted region, and thus the total amount of DNA mapping to that region is 90% (for the normal cells) plus (2+5)×10%/2 (for the tumor cells)=125%. Alternately in some embodiments, an allelic approach shows that the ratio of alleles at heterozygous loci averaged 25:20. Note that when using an allelic approach alone, a focal amplification of five-fold over a chromosomal region in a sample with 10% cfDNA may appear the same as a deletion over the same region in a sample with 40% cfDNA; in these two cases, the haplotype that is under-represented in the case of the deletion appears to be the haplotype without a CNV in the case with the focal duplication, and the haplotype without a CNV in the case of the deletion appears to be the over-represented haplotype in the case with the focal duplication. Combining the likelihoods produced by this allelic approach with likelihoods produced by a quantitative approach differentiates between the two possibilities.

Exemplary Counting Methods/Quantitative Methods Using Reference Samples

An exemplary quantitative method that uses one or more reference samples is described in U.S. Ser. No. 62/008,235, filed Jun. 5, 2014 and U.S. Ser. No. 62/032,785, filed Aug. 4, 2014, which is hereby incorporated by reference in its entirety. In some embodiments, one or more reference samples most likely to not have any CNVs on one or more chromosomes or chromosomes of interest (e.g., a normal sample) are identified by selecting the samples with the highest fraction of tumor DNA, selecting the samples with the z-score closest to zero, selecting the samples where the data fits the hypothesis corresponding to no CNVs with the highest confidence or likelihood, selecting the samples known to be normal, selecting the samples from individuals with the lowest likelihood of having cancer (e.g., having a low age, being a male when screening for breast cancer, having no family history, etc.), selecting the samples with the highest input amount of DNA, selecting the samples with the highest signal to noise ratio, selecting samples based on other criteria believed to be correlated to the likelihood of having cancer, or selecting samples using some combination of criteria. Once the reference set is chosen, one can make the assumption that these cases are disomic, and then estimate the per-SNP bias, that is, the experiment-specific amplification and other processing bias for each locus. Then, one can use this experiment-specific bias estimate to correct the bias in the measurements of the chromosome of interest, such as chromosome 21 loci, and for the other chromosome loci as appropriate, for the samples that are not part of the subset where disomy is assumed for chromosome 21. Once the biases have been corrected for in these samples of unknown ploidy, the data for these samples can then be analyzed a second time using the same or a different method to determine whether the individuals (such as fetuses) are afflicted with trisomy 21. For example, a quantitative method can be used on the remaining samples of unknown ploidy, and a z-score can be calculated using the corrected measured genetic data on chromosome 21. Alternately, as part of the preliminary estimate of the ploidy state of chromosome 21, a fetal fraction (or tumor fraction for samples from an individual suspected of having cancer) can be calculated. The proportion of corrected reads that are expected in the case of a disomy (the disomy hypothesis), and the proportion of corrected reads that are expected in the case of a trisomy (the trisomy hypothesis) can be calculated for a case with that fetal fraction. Alternately, if the fetal fraction was not measured previously, a set of disomy and trisomy hypotheses can be generated for different fetal fractions. For each case, an expected distribution of the proportion of corrected reads can be calculated given expected statistical variation in the selection and measurement of the various DNA loci. The observed corrected proportion of reads can be compared to the distribution of the expected proportion of corrected reads, and a likelihood ratio can be calculated for the disomy and trisomy hypotheses, for each of the samples of unknown ploidy. The ploidy state associated with the hypothesis with the highest calculated likelihood can be selected as the correct ploidy state.

In some embodiments, a subset of the samples with a sufficiently low likelihood of having cancer can be selected to act as a control set of samples. The subset can be a fixed number, or it can be a variable number that is based on choosing only those samples that fall below a threshold. The quantitative data from the subset of samples can be combined, averaged, or combined using a weighted average where the weighting is based on the likelihood of the sample being normal. The quantitative data can be used to determine the per-locus bias for the amplification the sequencing of samples in the instant batch of control samples. The per-locus bias may also include data from other batches of samples. The per-locus bias may indicate the relative over- or under-amplification that is observed for that locus compared to other loci, making the assumption that the subset of samples do not contain any CNVs, and that any observed over or under-amplification is due to amplification and/or sequencing or other bias. The per-locus bias may take into account the GC content of the amplicon. The loci can be grouped into groups of loci for the purpose of calculating a per-locus bias. Once the per-locus bias has been calculated for each locus in the plurality of loci, the sequencing data for one or more of the samples that are not in the subset of the samples, and optionally one or more of the samples that are in the subset of samples, can be corrected by adjusting the quantitative measurements for each locus to remove the effect of the bias at that locus. For example, if SNP 1 was observed, in the subset of patients, to have a depth of read that is twice as great as the average, the adjustment may involve replacing the number of reads corresponding from SNP 1 with a number that is half as great. If the locus in question is a SNP, the adjustment may involve cutting the number of reads corresponding to each of the alleles at that locus in half. Once the sequencing data for each of the loci in one or more samples has been adjusted, it can be analyzed using a method for the purpose of detecting the presence of a CNV at one or more chromosomal regions.

In an example, sample A is a mixture of amplified DNA originating from a mixture of normal and cancerous cells that is analyzed using a quantitative method. The following illustrates exemplary possible data. A region of the q arm on chromosome 22 is found to only have 90% as much DNA mapping to that region as expected; a focal region corresponding to the HER2 gene is found to have 150% as much DNA mapping to that region as expected; and the p-arm of chromosome 5 is found to have 105% as much DNA mapping to it as expected. A clinician may infer that the sample has a deletion of a region on the q arm on chromosome 22, and a duplication of the HER2 gene. The clinician may infer that since the 22q deletions are common in breast cancer, and that since cells with a deletion of the 22q region on both chromosomes usually do not survive, that approximately 20% of the DNA in the sample came from cells with a 22q deletion on one of the two chromosomes. The clinician may also infer that if the DNA from the mixed sample that originated from tumor cells originated from a set of genetically tumor cells whose HER2 region and 22q regions were homogenous, then the cells contained a five-fold duplication of the HER2 region.

In an example, Sample A is also analyzed using an allelic method. The following illustrates exemplary possible data.

The two haplotypes on same region on the q arm on chromosome 22 are present in a ratio of 4:5; the two haplotypes in a focal region corresponding to the HER2 gene are present in ratios of 1:2; and the two haplotypes in the p-arm of chromosome 5 are present in ratios of 20:21. All other assayed regions of the genome have no statistically significant excess of either haplotype. A clinician may infer that the sample contains DNA from a tumor with a CNV in the 22q region, the HER2 region, and the 5p arm. Based on the knowledge that 22q deletions are very common in breast cancer, and/or the quantitative analysis showing an under-representation of the amount of DNA mapping to the 22q region of the genome, the clinician may infer the existence of a tumor with a 22q deletion. Based on the knowledge that HER2 amplifications are very common in breast cancer, and/or the quantitative analysis showing an over-representation of the amount of DNA mapping to the HER2 region of the genome, the clinician may infer the existence of a tumor with a HER2 amplification.

In some embodiments, allelic data is obtained, wherein the allelic data includes quantitative measurement(s) indicative of the number of copies of a specific allele of a polymorphic locus. In some embodiments, the allelic data includes quantitative measurement(s) indicative of the number of copies of each of the alleles observed at a polymorphic locus. Typically, quantitative measurements are obtained for all possible alleles of the polymorphic locus of interest. For example, any of the methods discussed in the preceding paragraphs for determining the allele for a SNP locus, such as for example, microarrays, qPCR, DNA sequencing, such as high throughput DNA sequencing, can be used to generate quantitative measurements of the number of copies of a specific allele of a polymorphic locus. This quantitative measurement is referred to herein as allelic frequency data or measured genetic allelic data. Methods using allelic data are sometimes referred to as quantitative allelic methods; this is in contrast to quantitative methods which exclusively use quantitative data from non-polymorphic loci, or from polymorphic loci but without regard to allelic identity. When the allelic data is measured using high-throughput sequencing, the allelic data typically include the number of reads of each allele mapping to the locus of interest.

In some embodiments, non-allelic data is obtained, wherein the non-allelic data includes quantitative measurement(s) indicative of the number of copies of a specific locus. The locus can be polymorphic or non-polymorphic. In some embodiments when the locus is non-polymorphic, the non-allelic data does not contain information about the relative or absolute quantity of the individual alleles that can be present at that locus. Methods using non-allelic data only (that is, quantitative data from non-polymorphic alleles, or quantitative data from polymorphic loci but without regard to the allelic identity of each fragment) are referred to as quantitative methods. Typically, quantitative measurements are obtained for all possible alleles of the polymorphic locus of interest, with one value associated with the measured quantity for all of the alleles at that locus, in total. Non-allelic data for a polymorphic locus can be obtained by summing the quantitative allelic for each allele at that locus. When the allelic data is measured using high-throughput sequencing, the non-allelic data typically includes the number of reads of mapping to the locus of interest. The sequencing measurements could indicate the relative and/or absolute number of each of the alleles present at the locus, and the non-allelic data includes the sum of the reads, regardless of the allelic identity, mapping to the locus. In some embodiments the same set of sequencing measurements can be used to yield both allelic data and non-allelic data. In some embodiments, the allelic data is used as part of a method to determine copy number at a chromosome of interest, and the produced non-allelic data can be used as part of a different method to determine copy number at a chromosome of interest. In some embodiments, the two methods are statistically orthogonal, and are combined to give a more accurate determination of the copy number at the chromosome of interest.

In any of the embodiments provided herein, methods of the invention can include a quantitative method for determining copy number or ploidy, or detecting CNV or ancuploidy. Accordingly, methods for or determining copy number or ploidy, or detecting CNV or ancuploidy can further include performing a quantitative method to determine copy number or ploidy, or to detect CNV or aneuploidy. The quantitative method can, for example, be the Focal CNV detection using depth of read (FODDOR) classifier method. The method is used for classifying a sample as normal or abnormal. We do this by testing if all the regions of interest, referred to as genes in this discussion of FODDOR, of the sample have the same genetic copy number or different copy numbers. If our test determines that all the genes have the same copy number, we classify the sample as normal. If they have different copy numbers, we classify it as abnormal. Notice that this approach fails to detect abnormal samples that have equal amplifications/deletions in all the regions. The fundamental classifier that we use here is the Generalized likelihood ratio test (GLRT) detector. We frame the problem as follows:

Let N be the total number of target positions, $n_k$ be the copy number of gene $k \in \{1, \ldots, K\}$, where K is the total number of genes of interest and $x_i$ be the counts at target i, $i \in \{1, \ldots, N\}$, Let $g:\{1, \ldots, N\} \rightarrow \{1, \ldots, K\}$ be a map from targets to genes. Next, the data is modeled as follows:

$$\log x_i = \log c_s + \log n_{g(i)} + \alpha_s \beta_i + \gamma_s + w_i \tag{4}$$

$$\delta_s^2 \delta_i^2$$

where $w_i$=K log $\epsilon_i$ and $w_i$~N(0;). Let $y_i$=log $x_i$. Let v_k=log $c_s$+$\gamma_s$+ log($n_k$) for k ∈™ {1, . . . , K}. So, for a healthy gene we have $v_k$=log $c_s$+$\gamma_s$+ log(2), and for an abnormal gene k with a tumor copy number $a_k$(≠2) and tumor fraction f, we have $v_k$=log $c_s$+$\gamma_s$+ log(2*(1−f)+$a_k$*f). Notice that here we are assuming that the whole of gene k has the same copy number $a_k$. In reality the gene may have different copy numbers at different subsections of the gene in which case $a_k$ is the weighted average of the copy numbers of all the subsections of that gene, weighted by the sizes of those subsections. Let us define the virtual tumor fraction of a gene k as the amount of excess of that gene compared to the normal genes of that sample, assuming an abnormal copy number of 3 for that gene. So, the virtual tumor fraction is given by $$\delta_s^2 \delta_i^2$$

$$vtf_k=(a_k-2)*f \quad (5)$$

For two samples, one with an abnormal copy number of 3 and a tumor fraction f0 and the other with an abnormal copy number of 4 and a tumor fraction of $f_0/2$, the virtual tumor fraction is exactly the same. From the algorithm point of view, these two samples are equivalent. This is because it is theoretically not possible to uniquely determine the abnormal copy number and the true tumor fraction. Also, the vtf of a normal gene is zero. Now, if we let $T_s=\log c_s+\gamma_s$ be the sample dependent parameter, we can rewrite the parameter $v_k$ as $$v_k=T_s+\log(1+vtf_k) \quad (6)$$

For a particular gene k with $N_k$ loci, if $y_k=[y_1: : : y_{Nk}]^T$ is an $N_k\times 1$ vector of logspace normalized depth of reads at the $N_k$ loci and $\beta_k=[\beta_1: : : \beta_{Nk}]^T$, $\sigma_k=[\sigma_1: : : \sigma_{Nk}]^T$, $w_k=[w_1: : : w_{Nk}]^T$, $v_k=[v_1: : : v_{Nk}]^T$, and define an N×K matrix U as $$[U]_{ik}=\begin{cases}1 & \text{if } g(i)=k\\ 0 & \text{otherwise}\end{cases}$$

and $H=[U\beta]$ and $\theta=[v^T\alpha_s]^T$. So, in vector form we can rewrite (4) as $$y=H\theta+w \quad (7)$$

where $$w\sim N(0,\delta_s^2C(\rho)),$$

$\rho=[\rho_1 \ldots \rho_{Nk}]^T$, are the correlation coefficients of each of the genes and $C(\rho)=\text{diag}(C(\rho_1) \ldots C(\rho_k))$ is a block diagonal matrix where each of its submatrices are as defined in below $$C(\rho_k)=(1-\rho_k)\times\text{diag}(\delta_k^2)+\rho_k\times\sigma_k\sigma_k^T \quad (8)$$

Here (β, σ, ρ) are the model parameters which are estimated using known diploid samples as explained in [1]. We can prewhiten the data vector y by multiplying both sides of (7) with S(ρ) where S(ρ) is and N×N matrix such that $S(\rho)^T S(\rho)=C(\rho)^{-1}$. If we let $\tilde{y}=S(\rho)y$, $\tilde{H}=S(\rho)H$, and $\tilde{w}=S(\rho)w$ then we can rewrite (4) as $$\tilde{y}=\tilde{H}\theta+\tilde{w} \quad (9)$$

where $$\tilde{w}\sim N(0,\delta_s^2 I).$$

Here the unknown parameters are $$\{\theta^T,\delta_s^2\}.$$

Let A be a (K−1)×(K+1) "difference matrix" defined as $$A=\begin{bmatrix}1 & -1 & 0 & \ldots & 0 & 0 & 0\\ 0 & 1 & -1 & \ldots & 0 & 0 & 0\\ \vdots & \vdots & \vdots & \ddots & \vdots & \vdots & \vdots\\ 0 & 0 & 0 & \ldots & 1 & -1 & 0\end{bmatrix} \quad (10)$$

Notice here that the last column of A is a zero vector which is used to eliminate the nuisance parameter $\alpha_s$. The hypothesis test we are interested in is $$H_0.:A\theta=0$$

$$H_1:A\theta\neq 0$$

From Theorem 9.1, as defined by S. M. Kay (see Kay S. M. "Fundamentals of Statistical Signal Processing, Volume 2: Detection Theory". Upper Saddle River, NJ, USA: Prentice-Hall, Inc., 1998) the Generalized Likelihood Ratio Test (GLRT) for this hypothesis test is to decide $H_1$. if $$T(y)=\frac{N-(K+1)}{K}\frac{(A\hat{\theta}_1-0)^T\left[A(\tilde{H}^T\tilde{H})^{-1}A^T\right]^{-1}(A\hat{\theta}_1-0)}{\tilde{y}^T\left(I-\tilde{H}(\tilde{H}^T\tilde{H})^{-1}\tilde{H}^T\tilde{y}\right.}>\gamma' \quad (11)$$

where is $\check{\theta}_1=(\tilde{H}^T\tilde{H})^{-1}\tilde{H}^T\tilde{y}$ is the MLE of θ under $H_1$. Notice that the above likelihood ratio is simply a ratio of the sum of squares of multivariate normals due to our assumed noise model. Here T(y) is derived starting from the likelihood ratio, and is a monotonically increasing function of it that we have manipulated to turn it into an F-statistic. We assume we that the sample dependent variance $$(\delta_s^2)$$

of the noise is unknown and so an MLE for delta is built in to the likelihood function. The exact detection performance (holds for finite data records) is given by $$Q_{F_{K,N-(K+1)}}\gamma' Q_{F'_{K,N-(K+1)}}$$

$$P_{FA}=P_{D(1)}=_{(\lambda)}\gamma'$$

$$Q_{F_{K,N-(K+1)}}\gamma' Q_{F'_{K,N-(K+1)}} \quad (12)$$

where $P_{FA}$ is the probability of false alarm (false positives), $P_D$ is the probability of detection (true positives), $F_{K,N-(K+1)}$ an F distribution with K numerator degrees of freedom and N−(K+1) denominator degrees of freedom, and $F'_{K,N-(K+1)}(\lambda)$ denotes a noncentral F distribution with K numerator degrees of freedom, N−(K+1) denominator degrees of freedom and noncentrality parameter λ. The noncentrality parameter is given by $$\lambda = \frac{(A\theta_1 - 0)^T\left[A\left(\tilde{H}^T\tilde{H}\right)^{-1}A^T\right]^{-1}(A\theta_1 - 0)}{\delta_s^2} \quad (13)$$

where $\theta_1$ is the true value of θ under $H_1$. The Q function is the complement of the cumulative distribution function i.e, $Q(x)=1-F_X(x)$. The parameter γ′ can be set based on the desired performance metrics. For example, we can set the γ′ based on the desired $P_{FA}$ and the corresponding $P_D$ follows. Note that we cannot simultaneously increase the $P_D$ and decrease the $P_{FA}$ by simply changing the γ.

In the previous section discussing this FODDOR method, a classifier was designed that at a sample level can classify a sample as normal or abnormal. But that classifier does not tell us which of the genes of an abnormal sample are in deed abnormal. Here we will design a region level classifier which can also determine the individual abnormal genes of an abnormal sample. We do this by iteratively identifying and removing abnormal genes, one per iteration from an abnormal sample, until we find a subset of genes that are normal. Notice that in the previous section, while computing the test statistic, we also estimate the parameter $\theta=[v^T\ \alpha_s]^T$ and so we have an estimate of v. So, for an abnormal sample arg max v should give us the gene with the highest vtf. So, the steps for the iterative region level classifier are as follows:

- Classify a sample as normal or abnormal using the FODDOR classifier. If a sample is normal, then all the regions are normal. If the sample is abnormal go to next step.
- Identify the gene with the highest vtf as explained above. Remove this gene from the analysis and go to the previous step.

Notice that this approach has some drawbacks. This approach is less effective when a sample has deletions. When a sample has deletions the algorithm identifies all other regions including normal regions as abnormal and converges to the subset of genes that have deletions and classifies this subset as normal. Accordingly, a method herein can include a quantitative, non-allelic method and a quantitative, allelic method, as provided herein.

Amplification (e.g. PCR) Reaction Mixtures

Methods of the present invention, in certain embodiments, include forming an amplification reaction mixture, and as discussed above, such reaction mixture that include amplicons and/or primers of the present invention, themselves represent certain embodiments of the invention. A reaction mixture typically is formed by combining a polymerase, nucleotide triphosphates, nucleic acid fragments from a nucleic acid library generated from the sample, and a set of primer pairs that amplify a set of amplicon that each include a polymorphic loci. The reaction mixtures provided herein, themselves forming in illustrative embodiments, a separate aspect of the invention. In illustrative embodiments, the reaction mixtures are PCR reaction mixtures. PCR reaction mixtures typically include magnesium.

In some embodiments, the reaction mixture includes ethylenediaminetetraacetic acid (EDTA), magnesium, tetramethyl ammonium chloride (TMAC), or any combination thereof. In some embodiments, the concentration of TMAC is between 20 and 70 mM, inclusive. While not meant to be bound to any particular theory, it is believed that TMAC binds to DNA, stabilizes duplexes, increases primer specificity, and/or equalizes the melting temperatures of different primers. In some embodiments, TMAC increases the uniformity in the amount of amplified products for the different targets. In some embodiments, the concentration of magnesium (such as magnesium from magnesium chloride) is between 1 and 8 mM.

The large number of primers used for multiplex PCR of a large number of targets may chelate a lot of the magnesium (2 phosphates in the primers chelate 1 magnesium). For example, if enough primers are used such that the concentration of phosphate from the primers is ~9 mM, then the primers may reduce the effective magnesium concentration by ~4.5 mM. In some embodiments, EDTA is used to decrease the amount of magnesium available as a cofactor for the polymerase since high concentrations of magnesium can result in PCR errors, such as amplification of non-target loci. In some embodiments, the concentration of EDTA reduces the amount of available magnesium to between 1 and 5 mM (such as between 3 and 5 mM).

In some embodiments, the pH is between 7.5 and 8.5, such as between 7.5 and 8, 8 and 8.3, or 8.3 and 8.5, inclusive. In some embodiments, Tris is used at, for example, a concentration of between 10 and 100 mM, such as between 10 and 25 mM, 25 and 50 mM, 50 and 75 mM, or 25 and 75 mM, inclusive. In some embodiments, any of these concentrations of Tris are used at a pH between 7.5 and 8.5. In some embodiments, a combination of KCl and $(NH_4)_2SO_4$ is used, such as between 50 and 150 mM KCl and between 10 and 90 mM $(NH_4)_2SO_4$, inclusive. In some embodiments, the concentration of KCl is between 0 and 30 mM, between 50 and 100 mM, or between 100 and 150 mM, inclusive. In some embodiments, the concentration of $(NH_4)_2SO_4$ is between 10 and 50 mM, 50 and 90 mM, 10 and 20 mM, 20 and 40 mM, 40 and 60 mM, or 60 and 80 mM $(NH_4)_2SO_4$, inclusive. In some embodiments, the ammonium $[NH_4^+]$ concentration is between 0 and 160 mM, such as between 0 to 50, 50 to 100, or 100 to 160 mM, inclusive. In some embodiments, the sum of the potassium and ammonium concentration ($[K^+]+[NH_4^+]$) is between 0 and 160 mM, such as between 0 to 25, 25 to 50, 50 to 150, 50 to 75, 75 to 100, 100 to 125, or 125 to 160 mM, inclusive. An exemplary buffer with $[K^+]+[NH_4^+]=120$ mM is 20 mM KCl and 50 mM $(NH_4)_2SO_4$. In some embodiments, the buffer includes 25 to 75 mM Tris, pH 7.2 to 8, 0 to 50 mM KCl, 10 to 80 mM ammonium sulfate, and 3 to 6 mM magnesium, inclusive. In some embodiments, the buffer includes 25 to 75 mM Tris pH 7 to 8.5, 3 to 6 mM $MgCl_2$, 10 to 50 mM KCl, and 20 to 80 mM $(NH_4)_2SO_4$, inclusive. In some embodiments, 100 to 200 Units/mL of polymerase are used. In some embodiments, 100 mM KCl, 50 mM $(NH_4)_2SO_4$, 3 mM $MgCl_2$, 7.5 nM of each primer in the library, 50 mM TMAC, and 7 ul DNA template in a 20 ul final volume at pH 8.1 is used.

In some embodiments, a crowding agent is used, such as polyethylene glycol (PEG, such as PEG 8,000) or glycerol. In some embodiments, the amount of PEG (such as PEG 8,000) is between 0.1 to 20%, such as between 0.5 to 15%, 1 to 10%, 2 to 8%, or 4 to 8%, inclusive. In some embodiments, the amount of glycerol is between 0.1 to 20%, such as between 0.5 to 15%, 1 to 10%, 2 to 8%, or 4 to 8%, inclusive. In some embodiments, a crowding agent allows either a low polymerase concentration and/or a shorter annealing time to be used. In some embodiments, a crowding agent improves the uniformity of the DOR and/or reduces dropouts (undetected alleles). Polymerases In some embodiments, a polymerase with proof-reading activity, a polymerase without (or with negligible) proof-reading activity, or a mixture of a polymerase with proof-reading activity and a polymerase without (or with negligible) proof-reading activity is used. In some embodiments, a hot start polymerase, a non-hot start polymerase, or a mixture of a hot start polymerase and a non-hot start polymerase is used. In some embodiments, a HotStarTaq DNA polymerase is used (sec, for example, QIAGEN catalog No. 203203). In some embodiments, AmpliTaq Gold® DNA Polymerase is used. In some embodiments a PrimeSTAR GXL DNA polymerase, a high fidelity polymerase that provides efficient PCR amplification when there is excess template in the reaction mixture, and when amplifying long products, is used (Takara Clontech, Mountain View, CA). In some embodiments, KAPA Taq DNA Polymerase or KAPA Taq HotStart DNA Polymerase is used; they are based on the single-subunit, wild-type Taq DNA polymerase of the thermophilic bacterium *Thermus aquaticus*. KAPA Taq and KAPA Taq HotStart DNA Polymerase have 5'→3' polymerase and 5'-3' exonuclease activities, but no 3' to 5' exonuclease (proofreading) activity (sec, for example, KAPA BIOSYSTEMS catalog No. BK1000). In some embodiments, Pfu DNA polymerase is used; it is a highly thermostable DNA polymerase from the hyperthermophilic archaeum *Pyrococcus furiosus*. The enzyme catalyzes the template-dependent polymerization of nucleotides into duplex DNA in the 5'→3' direction. Pfu DNA Polymerase also exhibits 3'→5' exonuclease (proofreading) activity that enables the polymerase to correct nucleotide incorporation errors. It has no 5'→3' exonuclease activity (see, for example, Thermo Scientific catalog No. EP0501). In some embodiments Klentaq1 is used; it is a Klenow-fragment analog of Taq DNA polymerase, it has no exonuclease or endonuclease activity (see, for example, DNA POLYMERASE TECHNOLOGY, Inc, St. Louis, Missouri, catalog No. 100). In some embodiments, the polymerase is a PHUSION DNA polymerase, such as PHUSION High Fidelity DNA polymerase (M0530S, New England BioLabs, Inc.) or PHUSION Hot Start Flex DNA polymerase (M0535S, New England BioLabs, Inc.). In some embodiments, the polymerase is a Q5® DNA Polymerase, such as Q5® High-Fidelity DNA Polymerase (M0491S, New England BioLabs, Inc.) or Q5® Hot Start High-Fidelity DNA Polymerase (M0493S, New England BioLabs, Inc.). In some embodiments, the polymerase is a T4 DNA polymerase (M0203S, New England BioLabs, Inc.).

In some embodiment, between 5 and 600 Units/mL (Units per 1 mL of reaction volume) of polymerase is used, such as between 5 to 100, 100 to 200, 200 to 300, 300 to 400, 400 to 500, or 500 to 600 Units/mL, inclusive.

PCR Methods

In some embodiments, hot-start PCR is used to reduce or prevent polymerization prior to PCR thermocycling. Exemplary hot-start PCR methods include initial inhibition of the DNA polymerase, or physical separation of reaction components reaction until the reaction mixture reaches the higher temperatures. In some embodiments, slow release of magnesium is used. DNA polymerase requires magnesium ions for activity, so the magnesium is chemically separated from the reaction by binding to a chemical compound, and is released into the solution only at high temperature. In some embodiments, non-covalent binding of an inhibitor is used. In this method a peptide, antibody, or aptamer are non-covalently bound to the enzyme at low temperature and inhibit its activity. After incubation at elevated temperature, the inhibitor is released and the reaction starts. In some embodiments, a cold-sensitive Taq polymerase is used, such as a modified DNA polymerase with almost no activity at low temperature. In some embodiments, chemical modification is used. In this method, a molecule is covalently bound to the side chain of an amino acid in the active site of the DNA polymerase. The molecule is released from the enzyme by incubation of the reaction mixture at elevated temperature. Once the molecule is released, the enzyme is activated.

In some embodiments, the amount to template nucleic acids (such as an RNA or DNA sample) is between 20 and 5,000 ng, such as between 20 to 200, 200 to 400, 400 to 600, 600 to 1,000; 1,000 to 1,500; or 2,000 to 3,000 ng, inclusive.

In some embodiments a QIAGEN Multiplex PCR Kit is used (QIAGEN catalog No. 206143). For 100×50 μl multiplex PCR reactions, the kit includes 2× QIAGEN Multiplex PCR Master Mix (providing a final concentration of 3 mM $MgCl_2$, 3×0.85 ml), 5× Q-Solution (1×2.0 ml), and RNase-Free Water (2×1.7 ml). The QIAGEN Multiplex PCR Master Mix (MM) contains a combination of KCl and $(NH_4)_2SO_4$ as well as the PCR additive, Factor MP, which increases the local concentration of primers at the template. Factor MP stabilizes specifically bound primers, allowing efficient primer extension by HotStarTaq DNA Polymerase. HotStarTaq DNA Polymerase is a modified form of Taq DNA polymerase and has no polymerase activity at ambient temperatures. In some embodiments, HotStarTaq DNA Polymerase is activated by a 15-minute incubation at 95° C. which can be incorporated into any existing thermal-cycler program.

In some embodiments, 1× QIAGEN MM final concentration (the recommended concentration), 7.5 nM of each primer in the library, 50 mM TMAC, and 7 μl DNA template in a 20 μl final volume is used. In some embodiments, the PCR thermocycling conditions include 95° C. for 10 minutes (hot start); 20 cycles of 96° C. for 30 seconds; 65° C. for 15 minutes; and 72° C. for 30 seconds; followed by 72° C. for 2 minutes (final extension); and then a 4° C. hold.

In some embodiments, 2× QIAGEN MM final concentration (twice the recommended concentration), 2 nM of each primer in the library, 70 mM TMAC, and 7 μl DNA template in a 20 μl total volume is used. In some embodiments, up to 4 mM EDTA is also included. In some embodiments, the PCR thermocycling conditions include 95° C. for 10 minutes (hot start); 25 cycles of 96° C. for 30 seconds; 65° C. for 20, 25, 30, 45, 60, 120, or 180 minutes; and optionally 72° C. for 30 seconds); followed by 72° C. for 2 minutes (final extension); and then a 4° C. hold.

Another exemplary set of conditions includes a semi-nested PCR approach. The first PCR reaction uses 20 ul a reaction volume with 2× QIAGEN MM final concentration, 1-5 nM of each primer in the library, and DNA template. Thermocycling parameters include 95° C. for 10 minutes; 25 cycles of 96° C. for 30 seconds, 65° C. for 1 minute, 58° C. for 6 minutes, 60° C. for 8 minutes, 65° C. for 4 minutes, and 72° C. for 30 seconds; and then 72° C. for 2 minutes, and then a 4° C. hold. Next, 2 μl of the resulting product, diluted 1:200, is used as input in a second PCR reaction. This reaction can include, for example, a 10 μl reaction volume with 1× QIAGEN MM final concentration, 20 nM of each primer of a set of primer pairs. Thermocycling parameters can include, for example, 95° C. for 10 minutes; 15 cycles of 95° C. for 30 seconds, 65° C. for 1 minute, 60° C. for 5 minutes, 65° C. for 5 minutes, and 72° C. for 30 seconds; and then 72° C. for 2 minutes, and then a 4° C. hold. The annealing temperature can optionally be higher than the melting temperatures of some or all of the primers, as discussed herein.

The melting temperature ($T_m$) is the temperature at which one-half (50%) of a DNA duplex of an oligonucleotide (such as a primer) and its perfect complement dissociates and becomes single strand DNA. The annealing temperature ($T_A$) is the temperature one runs the PCR protocol at. For prior methods, it is usually 5° C. below the lowest $T_m$ of the primers used, thus close to all possible duplexes are formed (such that essentially all the primer molecules bind the template nucleic acid). While this is highly efficient, at lower temperatures there are more unspecific reactions bound to occur. One consequence of having too low a $T_A$ is that primers may anneal to sequences other than the true target, as internal single-base mismatches or partial annealing can be tolerated. In some embodiments of the present inventions, the $T_A$ is higher than $T_m$, where at a given moment only a small fraction of the targets have a primer annealed (such as only ~1-5%). If these get extended, they are removed from the equilibrium of annealing and dissociating primers and target (as extension increases $T_m$ quickly to above 70° C.), and a new ~1-5% of targets has primers. Thus, by giving the reaction a long time for annealing, one can get ~100% of the targets copied per cycle.

In various embodiments, the annealing temperature is between 1, 2, 3, 4, 5, 6, 7, 8, 9, 10, 11, 12, 13° C. and 2, 3, 4, 5, 6, 7, 8, 9, 10, 11, 12, 13, or 15° C. on the high end of the range, greater than the melting temperature (such as the empirically measured or calculated $T_m$) of at least 25, 50, 60, 70, 75, 80, 90, 95, or 100% of the non-identical primers. In various embodiments, the annealing temperature is between 1 and 15° C. (such as between 1 to 10, 1 to 5, 1 to 3, 3 to 5, 5 to 10, 5 to 8, 8 to 10, 10 to 12, or 12 to 15° C., inclusive) greater than the melting temperature (such as the empirically measured or calculated $T_m$) of at least 25; 50; 75; 100; 300; 500; 750; 1,000; 2,000; 5,000; 7,500; 10,000; 15,000; 19,000; 20,000; 25,000; 27,000; 28,000; 30,000; 40,000; 50,000; 75,000; 100,000; or all of the non-identical primers. In various embodiments, the annealing temperature is between 1 and 15° C. (such as between 1 to 10, 1 to 5, 1 to 3, 3 to 5, 3 to 8, 5 to 10, 5 to 8, 8 to 10, 10 to 12, or 12 to 15° C., inclusive) greater than the melting temperature (such as the empirically measured or calculated $T_m$) of at least 25%, 50%, 60%, 70%, 75%, 80%, 90%, 95%, or all of the non-identical primers, and the length of the annealing step (per PCR cycle) is between 5 and 180 minutes, such as 15 and 120 minutes, 15 and 60 minutes, 15 and 45 minutes, or 20 and 60 minutes, inclusive.

Exemplary Multiplex PCR Methods

In various embodiments, limiting primer concentrations and/or conditions are used. In various embodiments, the length of the annealing step is between 15, 20, 25, 30, 35, 40, 45, or 60 minutes on the low end of the range and 20, 25, 30, 35, 40, 45, 60, 120, or 180 minutes on the high end of the range. In various embodiments, the length of the annealing step (per PCR cycle) is between 30 and 180 minutes. For example, the annealing step can be between 30 and 60 minutes and the concentration of each primer can be less than 20, 15, 10, or 5 nM. In other embodiments the primer concentration is 1, 2, 3, 4, 5, 6, 7, 8, 9, 10, 15, 20, or 25 nM on the low end of the range, and 2, 3, 4, 5, 6, 7, 8, 9, 10, 15, 20, 25, and 50 on the high end of the range.

At high level of multiplexing, the solution can become viscous due to the large amount of primers in solution. If the solution is too viscous, one can reduce the primer concentration to an amount that is still sufficient for the primers to bind the template DNA. In various embodiments, between 500 and 100,000 different primers are used and the concentration of each primer is less than 20 nM, such as less than 10 nM or between 1 and 10 nM, inclusive.

Exemplary Kits

In one aspect, the invention features a kit, such as a kit for amplifying target loci in a nucleic acid sample for detecting deletions and/or duplications, or determining ploidy, or detecting chromosomal aneuploidy such as CNV or determining AAI, of target chromosome regions or entire chromosomes using any of the methods described herein. In some embodiments, the kit can include any of the primer sets, pools, libraries, or reaction mixtures (typically without the sample or nucleic acid derived therefrom) of the invention. In an embodiment, the kit comprises a plurality of inner forward primers and optionally a plurality of inner reverse primers, and optionally outer forward primers and outer reverse primers, where each of the primers is designed to hybridize to the region of DNA an effective distance upstream and/or downstream from one of the target sites (e.g., polymorphic sites) on the target chromosome(s) or chromosome region(s), and optionally additional chromosomes or chromosome regions. In some embodiments, the kit includes instructions for using the primer pool, set, or library to amplify the target loci, such as for detecting one or more deletions and/or duplications of one or more chromosome regions or entire chromosomes using any of the methods described herein. The kit can include or be linked to, a computer program for performing the analytical steps of the methods provided herein, such as estimating the phase, generating individual probabilities, generating joint probabilities, generating a set of hypothesis or models, and/or selecting a best fit model, using genetic data generated using the kit. In some embodiments, the kit includes reagents for isolating cfDNA from plasma.

As indicated, in certain embodiments, kits of the invention provide primers or primer pairs for detecting deletions and/or duplications, or determining ploidy, or detecting chromosomal aneuploidy such as CNV or detecting AAI, such as the primers or primer pairs for multiplex reactions disclosed herein. In these embodiments, the kits, for example, can include between at least 100, 200, 250, 300, 500, 1000, 2000, 2500, 3000, 5000, 10,000, 20,000, 25,000, 28,000, 50,000, or 75,000 and at most 200, 250, 300, 500, 1000, 2000, 2500, 3000, 5000, 10,000, 20,000, 25,000, 28,000, 50,000, 75,000, or 100,000 primer pairs that are shipped together and that bind to primer binding sites that map to haploblocks, that bind within haploblocks, and/or that bind to sample DNA an effective distance from a polymorphic loci within a haploblock, on one or more target chromosomes or chromosome regions of interest known to exhibit aneuploidy associated with a disease or disorder. The haploblock can include at least 2, 3, 4, 5, 6, 7, 8, 9, 10, 15, 20, or 25 polymorphic loci that are target polymorphic loci for a method using the kit. The primers or primer pairs, or pools, sets, or libraries thereof, can be contained in a single vessel, such as a single tube or box, or multiple tubes or boxes. In certain embodiments, the primer pairs are pre-qualified by a commercial provider and sold together, and in other embodiments, a customer selects custom gene targets from a server that lists such components together in a virtual kit, and/or primers and a commercial provider makes and ships the primer pool to the customer neither in one tube or a plurality of tubes. In certain exemplary embodiments, the kits include primers for detecting CNVs, especially CNVs known to be correlated with at least one type of cancer.

Kits for circulating DNA detection according to some embodiments of the present invention, include standards and/or controls for circulating DNA detection and can include reagents for isolating ctDNA from blood or a sample thereof, such as plasma. For example, in certain embodiments, the standards and/or controls are sold and optionally shipped and packaged together with primers used to perform the amplification reactions provided herein.

Example Computer Architecture

In certain embodiments, provided herein are computer programs and computer systems for performing the analytical steps of the methods provided herein, such as estimating the phase, generating individual probabilities, generating joint probabilities, generating a set of hypothesis or models, and/or selecting a best fit model, using genetic data generated using the kit. The computer programs in certain embodiments, are associated with pools, sets, pluralities, or libraries of primers as provided herein, for carrying out methods provided herein.

In some embodiments, provided herein is a system for detecting chromosomal ploidy in a sample of an individual. The system can include the following:

a. an input processor configured to receive allelic frequency data comprising the amount of each allele present in the sample at each loci of a plurality of polymorphic loci, for example a set of SNP loci, on a plurality of segments within the chromosomal region, wherein each segment comprises loci with strong linkage disequilibrium, or each segment is a haploblock;
b. a modeler configured to:
    i. generate phased allelic information for the set of polymorphic loci by estimating the phase of the allele frequency data taking into account an increased statistical correlation of polymorphic loci within the same segment;
    ii. generate individual probabilities of allele frequencies for the polymorphic loci for different ploidy states using the allele frequency data; and
    iii. generate joint probabilities for the set of polymorphic loci using the individual probabilities and the phased allelic information; and
c. a hypothesis manager configured to select, based on the joint probabilities, a best fit model indicative of chromosomal ploidy, thereby determining ploidy of the chromosomal region.

In certain system embodiments, the allele frequency data is generated by a nucleic acid sequencing system.

In another embodiment, provided herein is a nontransitory computer readable medium for detecting chromosomal ploidy in a sample of an individual, that, when executed by a processing device, causes the processing device to perform the following:

a. receive allele frequency data comprising the amount of each allele present in the sample at each loci of a plurality of polymorphic loci on a plurality of segments within the chromosomal region, wherein each segment comprises loci with strong linkage disequilibrium;
b. generate phased allelic information for the set of polymorphic loci by estimating the phase of the allele frequency data taking into account an increased statistical correlation of polymorphic loci within the same segment;
c. generate individual probabilities of allele frequencies for the polymorphic loci for different ploidy states using the allele frequency data;
d. generate joint probabilities for the set of polymorphic loci using the individual probabilities and the phased allelic information; and
e. select, based on the joint probabilities, a best fit model indicative of chromosomal ploidy, thereby determining ploidy of the chromosomal region.

In certain embodiments, the allele frequency data is generated from nucleic acid sequence data.

Figure 5:
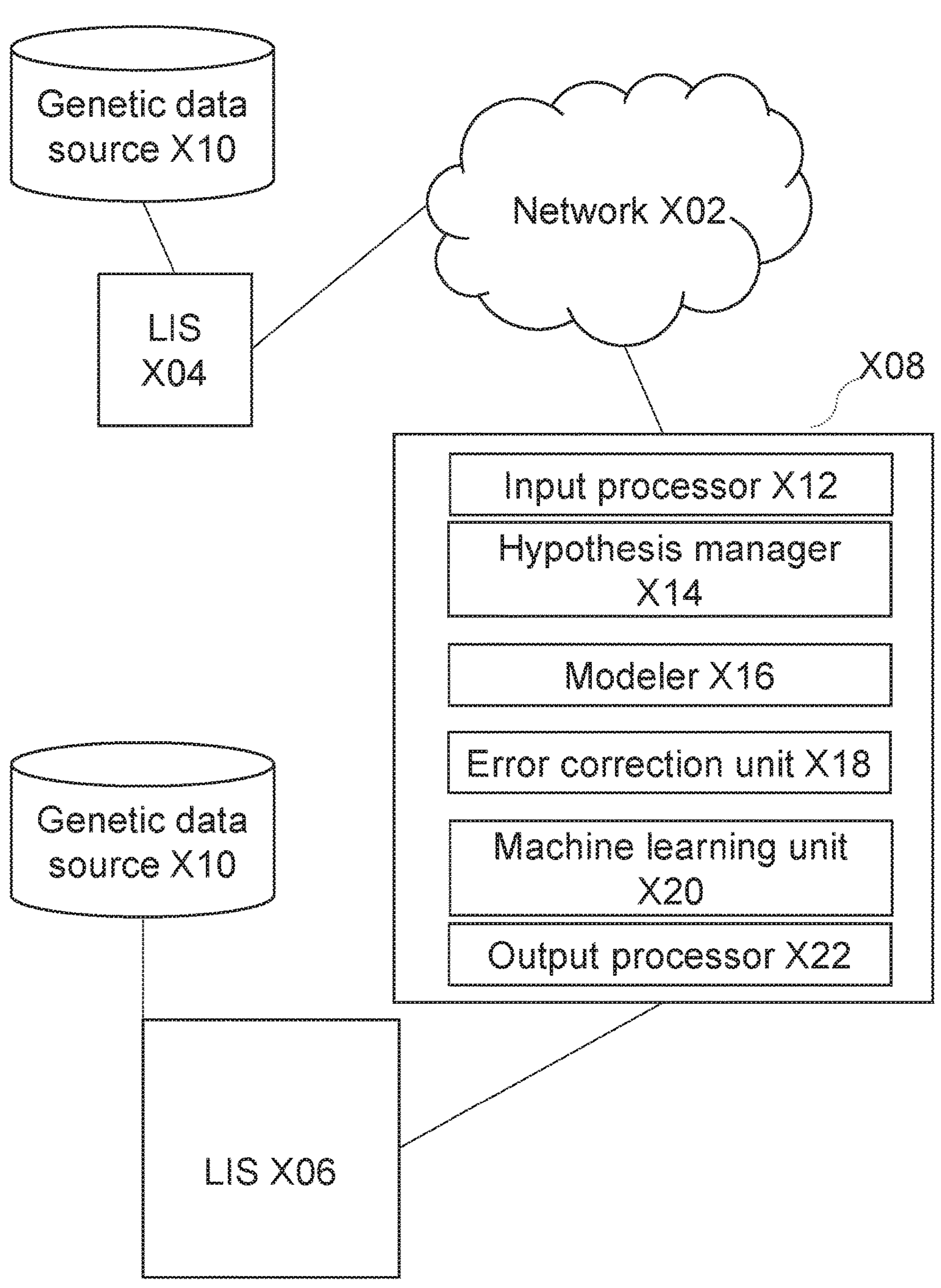
FIG. 5 shows an example system architecture X00 useful for performing embodiments of the present invention.

FIG. 5 shows an example system architecture X00 useful for performing embodiments of the present invention. System architecture X00 includes an analysis platform X08 connected to one or more laboratory information systems ("LISs") X04. As shown in FIG. 5, analysis platform X08 can be connected to LIS X04 over a network X02. Network X02 may include one or more networks of one or more network types, including any combination of LAN, WAN, the Internet, etc. Network X02 may encompass connections between any or all components in system architecture X00. Analysis platform X08 may alternatively or additionally be connected directly to LIS X06. In an embodiment, analysis platform X08 analyzes genetic data provided by LIS X04 in a software-as-a-service model, where LIS X04 is a third-party LIS, while analysis platform X08 analyzes genetic data provided by LIS X06 in a full-service or in-house model, where LIS X06 and analysis platform X08 are controlled by the same party. In an embodiment where analysis platform X08 is providing information over network X02, analysis platform X08 can be a server.

In an example embodiment, laboratory information system X04 includes one or more public or private institutions that collect, manage, and/or store genetic data. A person having skill in the relevant art(s) would understand that methods and standards for securing genetic data are known and can be implemented using various information security techniques and policies, e.g., username/password, Transport Layer Security (TLS), Secure Sockets Layer (SSL), and/or other cryptographic protocols providing communication security.

In an example embodiment, system architecture X00 operates as a service-oriented architecture and uses a client-server model that would be understood by one of skill in the relevant art(s) to enable various forms of interaction and communication between LIS X04 and analysis platform X08. System architecture X00 can be distributed over various types of networks X02 and/or may operate as cloud computing architecture. Cloud computing architecture may include any type of distributed network architecture. By way of example and not of limitation, cloud computing architecture is useful for providing software as a service (SaaS), infrastructure as a service (IaaS), platform as a service (PaaS), network as a service (NaaS), data as a service (DaaS), database as a service (DBaaS), backend as a service (BaaS), test environment as a service (TEaaS), API as a service (APIaaS), integration platform as a service (IPaaS) etc.

In an example embodiment, LISs X04 and X06 each include a computer, device, interface, etc. or any sub-system thereof. LISs X04 and X06 may include an operating system (OS), applications installed to perform various functions such as, for example, access to and/or navigation of data made accessible locally, in memory, and/or over network X02. In an embodiment, LIS X04 accesses analysis platform X08 through an application programming interface ("API"). LIS X04 may also include one or more native applications that may operate independently of an API.

In an example embodiment, analysis platform X08 includes one or more of an input processor X12, a hypothesis manager X14, a modeler X16, an error correction unit X18, a machine learning unit X20, and an output processor X18. Input processor X12 receives and processes inputs from LISs X04 and/or X06. Processing may include but is not limited to operations such as parsing, transcoding, translating, adapting, or otherwise handling any input received from LISs X04 and/or X06. Inputs can be received via one or more streams, feeds, databases, or other sources of data, such as can be made accessible by LISs X04 and X06. Data errors can be corrected by error correction unit X18 through performance of the error correction mechanisms described above.

In an example embodiment, hypothesis manager X14 is configured to receive the inputs passed from input processor X12 in a form ready to be processed in accordance with hypotheses for genetic analysis that are represented as models and/or algorithms. Such models and/or algorithms can be used by modeler X16 to generate probabilities, for example, based on dynamic, real-time, and/or historical statistics or other indicators. Data used to derive and populate such strategy models and/or algorithms are available to hypothesis manager X14 via, for example, genetic data source X10. Genetic data source X10 may include, for example, a nucleic acid sequencer. Hypothesis manager X14 can be configured to formulate hypotheses based on, for example, the variables required to populate its models and/or algorithms. Models and/or algorithms, once populated, can be used by modeler X16 to generate one or more hypotheses as described above. Hypothesis manager X14 may select a particular value, range of values, or estimate based on a most-likely hypothesis as an output as described above. Modeler X16 may operate in accordance with models and/or algorithms trained by machine learning unit X20. For example, machine learning unit X20 may develop such models and/or algorithms by applying a classification algorithm as described above to a training set database (not shown).

Once hypothesis manager X14 has identified a particular output, such output can be returned to the particular LIS 104 or 106 requesting the information by output processor X22.

Figure 6:
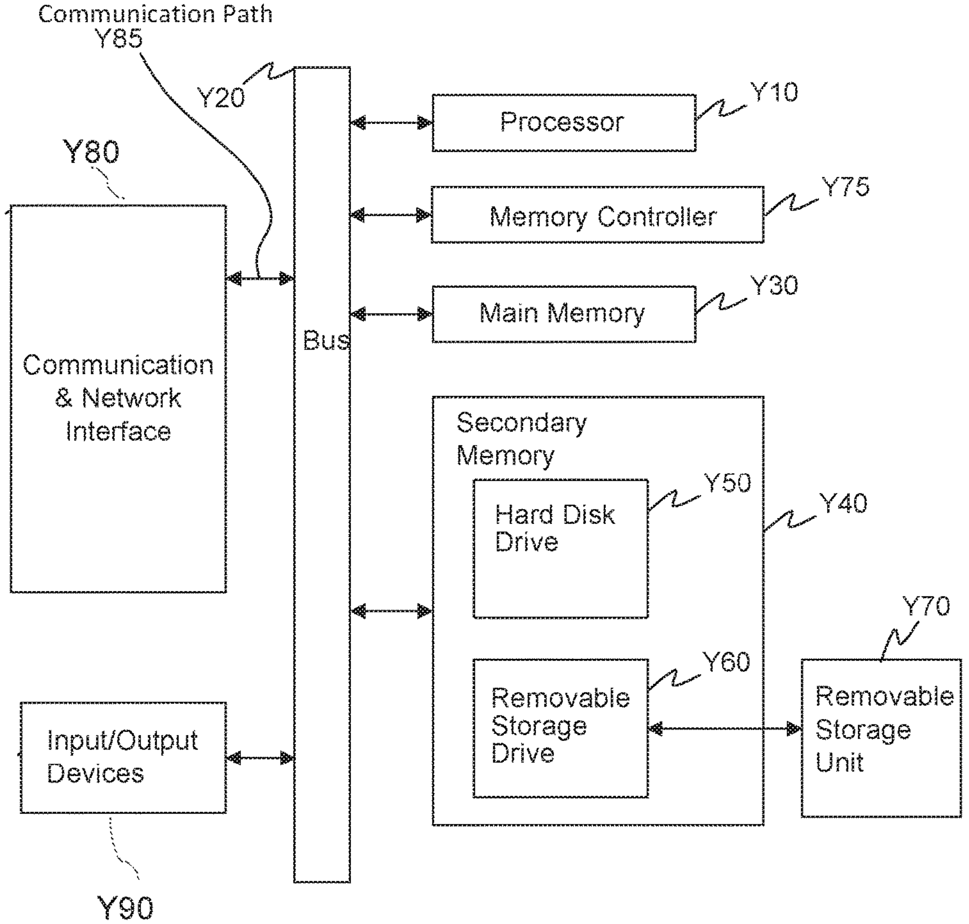
FIG. 6 illustrates an example computer system for performing embodiments of the present invention.

Various aspects of the disclosure can be implemented on a computing device by software, firmware, hardware, or a combination thereof. FIG. 6 illustrates an example computer system Y00 in which the contemplated embodiments, or portions thereof, can be implemented as computer-readable code. Various embodiments are described in terms of this example computer system Y00.

Processing tasks in the embodiment of FIG. 6 are carried out by one or more processors Y02. However, it should be noted that various types of processing technology can be used here, including programmable logic arrays (PLAs), application-specific integrated circuits (ASIcs), multi-core processors, multiple processors, or distributed processors. Additional specialized processing resources such as graphics, multimedia, or mathematical processing capabilities may also be used to aid in certain processing tasks. These processing resources can be hardware, software, or an appropriate combination thereof. For example, one or more of processors Y02 can be a graphics-processing unit (GPU). In an embodiment, a GPU is a processor that is a specialized electronic circuit designed to rapidly process mathematically intensive applications on electronic devices. The GPU may have a highly parallel structure that is efficient for parallel processing of large blocks of data, such as mathematically intensive data. Alternatively or in addition, one or more of processors Y02 can be a special parallel processing without the graphics optimization, such parallel processors performing the mathematically intensive functions described herein. One or more of processors Y02 may include a processing accelerator (e.g., DSP or other special-purpose processor).

Computer system Y00 also includes a main memory Y30, and may also include a secondary memory Y40. Main memory Y30 can be a volatile memory or non-volatile memory, and divided into channels. Secondary memory Y40 may include, for example, non-volatile memory such as a hard disk drive Y50, a removable storage drive Y60, and/or a memory stick. Removable storage drive Y60 may comprise a floppy disk drive, a magnetic tape drive, an optical disk drive, a flash memory, or the like. The removable storage drive Y60 reads from and/or writes to a removable storage unit 470 in a well-known manner. Removable storage unit Y70 may comprise a floppy disk, magnetic tape, optical disk, etc. which is read by and written to by removable storage drive Y60. As will be appreciated by persons skilled in the relevant art(s), removable storage unit Y70 includes a computer usable storage medium having stored therein computer software and/or data.

In alternative implementations, secondary memory Y40 may include other similar means for allowing computer programs or other instructions to be loaded into computer system Y00. Such means may include, for example, a removable storage unit Y70 and an interface (not shown). Examples of such means may include a program cartridge and cartridge interface (such as that found in video game devices), a removable memory chip (such as an EPROM, or PROM) and associated socket, and other removable storage units Y70 and interfaces which allow software and data to be transferred from the removable storage unit Y70 to computer system Y00.

Computer system Y00 may also include a memory controller Y75. Memory controller Y75 controls data access to main memory Y30 and secondary memory Y40. In some embodiments, memory controller Y75 can be external to processor Y10, as shown in FIG. 6. In other embodiments, memory controller Y75 may also be directly part of processor Y10. For example, many AMD™ and Intel™ processors use integrated memory controllers that are part of the same chip as processor Y10 (not shown in FIG. 6).

Computer system Y00 may also include a communications and network interface Y80. Communication and network interface Y80 allows software and data to be transferred between computer system Y00 and external devices. Communications and network interface Y80 may include a modem, a communications port, a PCMCIA slot and card, or the like. Software and data transferred via communications and network interface Y80 are in the form of signals which can be electronic, electromagnetic, optical, or other signals capable of being received by communication and network interface Y80. These signals are provided to communication and network interface Y80 via a communication path Y85. Communication path Y85 carries signals and can be implemented using wire or cable, fiber optics, a phone line, a cellular phone link, an RF link or other communications channels.

The communication and network interface Y80 allows the computer system Y00 to communicate over communication networks or mediums such as LANs, WANs the Internet, etc. The communication and network interface Y80 may interface with remote sites or networks via wired or wireless connections.

In this document, the terms "computer program medium," "computer-usable medium" and "non-transitory medium" are used to generally refer to tangible media such as removable storage unit Y70, removable storage drive Y60, and a hard disk installed in hard disk drive Y50. Signals carried over communication path Y85 can also embody the logic described herein. Computer program medium and computer usable medium can also refer to memories, such as main memory Y30 and secondary memory Y40, which can be memory semiconductors (e.g. DRAMs, etc.). These computer program products are means for providing software to computer system Y00.

Computer programs (also called computer control logic) are stored in main memory Y30 and/or secondary memory Y40. Computer programs may also be received via communication and network interface Y80. Such computer programs, when executed, enable computer system Y00 to implement embodiments as discussed herein. In particular, the computer programs, when executed, enable processor Y10 to implement the disclosed processes. Accordingly, such computer programs represent controllers of the computer system Y00. Where the embodiments are implemented using software, the software can be stored in a computer program product and loaded into computer system Y00 using removable storage drive Y60, interfaces, hard drive Y50 or communication and network interface Y80, for example.

The computer system Y00 may also include input/output/display devices Y90, such as keyboards, monitors, pointing devices, touchscreens, etc.

It should be noted that the simulation, synthesis and/or manufacture of various embodiments can be accomplished, in part, through the use of computer readable code, including general programming languages (such as C or C++), hardware description languages (HDL) such as, for example, Verilog HDL, VHDL, Altera HDL (AHDL), or other available programming tools. This computer readable code can be disposed in any known computer-usable medium including a semiconductor, magnetic disk, optical disk (such as CD-ROM, DVD-ROM). As such, the code can be transmitted over communication networks including the Internet.

The embodiments are also directed to computer program products comprising software stored on any computer-usable medium. Such software, when executed in one or more data processing devices, causes a data processing device(s) to operate as described herein. Embodiments employ any computer-usable or readable medium, and any computer-usable or readable storage medium known now or in the future. Examples of computer-usable or computer-readable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nano-technological storage devices, etc.), and communication mediums (e.g., wired and wireless communications networks, local area networks, wide area networks, intranets, etc.). Computer-usable or computer-readable mediums can include any form of transitory (which include signals) or non-transitory media (which exclude signals). Non-transitory media comprise, by way of non-limiting example, the aforementioned physical storage devices (e.g., primary and secondary storage devices).

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The following examples are put forth so as to provide those of ordinary skill in the art with a complete disclosure and description of how to use the embodiments provided herein, and are not intended to limit the scope of the disclosure nor are they intended to represent that the Examples below are all or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

EXAMPLES

Example 1. Creation of Primer Pool for Ovarian Cancer Polymorphic Loci within Haploblocks This example illustrates a method for identifying haploblocks within target chromosomal regions for detecting CNV in ovarian cancer, identifying target polymorphic loci within those segments, and selecting a pool of primers for amplifying nucleic acids including those target polymorphic loci. to the pool of primers allow the determination of allele frequencies at those polymorphic loci in experiments provided in other Examples herein. Accordingly, in this example, Ovarian cancer chromosome regions of interest were identified, haploblocks were identified, candidate SNPs were selected, and pools of primers were designed for amplifying the candidate SNPs.

Primer Pool Design.

The design process consists of these main steps:

a. Select candidate target SNPs for each region of interest.
b. Attempt to design up to five sets of right and left specific primers for each candidate target SNP.
c. Filter designs into haploblocks with at least 10 SNPs with designs.
d. Select compatible designs to form the primer pools.

Candidate SNPs Selection:

For each region of interest, we chose candidate SNPs satisfying the following criteria:

e. The SNP must be present in both dbSNP Common 138 and the 1000 Genomes project (the phase 1 version 3 variant calls released Apr. 30, 2012, "An integrated map of genetic variation from 1,092 human genomes," McVean et al, Nature 491: 56-65 (1 Nov. 2012) doi: 10.1038/nature 11632) variant call data set.
f. The SNP minor allele frequency from the 1000 Genomes project must be at least 10%.
g. The SNP location must be within one of the corresponding breakpoints in Table 4.

TABLE 4

| Chrom | Start | End | Event Type | No. Patients (COSMIC) | Cancer Census Gene |
|---|---|---|---|---|---|
| 8 | 115298000 | 145233000 | GAIN | 173 | MYC, MTSS1, NDRG1 |
| 3 | 166356000 | 180256000 | GAIN | 108 | PIK3CA, MECOM |
| 8 | 100758000 | 115298000 | GAIN | 101 | |
| 8 | 617000 | 37343000 | LOSS | 99 | |
| 19 | 28240000 | 33433000 | GAIN | 82 | CCNE1 |
| *20 | 29369569 | 63025520 | GAIN | 82 | |
| *20 | 1 | 26369569 | GAIN | 67 | |

TABLE 4-continued

| Chrom | Start | End | Event Type | No. Patients (COSMIC) | Cancer Census Gene |
|---|---|---|---|---|---|
| 12 | 18959000 | 29050000 | GAIN | 65 | KRAS |
| 19 | 34341000 | 40857000 | GAIN | 55 | AKT2 |
| 19 | 12042000 | 17796000 | GAIN | 54 | |
| 16 | 60437000 | 89380000 | LOSS | 50 | CDH1 |
| *17 | 25800001 | 31800000 | LOSS | 30 | NF1 |
| 22 | 42378000 | 49332000 | LOSS | 21 | |
| *17 | 10700001 | 16000000 | LOSS | 16 | MAP2K4 |

TABLE 5

Number of candidate SNPs selected for each region of interest.

| Chrom | Start | End | Candidate SNPs |
|---|---|---|---|
| 8 | 115298000 | 145233000 | 61,362 |
| 3 | 166356000 | 180256000 | 24,023 |
| 8 | 100758000 | 115298000 | 25,035 |
| 8 | 617000 | 37343000 | 96,572 |
| 19 | 28240000 | 33433000 | 10,294 |
| *20 | 29369569 | 63025520 | 60,135 |
| *20 | 1 | 26369569 | 54,321 |
| 12 | 18959000 | 29050000 | 19,888 |
| 19 | 34341000 | 40857000 | 11,607 |
| 19 | 12042000 | 17796000 | 12,303 |
| 16 | 60437000 | 89380000 | 66,790 |
| *17 | 25800001 | 31800000 | 7,699 |
| 22 | 42378000 | 49332000 | 17,705 |
| *17 | 10700001 | 16000000 | 12,111 |

Primer Design:

Primers were designed using primer3 release 2.3.6 (Whitehead Institute for Biomedical Research, Steve Rozen (Available on the Internet at //primer3.sourceforge.net/releases.php)) and then filtered in a reiterative fashion to check primer specificity. For each candidate SNP primer3 was used to design left and right primers (two-sided) with an amplicon length within a range of 50 to 75 bp and a melting temperature between 53-60° C. Primer3 was configured to use the SantaLucia salt correction and melting temperature formulae (SantaLucia JR (1998) "A unified view of polymer, dumbbell and oligonucleotide DNA nearest-neighbor thermodynamics", *Proc Natl Acad Sci* 95:1460-65).

Primer locations are restricted to be at least 2 bp away from any SNP which is present either in dbSNP Common 138, or in the 1000 Genomes project with minor allele frequency larger than 1%. Up to five designs can be generated per target. The parameters in Table 6 were used for primer design.

TABLE 6

Exemplary design parameters:

| Name | Original Value | Description |
|---|---|---|
| target_padding | 2 | Primers should end at least 2 bases away from the target loci |
| min_amplicon_size | 50 | |
| max_amplicon_size | 75 | |
| PRIMER_MAX_SIZE | 30 | |
| PRIMER_OPT_SIZE | 24 | |
| PRIMER_MIN_SIZE | 18 | |
| PRIMER_WT_SIZE_LT | 0 | |
| PRIMER_WT_SIZE_GT | 1 | Penalty for primer longer than optimal |
| PRIMER_PAIR_WT_PRODUCT_SIZE_LT | 0 | |
| PRIMER_PAIR_WT_PRODUCT_SIZE_GT | 3 | Significant penalty for amplicon longer than optimal |
| PRIMER_MAX_TM | 60 | |
| PRIMER_OPT_TM | 56 | |
| PRIMER_MIN_TM | 53 | |
| PRIMER_WT_TM_LT | 1.5 | Penalty for TM lower than optimal |
| PRIMER_WT_TM_GT | 1 | Penalty for TM higher than optimal |
| PRIMER_MAX_GC | 70 | |
| PRIMER_OPT_GC_PERCENT | 50 | |
| PRIMER_MIN_GC | 30 | |
| PRIMER_WT_GC_PERCENT_LT | 1 | |
| PRIMER_WT_GC_PERCENT_GT | 1 | |
| PRIMER_MAX_END_GC | 3 | |
| PRIMER_SALT_CORRECTIONS | 1 | |
| PRIMER_MAX_POLY_X | 10 | |
| PRIMER_INTERNAL_MAX_POLY_X | 10 | |

The designs generated by primer3 were then filtered:

h. if the amplicon GCcontent is not in a safe range [30%-70%].

i. if primer pairs are susceptible to mispriming and amplicons that are not sufficiently unique in the genome to map confidently.

Finally, for SNPs with multiple remaining design pairs we keep the shortest amplicon. The following table shows the number of SNPs with passing designs. It should be noted that many if not most candidate SNPs do not have any feasible design.

TABLE 7

Number of SNPs with designed assays for each region of interest.

| Chrom | Start | End | SNPs with design | Yield |
|---|---|---|---|---|
| 8 | 115298000 | 145233000 | 15,993 | 26.1% |
| 3 | 166356000 | 180256000 | 4,194 | 17.5% |
| 8 | 100758000 | 115298000 | 4,644 | 18.6% |
| 8 | 617000 | 37343000 | 16,503 | 17.1% |
| 19 | 28240000 | 33433000 | 3,041 | 29.5% |
| *20 | 29369569 | 63025520 | 17,371 | 28.9% |
| *20 | 1 | 26369569 | 12,955 | 23.8% |
| 12 | 18959000 | 29050000 | 3,289 | 16.5% |
| 19 | 34341000 | 40857000 | 2,649 | 22.8% |
| 19 | 12042000 | 17796000 | 2,510 | 20.4% |
| 16 | 60437000 | 89380000 | 15,082 | 22.6% |
| *17 | 25800001 | 31800000 | 1,842 | 23.9% |
| 13 | 48765000 | 49720000 | 230 | 19.5% |
| 22 | 42378000 | 49332000 | 5,756 | 32.5% |
| *17 | 10700001 | 16000000 | 2,541 | 21.0% |

Haploblocks were identified by identifying polymorphic loci with strong linkage disequilibrium using a D'>95% cutoff where 95% of pairwise SNP comparisons showed a strong linkage disequilibrium. SNPs with minor allele frequency of less than 5% were ignored by the method. The program called plink was used to estimate haploblocks (http://pngu.mgh.harvard.edu/~purcell/plink/ld.shtml #blox). The program estimates haploblocks for a given set of SNPs based on a given reference panel.

For wet lab experiments confirming the in silico results, amplicons can be identified that include the SNPs, with lengths between 50 and 75 bp, with a Tm of between 53-66C and with a GC content of 30-70 and MAF of 10-50%.

We used the 1000 genomes project haplotypes as the reference panel (1000 genomes project haplotypes release September 2013). The release contains haplotypes on 1092 samples (#haplotypes=2184) for 36.8 million SNPs. The haploblocks in Table 8 were identified.

TABLE 8

Identified haploblocks for SNPs with designed assays for each region of interest

| Index | Chrom | start_bp | end_bp | designs in haploblocks >-10 | Yield | designs in haploblocks >20 | Longest _Block |
|---|---|---|---|---|---|---|---|
| 1 | 12 | 18,959,000 | 29,050,000 | 645 | 77% | 221 | 42 |
| 3 | 16 | 60,437,000 | 89,380,000 | 1170 | 95% | 670 | 44 |
| 4 | 19 | 12,042,000 | 17,796,000 | 405 | 72% | 104 | 29 |
| 5 | 19 | 28,240,000 | 33,433,000 | 836 | 82% | 343 | 61 |
| 6 | 19 | 34,341,000 | 40,857,000 | 704 | 84% | 402 | 42 |
| 7 | 22 | 42,378,000 | 49,332,000 | 547 | 70% | 156 | 57 |
| 8 | 3 | 166,356,000 | 180,256,000 | 771 | 78% | 266 | 37 |
| 9 | 8 | 617,000 | 37,343,000 | 1225 | 92% | 624 | 55 |
| 10 | 8 | 115,298,000 | 145,233,000 | 1173 | 91% | 708 | 57 |
| 11 | 8 | 100,758,000 | 115,298,000 | 1309 | 97% | 628 | 64 |
| 12 | 20 | 1 | 26,369,569 | 1016 | 96% | 769 | 77 |
| 13 | 20 | 29,369,569 | 63,025,520 | 1238 | 96% | 965 | 50 |
| 14 | 17 | 25,800,001 | 31,800,000 | 457 | 78% | 173 | 24 |
| 15 | 17 | 10,700,001 | 16,000,000 | 332 | 84% | 126 | 24 |

Pooling:

Candidate PCR assays are ranked and selected on the basis of number of patients having a CNV spanning over the SNP location, the haploblock size in terms of number of SNPs with haploblocks with more SNPs being favored, target SNP minor allele frequency, observed heterozygosity rate (from dbSNP), presence in HapMap, type of mutation (transversions are preferred over transitions), amplicon GC-content and amplicon length.

Results

Table 9 provides details regarding haploblocks (i.e. target segments) within chromosome regions of interest. As indicated, for each segment there were at least 81 SNPs in haploblocks (i.e. segments) with greater than 20 SNPs. The longest haploblock per chromosome region of interest varied from 24 to 79 SNPs (Table 9).

TABLE 9

Final pool configuration for each region of interest.

| Chrom | Start | End | Number of assays | expected_no.hets | Number of SNPs in Blocks >20 | Longest block |
|---|---|---|---|---|---|---|
| 8 | 115298000 | 145233000 | 1296 | 507 | 829 | 56 |
| 3 | 166356000 | 180256000 | 992 | 365 | 290 | 40 |
| 8 | 100758000 | 115298000 | 1354 | 512 | 729 | 61 |
| 8 | 617000 | 37343000 | 1332 | 512 | 608 | 55 |
| 19 | 28240000 | 33433000 | 1019 | 388 | 336 | 54 |
| *20 | 29369569 | 63025520 | 1290 | 508 | 1041 | 50 |
| *20 | 1 | 26369569 | 1055 | 406 | 790 | 79 |
| 12 | 18959000 | 29050000 | 843 | 294 | 221 | 42 |
| 19 | 34341000 | 40857000 | 838 | 317 | 393 | 42 |
| 19 | 12042000 | 17796000 | 563 | 208 | 81 | 30 |
| 16 | 60437000 | 89380000 | 1235 | 453 | 720 | 43 |
| *17 | 25800001 | 31800000 | 588 | 230 | 174 | 24 |
| 22 | 42378000 | 49332000 | 783 | 307 | 201 | 57 |
| *17 | 10700001 | 16000000 | 395 | 144 | 125 | 24 |

Example 2

In this in silico experiment the accuracy of the informatics haplotyping was determined. To estimate haplotypes, the tool ShapeIt was used (available at the hypertext transfer protocol secure site at mathgen.stats.ox.ac.uk/genetics_software/shapeit/shapeit.html). ShapeIt takes as input a list of genotypes along with haplotyping likelihoods based on SNP loci locations and population cross-over data, and outputs estimated haplotypes for the inputted genotypes. It estimates haplotypes for each chromosome separately.

The 1000 genomes project has existing high confidence genotype calls for many individuals publicly available. The entirety of this high quality genotype dataset was used as a test dataset for the haplotyping validation. Similarly, the 1000 genomes project has available high quality haplotyping information for each dataset. The 1000 genomes haplotyping data can be used as a best guess truth dataset for comparison.

Comparing haplotypes estimated by ShapeIt to known, curated haplotypes from 1000 genomes provides us with a measure of the level of haplotyping accuracy and error of the primer pool. When comparing errors in haplotyping, it is important to also consider if the mis-haplotyping is occurring within a known haploblock or outside of a haploblock. SNPs within a haploblock are genetically linked and generally exist together. Thus, one can conclude that the mis-haplotyping switch error will be lesser within haploblocks and greater outside of haploblocks.

1092 genotype samples from the 1000 genomes dataset were used for the validation. All samples were run through Shapelt for haplotype estimation. The resulting haplotypes were compared to existing, curated 1000 genomes haplotypes to determine the level of error in haplotyping for the primer pool set. Each haplotyping event was carried out on each region independently.

The Haplotyping Error is Calculated as:

Haplotyping Error=(Number of switched haplotype calls at SNP X)/(Number of heterozygous genotypes). It was observed that haplotying error rates were decreased within haplblocks in simulations.

Example 3

In this in silico experiment, it was observed that by analyzing polymorphic data as if the polymorphic loci were within haploblocks, allelic imbalance was detected at similar rates to calculations using perfect haplotype data, in samples down to allelic imbalances of 1%, provided that a sufficient number of polymorphic loci per target chromosome region were analyzed that were within haploblocks having a minimum number of polymorphic loci per haploblock. Two artificial titration experiments using breast cancer cell lines (HCC1954 and HCC2218) were performed to evaluate the performance of the CNV calling algorithm in plasma samples. More specifically, titrations were prepared from pairs of matched tumor and normal cell line samples and having CNVs on chromosome 1 or chromosome 2.

Cell line HCC1954 was evaluated for chromosome 1, and cell line HCC2218 was evaluated for chromosome 2. For each chromosome, 1248 SNPs were analyzed.

We assigned certain numbers of consecutive SNPs to haploblocks to evaluate the theoretical performance of the CNV calling algorithm in the potential product. The allele count data from published titration experiments (Kirkizlar et al. 2015 (Kirkizlar et al., *Translational Oncology,* 8 407-416)) were used. The probes of Kirkizlar et al. 2015 were used, except that if there were more than 1248 SNPs in a probe design, only the first 1248 SNPs were used.

We assumed that we had perfect haplotype information within the blocks, and no haplotype information between the blocks. Referring to the formula provided herein in the section on combining likelihoods, (Combined_Likelihoods), in the presence of perfect haplotype information, we have c=0 or c=1. In the present simulation to determine the optimal block size, we assumed perfect haplotypes within the blocks (i.e., c=0 or c=1) and we assumed no haplotype information between the blocks (i.e., c=0.5). Note that as the minimum block size increases, the number of total SNPs decreases. We attempted to determine the optimal minimum block size that also has a sufficient number of SNPs. We ran our algorithm for minimum block sizes of 1, 10, 15 and 20; and compared our results with the system that had perfect haplotype information.

For minimum block size of 1 (i.e., no haploblock requirement), especially regions with very few good blocks had false positives (with >1.0% allelic imbalance detected for multiple regions that were negative). The quantification of the allelic imbalance value became more accurate for >2.0% allelic imbalance.

Performance of the algorithm was similar to the perfect haplotype case for minimum block size of 10 and maximum block size of 100, and sufficient number of SNPs (≥1000). More specifically, for such cases, there have been scenarios with false positives (allelic imbalance of >0.50%), but generally the detection of true positives has been successful (for each case with ≥1000 SNPs in haploblocks that had allelic imbalance of >1.0% originally, the allelic imbalance was detected to be >1.0% in the imperfect haplotype scenario).

However, for scenarios with a low number of SNPs (i.e. 125 to 250), the algorithm failed to detect even allelic imbalance of >2.5%. Hence, a minimum block size of 10 and at least 350 SNPs in each region, proved to be especially effective for the Ovarian cancer arm length CNV analysis performed in this simulation. Note that for other cancers and for focal chromosome regions, smaller numbers of SNPs and smaller minimum number of SNPs per haploblock can be successfully employed (See Example 5-lung cancer focal chromosome region analysis).

Example 4

This example confirms the effectiveness of the methods provided herein, particularly methods that include the haploblock assay/primer design step of Example 1, in a wet lab environment with patient samples, biochemical methods. Accordingly, for this experiment the primers/assays for ovarian cancer identified in Example 1, were used.

Sample Preparation

DNA extraction and QC. All the plasma aliquots from each patient were pooled prior to cfDNA extraction, and the hemolysis grade of each pooled plasma sample was evaluated visually (no hemolysis, mild hemolysis or severe hemolysis). cfDNA was extracted using the Qiagen NA kit (Valencia, CA) following a protocol optimized for 5 ml of plasma. All cfDNA samples were QCed on Bioanalyzer High Sensitivity chips (Agilent, Santa Clara, CA). The same Bioanalyzer High Sensitivity runs were also used to quantify the cfDNA samples by interpolation of the mononucleosomal peak height on a calibration curve prepared from a pure cfDNA sample that was previously quantified. This was necessary because cfDNA sometimes contains an intact DNA fraction that overlaps with the high size marker on the chip, which makes quantification of the mononucleosomal peak unreliable. A representative subset of the purified genomic DNA samples was quantified using Nanodrops (Wilmington, DE). All of the samples quantified were in the expected range (~10 ng/μl).

cfDNA library preparation. The entire cfDNA amount from each plasma sample was used as input into Library Prep using the Natera library prep kit and following the kit instructions. Libraries were generated from the samples above. Adapters were ligated to DNA fragments and the fragments were amplified using the following protocol:

95° C., 2 min; 15×[95° C., 20 sec, 55° C., 20 sec, 68° C., 20 sec], 68° C. 2 min, 4° C. hold. The libraries were amplified to plateau and then purified using Ampure beads (Beckman Coulter, Brea, CA) following the manufacturer's protocol. The purified libraries were QCed on the LabChip.

cfDNA multiplex PCR and Sequencing. The library material from each plasma sample was used as input DNA into multiplex PCR (mPCR) reactions in the relevant assay pool and an optimized plasma mPCR protocol. The primers of Table 9 of Example 1 were obtained (IDT, Coralville, Iowa) as a pool. A 10 nM primer concentration was used for each primer. The reactions were performed using the following protocol: PCR amplified: 95 C 10 min, 25× [96 C 30 sec, 65 C 20 min, 72 C 30 sec], 72 C 2 min, 4C hold. The amplification product was diluted 1:2,000 in water and 1 µl added to the Barcoding-PCR in a 10 uL reaction volume. The barcoded PCR products were pooled and the pools were purified using Ampure beads following the manufacturer's protocol, QCed on a Bioanalyzer DNA 1000 chip (Agilent, Santa Clara, CA), and quantified using the Qubit dsDNA Broad Range kit (Thermo Fisher Scientific, Waltham, MA). Each pool was sequenced on a separate HiSeq 2500 Rapid run (Illumina, San Diego, CA) with 50 cycle paired end single index reads.

Tables 10-14 provide characteristics of the samples based on prior characterization. The number of samples per stage is shown in Table 10 based on histological analysis. Tables 11-14 are based on next generation sequencing analysis of tumor samples. The number of tumor samples with a CNV covering a at least 50% of the region is shown in Table 11. The number of tumor samples with a CNV covering at least 25% of the region is shown in Table 12. The number of regions with large abnormalities (at least 50% of the region) per patient is shown in Table 13. The number of regions with smaller abnormalities (at least 25% of the region) per patient is shown in Table 14.

TABLE 10

| Patient Coverage in Tumor Samples | | | | | | | |
|---|---|---|---|---|---|---|---|
| Stage | I | II | III | IV | All Malignant | Benign | Total |
| Num of Samples | 11 | 10 | 11 | 8 | 40 | 40 | 80 |

TABLE 11

| Summary Per Region (CNV covering 50%) | | | | | | |
|---|---|---|---|---|---|---|
| Chr | Region | I | II | III | IV | Benign |
| 12 | 1 | 6 | 3 | 0 | 3 | 0 |
| 16 | 3 | 3 | 3 | 1 | 5 | 0 |
| 19 | 4 | 7 | 5 | 0 | 0 | 1 |
| 19 | 5 | 6 | 2 | 0 | 1 | 1 |
| 19 | 6 | 5 | 1 | 0 | 3 | 0 |
| 22 | 7 | 4 | 1 | 3 | 6 | 1 |
| 3 | 8 | 3 | 2 | 3 | 5 | 0 |
| 8 | 9 | 6 | 2 | 3 | 5 | 1 |
| 8 | 10 | 8 | 4 | 2 | 5 | 1 |
| 8 | 11 | 7 | 3 | 1 | 2 | 1 |
| 20 | 12 | 3 | 1 | 1 | 1 | 1 |
| 20 | 13 | 1 | 3 | 3 | 3 | 0 |
| 17 | 14 | 6 | 4 | 3 | 5 | 1 |
| 17 | 15 | 7 | 5 | 4 | 6 | 1 |

TABLE 12

| Summary Per Region (CNV covering 25%) | | | | | | |
|---|---|---|---|---|---|---|
| Chr | Region | I | II | III | IV | Benign |
| 12 | 1 | 7 | 3 | 1 | 4 | 1 |
| 16 | 3 | 3 | 5 | 2 | 6 | 0 |
| 19 | 4 | 7 | 5 | 1 | 1 | 1 |
| 19 | 5 | 6 | 4 | 0 | 2 | 1 |
| 19 | 6 | 7 | 1 | 0 | 3 | 0 |
| 22 | 7 | 6 | 4 | 3 | 7 | 1 |
| 3 | 8 | 3 | 2 | 3 | 5 | 1 |
| 8 | 9 | 7 | 2 | 3 | 7 | 1 |
| 8 | 10 | 8 | 4 | 2 | 5 | 1 |

TABLE 12-continued

| Summary Per Region (CNV covering 25%) | | | | | | |
|---|---|---|---|---|---|---|
| Chr | Region | I | II | III | IV | Benign |
| 8 | 11 | 8 | 3 | 1 | 5 | 1 |
| 20 | 12 | 4 | 3 | 2 | 1 | 1 |
| 20 | 13 | 4 | 3 | 3 | 4 | 1 |
| 17 | 14 | 6 | 4 | 4 | 5 | 1 |
| 17 | 15 | 7 | 5 | 4 | 7 | 2 |

TABLE 13

| Summary of abnormalities per patient (abnormality at least 50%) | | | | | |
|---|---|---|---|---|---|
| Stage | >0 | >1 | >3 | >5 | All Samples |
| I | 9 | 9 | 9 | 5 | 11 |
| II | 5 | 5 | 5 | 5 | 10 |
| III | 5 | 5 | 4 | 3 | 11 |
| IV | 8 | 8 | 8 | 4 | 8 |
| All | | | | | 40 |
| Malignant | 27 | 27 | 26 | 17 | |
| Benign | 1 | 1 | 1 | 1 | 40 |

TABLE 14

| Summary of abnormalities per patient (abnormality at least 25%) | | | | | |
|---|---|---|---|---|---|
| Stage | >0 | >1 | >3 | >5 | All Samples |
| I | 9 | 9 | 9 | 5 | 11 |
| II | 5 | 5 | 5 | 5 | 10 |
| III | 5 | 5 | 4 | 3 | 11 |
| IV | 8 | 8 | 8 | 6 | 8 |
| All | | | | | 40 |
| Malignant | 27 | 27 | 26 | 19 | |
| Benign | 2 | 1 | 1 | 1 | 40 |

CNV was detected in 68% of tumor samples. We had two positives among benign samples, but one clearly seemed positive across all samples and one had a large duplication in the region in question.

Performance of ShapeIT

Summary Per Region

We calculated the errors made by ShapeIT to assess the effectiveness of our informatics haplotyping used in certain embodiments of methods herein. More specifically, among all the haplotype estimates made by ShapeIT between two consecutive heterozygous SNPs, we calculated the % of the SNPs where ShapeIT made an error. We also considered errors in SNP haplotypes where SNP calls were made with high confidence (>95% confidence) vs. low confidence errors (≤95% confidence). As shown in Table 15, ShapeIT errors were observed on all chromosomes tested, and errors were much higher in low confidence call samples.

TABLE 15

| ShapeIt Error by Region | | | | |
|---|---|---|---|---|
| Chr | Region | Error % | High Conf Error % | Low Conf Error % |
| 12 | 1 | 2.51% | 0.61% | 15.79% |
| 16 | 3 | 1.58% | 0.27% | 11.66% |
| 19 | 4 | 2.92% | 0.37% | 20.51% |
| 19 | 5 | 1.07% | 0.00% | 11.96% |
| 19 | 6 | 1.25% | 0.23% | 10.71% |
| 22 | 7 | 2.03% | 0.32% | 16.51% |
| 3 | 8 | 2.95% | 0.45% | 24.06% |
| 8 | 9 | 3.08% | 1.25% | 18.68% |

TABLE 15-continued

| ShapeIt Error by Region | | | | |
|---|---|---|---|---|
| Chr | Region | Error % | High Conf Error % | Low Conf Error % |
| 8 | 10 | 1.03% | 0.59% | 5.28% |
| 8 | 11 | 1.20% | 1.13% | 1.99% |
| 20 | 12 | 1.34% | 0.84% | 7.08% |
| 20 | 13 | 1.47% | 0.41% | 10.24% |
| 17 | 14 | 2.13% | 0.47% | 22.31% |
| 17 | 15 | 3.60% | 0.47% | 29.92% |

Summary Per Sample

Next, among the 9 cancer samples that were not contaminated, we compared the ShapeIT haplotypes with the haplotypes estimated from matched tumor samples. Haplotype estimation from tumor samples is believed to be accurate because the large allelic imbalance makes it relatively easy to determine haplotypes with high confidence. Table 16 provides ShapeIt results for each sample. Total error rate across all samples and all regions was 1.95%. The high confidence error rate was 0.60%, wherein the low confidence error rate was 14.25%.

TABLE 16

| SharpeIt Error by Sample | | | |
|---|---|---|---|
| Sample | Error % | HighConfError % | LowConfError % |
| DLS15-10446 | 3.02% | 1.21% | 21.30% |
| DLS14-23566 | 2.97% | 0.80% | 23.04% |
| DLS14-23548 | 1.76% | 0.59% | 16.17% |
| DLS14-23574 | 1.37% | 0.30% | 11.27% |
| DLS14-23570 | 2.02% | 0.75% | 15.66% |
| DLS15-10457 | 1.44% | 0.32% | 14.67% |
| DLS15-10447 | 1.53% | 0.36% | 8.88% |
| 522 | 1.43% | 0.43% | 9.40% |
| 528 | 2.10% | 0.58% | 16.44% |

Performance of CNV Algorithm

We analyzed the data using a CNV algorithm with two main outputs: (1) Confidence and (2) Average allelic imbalance (AAI). When making a determination of copy number variability in a region, we used the confidence estimate (which is a function of the AAI estimate, number of SNPs, etc.). In plasma samples, CNVs were identified by a maximum likelihood algorithm that searched for plasma CNVs in regions where the tumor sample from the same individual also had CNVs using haplotype information deduced from the tumor sample. In the negative control samples, haplotype information was deduced from parental genotypes. The CNV detection algorithm modeled expected allelic frequencies across all allelic imbalance ratios at 0.025% intervals for three sets of hypotheses: (1) all cells are normal (no allelic imbalance), (2) some/all cells have a homolog 1 deletion or a homolog 2 amplification, or (3) some/all cells have a homolog 2 deletion or a homolog 1 amplification. The likelihood of each hypothesis was determined at each SNP using a Bayesian classifier based on expected and observed allele frequencies at all heterozygous SNPs, and then the joint likelihood across multiple SNPs was calculated. Finally, the hypothesis with the maximum likelihood was selected. This algorithm also calculates the confidence of each CNV call by comparing the likelihoods of different hypotheses. A minimum confidence threshold of 99.9% was used in plasma samples from patients with cancer to minimize false-positive results. Further details regarding the analytical method used are provided in the section herein that discusses the Allelic_Analysis_Example.

We performed two sets of plasma runs, one with 1 ml input DNA, the other one with 5 ml input DNA.

1 ml Input DNA Runs:

Runs SQ1179-SQ1185 included a total of 28 samples (24 cancer samples and 4 normal model samples). Nine malignant, 2 benign, and 4 normal model samples (hence, 9 positives and 6 alleged negatives) were analyzed.

In tumor, a region was counted as positive for CNV if the CNV covered at least 25% of the region. We used a 95% confidence cutoff when calling a region positive in plasma. Based on that, the following table summarizes results.

TABLE 17

| Results of CNV determinations (1 ml samples) | | | |
|---|---|---|---|
| Sample | Stage | Tumor CNVs | Plasma CNVs |
| DLS15-10446 | 4 | 11 | 1 |
| DLS14-23566 | 4 | 9 | 8 |
| DLS14-23548 | 3 | 6 | 1 |
| DLS14-23574 | 3 | 6 | 0 |
| DLS14-23570 | 4 | 8 | 8 |
| DLS15-10457 | 1 | 11 | 0 |
| DLS15-10447 | 1 | 14 | 0 |
| 522 | 3 | 13 | 10 |
| 528 | 3 | 11 | 0 |
| DLS14-23595 | benign | 0 | 0 |
| DLS14-23531 | benign | 0 | 0 |
| N020186-DNA | Normal | N/A | 0 |
| N020180-DNA | Normal | N/A | 0 |
| N020178-DNA | Normal | N/A | 0 |
| N029430-DNA | Normal | N/A | 0 |

The maximum confidence indicating an abnormality in the negative samples was 86%, hence a 95% confidence threshold seems a conservative but reasonable choice. Further experiments and data may provide more evidence for decreasing the confidence cutoff for making a positive call (for example a confidence cutoff of 90% would have resulted in two plasma CNV calls in the samples where we had only one positive call with the 95% threshold, but it would not have changed the result for the samples with no positive calls). Accordingly, although in some embodiments a 90%, 91%, 92%, 93%, 94%, 95%, 96%, 97%, 98%, and 99% cutoff are used, in illustrative embodiments a 90%, 91%, 92%, 93%, 94%, or 95% confidence cutoff is used.

The AAI estimate in the samples and regions where positive calls were made ranged from 1.39% to 14.91%. If the confidence cutoff were decreased to 90%, this range would have been 1.09% to 14.91%.

In certain embodiments, a no call range is defined as well. More specifically, a confidence range could be defined calls are not made on a region (e.g., in one embodiment <80% confidence is reported as low risk of CNV, 80% to 90% is reported as a no call, and >90% is reported as high risk). The specific ranges could be modified. For example, in one embodiment, less than 75% confidence in CNV is reported as low risk of CNV, 75% to 85% is reported as a no call, and greater than 85% is reported as high risk for CNV.

5 ml Input DNA Runs

Runs SQ1211 and SQ1212 included a total of 8 cancer samples. Three malignant and 1 benign sample were analyzed (i.e., 3 positives and 1 alleged negative).

Using similar methods and cutoffs as above to call positives in tumor and plasma, we obtained the results provided in Table 18.

TABLE 18

| Results of CNV determinations (5 ml samples) | | | |
|---|---|---|---|
| Sample | Stage | Tumor CNVs | Plasma CNVs |
| DLS15-10457 | 1 | 11 | 0 |
| DLS15-10447 | 1 | 14 | 0 |
| DLS14-23590 | 2 | 10 | 1 |
| DLS14-23580 | benign | 0 | 0 |

The maximum confidence on an abnormality was 85% in the benign sample. Therefore, a 95% confidence cutoff for making a positive call again seems reasonable. However, in some embodiments, a 90% confidence cutoff is used.

Summary of all Samples

The following Table 19, is a summary of positive call rate in the plasma summarized by cancer stage:

TABLE 19

| Positive call rate in plasma by cancer stage | | |
|---|---|---|
| Stage | Positive Calls | Total Samples |
| I | 0 | 2 |
| II | 1 | 1 |
| III | 2 | 4 |
| IV | 3 | 3 |
| All Malignant | 6 | 10 |
| All Negative (Benign or Normal Sample) | 0 | 7 |

Based on these results, the sensitive achieved was 60% and the specificity was 100%.

CONCLUSIONS

The selection of target sites for amplification, within haploblocks, yielded acceptable improved results for CNV detection in ctDNA. A high number of samples from malignant tumors did not exhibit any detectable abnormalities in the regions selected. This could be due to the biopsy or it could be due to the region selection.

ShapeIT performance for informatics haplotyping was acceptable and consistent with expectations. Furthermore, ShapeIT performance was consistent across patients.

The plasma CNV calling algorithm used in this embodiment did not detect CNVs in Stage I cancer samples, and did not detect all Stage 3 samples. It is possible that due to the biology of the ovarian tumors, the circulating free DNA amount in the plasma is not sufficient enough to catch certain CNVs. This is consistent with our observations related to SNVs. It is possible that further design improvements will provide sufficient sensitivity to detect CNVs in ctDNA in all Ovarian cancer patients. Nonetheless, the methods provided herein, which in illustrative examples as illustrated in Example 1, utilize pools of primers that target SNPs that are found within haploblocks and then utilize analytical methods with imperfect estimates of haplotypes, that take advantage of the fact that loci are selected that are within haploblocks, represent an important step in improved detection of CNVs in ctDNA in cancer.

Example 5

This example provides details regarding the identification of a panel of target chromosomal regions across eight driver genes, a primer pool for amplifying segments within such target chromosomal regions, which exhibit high somatic copy number variation (CNV) in lung cancer, wherein the primer pool is focused on primers that amplify SNPs within haploblocks, and analytical methods to assess copy number. The primer pool includes primer pairs (i.e. forward and reverse primers) for amplifying loci with strong linkage disequilibrium to other loci (i.e. loci within a set of haploblocks within target chromosomal regions known to exhibit CNV where a therapeutic has been identified), thereby useful for enrichment of target SNPs within haploblocks, for detecting CNV for a lung cancer therapy selection panel. The primer pairs are used to generate amplicons that can be analyzed, for example by high throughput sequencing. The primer pool was used to establish the feasibility of detecting lung cancer-relevant CNVs in plasma samples. The identified chromosomal regions in this design are focal CNVs and in fact, cover regions less than 2.5 megabases.

The Lung Cancer Therapy Selection Panel analyzed in this Example is a RUO liquid biopsy test targeted towards patients with a known diagnosis of lung cancer. It focuses on multiple types of lung cancer alterations that impact therapy decisions and detects single nucleotide variations (SNVs), copy number variations (CNVs), and gene fusions. The panel is intended to be used on plasma cfDNA samples.

In particular, this example illustrates the analytical performance of the focal CNV (fCNV) component of this test. Focal CNVs in this example are generally covering short regions (<2.5 Mb). The current version of the Lung Cancer Therapy Selection Panel aims to detect fCNVs surrounding eight targeted genes including BRAF, EGFR, ERBB2, FGFR1, KRAS, MET, MYC, and PIK3CA.

This example also provides detailed copy number determinations obtained by analyzing the samples using the quantitative, non-allelic FODDOR method, and illustrates the complementary nature of a quantitative, non-allelic method like the FODDOR method with the allele-based haploblock method.

The FODDOR algorithm can be used for classifying a sample as either positive or negative. This is done by checking if all the regions of interest in the sample have the same copy number or if they have different copy numbers.

In addition to classifying a sample as positive or negative, FODDOR can also estimate the virtual tumor fraction (VTF) of the region with maximum abnormality. VTF of a region is defined as the tumor cell fraction of a tumor with copy number equal to 3 in that region that is required to generate the copy number observed in that region. That is, suppose that a hypothetical tumor has a copy number equal to 4 in just one abnormal region and suppose that tumor's cell fraction in the corresponding plasma is 0.05. The VTF of this region is the tumor cell fraction that is required to generate the equivalent excess of this region assuming that the region's average copy number is 3. The conversion from VTF to TCF is given by: $VTF=(N-2)\times TCF$, where N is the average copy number of that region in the tumor. We estimate the VTF by estimating the excess of a region compared to the average of all the other regions.

Using the above two features of FODDOR, we also designed an estimator which, subject to certain conditions, can make calls on and estimate the individual region copy numbers. This is done by iteratively running FODDOR to pick out one abnormal region per iteration until FODDOR identifies a subset of regions that all have the same copy number. In case FODDOR cannot identify a subset of at least two regions with same copy number, the sample is no-called. More information about the FODDOR method is provided in a separate section in this specification.

The fCNV panel includes genes with recurrent fCNVs that are demonstrated to have clinical utility in the treatment of patients with lung cancer. This utility is based on meeting at least one of the following criteria: (1) Credentialed per NCCN guidelines or FDA-labeling for selection of an approved treatment target in a lung cancer; (2) Credentialed per NCCN guidelines or FDA-labeling for selection of an approved treatment target in any malignancy but robust clinical data are lacking demonstrating efficacy in lung cancer (i.e. "Off-Label"); (3) The mutation is an eligibility criteria for an ongoing clinical trial (per ClinicalTrials.gov).

The eight target genes that are all amplified oncogenes that are targets of existing therapeutic agents (FDA-approved use or off-label use), or therapeutic agents in development (clinical or pre-clinical), were identified (See Table 20). Of the 8 genes, MET amplification is credentialed (category 2A) in NCCN Non-Small Cell Lung Clinical Guidelines (version 6.2015) as an emerging target for Crizotinib treatment (Ou, 2006). For these genes, target regions that are known to be amplified in lung cancer are shown in Table 20 along with a therapeutic targeted to the gene with the CNV.

TABLE 20

Target lung cancer genes, chromosomal regions, and justification of therapeutic utility (([a]FDA-Approved/[b]Off-Label/[c]Clinical Trial/[d]Preclinical)

| Gene Name | Gene Coordinates (hg19) | length [kb] | Indicated Targeted Therapeutic |
|---|---|---|---|
| BRAF | chr7:140433813-140624564 | 191 | vemurafenib[b]; dabrafenib[b] (approved for gene mutations) |
| EGFR | chr7:55086725-55275031 | 188 | cetuximab[a]; erlotinib[a]; gefitinib[a]; afatinib[a]; panitumumab[b]; vandetanib[b]; lapatinib[b] |
| ERBB2 | chr17:37856231-37884915 | 29 | afatinib[3]; ado-trastuzumab emtansine[b]; pertuzumab[b]; trastuzumab[b]; lapatinib[b] |
| FGFR1 | chr8:38268656-38325363 | 57 | ponatinib[b] |
| KRAS | chr12:25358180-25403854 | 46 | Mekinist[a] Selumetinib[c] (for gene mutations) |
| MET | chr7:1163 12459-116438440 | 126 | crizotinib[a]; cabozantinib[a] |
| MYC | chr8:128748315-128753680 | 5 | gefitinib (high copy number may confer increased EGFR tyrosine kinase sensitivity) |
| PIK3CA | chr3:178866311-178952497 | 86 | Dactolisib[c] Buparlisib[c] (for gene mutations) |

Target chromosomal regions of each gene of interest were identified based on the following considerations: There are three main papers that studied lung cancer by analyzing large number of samples, each on a different subtype of Lung cancer.

TCGA 2012-178 SQCC (Lung Squamous Cell Carcinoma) samples (Nature 489:519-25 (2012). doi:10.1038/nature11404);

TCGA 2014-230 ADC (Lung Adenocarcinoma) samples (Nature 511:543-50 (2014). doi: 10.1038/nature13385); and George et al. 2015-110 SCLC (Small Cell Lung Cancer) samples (Nature 524:47-53 (2015). doi: 10.1038/nature14664).

Table 21 presents regions identified by three main lung cancer studies with statistically significant focal copy number alteration (q-value<0.05) for the eight target genes reported in these studies.

TABLE 21

Chromosomal regions with focal copy number alterations

| Subtype | Gene | Chr | Start (hg19) | End (hg19) | Length (Mb) | q-value | CNV type |
|---|---|---|---|---|---|---|---|
| ADC | KRAS | 12 | 25402469 | 26433911 | 1.03 | 1.330E−05 | Amp |
| ADC | EGFR | 7 | 54535672 | 55737616 | 1.20 | 1.520E−05 | Amp |
| ADC | MET | 7 | 116283302 | 116449049 | 0.17 | 5.913E−04 | Amp |
| ADC | MET* | 7 | 115368861 | 117051327 | 1.68 | 2.483E−04 | Amp |
| ADC | ERBB2 | 17 | 37804811 | 38011853 | 0.21 | 1.902E−02 | Amp |
| SQCC | FGFR1 | 8 | 38170522 | 38286018 | 0.12 | 1.19E−30 | Amp |
| SQCC | MYC | 8 | 128202879 | 128788635 | 0.59 | 6.79E−10 | Amp |
| SQCC | EGFR | 7 | 54642932 | 55858372 | 1.22 | 8.85E−07 | Amp |
| SCLC | PIK3CA | 3 | 178430118 | 186909171 | 8.48 | 2.44E−10 | Amp |

We also investigated the dataset of COSMIC ASCAT CNV Events to inspect recurrent CNV regions covering the target genes. Cosmic uses ICGC CNV profiles where available, otherwise Cosmic reanalyzed TCGA with ASCAT. ASCAT accounts for normal cell admixture and tumor aneuploidy in CNV estimation using B-allele frequencies. Note that COSMIC is more conservative with respect to CNV calls. Table 22 provides the results from the COSMIC analysis. The CNV affected regions in each gene vary among patients and they are longer than the coding region of the gene. As can be seen in the table below, the average length of CNV region per each gene is from 0.5 Mb to 33 Mb. We also observe that the majority of CNVs in the target genes are high level amplification (with median copy number (50th percentile≥9) (Table 22).

TABLE 22

Recurrent CNV regions from analysis of COSMIC lung cancer data

| Gene Name | # Samples from Cosmic | copy number 5th PCTL | copy number 50th PCTL | copy number 90the PCTL | Major to Minor Haplotype ratio 5th PCTL | Major to Minor Haplotype ratio 50th PCTL | Major to Minor Haplotype ratio 90the PCTL | length [Mb] 5th PCTL | length [Mb] 50th PCTL | length [Mb] 90the PCTL |
|---|---|---|---|---|---|---|---|---|---|---|
| BRAF | 19 | 2 | 9 | 14 | 1.3 | 2.0 | 9.2 | 1.10 | 33.04 | 50.50 |
| EGFR | 85 | 5 | 12 | 36 | 1.0 | 5.0 | 22.0 | 0.46 | 3.09 | 49.15 |
| ERBB2 | 18 | 7 | 16 | 62 | 1.4 | 5.0 | 18.5 | 0.20 | 0.50 | 10.33 |
| FGFR1 | 110 | 1 | 10 | 27 | 1.3 | 5.8 | 16.7 | 0.37 | 1.76 | 15.31 |
| KRAS | 61 | 5 | 10 | 19 | 1.2 | 4.0 | 13.0 | 0.31 | 5.37 | 27.12 |
| MET | 37 | 5 | 10 | 37 | 1.2 | 4.0 | 12.0 | 0.38 | 7.53 | 49.95 |
| MYC | 107 | 5 | 10 | 24 | 1.0 | 4.5 | 13.0 | 0.12 | 2.01 | 30.65 |
| PIK3CA | 182 | 5 | 9 | 18 | 1.0 | 4.0 | 9.3 | 1.46 | 11.96 | 40.85 |

We applied additional processing to these reported regions to determine target regions for our panel:

KRAS-reported statistically significant region by TCGA for subtype ADC has been chosen as the target region.

MYC-reported statistically significant region by TCGA for subtype SQCC has been chosen as the target region.

EGFR—the overlap between the two statistically significant regions identified by TCGA for subtypes ADC and SQCC has been considered as the target region.

MET—the region reported in Table 21 is small and therefore not feasible for design. However, the same study identified a larger region (1.68 Mb) including MET with statistically significant CNV for a sub-group of patients (n=87). We decided to choose that region as the target region.

It is noteworthy that TCGA considered these genes as "drivers": KRAS, EGFR, ERBB2, BRAF, MET, ALK fusion genes, RET fusion genes, ROS1 fusion genes, HRAS, NRAS, and MAP2K1.

Next, mutations were filtered to include only those with either evidence of recurrence within the COSMIC database3 (>3 independent mutations at the same site) or evidence of functional impact (e.g. MAP2K1 p.C121S4 and MET exon 14 deletions 5, 6).

After mutation filtering, we considered any sample having a mutation in one of the above listed genes listed as belonging to the "oncogene-positive" group (n=143). Samples lacking any of the mutations were considered "oncogene-negative" (n=87).

ERBB2 and FGFR1—the region reported in Table 21 is small and therefore not feasible for design. COSMIC data shows the CNV regions are quite variable for these genes, which makes it hard to identify the most common CNV region. Therefore, we decided to target a window of 1.5 Mb around the gene.

PIK3CA-reported region for SCLC is quite large. We chose a common CNV region among 80% of samples (141 out of 177) in COSMIC data. Note that we filtered for non TCGA samples or loss CNVs in Cosmic data.

BRAF—there is no statistically significant CNV region reported in the literature. We chose a common CNV region among 80% of samples (13 out of 16) in COSMIC data. Note that we filtered for non TCGA samples or loss CNVs in Cosmic data.

Based on the above considerations, the chromosomal regions that were selected as target chromosomal regions are shown in Table 23.

TABLE 23

Selected target chromosomal regions

| Gene | Chr | Start (hg19) | End (hg19) | Length (Mb) | Total SNPs MAE >= .1 |
|---|---|---|---|---|---|
| KRAS | 12 | 25402469 | 26433911 | 1.03 | 2184 |
| EGFR | 7 | 54642932 | 55737616 | 1.09 | 2377 |
| MET | 7 | 115368861 | 117051327 | 1.68 | 2267 |
| FGFR1 | 8 | 37500000 | 39000000 | 1.50 | 1740 |
| PIK3CA | 3 | 178431895 | 179540177 | 1.11 | 1820 |
| MYC | 8 | 128202879 | 128788635 | 0.59 | 1432 |
| BRAF | 7 | 138448946 | 140783654 | 2.33 | 3631 |
| ERBB2 | 17 | 37000000 | 38500000 | 1.50 | 1844 |

SNP Loci And Primer Design Requirements

The following pool design requirements were specified:

Target the top regions in ovarian cancer such that at least 80% of patients reported in TCGA are covered;

SNPs should be part of relatively large haplotype blocks such that the informatics phasing error rate is less than 5% on average for each region of interest;

SNPs covering specific cancer-related genes in regions of interest should be given high priority;

At least 1,000 SNPs should be identified per target chromosome region;

All primer designs compatible with mmPCR in one pool, meaning all dual extensible interactions in one pool, should have deltaG higher than-4 kcal/mol;

The SNP target loci should be located in the first 50 bases of amplicon;

The SNP loci allele determination should be compatible with HiSeq 2500 50 bp single-end sequencing (note that not all assays necessarily satisfy the Nextseq 75 bp paired-end requirements);

The following were the main primer design requirements:

One pair of left and right primers per target SNP;

Optimal Tm 56C, allowed range [53C-59C];

Amplicon length 50-75 bp;

GCcontent 30-70%;

Maximum GC clamp 4;

Pool Design;

The design process consisted of these main steps:

Select candidate target SNPs for each region of interest;

Attempt to design up to five sets of right and left specific primers for each candidate target SNP;

Identify known haplotype blocks for SNPs with a design;

Select compatible designs to form the primer pool(s);

Candidate SNPs Selection

For each region of interest we chose candidate SNPs satisfying following criteria:

The SNP must be present in both dbSNP Common 138 and the 1000 Genomes project (the phase 1 version 3 variant calls released Apr. 30, 2012) variant call data set;

The SNP minor allele frequency from the 1000 Genomes project must be at least 10%;

The SNP location must be within one of the corresponding breakpoints in Table 20.

Primer Design

The primers were designed using Primer3 release 2.3.6 and the RunPrimer3 Java program using the design parameters in Table 24. For each candidate SNP Primer3 was used to design left and right primers (two-sided) with amplicon length within a range of 50 to 75 bp and melting temperature between 53-59° C. optimized at 56° C. Primer3 was configured to use the SantaLucia salt correction and melting temperature formulae. Primer locations were restricted to be at least 2 bp away from any SNP which is present either in dbSNP Common 138, or in the 1000 Genomes project with minor allele frequency greater than 1%. Up to five designs can be generated per target. Since previously we did not identify an issue for test primers with 4 GC clamp, we decided to limit the GC clamp to 4.

TABLE 24

Primer design parameters

| Name | Value | |
|---|---|---|
| target_padding | 2 | Primers should end at least 2 bases away from the target loci |
| PRIMER_MAX_SIZE | 30 | |
| PRIMER_OPT_SIZE | 24 | |
| PRIMER_MIN_SIZE | 18 | |

TABLE 24-continued

| Primer design parameters | | |
|---|---|---|
| Name | Value | |
| PRIMER_WT_SIZE_LT | 0.5 | |
| PRIMER_WT_SIZE_GT | 0.5 | Penalty for primer longer than optimal |
| PRIMER_PAIR_WT_PRODUCT_SIZE_LT | 0 | |
| PRIMER_PAIR_WT_PRODUCT_SIZE_GT | 1 | Penalty for amplicon longer than optimal |
| PRIMER_MAX_TM | 59 | |
| PRIMER_OPT_TM | 56 | |
| PRIMER_MIN_TM | 53 | |
| PRIMER_WT_TM_LT | 1 | Penalty for TM lower than optimal |
| PRIMER_WT_TM_GT | 1 | Penalty for TM higher than optimal |
| PRIMER_MAX_GC | 70 | |
| PRIMER_OPT_GC_PERCENT | 50 | |
| PRIMER_MIN_GC | 30 | |
| PRIMER_WT_GC_PERCENT_LT | 1 | |
| PRIMER_WT_GC_PERCENT_GT | 1 | |
| PRIMER_MAX_END_GC | 4 | |
| PRIMER_MAX_POLY_X | 5 | |
| PRIMER_INTERNAL_MAX_POLY_X | 5 | |
| PRIMER_SALT_CORRECTIONS | 1 | |
| PRIMER_SALT_DIVALENT | 0 | |
| PRIMER_DNTP_CONC | 0 | |
| PRIMER_THERMODYNAMIC_OLIGO_ALIGNMENT | 1 | |
| PRIMER_THERMODYNAMIC_TEMPLATE_ALIGNMENT | 1 | |
| PRIMER_MISPRIMING_LIBRARY | Human | The mispriming library containing microsatellites downloadable from Primer 3 website. |
| PRIMER_LIB_AMBIGUITY_CODES_CONSENSUS | 1 | |

We skipped the filtering for the probable mispriming. We found that mispriming filtering was too stringent and it over-filtered designed primers. Finally, if a SNP target has multiple designs we chose the design with the shortest amplicon length.

Haplotype Block Identification

We used a program called plink (v1.90b3p 64-bit (10 Oct. 2014)) to identify haplotype blocks for our regions of interest based on the definition provided herein. The program has been run for each region separately on the set of SNPs with proper designs produced in the previous step. The 1000 genomes project haplotypes release on 2013-09 was used at the reference panel. The release contains haplotypes on 1092 samples (#haplotypes=2184) for 36.8 million SNPs.

Pooling

The final step of the design process was to choose a subset of the candidate SNPs with designs that could be combined into a single multiplex primer pool. To be able to pool the set of designed primers we needed to minimize the possibility of primer-dimer formation. The tendency of two primers to bind to each other can be estimated by the Gibbs free energy and/or the melting temperature of their most stable interaction.

For every pair of primers in the design set we calculated the Gibbs free energy (deltaG) and the corresponding melting temperature ($T_m$) for three types of interactions including the strongest dual extensible, the extensible, as well as any. An extensible interaction is defined as one with at least three base matches at the 3'end of the primer. All calculations were based on a thermodynamic approach using the following design parameters:

temperature=56 C;
primer_concentration=50 nM;
salt_concentration=50 mM;

```
forward_tag = ACACGACGCTCTTCCGATCT;

reverse_tag = AGACGTGTGCTCTTCCGATCT;
```

The interaction score for each pair of primers was set to max {deltaG2, 90%*deltaG12, 65%*deltaG012}. Based on prior experience we believe primers with interaction score weaker than-4 kcal/mol are less likely to create primer-dimers, and thus can be in a multiplex primer pool.

We ran a pooling algorithm that analyzed primer dimers with the above considerations to select an optimized set of designs with no high-scoring interactions (<−4 kcal/mol). The algorithm is a heuristic method that attempts to choose a required compatible number of SNPs from large halplotype blocks. Based on simulation results in Example 3 SNPs in haplotype blocks smaller than 10 were less likely to contribute to the CNV detection algorithm. Therefore, we decided to ignore any block smaller than 10. The utility score of a target includes the following weighted factors: number of patients having a CNV spanning over the SNP location (w=.5); the haplotype block size that a SNP belongs to (w=.2), target SNP minor allele frequency (w=.3), observed heterozygosity rate (w=.1), presence in HapMap (w=.1), transversion mutation (w=.1), amplicon GC-content (w=.1) and amplicon length (w=.1). The pooling algorithm first builds a conflict graph, where assays are nodes and the edge between two nodes represents a high score interaction between the primers of corresponding assays. Then it tries to find the Maximal Independent Set by iteratively removing the highest degree node at each step. In case there are several nodes with highest degree, the one with the lowest utility score is removed.

General Methodology

In this study we analyzed cell-line derived cfDNA titrations and plasma from healthy individuals. Unless indicated otherwise, sample preparation and sequencing analysis was performed as set out in Example 4. Briefly, samples were made into libraries by ligation of adapters followed by PCR to amplify the available cfDNA. The selected SNPs in the target genetic regions were then amplified by massively multiplexed PCR. The amplification protocol for multiplex PCR was as follows: 95C 15 min, 17×[95C 30 sec, 62.5C 15 min, 72C 5 min], 72C 2 min, 4C hold.

The resultant amplicon pool was sequenced using next generation sequencing and the resulting data was analyzed to determine the presence of fCNVs in the target genes that are listed in Table 23.

Scope

Artificial cfDNA samples were generated with known relative copy number changes that ranged from above to below the expected limit of detection of our method, resulting in <1% to >40% expected average allelic imbalance (AAI). These known positive samples were then used to assess the sensitivity of our technology.

Specificity was tested using both negative artificial cfDNA and cfDNA extracted from standard plasma samples from healthy individuals.

Exemplary abbreviations used specifically in this Example:

AAI Average Allelic Imbalance;
fCNV focal CNV;
FODDOR Focal CNV Detection using Depth of Read;
NAT normal adjacent tissue;

NCCN National Comprehensive Cancer Network;
NGS Next Generation Sequencing;
NIPT Non-invasive prenatal testing
Plasmart Artificially created plasma sample;
SNV Single Nucleotide Variation;
TCF Tumor Cell Fraction;
VTF Virtual Tumor Fraction.

Samples Description

Three pairs of matching (one pair per individual) CNV-affected tumor and non-affected wild type cell lines were purchased from ATCC and cultured according to ATCC recommendations.

The presence of CNVs was confirmed using Oncoscan and NGS data. More specifically, the regions shown in Table 25 were found to be good candidates in each cell line (i.e., they had obvious copy number differences between the homologs).

TABLE 25

Samples used in titration experiment

| Matched Cell Line Pairs | Regions |
|---|---|
| Cell Line Pair A | EGFR, ERBB2, FGFR1, KRAS, MET, PIK3CA |
| Cell Line Pair B | BRAF, ERBB2, FGFR1, MET |
| Cell Line Pair C | BRAF, ERBB2, FGFR1, KRAS, MYC, PIK3CA |

These titrations simulate the stated tumor cell fractions (TCF) of 1%, 2%, 3%, 5%, 7%, 10%, and 20%. A sample with 1% TCF refers to a sample containing DNA from 1 tumor cell per 99 wild type cells.

These synthetic samples simulate cfDNA extracted from plasma of cancer patients with known CNVs and were used to determine the limit of detection based on known TCF. Note that the level of abnormality is unknown in real cancer plasmas, hence they cannot be used to determine the limit of detection.

Negative control libraries were generated from both mononucleosomal DNA from wild type cell lines and from cfDNA extracted from standard plasma samples from healthy individuals.

Matching Tumor and Normal Cell Lines

Pairs of matching tumor and normal cell lines were generated from the same individual cancer patient and were purchased from ATCC. Cell lines were not selected for tumor origin but data availability in public databases that indicated CNVs affecting the coding region of assay panel covered target genes. A list of the selected cell lines and additional information such as tissue origination and cancer stage are shown in Table 26.

TABLE 26

Tumor cell lines used in this study (Gazdar et. al. 1998)

| cell line | tissue | primary stage | cell line characteristics | patient |
|---|---|---|---|---|
| HCC1954 | mammary gland; breast/duct; epithelial | IIA, grade 3 invasive ductal carcinoma with no lymph node metastases | poorly differentiated cell line initiated on Oct. 30, 1995; it took about 4 months to establish | 61 years adult, East Indian, Female |
| HCC2218 | mammary gland; breast/duct; epithelial | TNM stage IIIA, grade 3, primary invasive ductal carcinoma with metastases in 42/43 lymph nodes | poorly differentiated cell line initiated on Apr. 10, 1996, and took 6 months to establish | 38 years, Caucasian, White, Female |
| HCC38 | mammary gland; breast/duct; epithelial | TNM stage IIB, grade 3, primary ductal carcinoma | initiated on Apr. 27, 1992 and took 32 months to establish | 50 years, Caucasian, White, Female |

Normal Reference Cell Lines

Normal reference cell lines are generated from leukocytes of the cancer patient by EBV-transformation.

Tumor Cell Lines

Matching tumor cell lines are made from various kinds of tumor tissues or metastases by months of repeated subclonation. This process can cause subclonal CNV and SNV occurrence within a cell line during cultivation and causes CNVs of larger genome regions than commonly seen in true tumor biopsies. However, genome rearrangements in DNA samples extracted from the same culture have CNVs that remain constant throughout experiments conducted with those samples.

Artificial cfDNA Preparation

We used the MNase-based shearing of cell line DNA into mononucleosomal DNA fragments to simulate cfDNA. Mononucleosomal DNA (150 bp fragments) from each of these CNV-affected and non-affected cell line pairs was purified and mixed to generate a range of known CNV titrations.

DNA samples were characterized with Oncoscan to establish the exact CN for each genome region. Tumor and normal DNA were titrated over a range of tumor fractions to create artificial samples. These have a known CNV copy number and tumor fraction for each CNV in each sample.

DNA Yield Consideration

Reference cell lines grown in suspension at high cell counts and high yield for mononucleosomal DNA were used as artificial cfDNA. In contrast to this, adherent growing tumor cell lines have lower cell counts per culture and MNase-treatment yields much less mononucleosomal DNA.

Considerations on Compatibility of Cell Lines with Bias Model

Artificial samples prepared from cell lines have previously shown performance inconsistent with patient plasma, suspected to be due to differences in resulting data characteristics. A simple method to measure similarity between artificial samples and a set of reference data such as real plasma is to compare the distribution of reads over the individual targets. This can be computed as a correlation coefficient between average per-target amplification rates, calculated between a set of artificial samples and a set of reference samples. Table 27 shows the correlation coefficients calculated for various data sets compared to their corresponding references.

TABLE 27

| Amplification correlation coefficients for various data sets measured against corresponding reference data | |
|---|---|
| Data set | Amplification correlation coefficient against reference data |
| Microdeletions validation study plasmart | 0.96 |
| Panorama V3 feasibility study plasmart | 0.88 |
| Panorama commercial data affected by poor quality extraction reagents | 0.87 |
| Focal CNV cell line titration study | 0.87 |

Samples

CNVs including "focal" CNVs are larger than hundreds of kb in length which is too large to use synthetic DNA to generate artificial DNA samples with known CNVs, similar to what was used for SNV-spikes. Additionally, the AAI-approach requires normal and CNV-affected samples to have the same SNP-pattern and to be derived from the same donor. Two kinds of test samples used for this study fulfill these requirements: cell lines and lung cancer patient samples.

Tissue DNA Preparation for Reference Experiments

Four FFPE- and 38 FF matching sample sets of lung cancer patients of various carcinoma types and stages purchased from CRO were included in this experiment as shown in Table 28. Tumor- and normal tissue DNA and plasma cfDNA were extracted and used for subsequent analysis.

TABLE 28

Overview of patient samples.

| Histological diagnosis | sample count | Stage | sample count | Highest Stage | sample count |
|---|---|---|---|---|---|
| adenocarcinoma | 15 | I | 9 | IA | 9 |
| small cell carcinoma | 2 | II | 18 | IB | 21 |
| squamous cell carcinoma | 20 | III | 11 | IIA | 0 |
| bronchioloalveolar adenocarcinoma | 3 | IV | 0 | IIB | 7 |
| adesquamous carcinoma | 2 | n/a | 4 | IIIA | 4 |
| total | 42 | total | 42 | IIIB | 0 |
| | | | | IV | 1 |
| | | | | total | 42 |

Sample Preparation

Mononucleosomal DNA from cell lines was prepared according to the protocol described in Wapner et al. 2014 and mixed.

Library Preparation

The titration and real cfDNA samples were converted into libraries using the Natera library preparation kit. Libraries were prepared from the cell line MNased DNA samples, cell line titrations, and patient plasma cfDNA. The cell line derived sample and titration libraries contained 10 k haploid genome copies (~33 ng) of DNA input material. Due to the large variance in total cfDNA available per patient, one library per patient was prepared with 40 μl cfDNA. All libraries were made with 15 cycles of library amplification and were purified using AMPure (Beckman Coulter, Brea, CA).

Multiplex PCR

The multiplex PCR protocol as disclosed in Example 4 above, was performed on each library using the Lung fCNV Primer Pool except that a 62.5° C. annealing temperature was used. Accordingly, the cycling conditions for the multiplex PCR was as follows: 95C 15 min, 17×[95C 30 sec, 62.5C 15 min, 72C 5 min], 72C 2 min, 4C hold Multiplex reactions using titration and plasma cfDNA libraries contained 6.7 μl of purified library input while the pure cell line reactions used 3 μl of purified library. Each reaction was done in triplicate. Each reaction contained approximately 15 k haploid genome copies (50 ng).

Barcoding PCR, Pooling and Sequencing

Each OneSTAR PCR reaction was barcoded. To fit the needs of AAI analysis the titration and plasma cfDNA reactions were pooled with 16 samples per pool to maintain an average DOR/assay >4,000. The titration and plasma cfDNA reactions were pooled into two additional and separate FODDOR pools containing 240 samples each. This creates an average DOR/assay of 290. Barcoded reactions of cancer-free patient plasmas used in the Bias Model experiment were included in the two FODDOR pools to ensure a final reaction count of 240 samples per pool. The patient tumor and normal tissue barcoded reactions were pooled with the pure cell line reactions and had an approximate DOR/assay of 615.

fCNV Workflow

Library products were subjected to the fCNV workflow and products were barcoded and pooled. The pools were quantified and sequenced. The sequence data was analyzed to determine sensitivity and specificity.

Defining True CNV Status for Use as Reference

Two external methods were used to establish CNV-truth for cell lines and tissues, OneSTAR Truth and Oncoscan. In addition, we also sequenced the tumor cell-line as a genomic sample and as a library.

OneSTAR Truth

OneSTAR PCR with the lungTSP fCNV panel was used to measure AAI in DNA samples from tumor/wild type cell lines and tumor/normal reference tissues. This method provides AAI but not an absolute CN per CNV.

Oncoscan

Oncoscan uses a different, much larger set of SNP-probes than the lungTSP fCNV panel to estimate genome-wide CNs (Table 29). The CN estimate is based on both allele frequency and probe intensity.

TABLE 29

The number of SNP-probes present within each gene region in NGS and Oncoscan.

| Gene | Chr | StartPos | EndPos | SNPs in NGS | SNPs in Oncoscan |
|---|---|---|---|---|---|
| BRAF | 7 | 138449419 | 140782039 | 836 | 304 |
| EGFR | 7 | 54646322 | 55737172 | 611 | 272 |
| ERBB2 | 17 | 37000013 | 38496752 | 497 | 269 |
| FGFR1 | 8 | 37501860 | 38993605 | 495 | 149 |
| KRAS | 12 | 25404604 | 26430452 | 493 | 78 |
| MET | 7 | 115376764 | 117048082 | 539 | 286 |
| MYC | 8 | 128203857 | 128788247 | 426 | 157 |
| PIK3CA | 3 | 178435382 | 179540177 | 430 | 120 |

Oncoscan was used to establish CNVs and CNs for the genomes of the tumor cell lines used for titrations, and to make predictions about AAI in cfDNA titration samples. Oncoscan was not used for patient tumor samples.

Cosmic

The Cosmic database was used to initially choose tumor cell lines with CNVs in the assay covered regions. The DNA preparations of these cell lines were then validated by Oncoscan.

In several cases the target gene coding region fell into a gap between CNVs reported in Cosmic, leading to an absence of a CN-call in Cosmic. However, Oncoscan data of the same cell line for the same region shows a continuous CNV. This is probably caused by Cosmic only annotating the highest CN of a region while slightly less affected regions are not annotated as CNV-affected, leading to many false negative calls. Discrepancies between Cosmic and Oncoscan CN-calls for the genes and cell lines used in this study are listed in Table 30.

Cosmic and Oncoscan agree on the locations of CN-transitions in these regions, which can be interpreted as a) the cell line genome is stable enough to allow reproduction of results between the experiment represented in Cosmic data and our DNA prep and b) the reported gaps in Cosmic are most likely misrepresentations and the not reported CNs are false negatives.

TABLE 30

| Comparison of COSMIC and OncoScan CN-calls ("Cosmic CN"/"Oncoscan CN") | | | | | | | | |
|---|---|---|---|---|---|---|---|---|
| COSMIC/ Oncoscan CN Call | BRAF | PIK3CA | MYC | MET | KRAS | FGFR1 | ERBB2 | EGFR |
| HCC1954 | 2/2.3 | 2/3 | 2/10 | 2/2.6 | 2/2 | 2/2 | 14/69 | 2/3 |
| HCC2218 | 2/4 | 2/2 | 2/6 | 2/4 | 2/2 | 2/2 | 14/23 | 2/2 |
| HCC38 | 2/2.3 | 2/2.6 | 2/3.3 | 2/2 | 2/2 | 2/2 | 2/2 | 2/2 |

Briefly, the algorithm computes an average AAI value that fits the data best at each region together with the corresponding confidence. We use the AAI and confidence values together to make the final call.

More specifically, we analyzed the data using a CNV algorithm with two main outputs: (1) Confidence and (2) Average allelic imbalance (AAI). When making a determination of copy number variability in a region, we used the confidence estimate (which is a function of the AAI estimate, number of SNPs, etc.). In plasma samples, CNVs were identified by a maximum likelihood algorithm that searched for plasma CNVs in regions where the tumor sample from the same individual also had CNVs using haplotype information deduced from the tumor sample. In the negative control samples, haplotype information was deduced from parental genotypes. The CNV detection algorithm modeled expected allelic frequencies across all allelic imbalance ratios at 0.025% intervals for three sets of hypotheses: (1) all cells are normal (no allelic imbalance), (2) some/all cells have a homolog 1 deletion or a homolog 2 amplification, or (3) some/all cells have a homolog 2 deletion or a homolog 1 amplification. The likelihood of each hypothesis was determined at each SNP using a Bayesian classifier based on expected and observed allele frequencies at all heterozygous SNPs, and then the joint likelihood across multiple SNPs was calculated. Finally, the hypothesis with the maximum likelihood was selected. This algorithm also calculates the confidence of each CNV call by comparing the likelihoods of different hypotheses. A minimum confidence threshold of 99.9% was used in plasma samples from patients with cancer to minimize false-positive results. Further details regarding the analytical method used in this Example are provided in the analytical method called the Allelic_Analysis_Example discussed herein.

AAI can be interpreted as the average difference between the copy numbers of the homologs, and is analogous to the Truth Used for Final Analysis As explained previously, we estimated the true copy number and AAI of each of the regions in the three cell-lines using several different techniques. The results were not completely concordant, but were merged into a final "best estimate" truth that we used for analyzing the performance of the algorithms. Table 31 lists this "best estimate" truth. All of the regions are considered affected by a CNV except as described below the table.

TABLE 31

| Best estimate of true copy number, used as reference for performance analysis | | | | | | | | |
|---|---|---|---|---|---|---|---|---|
| | BRAF | EGFR | ERBB2 | FGFR1 | KRAS | MET | MYC | PIK3CA |
| HCC38 | 2.06 | 2[1] | 2 | 2.33 | 2.275 | 2[2] | 3.33 | 2.67 |
| HCC1954 | 3[3] | 3 | 37.38 | 0 | 0 | 3 | 6.59[4] | 2.85 |
| HCC2218 | 2.67 | 2[5] | 6.32 | 1 | 2[6] | 3.00 | 4[7] | 2[8] |

[1]EGFR (not >99% confident about >0% AAI in the TCF = 20% sample despite clear abnormality in tumor).
[2]MET (0% AAI in the TCF = 20% sample despite clear abnormality in tumor).
[3]Excluded region. BRAF (0% AAI in the TCF = 20% sample despite clear abnormality in tumor.
[4]Excluded region. MYC (balanced duplication covering most of the region, with a small unbalanced duplication).
[5]EGFR (CN = 2 in tumor).
[6]KRAS (CN = 2 in tumor).
[7]MYC (balanced duplication).
[8]PIK3CA (CN = 2 in tumor).

Average Allelic Imbalance Algorithm

An improved version of the CNV calling algorithm described at Kirkizlar et al. 2015 (Kirkizlar et al., *Translational Oncology,* 8 407-416) was used to make the fCNV calls. The algorithm uses haplotype information estimated through informatic methods rather than the perfect haplotype information obtained through tumor samples. Note that haplotype information predicts which alleles are present on a single chromosome homolog and would therefore be present with the same homolog copy number.

variant allele frequency in SNV detection. The reason behind using AAI as the main performance measure is due to the fact that the TCF can be ambiguous for the regions with multiple abnormalities. In order to relate AAI to TCF, one could assume that a region has a constant copy number, for example, one extra copy throughout the region, and then compute the corresponding TCF from the observed AAI. Table 32 below shows the relationship between AAI and TCF under the assumption that one homolog always has one copy and the second homolog is amplified.

TABLE 32

AAI as a function of TCF and tumor copy number

| TCF | CN = 3 | CN = 4 | CN = 5 | CN = 6 |
|---|---|---|---|---|
| 1% | 0.50% | 0.99% | 1.48% | 1.96% |
| 2% | 0.99% | 1.96% | 2.91% | 3.85% |
| 3% | 1.48% | 2.91% | 4.31% | 5.66% |
| 5% | 2.44% | 4.76% | 6.98% | 9.09% |
| 7% | 3.38% | 6.54% | 9.50% | 12.28% |
| 10% | 4.76% | 9.09% | 13.04% | 16.67% |
| 15% | 6.98% | 13.04% | 18.37% | 23.08% |
| 20% | 9.09% | 16.67% | 23.08% | 28.57% |

The Table presented in FIG. 8 provides the AAI estimate as a function of TCF values and total copy number of the tumor cells (assuming an unbalanced duplication where one homolog has one copy). Note that due to the mosaic nature of the cell lines and complex duplication patterns, FIG. 8 only provides an approximation to our observed AAI.

As for AAI method, we use the average AAI estimate at 20% TCF as the truth (Table 33).

TABLE 33

Observed AAI at 20% TCF

| AAI % | BRAF | EGFR | ERBB2 | FGFR1 | KRAS | MET | MYC | PIK3CA |
|---|---|---|---|---|---|---|---|---|
| HCC38 | 0 | 3.73 | 81.82 | 6.34 | 10.37 | 3.64 | 1.08 | 7.06 |
| HCC1954 | 10.50 | 1.31 | 16.87 | 4.99 | 1.12 | 19.29 | 0.86 | 0 |
| HCC2218 | 7.18 | 1.72 | 19.76 | 6.49 | 2.7 | 0 | 2.68 | 17.19 |

DNA Extraction

Genomic DNA from tumor and normal cell lines were extracted and enzymatically fragmented into "MNased DNA."

cfDNA was extracted from each of the 42 patient plasma samples using the QIAamp Circulating Nucleic Acid kit (Qiagen, Hilden, Germany) and was eluted in 50 μl of DNA Suspension Buffer. DNA was extracted from the matching tumor and normal tissue from the same 42 patients using the Qiagen GeneRead DNA FFPE Kit protocol optimized for our FFPE slice thicknesses.

DNA Quantification and Characterization

The MNased DNA samples from the cell lines were quantified using the Quant-it Broad Range kit (Thermo Fisher Scientific, Waltham, MA) and characterized using the Bioanalyzer 1K kit (Agilent, Santa Clara, CA). To simulate cfDNA, the mononucleosomal fragments (150 bp) of each cell line were isolated via size selection and re-quantified and characterized to confirm target fragment size.

cfDNA extracted from the patient plasma was quantified using the Bioanalyzer High Sensitivity Kit (Agilent, Santa Clara, CA). The Bioanalyzer electropherograms were also used to characterize DNA fragment sizes in patient samples. The DNA extracted from the patient tissues was quantified via NanoDrop (Thermo Fisher Scientific, Waltham, MA).

Tumor Cell Line Titrations

Mononucleosomal DNA from each CNV-affected and non-affected cell line pair was purified and mixed to generate a range of known CNV titrations. These titrations simulate the stated TCFs of 1%, 2%, 3%, 5%, 7%, 10%, and 20%.

Tumor Cell Fraction

A sample with 1% TCF refers to a sample containing DNA from 1 tumor cell per 99 wild type cells. TCF as a unit was used to correctly describe titrations. TCF incorporates the increase in genome weight in strongly CNV-affected samples. Not adjusting for this genome weight gain causes unaffected regions to be present at CN<2.

Results

Figure 7:
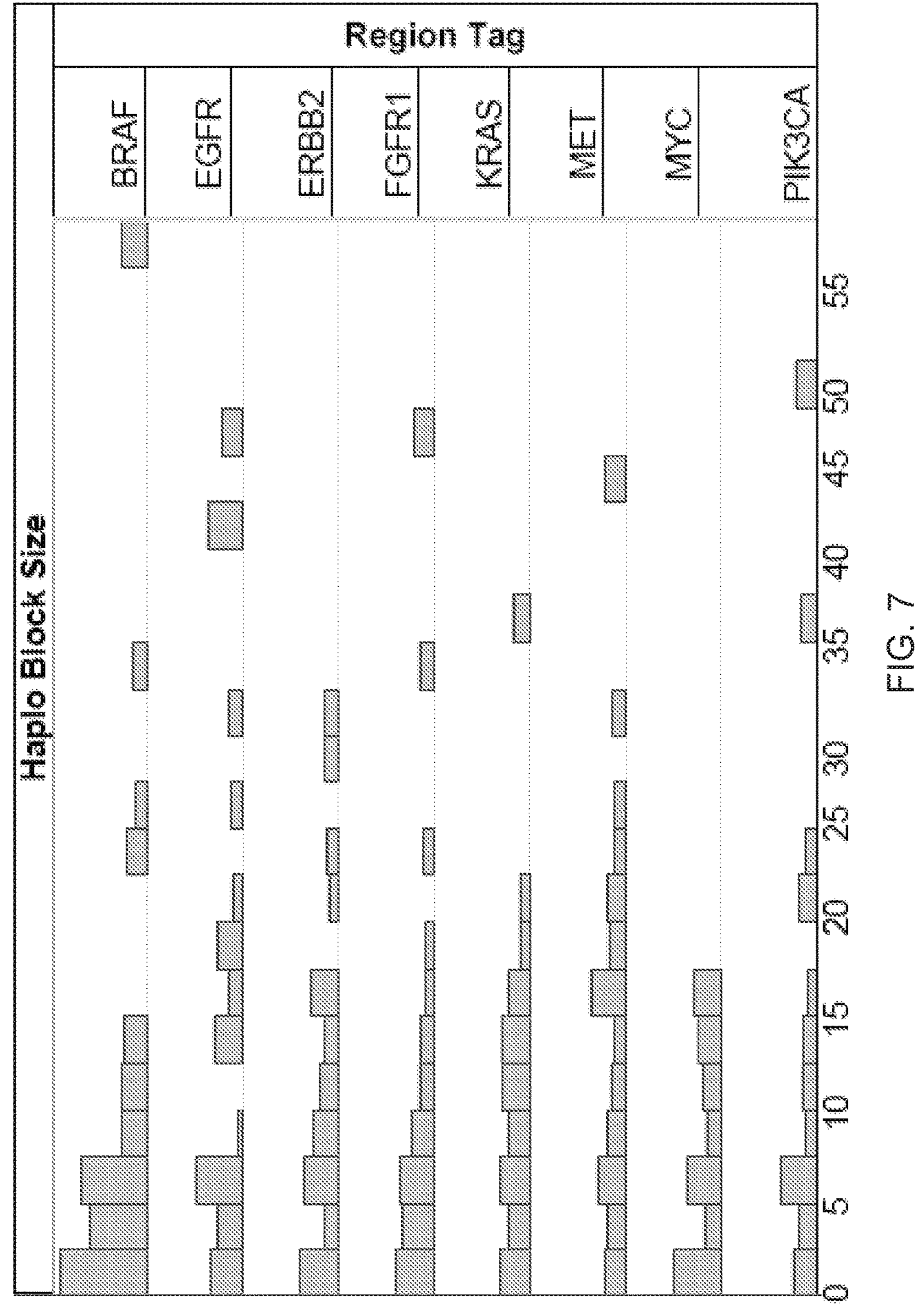
FIG. 7 is a graph of haploblock size for target chromosome regions of 8 target lung cancer-associated genes analyzed in Example 5.

Table 34 provides the combined pool configuration for each region of interest. As indicated, using the above criteria, between 81 and 98% of available SNPs were selected and a pool of 4327 SNPs was selected. The primer pools included SNPs with minor allele frequencies between 0.10 and 0.50. Haploblock sizes are shown in FIG. 7. Block sizes range from 2 to 57 SNPs.

TABLE 34

Final pool configuration for each region of interest.

| Gene | Number of assays | Expected no. heterozygous SNPs | Number of SNPs in blocks >= 10 | Longest block |
|---|---|---|---|---|
| KRAS | 493 | 124 | 254 | 36 |
| EGFR | 611 | 169 | 359 | 47 |
| MET | 539 | 139 | 345 | 44 |
| FGFR1 | 495 | 126 | 198 | 47 |
| PIK3CA | 430 | 117 | 227 | 49 |
| MYC | 426 | 121 | 161 | 17 |
| BRAF | 836 | 231 | 273 | 57 |
| ERBB2 | 497 | 150 | 236 | 30 |

Copy Number Truth Analysis in Cell Lines

We observed that the Oncoscan results may not correspond to the copy numbers observed by other methods. For example, the PIK3CA region of HCC1954 and the presence of an abnormal "allele ratio from 0.5" [absolute value of (β-Allele Frequency-0.5)] that suggests a CNV beginning upstream from the copy number call made by Oncoscan.

In addition, consider for example HCC1954 in chromosome 7 (including the genes BRAF, EGFR and MET), where the BAF looked stable in Oncoscan data across the whole chromosome. According to our initial analysis, we would expect approximately 9% to 12% AAI in each of these regions for 20% TCF. However, we observed 0% AAI in BRAF and ~3.5% AAI in EGFR and MET.

Another example is the FGFR in HCC2218. Oncoscan data suggested a one copy deletion that should have resulted in 9% AAI for 20% TCF. We observed ~5% AAI for this titration.

Hence, we have decided to use the 20% TCF sample together with the Oncoscan data to determine an approximate truth for each region. More specifically, let $H_1$ and $H_2$ denote the copy numbers of the homologs, and let $AAI_{20}$ denote the AAI found from 20% TCF sample. We only considered the regions where the average confidence on the AAI call across three replications was 99% for TCF=20%, and we calculated the average AAI of three replications to find $AAI_{20}$.

We used the formula $AAI=TCF*(H_1-H_2)/[(1-TCF)*2+TCF*(H_1+H_2)]$, and plug in $AAI_{20}$, TCF=20%, and $H_1+H_2$ found from Oncoscan analysis to estimate $(H_1-H_2)$. Then, we use this estimate to find the approximate expected AAI for TCF=1%, 2%, 3%, 5%, 7%, 10%.

More specifically, the regions shown in Table 35 were found to be good candidates in each cell line (i.e., they had obvious copy number differences between the homologs). This method provided successful AAI estimations for several gene regions including HCC2218 KRAS (a non-affected region) and MET (a CNV affected region).

TABLE 35

Samples used in the titration experiment.

| Matched Cell Line Pairs | Regions Included | Regions Excluded |
|---|---|---|
| HCC1954 | EGFR, ERBB2, FGFR1, KRAS, MET, PIK3CA | BRAF (0% AAI in the TCF = 20% sample despite clear abnormality in tumor) MYC (balanced duplication covering most of the region, with a small unbalanced duplication) |
| HCC2218 | BRAF, ERBB2, FGFR1, MET | EGFR (CN = 2 in tumor) KRAS (CN = 2 in tumor) MYC (balanced duplication) PIK3CA (CN = 2 in tumor) |
| HCC38 | BRAF, ERBB2, FGFR1, KRAS, MYC, PIK3CA | EGFR (not > 99% confident about > 0% AAI in the TCF = 20% sample despite clear abnormality in tumor) MET (0% AAI in the TCF = 20% sample despite clear abnormality in tumor) |

Results of NGS Analysis of Geneticist Tumor Samples

For each tumor sample, regions with significant AAI were determined using the tumor analysis described in Kirkizlar et al. (Kirkizlar, Eser et al. Detection of Clonal and Subclonal Copy-Number Variants in Cell-Free DNA from Patients with Breast Cancer Using a Massively Multiplexed PCR Methodology. Translational Oncology 8.5 (2015): 407-416). Due to the mosaic nature of the tumor samples, we only aimed to determine the percentage of the SNPs affected by a CNV.

To summarize, out of 42 samples, 27 of them had at least one region with >50% of the SNPs affected and 30 of them had at least one region with >25% of the SNPs affected.

More specifically, Table 36 provides the number of samples vs. number of abnormal regions (where the abnormality is defined as >50% SNPs or >25% SNPs being affected in a region). Note that due to subclonality, the absence of CNVs in the tumor samples do not imply the absence of CNVs in the plasma.

TABLE 36

Summary of affected regions.

| | Number of Regions with Abnormality | | | | | |
|---|---|---|---|---|---|---|
| | 0 | 1 | 2 | 3 | 4 | >5 |
| >50% SNPs affected | 15 | 9 | 10 | 2 | 4 | 2 |
| >25% SNPs affected | 12 | 5 | 11 | 6 | 4 | 4 |

Analysis Using AAI Method

Due to the complex and mosaic nature of CNVs present in the cell lines (confirmed with non-integer copy number calls in Oncoscan data), the titration samples with 20% TCF were used in addition to Oncoscan when determining the expected AAI in each region of each cell line. FIG. 8 provides the AAI estimate as a function of TCF values and total copy number of the tumor cells (assuming an unbalanced duplication where one homolog has one copy).

In six titrations (TCF=1%, 2%, 3%, 5%, 7%, 10%) we found a total of 62 regions with at least 1% expected AAI across three cell lines and six titrations. Since we had three replicates at each TCF level, we made a total of 186 calls in these regions. Note that in this approach, balanced CNVs are not detected in the reference method, and so do not detract from sensitivity.

We called a region as positive if one of the following conditions satisfied: (i) AAI and confidence estimates found using all the SNPs in a region exceeded the region-level thresholds (ii) there exists a subregion with at least 50 consecutive SNPs that had AAI and confidence estimates that exceeded the subregion thresholds.

The sensitivity was 100%(51/51) for AAI ≥5%, 100% (60/60) for AAI ≥4%, 97.6% (82/84) for AAI ≥3%, and 91.5% (107/117) for AAI ≥2%. The observed specificity was 100% (336/336).

Moreover, note that TCF=5% with a CNV of 3 copies corresponds to AAI=2.44%. We observed that our sensitivity for AAI≥2.44% was 96% (95/99).

Furthermore, specificity was determined using 24 putative normal plasma samples and six replicates of each cell line at 0% TCF, resulting in 42*8=336 regions with 0% target AAI.

The sensitivity at each expected AAI range and specificity is as in Table 37. This represents the fraction of CNVs that were successfully detected, for affected genes with expected AAI in the identified range (based on Oncoscan and 20% titration samples).

TABLE 37

Sensitivity and specificity at various AAI levels

| Expected AAI | TCF (for CN = 3) | Called | Eligible | Sensitivity |
|---|---|---|---|---|
| [1%, 2%) | [2.02%, 4.08%) | 22 | 69 | 31.88% |
| [2%, 3%) | [4.08%, 6.19%) | 25 | 33 | 75.76% |
| [3%, 4%) | [6.19%, 8.33%) | 22 | 24 | 91.67% |
| [4%, 5%) | [8.33%, 10.53%) | 9 | 9 | 100.00% |
| [5%, 8%) | [10.53%, 17.39%) | 24 | 24 | 100.00% |
| ≥8% | ≥17.39% | 27 | 27 | 100.00% |

TABLE 37-continued

| Sensitivity and specificity at various AAI levels | | | | |
|---|---|---|---|---|
| Expected AAI | | Called | Eligible | Specificity |
| 0% | 0% | 0 | 336 | 100.00% |

Table 38 provides the sensitivity and specificity at each region in the base case scenario (note that we merged some expected AAI buckets due to the low number of regions available). Note that N/A denotes the absence of any samples within the expected AAI range under consideration. Sample size at each region is given in parentheses.

TABLE 38

| Sensitivity, specificity, and sample size per gene at various AAI levels in the base case (Titration) | | | | | | | | |
|---|---|---|---|---|---|---|---|---|
| | BRAF | EGFR | ERBB2 | FGFRI | KRAS | MET | MYC | PIK3CA |
| NumSNPs → | 836 | 611 | 497 | 495 | 493 | 539 | 426 | 530 |
| Target AAI | Sensitivity | | | | | | | |
| [1%, 2%) | 41.67% (12) | 83.33% (6) | 16.67% (6) | 53.33% (15) | 16.67% (6) | 0.00% (9) | 33.33% (6) | 0.00% (9) |
| 2%, 4%) | 100.00% (12) | N/A (0) | 66.67% (9) | 86.67% (15) | 100.00% (6) | 50.00% (6) | N/A (0) | 77.78% (9) |
| ≥4% | 100.00% (3) | N/A (0) | 100.00% (36) | N/A (0) | 100.00% (3) | 100.00% (9) | N/A (0) | 100.00% (9) |
| Target AAI | Specificity | | | | | | | |
| 0% | 100.00% (42) | 100.00% (42) | 100.00% (42) | 100.00% (42) | 100.00% (42) | 100.00% (42) | 100.00% (42) | 100.00% (42) |

Table 39 provides the minimum expected AAI level at which all three replicates were called as positive for a given cell line and region. For regions annotated with N/A, allelic imbalance was not detected in Oncoscan and NGS. Note that no CNVs were detected at any titration level for genes that were known to be unaffected based on the reference data. This table also provides minimum AAI detected in each region (last column) and in each cell line (last row).

TABLE 39

| Minimum expected AAI detected in all three replicates in each region and cell line in the base case (Titration) | | | | |
|---|---|---|---|---|
| | HCC1954 | HCC2218 | HCC38 | Min |
| BRAF | N/A | 2.75% | 1.80% | 1.80% |
| EGFR | 1.90% | N/A | N/A | 1.90% |
| ERBB2 | 6.12%[1] | 5.45% | 2.96% | 2.96% |
| FGFR1 | 3.01% | 1.15% | 1.66% | 1.15% |
| KRAS | 2.39% | N/A | 2.70% | 2.39% |
| MET | 3.64% | 3.14% | N/A | 3.14% |
| MYC | N/A | N/A | 2.68% | 2.68% |
| PIK3CA | 3.58% | N/A | 2.72% | 2.72% |
| Min | 1.90% | 1.15% | 1.66% | |

[1]6.12% AAI for ERBB2 region of HCC1954 corresponded to the lowest TCF (1%) in the experiment. Hence, performance in ERBB2 is potentially closer to the one observed in HCC38.

Next, we revised our confidence & AAI thresholds to see how the sensitivity & specificity changes. More specifically, we decreased the confidence & AAI thresholds gradually, and Table 40 below summarizes our findings.

TABLE 40

| Sensitivity vs. specificity as a function of calling thresholds (Titration) | | | | | | |
|---|---|---|---|---|---|---|
| | Base Case | 5% lower | 10% lower | 15% lower | 20% lower | 25% lower |
| Expected AAI | Sensitivity | | | | | |
| [1%, 2%) | 31.88% | 42.03% | 52.17% | 57.97% | 69.57% | 73.91% |
| [2%, 3%) | 75.76% | 75.76% | 78.79% | 78.79% | 81.82% | 87.88% |
| [3%, 4%) | 91.67% | 91.67% | 91.67% | 95.83% | 100.00% | 100.00% |
| [4%, 5%) | 100.00% | 100.00% | 100.00% | 100.00% | 100.00% | 100.00% |
| [5%, 8%) | 100.00% | 100.00% | 100.00% | 100.00% | 100.00% | 100.00% |
| ≥8% | 100.00% | 100.00% | 100.00% | 100.00% | 100.00% | 100.00% |
| Expected AAI | Specificity | | | | | |
| 0% | 100.00% | 98.51% | 97.32% | 94.64% | 93.75% | 92.56% |

Analysis of Cell Line Titrations and Plasmas Using FODDOR Method

Sample Classifier

We used FODDOR to simply classify the plasmART samples as positive/negative. The VTF is calculated from the TCF using the numbers in Table 33.

HCC38

The performance of FODDOR on this cell line is listed in Table 41. This table shows that the FODDOR sensitivity and specificity around a VTF of 5% are 100% and 97.5% respectively.

TABLE 41

FODDOR classifier sample level calls on cell line HCC38 at different TCF titrations.

| TCF (%): | 0 | 0.1 | 0.2 | 1 | 2 | 3 | 5 | 10 | 20 |
|---|---|---|---|---|---|---|---|---|---|
| VTF (%): | 0 | 0.133 | 0.266 | 1.33 | 2.66 | 3.99 | 6.65 | 13.3 | 26.6 |
| Total | 40 | 5 | 5 | 5 | 5 | 5 | 5 | 5 | 5 |
| Positive Calls | 1 | 2 | 0 | 0 | 3 | 5 | 5 | 5 | 5 |
| Negative Calls | 39 | 3 | 5 | 5 | 2 | 0 | 0 | 0 | 0 |

HCC1954

The performance of FODDOR on this cell line is listed in Table 42. This table shows that the FODDOR sensitivity and specificity around a VTF 5% are 70% and 97.5% respectively. But notice that this cell line has multiple (in fact, all) regions with abnormal copy numbers. So, the VTF estimate is not accurate.

TABLE 42

FODDOR classifier sample level calls on cell line HCC1954 at different TCF titrations.

| TCF (%): | 0 | 0.1 | 0.2 | 1 | 2 | 3 | 5 | 10 | 20 |
|---|---|---|---|---|---|---|---|---|---|
| VTF (%): | 0 | 3.5385 | 7.077 | 35.385 | 70.77 | 106.155 | 176.925 | 353.85 | 707.7 |
| Total | 40 | 5 | 5 | 5 | 5 | 5 | 5 | 5 | 5 |
| Positive Calls | 1 | 4 | 3 | 5 | 5 | 5 | 5 | 5 | 5 |
| Negative Calls | 39 | 1 | 2 | 0 | 0 | 0 | 0 | 0 | 0 |

HCC2218

The performance of FODDOR on this cell line is listed in Table 43. This table shows that the FODDOR sensitivity even up to VTF of 10% is just 20%. This cell line is listed as having a copy number of 6.32 for the ERBB2 region. But, we noticed that this region has both deletions and duplications and so we are running into one of the limitations of the FODDOR classifier here. The specificity is 97.5%.

TABLE 43

FODDOR classifier sample level calls on cell line HCC2218 at different TCF titrations.

| TCF (%): | 0 | 0.1 | 0.2 | 1 | 2 | 3 | 5 | 10 | 20 |
|---|---|---|---|---|---|---|---|---|---|
| VTF (%): | 0 | 0.432 | 0.864 | 4.32 | 8.64 | 12.96 | 21.6 | 43.2 | 86.4 |
| Total | 40 | 5 | 5 | 5 | 5 | 5 | 5 | 5 | 5 |
| Positive Calls | 1 | 1 | 0 | 1 | 1 | 2 | 5 | 5 | 5 |
| Negative Calls | 39 | 4 | 5 | 4 | 4 | 3 | 0 | 0 | 0 |

Iterative Estimator

HCC38

Next we ran the iterative region level estimator to make calls on individual regions. At 5% TCF, the region level VTF estimates are as follows. This algorithm identifies EGFR, KRAS and MET as normal regions and the remaining regions as abnormal with VTF estimates listed in Table 44.

TABLE 44

| FODDOR based iterative estimator's region level VTF estimates on cell line HCC38. | | | | | | | |
|---|---|---|---|---|---|---|---|
| BRAF | EGFR | ERBB2 | FGFR1 | KRAS | MET | MYC | PIK3CA |
| 0.024312 | 0 | 0.046294 | 0.070133 | 0 | 0 | 0.055685 | 0.016963 |

These results are in line with the AAI calls at 5% TCF, except for the MYC region. FODDOR identifies MYC as abnormal but AAI does not have enough confidence at 5% TCF to identify this region as abnormal. AAI successfully identifies this region as abnormal at 20% TCF as seen in Table 45. This is one of the benefits of using FODDOR in combination with AAI.

TABLE 45

| AAI region level positive call confidences on cell line HCC38 at 5% TCF. | | | | | | | |
|---|---|---|---|---|---|---|---|
| BRAF | EGFR | ERBB2 | FGFR1 | KRAS | MET | MYC | PIK3CA |
| 99.79% | 6.80% | 100% | 100% | 57.78% | 41.32% | 77.73% | 100% |

For TCF higher than 5% FODDOR fails to make calls on any of the regions. This is because FODDOR is unable to identify a subset of at least two regions which it can use as reference regions. This seems to be the case for this cell line as can be noticed in Table 46.

TABLE 46

| AAI region level positive call confidences on cell line HCC38 at 20% TCF. | | | | | | | |
|---|---|---|---|---|---|---|---|
| BRAF | EGFR | ERBB2 | FGFR1 | KRAS | MET | MYC | PIK3CA |
| 100% | 92.12% | 100% | 100% | 99.54% | 38.21% | 99.74% | 100% |

HCC1954

At 5% TCF, the region level VTF estimates are as follows. According to Table 31, all the regions in this cell line are abnormal. Since there are no reference regions, FODDOR is not applicable for this sample. So FODDOR results on this sample must be carefully interpreted.

First, the regions FGFR1 and KRAS have both copy deletions and so their copy number is 0. Since these regions have the least copy number, FODDOR will see these regions are normal and use them as reference regions to estimate the VTF of the other regions. In fact that is exactly what FODDOR is doing as can be seen in Table 47.

From Table 31, we see that the ERBB2 region has the highest copy number of 37. FODDOR's estimate of region level VTF's also shows that ERBB2 is the region with the highest copy number. So, even though FODDOR doesn't find a valid reference region, it is still able to pick up an extremely amplified region.

The MYC region, according to the Table 31, has a copy number of 6.59 with partial segments having balanced duplications. As a result, AAI algorithm fails to detect the abnormality in this region. Even though FODDOR doesn't have a valid reference region, we can see that FODDOR algorithm calls this regions as abnormal with a large VTF estimate. Of course, in this particular example, FODDOR was unfairly enabled to call the MYC region as abnormal. But the fact that FODDOR has a large VTF estimate for this region suggests that even if the deleted regions were actually balanced, FODDOR would have still caught the MYC abnormality. The takeaway from this example is that FODDOR is not affected by balanced CNVs and so using it in combination with AAI will enable us to catch balanced CNVs that AAI fails to catch (Table 48).

TABLE 47

FODDOR based iterative estimator's region level VTF estimates on cell line HCC1954

| BRAF | EGFR | ERBB2 | FGFR1 | KRAS | MET | MYC | PIK3CA |
|---|---|---|---|---|---|---|---|
| 0.042896 | 0.039741 | 0.50063 | 0 | 0 | 0.049237 | 0.10048 | 0.054556 |

TABLE 48

AAI region level positive call confidences on cell line HCC1954 at 5% TCF.

| BRAF | EGFR | ERBB2 | FGFR1 | KRAS | MET | MYC | PIK3CA |
|---|---|---|---|---|---|---|---|
| 23.67% | 90.31% | 100% | 41.26% | 99.98% | 35.75% | 53.59% | 70.49% |

For TCF higher than 5% FODDOR fails to make calls on any of the regions. This is because FODDOR is unable to identify a subset of at least two regions which it can use as reference regions. This, in fact seems to be the case for this cell line as can be noticed in the Table 49.

TABLE 49

AAI region level positive call confidences on cell line HCC1954 at 20% TCF.

| BRAF | EGFR | ERBB2 | FGFR1 | KRAS | MET | MYC | PIK3CA |
|---|---|---|---|---|---|---|---|
| 26.56% | 100% | 100% | 100% | 100% | 100% | 54.79% | 100% |

HCC2218

At 5% TCF, the region level VTF estimates are in Table 50.

TABLE 50

FODDOR based iterative estimator's region level VTF estimates on cell line HCC2218

| BRAF | EGFR | ERBB2 | FGFR1 | KRAS | MET | MYC | PIK3CA |
|---|---|---|---|---|---|---|---|
| 0.024168 | 0 | 0 | 0 | 0.0058011 | 0.038968 | 0.061569 | 0.013419 |

According to the Table 31 only the EGFR and KRAS regions are normal. The FGFR1 has a deletion resulting in a copy number of 1. But since FODDOR assumes the regions with the least copy number as normal, it incorrectly sees FGFR1 as normal and as a consequence sees KRAS and PIK3CA as abnormal. In this cell line, the ERBB2 region has both deletion and duplication which effectively canceled each other and so FODDOR identified this region as normal.

Next, we removed the FGFR1 region from the analysis and re-ran the FODDOR based iterative estimator on the rest of the regions. Since there are no deletions in any of the other regions, we expected FODDOR to perform correctly. The new VTF estimates are in Table 51.

TABLE 51

FODDOR based iterative estimator's region level VTF estimates on cell line HCC2218 after eliminating the FGFR1 region.

| BRAF | EGFR | ERBB2 | FGFR1 | KRAS | MET | MYC | PIK3CA |
|---|---|---|---|---|---|---|---|
| 0 | 0 | 0 | N/A | 0 | 0.0197 | 0.0459 | 0.0045 |

Now, the results look reasonable. FODDOR correctly identified MYC and MET as abnormal regions. In 1 out of 5 replicates, it identified PIK3CA as abnormal. Also, it correctly called EGFR and KRAS as normal. FODDOR failed to detect the BRAF abnormality. The ERBB2 abnormality was again not detected as expected due to the reason previously explained. You can compare FODDOR results against the AAI results listed in Table 52.

TABLE 52

AAI region level positive call confidences on cell line HCC2218 at 5% TCF.

| BRAF | EGFR | ERBB2 | FGFR1 | KRAS | MET | MYC | PIK3CA |
|---|---|---|---|---|---|---|---|
| 100% | 70.95% | 90.49% | 95.64% | 8.12% | 100% | 47.89% | 43.81% |

Here again, the MYC region has balanced duplications. As a result, the AAI algorithm failed to detect the abnormality in this region. But FODDOR algorithm was able to successfully detect this abnormality. Notice that AAI fails to detect the MYC abnormality even at 20% TCF as shown in Table 53.

TABLE 53

AAI region level positive call confidences on cell line HCC2218 at 20% TCF.

| BRAF | EGFR | ERBB2 | FGFR1 | KRAS | MET | MYC | PIK3CA |
|---|---|---|---|---|---|---|---|
| 100% | 81.73% | 100% | 100% | 74.46% | 100% | 58.7% | 22.96% |

Stand Alone FODDOR Performance

Here, we analyzed the stand-alone performance of the FODDOR based iterative estimator. We used the AAI calls at 20% TCF as the truth and compared the FODDOR results to this truth. Since the AAI has some limitations, using the AAI results as the truth to estimate FODDOR performance, especially the sensitivity, gave us the lower limit of the true performance.

HCC38

Here, we know from AAI that ERBB2 is abnormal, but since we do not have the copy number estimate of this region we assumed ERBB2 was normal for this analysis. The individual region copy numbers that we used for computing the VTF from the TCF are obtained from Table 31. The results are shown in Table 54.

TABLE 54

FODDOR performance on cellline HCC38 using AAI calls at 20% TCF as truth.

| VTF | 0.01 | 0.02 | 0.03 | 0.04 | 0.05 | 0.06 | 0.07 |
|---|---|---|---|---|---|---|---|
| Positives | 45 | 25 | 15 | 5 | 5 | 5 | 0 |
| True Positives | 22 | 17 | 13 | 5 | 5 | 5 | 0 |
| Sensitivity | 48.889% | 68% | 86.667% | 100% | 100% | 100% | NaN |

HCC1954

Here we assumed that FGFR1 and KRAS are normal and analyzed the calls on the rest of the regions. The results are shown in Table 55.

TABLE 55

FODDOR performance on cellline HCC1954 using AAI calls at 20% TCF as truth.

| VTF >= | 0.01 | 0.02 | 0.03 | 0.04 | 0.05 | 0.06 | 0.07 |
|---|---|---|---|---|---|---|---|
| Positives | 125 | 105 | 85 | 65 | 55 | 40 | 40 |
| True Positives | 72 | 71 | 66 | 57 | 52 | 37 | 37 |
| Sensitivity | 57.6% | 67.619% | 77.647% | 87.692% | 94.545% | 92.5% | 92.5% |

HCC2218

Here we assumed that ERBB2 is normal because there is both deletion and duplication on this region which effectively makes the abnormality invisible to FODDOR. The results are shown in Table 56.

TABLE 56

FODDOR performance on cellline HCC2218 using AAI calls at 20% TCF as truth.

| VTF | 0.01 | 0.02 | 0.03 | 0.04 | 0.05 | 0.06 | 0.07 |
|---|---|---|---|---|---|---|---|
| Positives | 55 | 45 | 30 | 20 | 15 | 5 | 5 |
| True Positives | 17 | 16 | 16 | 11 | 11 | 5 | 5 |
| Sensitivity | 30.909% | 35.556% | 53.333% | 55% | 73.333% | 100% | 100% |

Combining the results from the three cell line samples with a VTF estimate of at least 5%, we estimate the sensitivity of FODDOR region level estimator to be 92.35%.

In addition to the above titration samples, we also ran FODDOR on 120 wild type samples. One these FODDOR made positive calls on 2 samples (2 regions on one and 5 regions on the other). 2 other samples had extremely bad K-S statistics suggesting that something unusual was happening with theses samples. So, we removed these 2 samples from our analysis. Using these numbers the estimated specificity of 99.26%.

SUMMARY

The FODDOR based iterative estimator by itself has lower performance than AAI. But when combined with AAI, it can improve the overall performance by detecting abnormalities that AAI fails to detect, due to fundamental limitations of AAI.

Sample QC

As a part of sample QC, we determined the following: (1) Match between the tumor and plasma samples (to make sure that the plasma sample is coming from the same person whose tumor we analyzed) 2) Contamination checks to determine the presence of ambient or genotyped contamination. We used a tentative 0.2% threshold to determine if a sample is contaminated or not.

Based on this analysis, we observed that two cancer plasma samples, namely 9770Vd(303) and 9545 VH with sequencing ids 2330093 and 2330135, did not match the genotypes of their corresponding tumor sample and were eliminated from further analysis (note that to ensure that the abnormality in the tumor is not causing the mismatch, we only looked at the heterozygous SNPs when making this determination).

Furthermore, cancer plasmas 2872/12 and 5679/12 with sequencing ids 2330110 and 2330114, had high level of genotyped contamination (>2%) and were also eliminated from further analysis.

Two negative samples (Neg-9 and Neg-37 with sequencing ids 2330145 and 2370513), were mixtures of multiple plasmas. One other negative sample (Neg-22 with sequencing id 2370501) had higher than usual contamination (0.3% ambient and 0.9% genotyped contamination). These three samples were also eliminated from further analysis. Hence, a total of 4 cancer and 3 negative plasmas failed the QC, resulting in remaining 38 cancer and 83 negatives for the further analysis.

Analysis Using AAI Method

Sample level calls using the base case thresholds using in the titration analysis were as in Table 57. Note that the sensitivity and specificity is not exactly well defined in this context, although we still use these terms loosely. More specifically, we detected 34.21% of all cancer samples as positives. Moreover, one normal sample was called as positive with 100% confidence and an AAI of 4.22% (Neg-91 with sequencing id 2370539). This sample actually seems to have an abnormality that is visible in the het rate plot hence we believe it is very likely to be a correct call for analytical purposes.

TABLE 57

Sample level sensitivity vs. specificity in the base case (Geneticist)

| Stage | Called | Eligible | Sensitivity |
|---|---|---|---|
| IA | 3 | 8 | 37.50% |
| IB | 7 | 19 | 36.84% |

TABLE 57-continued

| Sample level sensitivity vs. specificity in the base case (Geneticist) | | | |
|---|---|---|---|
| IIB | 3 | 6 | 50.00% |
| IIIA | 0 | 4 | 0.00% |
| IV | 0 | 1 | 0.00% |
| All Cancer | 13 | 38 | 34.21% |
| | Called | Eligible | Specificity |
| Normal | 1 | 83 | 98.80% |

Next, we provide the sensitivity in the samples with positive tumors. More specifically, we define a tumor as positive if there is at least one sample with at least 50% SNPs covered with a CNV based on the previous analysis. Table 58 below provides the sensitivity for plasmas with positive and negative tumors.

TABLE 58

| Sample level sensitivity as a function of presence of CNVs in the tumor (Geneticist) | | |
|---|---|---|
| | TumorPos | TumorNeg |
| PlasmaPos | 50.00% | 7.14% |
| PlasmaNeg | 50.00% | 92.86% |
| NumSamples | 24 | 14 |

Note that the sensitivity seems significantly higher in the plasmas with corresponding positive tumors (50.00%) compared to plasmas with negative tumors (7.14%).

Finally, in Table 59 we study the sensitivity vs. specificity tradeoff as a function of calling thresholds.

TABLE 59

| Sample level sensitivity vs. specificity as a function of calling thresholds (Geneticist) | | | | | | |
|---|---|---|---|---|---|---|
| | Base Case | 5% lower | 10% lower | 15% lower | 20% lower | 25% lower |
| Stage | Sensitivity | | | | | |
| IA | 37.50% | 37.50% | 50.00% | 50.00% | 50.00% | 50.00% |
| IB | 36.84% | 36.84% | 36.84% | 36.84% | 42.11% | 42.11% |
| IIB | 50.00% | 50.00% | 50.00% | 66.67% | 66.67% | 66.67% |
| IIIA | 0.00% | 0.00% | 0.00% | 0.00% | 25.00% | 25.00% |
| IV | 0.00% | 0.00% | 0.00% | 0.00% | 0.00% | 0.00% |
| All Cancer | 34.21% | 34.21% | 36.84% | 39.47% | 44.74% | 44.74% |
| Normal | Specificity | | | | | |
| | 98.80% | 97.59% | 97.59% | 96.39% | 93.98% | 91.57% |

Analysis Using FODDOR Method

First we ran the FODDOR classifier to simply classify a sample as positive/negative. The performance of the classification had a sensitivity estimate of 42.105% (38 positives, 16 true positive calls) and specificity estimate of 95.213% (188 negatives, 9 false positive calls). Note that a sample marked as positive may not necessarily have a CNV in the plasma. Also, we do not know the TCF in the plasma sample.

This specificity estimate is very close to our specificity estimate using the zero-titration samples before. Here FODDOR identified the following 7 additional samples that were not identified as positive by AAI. These samples demonstrate the benefit of using FODDOR in combination with AAI. It is important to note that FODDOR and AAI identified different cancer samples as positives. So together they identified 21 samples as positives which gives us a combined sensitivity estimate of 60.53%

Next we ran the region level estimator. As truth we used the individual region copy numbers determined previously in the CNV-truth Geneticist samples. The sensitivity estimate is 16.176% (68 positives, 11 true positive calls) and the specificity estimate is 97.065% (1772 negatives, 52 false negative calls). Note that the abnormal region in the tumor does not mean that the region is abnormal in the plasma. So, the sensitivity estimate above is only a lower bound of the true sensitivity. Also, note that we do not know the TCF here.

Using the AAI calls on individual regions, the sensitivity estimate is 31.579% (38 positives, 12 true positives) and the specificity estimate is 97.17% (1802 negatives, 51 false positives).

The sensitivity estimate above is only a lower bound of the true sensitivity.

Comparison to Performance Objectives

The performance objectives for fCNV technology were as follows, measured as analytical performance per gene region tested: (1) Sensitivity≥95% for TCF≥5% assuming copy number change ≥1 and (2) [SEP] Specificity≥99%.

The sensitivity objective can be evaluated with respect to the AAI method or the combination. The AAI method detected 96% (95/99) of regions with AAI corresponding to a one copy change at TCF≥5%, for regions where an allelic imbalance was present in the reference data. There were two genes with balanced CNVs, which if included in the sensitivity calculation, reduce the AAI sensitivity to 90% (95/105). These were both detectable by FODDOR, leading to a combined method sensitivity of 96% (101/105).

Specificity can be observed from real plasma that is assumed to be unaffected by a CNV because it was collected from subjects presumed to be healthy, but there is still some risk of a CNV being present. Specificity could also be estimated from samples prepared from pure wild-type cell line. Thus the observed specificity might be an underestimate of the true specificity.

The specificity of the AAI method in presumed-negative plasma samples was 98.8% (82/83) by sample or 99.8% (663/664) by region, but the sample called positive was confirmed to have an allelic imbalance visible by inspection. Therefore the estimated analytical specificity could be considered 100%. The specificity in the cell line titrations was also 100%. The specificity demonstrated by the FODDOR method was 95% in real plasma and 98% in pure wild-type cell lines.

Performance on Affected Patient Samples

The following conclusions can be drawn: (1) samples that do not show an allelic imbalance in the tumor tissue are far less likely to show one in plasma; (2) a significant number of samples are identified as positive using one algorithm but not the other, bidirectionally; and (3) some samples are not identified as positive by either algorithm, even conditioned on the presence of allelic imbalance in the tumor tissue. [SEP] The fact that the two algorithms identify different sets of positive samples is expected due to their differing methods and could indicate that balanced CNVs are more common than expected.

Discussion

The results of this study are equivalent to detecting a CNV with copy number of 6 and a TCF of 2%, with 100% sensitivity and 100% specificity in liquid biopsies.

To put our results into context with published results, Lanman et al. 2015 (PLoS ONE 10(10): e0140712. doi: 10.1371/journal.pone.0140712) (Guardant Health) shows plasma fCNV limit of detection of 5% TCF with a copy number of 6; this means that they are able to detect an AAI of ~9.1% (More specifically, the limit of detection mentioned is an additional 0.2 copies in EGFR and MET. This corresponds to an AAI of 0.2/2.2=9.09%. For ERBB2 the limit is higher at 0.5 copies, or an AAI of 0.5/2.5=20%.) compared to the observed 100% sensitivity at AAI of 4% demonstrated in this Example.

In FIG. 8, example AAI values that were detected with 100% sensitivity using the fCNV method herein are marked with a dot pattern, and the limit of detection claimed by Lanman et al. is marked with a line pattern.

Some of the methods provided herein, are set out with the following clauses:

Clause 1. A method for determining ploidy of a chromosomal segment in a sample of an individual, the method comprising:

a. receiving sequencing data for amplicons spanning each loci of a plurality of polymorphic loci on a plurality of subsegments within the chromosomal segment, wherein each subsegment comprises loci with strong linkage disequilibrium;
b. generating allele frequency data comprising the amount of each allele present in the sample at each loci from the sequencing data;
c. generating phased allelic information for the plurality of polymorphic loci by estimating the phase of the allele frequency data taking into account an increased statistical correlation of polymorphic loci within the same subsegment;
d. generating individual probabilities of allele frequencies for the polymorphic loci for different ploidy states using the allele frequency data;
e. generating joint probabilities for the plurality of linked polymorphic loci using the individual probabilities and the phased allelic information; and
f. selecting, based on the joint probabilities, a best fit model indicative of chromosomal ploidy, thereby determining ploidy of the chromosomal segment.

Clause 2. A method according to clause 1, wherein each subsegment includes between 10 and 500 polymorphic loci.

Clause 3. A method according to clause 2, wherein allele frequency data is generated for at least 300 loci within the chromosome segment.

Clause 4. A method according to clause 2, wherein allele frequency data is generated for at least 1000 loci within the chromosome segment.

Clause 5. A method according to clause 2, wherein between 10 and 100 of the polymorphic loci are located within each subsegment.

Clause 6. The method according to clause 2, further comprising an amplification reaction using a set of non-interactive primers, wherein the set of non-interactive primers are chosen such that each primer pair of the set amplify an amplicon comprising one loci of the plurality of polymorphic loci.

Clause 7. A method according to clause 2, wherein the method is performed on a plurality of chromosome segments.

Clause 8. A method according to clause 7, wherein the sample is a plasma sample from an individual and the method further comprises determining, based on the selecting, whether cancer is present in the individual.

Clause 9. A method of clause 8, wherein the plurality of chromosome segments comprise at least two segments selected from the group of chromosome segments consisting of at least: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, and chromosome 17 nucleotides 10700001-16000000.

Clause 10. A method according to clause 9, wherein the method further comprises determining, based on the selecting, whether Ovarian cancer is present in the individual.

Clause 11. A method for determining ploidy of a chromosomal segment in a sample of an individual, the method comprising:

a. receiving allele frequency data for each loci of a plurality of polymorphic loci on a plurality of subsegments within the chromosomal segment, wherein each subsegment comprises loci with strong linkage disequilibrium, wherein the allele frequency data comprises the amount of each allele present in the sample at each loci;
b. generating phased allelic information for the plurality of polymorphic loci by estimating the phase of the allele frequency data taking into account an increased statistical correlation of polymorphic loci within the same subsegment;
c. generating individual probabilities of allele frequencies for the polymorphic loci for different ploidy states using the allele frequency data;
d. generating joint probabilities for the plurality of linked polymorphic loci using the individual probabilities and the phased allelic information; and
e. selecting, based on the joint probabilities, a best fit model indicative of chromosomal ploidy, thereby determining ploidy of the chromosomal segment.

Clause 12. A method according to clause 11, wherein each subsegment includes between 10 and 100 polymorphic loci.

Clause 13. A method according to clause 12, wherein allele frequency data is generated for at least 300 loci within the chromosome segment.

Clause 14. A method according to clause 12, wherein allele frequency data is generated for at least 1000 loci within the chromosome segment.

Clause 15. A method for determining whether circulating tumor nucleic acids from an Ovarian cancer are present in a liquid sample from an individual, comprising a. analyzing the sample to determine a ploidy at a plurality of chromosome segments in the individual, wherein the analyzing comprises separately analyzing SNP allelic data for between 10 and 100 SNP loci within each subsegment of a set of chromosome subsegments from each of the plurality of chromosome segments, wherein each subsegment comprises loci with strong linkage disequilibrium, and then combining the separate SNP allelic data to determine a subsegment allele for each of the set of chromosome subsegments, and then combining subsegment allelic data for subsegments on the same chromosome segment to determine ploidy of each of the chromosome segments; and b. determining the level of allelic imbalance present for each chromosome segment of the plurality of chromosome segments based on the ploidy determination, whereby an allelic imbalance above a cutoff value is indicative of the presence of circulating tumor nucleic acids.

Clause 16. A method according to clause 15, wherein an average allelic imbalance cutoff value above 0.45 is indicative of the presence of circulating tumor nucleic acids.

Clause 17. A method according to clause 15, wherein the plurality of chromosome segments comprise at least two segments selected from the group of chromosome segments consisting of at least 90% of the contiguous nucleotides of the following plurality of chromosome segments: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, and chromosome 17 nucleotides 10700001-16000000.

Clause 18. A method according to clause 17, wherein the group of chromosome segments consists of at least 95% of the contiguous nucleotides of the plurality of chromosome segments.

Clause 19. The method according to clause 15, wherein the plurality of chromosome segments comprise of at least two segments selected from the group of chromosome segments consisting of at least: chromosome 3, chromosome 8, chromosome 12, chromosome 13, chromosome 16, chromosome 19, chromosome 20, and chromosome 22.

Clause 20. The method according to clause 15, wherein the plurality of chromosome segments comprise at least three segments selected from the group of chromosome segments consisting of at least the following plurality of chromosome segments: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, and chromosome 17 nucleotides 10700001-16000000.

Clause 21. The method according to clause 17, wherein within the set of chromosome subsegments from each of the plurality of chromosome segments a plurality of subsegments comprise between:

a. 50%-100% of the chromosome subsegments, b. 60%-99% of the chromosome subsegments, c. 65%-95% of the chromosome subsegments, d. 70%-90% of the chromosome subsegments, and e. 75%-85% of the chromosome subsegments.

Clause 22. A method according clause 15, wherein the analyzing is performed using high throughput nucleic acid sequencing by determining the nucleic acid sequence of less than 10% of the nucleotides within each segment of the plurality of chromosome segments.

Clause 23. A method for determining whether circulating tumor nucleic acids from an Ovarian cancer are present in a liquid sample from an individual, comprising a. analyzing the sample to determine a ploidy at a plurality of chromosome segments in the individual, wherein the chromosome segments comprise at least two segments that exhibit copy number variation in at least 50% of Ovarian cancer patients; and b. determining the level of allelic imbalance present for each chromosome segment of the set of chromosome segments based on the ploidy determination, wherein an allelic imbalance equal to or greater than 0.45% for any of the chromosome segments is indicative of the presence of circulating tumor nucleic acids in the sample.

Clause 24. A method according to clause 23, wherein the analyzing comprises separately analyzing SNP allelic data for between 10 and 100 SNP loci with strong linkage disequilibrium within each subsegment of a set of chromosome subsegments from each of the plurality of chromosome segments, and then combining the separate SNP allelic data to determine a subsegment allele for each of the set of chromosome subsegments, and then combining subsegment allelic data for subsegments on the same chromosome segment to determine ploidy of each of the chromosome segments.

Clause 25. A method according to clause 23, wherein the analyzing comprises analyzing at least two chromosome segments selected from the group of chromosome segments consisting of the following plurality of chromosome segments: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, and chromosome 17 nucleotides 10700001-16000000 for an average allelic imbalance indicative of a deletion of the segment.

Clause 26. A method according to clause 23, wherein the analyzing comprises analyzing at least two chromosome segments from the group of chromosome segments consisting of the following plurality of chromosome segments: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-

63025520, chromosome 17 nucleotides 25800001-31800000, and chromosome 17 nucleotides 10700001-16000000.

Clause 27. A method according to clause 23, wherein the analyzing comprises analyzing at least three chromosome segments selected from the group of chromosome segments consisting of the following plurality of chromosome segments: chromosome 8 nucleotides 115,298,000-145,233,000, chromosome 8 nucleotides 100758000-115298000, chromosome 8 nucleotides 617000-37343000, chromosome 3 nucleotides 166356000-180256000, chromosome 22 nucleotides 42378000-49332000, chromosome 19 nucleotides 34341000-40857000, chromosome 19 nucleotides 28240000-33433000, chromosome 19 nucleotides 12042000-17796000, chromosome 16 nucleotides 60437000-89380000, chromosome 12 nucleotides 18959000-29050000, chromosome 20 nucleotides 1-26369569, chromosome 20 nucleotides 29369569-63025520, chromosome 17 nucleotides 25800001-31800000, and chromosome 17 nucleotides 10700001-16000000.

Clause 28. A method according to clause 23, further comprising detecting a single nucleotide variant at a single nucleotide variance site in a set of single nucleotide variance locations, wherein detecting either an allelic imbalance equal to or greater than 0.45% or detecting the single nucleotide variant, or both, is indicative of the presence of circulating tumor nucleic acids in the sample.

Clause 29. A method according to clause 23, wherein the method further comprises performing the method on an Ovarian cancer control nucleic acid sample with a known average allelic imbalance ratio.

Clause 30. A method according to clause 29, wherein the control is a chromosomal segment sample from the tumor of the individual.

Clause 31. A method according to clauses 23-26, wherein analyzing the sample comprises performing a multiplex PCR to amplify amplicons across 1000 to 50,000 polymeric loci on the set of chromosome segments.

Clause 32. A system for detecting chromosomal ploidy in a sample of an individual, the system comprising:

a. an input processor configured to receive allelic frequency data comprising the amount of each allele present in the sample at each loci of a plurality of polymorphic loci on a plurality of subsegments within the chromosomal segment, wherein each subsegment comprises loci with strong linkage disequilibrium;

b. a modeler configured to:

c. generate phased allelic information for the set of polymorphic loci by estimating the phase of the allele frequency data taking into account an increased statistical correlation of polymorphic loci within the same subsegment;

d. generate individual probabilities of allele frequencies for the polymorphic loci for different ploidy states using the allele frequency data; and e. generate joint probabilities for the set of polymorphic loci using the individual probabilities and the phased allelic information; and f. a hypothesis manager configured to select, based on the joint probabilities, a best fit model indicative of chromosomal ploidy, thereby determining ploidy of the chromosomal segment.

Clause 33. A system according to clause 32, wherein the allele frequency data is generated by a nucleic acid sequencing system.

Clause 34. A nontransitory computer readable medium for detecting chromosomal ploidy in a sample of an individual, comprising computer readable code that, when executed by a processing device, causes the processing device to:

a. receive allele frequency data comprising the amount of each allele present in the sample at each loci of a plurality of polymorphic loci on a plurality of subsegments within the chromosomal segment, wherein each subsegment comprises loci with strong linkage disequilibrium;

b. generate phased allelic information for the set of polymorphic loci by estimating the phase of the allele frequency data taking into account an increased statistical correlation of polymorphic loci within the same subsegment;

c. generate individual probabilities of allele frequencies for the polymorphic loci for different ploidy states using the allele frequency data;

d. generate joint probabilities for the set of polymorphic loci using the individual probabilities and the phased allelic information; and e. select, based on the joint probabilities, a best fit model indicative of chromosomal ploidy, thereby determining ploidy of the chromosomal segment.

Clause 35. A computer readable medium according to clause 34, wherein the allele frequency data is generated from nucleic acid sequence data.

The invention claimed is:

1. A method for amplifying and sequencing DNA, comprising:

(i) extracting cell-free DNA from a biological sample of a human subject to obtain extracted DNA;

(ii) performing target multiplex amplification by forming a reaction mixture comprising the extracted DNA or DNA derived therefrom and a pool of primers and subjecting the reaction mixture to amplification conditions to obtain a plurality of amplicons comprising one or more SNP or SNV loci, wherein the pool of primers comprise 200 to 10,000 target-specific primers that each specifically bind to a different primer binding sequence that is located within an effective distance of one or more SNP or SNV loci to obtain the plurality of amplicons comprising one or more SNP or SNV loci, wherein at least 90% of the primer binding sequences are located within a plurality of haploblocks that may exhibit genetic variation associated with cancer, wherein each haploblock comprises at least 2 of the primer binding sequences, and wherein each haploblock comprises two or more SNP or SNV loci having strong linkage disequilibrium; and (iii) sequencing the amplicons to obtain phased allelic data of the SNP or SNV loci.

2. The method of claim 1, wherein the biological sample is a blood, serum, plasma, or urine sample.

3. The method of claim 1, wherein the sequencing in step (iii) is high-throughput sequencing.

4. The method of claim 1, wherein the genetic variation comprises a mutation, insertion or deletion associated with cancer.

5. The method of claim 1, wherein the genetic variation comprises deletion or duplication of a chromosomal region associated with cancer.

6. The method of claim 1, wherein the pool of primers comprises 300 to 5,000 target-specific primers that each specifically bind to a different primer binding sequence.

7. The method of claim 1, wherein the pool of primers comprises 400 to 2,500 target-specific primers that each specifically bind to a different primer binding sequence.

8. The method of claim 1, wherein the pool of primers comprises 500 to 1,000 target-specific primers that each specifically bind to a different primer binding sequence.

9. The method of claim 1, wherein at least 95% of the primer binding sequences are located within the plurality of haploblocks.

10. The method of claim 1, wherein at least 99% of the primer binding sequences are located within the plurality of haploblocks.

11. The method of claim 1, wherein each haploblock comprises at least 3 of the primer binding sequences.

12. The method of claim 1, wherein each haploblock comprises at least 5 of the primer binding sequences.

13. The method of claim 1, wherein the pool of primers comprises 200 to 10,000 target-specific primers targeting 200 to 10,000 SNP or SNV loci located within the plurality of haploblocks.

14. The method of claim 1, wherein the pool of primers comprises 300 to 5,000 target-specific primers targeting 300 to 5,000 SNP or SNV loci located within the plurality of haploblocks.

15. The method of claim 1, wherein the pool of primers comprises 400 to 2,500 target-specific primers targeting 400 to 2,500 SNP or SNV loci located within the plurality of haploblocks.

16. The method of claim 1, wherein the pool of primers comprises 500 to 1,000 target-specific primers targeting 500 to 1,000 SNP or SNV loci located within the plurality of haploblocks.

17. The method of claim 1, wherein at least 95% of the SNP or SNV loci are located within the plurality of haploblocks.

18. The method of claim 1, wherein at least 99% of the SNP or SNV loci are located within the plurality of haploblocks.

19. The method of claim 1, wherein each haploblock comprises at least 3 of the SNP or SNV loci.

20. The method of claim 1, wherein each haploblock comprises at least 5 of the SNP or SNV loci.

* * * * *

SEQUENCE LISTING

```
Sequence total quantity: 2
SEQ ID NO: 1            moltype = DNA  length = 20
FEATURE                 Location/Qualifiers
misc_feature            1..20
                        note = primer tag
source                  1..20
                        mol_type = other DNA
                        organism = synthetic construct
SEQUENCE: 1
acacgacgct cttccgatct                                                  20

SEQ ID NO: 2            moltype = DNA  length = 21
FEATURE                 Location/Qualifiers
misc_feature            1..21
                        note = primer tag
```

-continued

```
source                  1..21
                        mol_type = other DNA
                        organism = synthetic construct
SEQUENCE: 2
agacgtgtgc tcttccgatc t                                            21
```